(12) United States Patent
Jin et al.

(10) Patent No.: US 10,787,430 B2
(45) Date of Patent: Sep. 29, 2020

(54) HEMOGLOBIN MODIFIER COMPOUNDS AND USES THEREOF

(71) Applicant: FronThera U.S. Pharmaceuticals LLC, San Diego, CA (US)

(72) Inventors: Bohan Jin, San Diego, CA (US); Qing Dong, San Diego, CA (US); Gene Hung, San Diego, CA (US)

(73) Assignee: FRONTHERA U.S. PHARMACEUTICALS LLC, San Diego, CA (US)

( * ) Notice: Subject to any disclaimer, the term of this patent is extended or adjusted under 35 U.S.C. 154(b) by 0 days.

(21) Appl. No.: 16/310,258

(22) PCT Filed: Jun. 16, 2017

(86) PCT No.: PCT/US2017/037983
§ 371 (c)(1),
(2) Date: Dec. 14, 2018

(87) PCT Pub. No.: WO2017/218960
PCT Pub. Date: Dec. 21, 2017

(65) Prior Publication Data
US 2019/0330181 A1 Oct. 31, 2019

Related U.S. Application Data

(60) Provisional application No. 62/351,708, filed on Jun. 17, 2016.

(51) Int. Cl.
| | |
|---|---|
| *C07D 401/04* | (2006.01) |
| *C07D 403/04* | (2006.01) |
| *C07D 413/14* | (2006.01) |
| *C07D 491/048* | (2006.01) |
| *C07D 405/14* | (2006.01) |
| *C07D 417/14* | (2006.01) |
| *C07D 471/04* | (2006.01) |
| *C07D 401/14* | (2006.01) |
| *C07D 409/14* | (2006.01) |
| *C07D 417/04* | (2006.01) |
| *C07D 413/04* | (2006.01) |
| *A61K 31/155* | (2006.01) |
| *A61K 31/198* | (2006.01) |
| *C07K 16/28* | (2006.01) |

(52) U.S. Cl.
CPC ......... *C07D 401/04* (2013.01); *C07D 401/14* (2013.01); *C07D 403/04* (2013.01); *C07D 405/14* (2013.01); *C07D 409/14* (2013.01); *C07D 413/04* (2013.01); *C07D 413/14* (2013.01); *C07D 417/04* (2013.01); *C07D 417/14* (2013.01); *C07D 471/04* (2013.01); *C07D 491/048* (2013.01); *A61K 31/155* (2013.01); *A61K 31/198* (2013.01); *C07K 16/2854* (2013.01)

(58) Field of Classification Search
CPC .. C07D 401/04; C07D 401/14; C07D 403/04; C07D 405/14; C07D 409/14; C07D 413/04; C07D 413/14; C07D 417/04; C07D 417/14; C07D 471/04; C07D 491/048; A61K 31/155; A61K 31/198; C07K 16/2854
USPC ....................................................... 514/256
See application file for complete search history.

(56) References Cited

U.S. PATENT DOCUMENTS

| | | |
|---|---|---|
| 2013/0040997 A1 | 2/2013 | Kim et al. |
| 2013/0190315 A1 | 7/2013 | Metcalf et al. |
| 2013/0190316 A1 | 7/2013 | Metcalf et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2015/0057251 A1 | 2/2015 | Harris |
| 2015/0209443 A1 | 7/2015 | Metcalf et al. |
| 2015/0344483 A1 | 12/2015 | Metcalf et al. |
| 2016/0046613 A1 | 2/2016 | Metcalf et al. |

FOREIGN PATENT DOCUMENTS

| | | |
|---|---|---|
| WO | WO-2013102142 A1 | 7/2013 |
| WO | WO-2014150256 A1 | 9/2014 |
| WO | WO-2014150258 A1 | 9/2014 |
| WO | WO-2014150261 A1 | 9/2014 |
| WO | WO-2014150276 A1 | 9/2014 |
| WO | WO-2014150289 A1 | 9/2014 |
| WO | WO-2015031284 A1 | 3/2015 |
| WO | WO-2015031285 A1 | 3/2015 |
| WO | WO-2015116061 A1 | 8/2015 |
| WO | WO-2015120133 A1 | 8/2015 |
| WO | WO-2015125085 A1 | 8/2015 |
| WO | WO-2017218960 A1 | 12/2017 |

OTHER PUBLICATIONS

PCT/US2017/037983 International Search Report and Written Opinion dated Oct. 20, 2017.

*Primary Examiner* — Kristin A Vajda
(74) *Attorney, Agent, or Firm* — Wilson Sonsini Goodrich & Rosati

(57) ABSTRACT

Described herein are compounds, including pharmaceutically acceptable salts thereof, methods of making such compounds, pharmaceutical compositions comprising such compounds, and methods of using such compounds to treat, prevent or diagnose blood-based diseases, disorders or conditions.

18 Claims, 3 Drawing Sheets

Example 29e (top curve)

GBT440 (bottom curve)

Example 29e (top curve - circles)

GBT440 (bottom curve - squares)

HEMOGLOBIN MODIFIER COMPOUNDS AND USES THEREOF

CROSS-REFERENCE

This application is a national stage entry of PCT/US2017/037983, filed on Jun. 16, 2017, and claims the benefit of U.S. Application Ser. No. 62/351,708 filed Jun. 17, 2016, all of which is incorporated by reference in their entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose blood-based diseases, disorders or conditions.

BACKGROUND OF THE INVENTION

Blood-based proteins, such as hemoglobin, are responsible for delivering oxygen from the lungs to all parts of the body. Described herein are compounds that modulate the activity of blood-based proteins and find use in the treatment of blood-based diseases, disorders or conditions.

SUMMARY OF THE INVENTION

In one aspect, described herein are compounds, or pharmaceutically acceptable salts or solvates thereof, that modulate hemoglobin. In some embodiments, compounds, or pharmaceutically acceptable salts or solvates thereof, modulate hemoglobin in such a manner so as to maintain hemoglobin in an oxygenated state. In other embodiments, compounds, or pharmaceutically acceptable salts or solvates thereof, increase tissue oxygenation.

Presented herein are compounds of Formula Formula (V), or a pharmaceutically acceptable salt or solvate thereof:

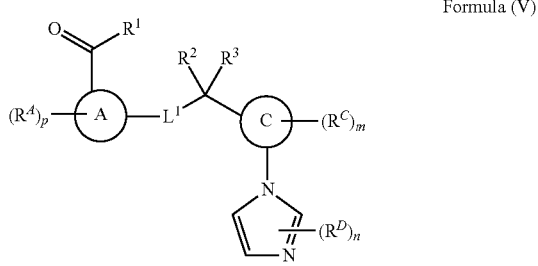

Formula (V)

wherein, $R^1$ is H or D;

$L^1$ is X or —C($R^7$)($R^8$)—;

X is —O—, —S—, —S(O)—, —S($O_2$)— or —$NR^4$—;

$R^7$ and $R^8$ are each independently H, D, substituted or unsubstituted $C_1$-$C_6$alkyl, or substituted or unsubstituted $C_1$-$C_6$deuteroalkyl;

$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

$R^2$ is H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

$R^3$ is H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

or $R^2$ and $R^3$ together with the carbon that they are attached to form a substituted or unsubstituted $C_3$-$C_6$cycloalkyl or a substituted or unsubstituted $C_2$-$C_8$heterocycloalkyl;

ring A is a monocyclic carbocycle, monocyclic heterocycle, bicyclic carbocycle, or bicyclic heterocycle;

ring C is a monocyclic heterocycle or a monocyclic carbocycle;

each $R^A$, $R^C$, and $R^D$ is independently H, D, halogen, —CN, —OH, —$OR^5$, —$SR^5$, —S(=O)$R^6$, —$NO_2$, —N($R^5$)$_2$, —S(=O)$_2R^6$, —NHS(=O)$_2R^6$, —S(=O)$_2$N(R)$_2$, —C(=O)$R^6$, —OC(=O)$R^6$, —$CO_2R^5$, —$OCO_2R^6$, —C(=O)N(R)$_2$, —OC(=O)N(R)$_2$, —$NR^5$C(=O)N(R)$_2$, —$NR^5$C(=O)$R^6$, —$NR^5$C(=O)$OR^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;

each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

or two $R^5$ on the same N atom are taken together with the N atom to which they are attached to form a N-containing heterocycloalkyl;

each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

p is 0, 1, 2 or 3;

m is 0, 1, 2 or 3; and n is 0, 1, 2 or 3.

In some embodiments the compound of Formula (V) has the structure of Formula (Va), or a pharmaceutically acceptable salt or solvate thereof:

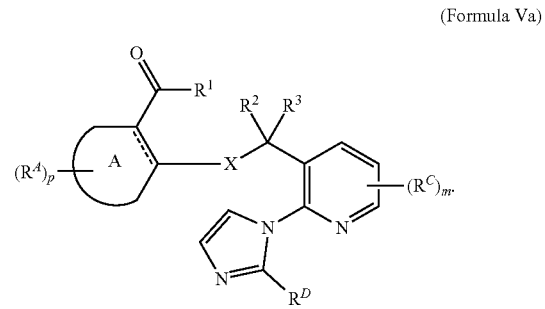

(Formula Va)

Presented herein are compounds of Formula Formula (II), or a pharmaceutically acceptable salt or solvate thereof:

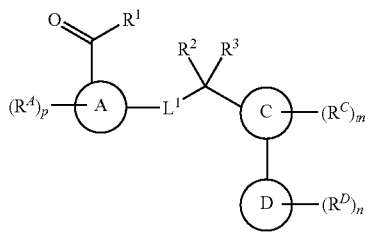

Formula (II)

wherein,

R¹ is H or D;

L¹ is X or —C(R⁷)(R⁸)—;

X is —O—, —S—, —S(O)—, —S(O₂)— or —NR⁴—;

R⁷ and R⁸ are each independently H, D, substituted or unsubstituted $C_1$-$C_6$alkyl, or substituted or unsubstituted $C_1$-$C_6$deuteroalkyl;

R⁴ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

R² is H, D, substituted or unsubstituted $C_1$-$C_6$alkyl, or substituted or unsubstituted $C_1$-$C_6$deuteroalkyl;

R³ is D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

or R² and R³ together with the carbon that they are attached to form a substituted or unsubstituted $C_3$-$C_6$cycloalkyl or a substituted or unsubstituted $C_2$-$C_8$heterocycloalkyl;

or R⁷ and R³ are taken together with the carbons that they are attached to form a substituted or unsubstituted $C_3$-$C_6$cycloalkyl or a substituted or unsubstituted $C_2$-$C_8$heterocycloalkyl;

or R³ and R^C are taken together with the carbons that they are attached to form a substituted or unsubstituted $C_3$-$C_6$cycloalkyl or a substituted or unsubstituted $C_2$-$C_8$heterocycloalkyl;

or R³ and R^A are taken together with the carbons that they are attached to form a substituted or unsubstituted $C_3$-$C_6$cycloalkyl or a substituted or unsubstituted $C_2$-$C_8$heterocycloalkyl;

ring A is a monocyclic carbocycle, monocyclic heterocycle, bicyclic carbocycle, or bicyclic heterocycle;

ring C is a monocyclic heterocycle or a monocyclic carbocycle;

ring D is a monocyclic heterocycle, bicyclic heterocycle, monocyclic carbocycle, or a bicyclic carbocycle;

each R^A, R^C, and R^D is independently H, D, halogen, —CN, —OH, —OR⁵, —SR⁵, —S(═O)R⁶, —NO₂, —N(R⁵)₂, —S(═O)₂R⁶, —NHS(═O)₂R⁶, —S(═O)₂N(R⁵)₂, —C(═O)R⁶, —OC(═O)R⁶, —CO₂R⁵, —OCO₂R⁶, —C(═O)N(R)₂, —OC(═O)N(R)₂, —NR⁵C(═O)N(R)₂, —NR⁵C(═O)R⁶, —NR⁵C(═O)OR⁶, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;

each R⁵ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

or two R⁵ on the same N atom are taken together with the N atom to which they are attached to form a N-containing heterocycloalkyl;

each R⁶ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

p is 0, 1, 2 or 3;

m is 0, 1, 2 or 3; and n is 0, 1, 2 or 3.

In some embodiments the compound of Formula (II) has the structure of Formula (IIa), or a pharmaceutically acceptable salt or solvate thereof:

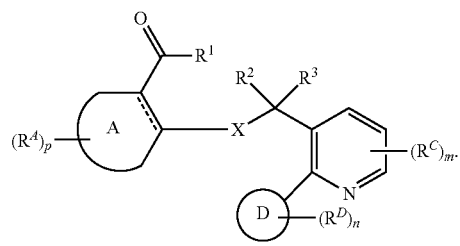

(Formula IIa)

In some embodiments the compound of Formula (II) has the structure of Formula (IIa), or a pharmaceutically acceptable salt or solvate thereof:

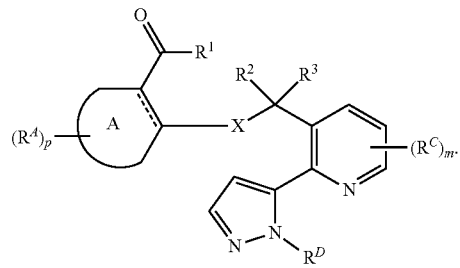

(Formula IIb)

In some embodiments the compound of Formula (II) has the structure of Formula (IIc), or a pharmaceutically acceptable salt or solvate thereof:

(Formula IIc)

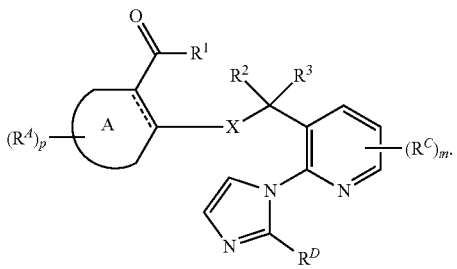

Presented herein are compounds of Formula Formula (IV), or a pharmaceutically acceptable salt or solvate thereof:

Formula (IV)

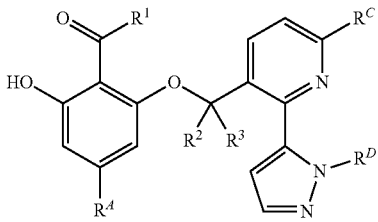

wherein,
$R^1$ is H or D;
$R^2$ is H or D;
$R^3$ is H or D;
$R^A$ is H, D, or F;
$R^C$ is H, D, or F; and
$R^D$ is H, D, $C_1$-$C_6$alkyl, or $C_1$-$C_6$deuteroalkyl;
provided that when $R^D$ is H or $C_1$-$C_6$alkyl then at least one of $R^1$, $R^2$, $R^3$, $R^A$, and $R^C$ is D.

Also provided herein are pharmaceutical compositions comprising any one of the compounds disclosed herein, or a pharmaceutically acceptable salt thereof, and at least one pharmaceutically acceptable excipient.

In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

Also provided herein in one aspect are compounds of Formula (I), (II), (II'), (III), (IV), (V), (VI), or (VII), or a pharmaceutically acceptable salt or solvate thereof, that are suitable for use in medicine.

In some embodiments, presented herein are compounds selected from active metabolites, tautomers, pharmaceutically acceptable solvates, pharmaceutically acceptable salts or prodrugs of a compound of Formula (I), (II), (II'), (III), (IV), (V), (VI), or (VII).

Also described are pharmaceutical compositions comprising a therapeutically effective amount of a compound of Formula (I), (II), (II'), (III), (IV), (V), (VI), or (VII), or a pharmaceutically acceptable salt thereof. In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a suspension, a solution, an emulsion, an ointment, or a lotion.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In such embodiments, the compound of Formula (I), (II), (II'), (III), (IV), (V), (VI), or (VII), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compounds of Formula (I), (II), (II'), (III), (IV), (V), (VI), or (VII), or a pharmaceutically acceptable salt thereof, are administered topically to the skin of mammal.

In any of the aforementioned aspects are further embodiments in which the effective amount of the compound of Formula (I), (II), (II'), (III), (IV), (V), (VI), or (VII), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Articles of manufacture, which include: packaging material; a compound of Formula (I), (II), (II'), (III), (IV), (V), (VI), or (VII), or a pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for modifying hemoglobin activity, are provided.

Also presented herein are methods of treating a disease or condition in a subject comprising administering the compound disclosed herein.

In some embodiments, the disease or condition is associated with oxygen deficiency.

In some embodiments, the disease or condition is selected from sickle-cell disease, cancer, a pulmonary condition, stroke, high altitude sickness, an ulcer, a pressure sore, Alzheimer's disease, acute respiratory disease syndrome, and a wound.

In some embodiments, the disease or condition is sickle-cell disease.

In some embodiments, the disease or condition is a mitochondrial disease.

In some embodiments, the mitochondrial disease is selected from mitochondrial myopathy, Leber's hereditary optic neuropathy (LHON), Leigh syndrome, neuropathy/ataxia/retinitis pigmentosa (NARP), myoneurogenic gastrointestinal encephalopathy (MNGIE), myoclonic epilepsy with ragged red fibers (MERRF), mitochondrial myopathy/encephalomyopathy/lactic acidosis/stroke-like symptoms (MELAS), mitochondrial neurogastrointestinal encephalomyopathy (MNGIE), and any combination thereof. In some embodiments, the mitochondrial disease is Leigh syndrome.

In some embodiments, the disease or condition is a hypoxemic pulmonary disorder. In some embodiments, the hypoxemic pulmonary disorder is selected from idiopathic pulmonary fibrosis (IPF), acute respiratory distress syndrome (ARDS), chronic obstructive pulmonary disease (COPD), and any combinations thereof. In some embodiments, the hypoxemic pulmonary disorder is idiopathic pulmonary fibrosis (IPF).

In some embodiments, the method further comprises administering a second therapeutic agent. In some embodiments, the second therapeutic agent is selected from metformin, a P-selectin inhibitor, L-glutamine, and any combinations thereof. In some embodiments, the second therapeutic agent is metformin. In some embodiments, the second therapeutic agent is L-glutamine. In some embodiments, the second therapeutic agent is a P-selectin inhibitor. The method of claim 110, wherein the P-selectin inhibitor is selected from crizanlizumab, PSI-697 (2-(4-chlorobenzyl)-3-hydroxy-7,8,9,10-tetrahydrobenzo[h] quinoline-4-carboxylic acid), rivipansel, and any combinations thereof. In some embodiments, the P-selectin inhibitor is crizanlizumab. In some embodiments, the frequency of sickle-cell crisis in the subject is reduced as compared to a subject being administered the first therapeutic agent alone. In some embodiments, the sickle-cell crisis is selected from a vaso-occlusive crisis, an aplastic crisis, a sequestration crisis, haemolytic crisis, and any combinations thereof.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
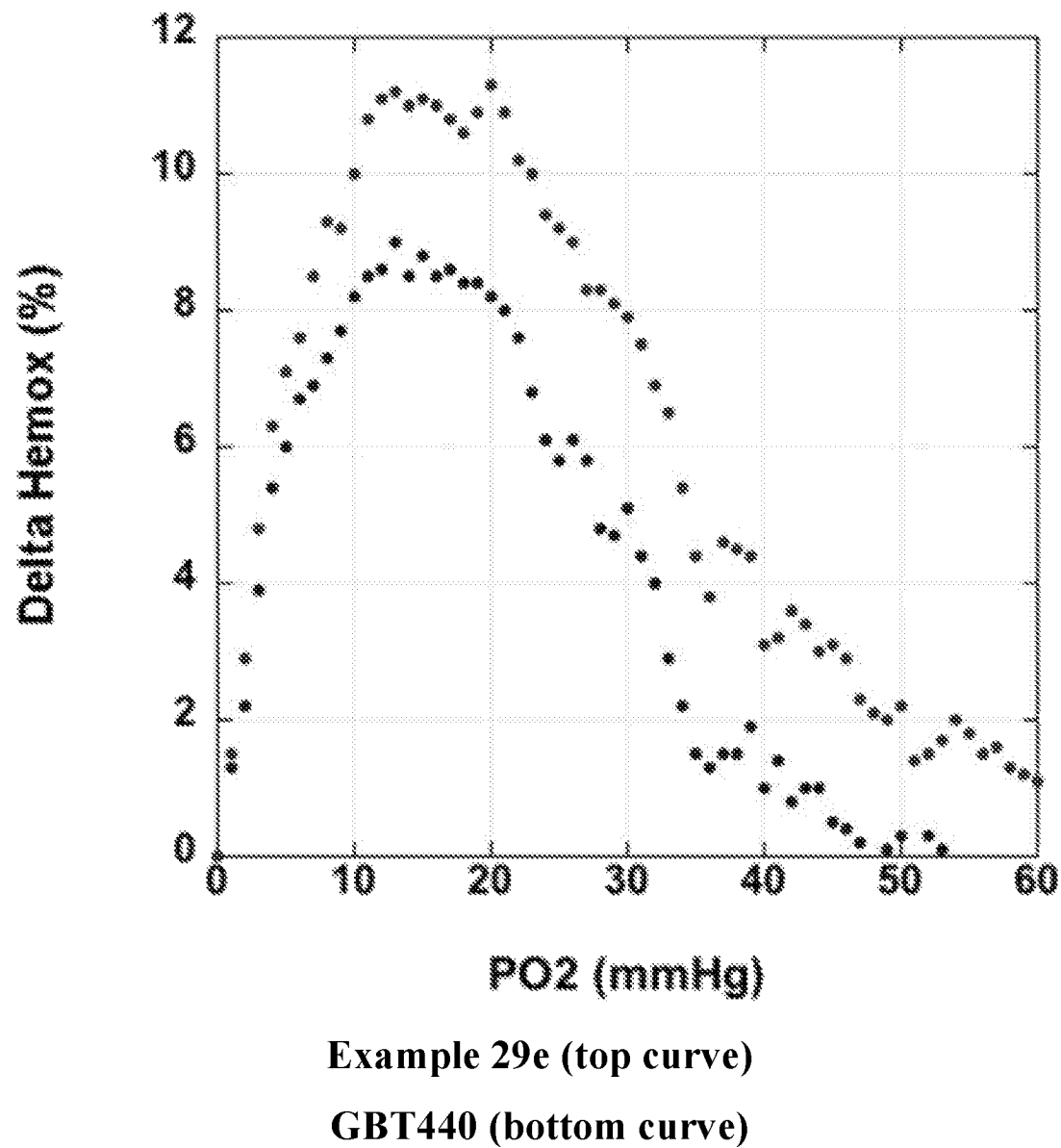
FIG. 1A shows the delta hemox (%) of example 29e as compared with GBT440 at 0.2 mM.

Blood-based proteins, such as hemoglobin, are responsible for delivering oxygen from the lungs to all parts of the body. Sickle cell disease is a genetic, chronic disease that is caused by sickle hemoglobin, which are abnormal hemoglobin that have a sickle shape. Sickle hemoglobin cells tend to stick to vessel walls, causing a blockage that impedes the blood flow and prevents oxygen from reaching nearby tissues. The symptoms of sickle cell disease vary in severity and include acute pain, chronic pain, anemia, and organ damage resulting from prolonged periods without adequate oxygen. The only cure available to treat sickle-cell disease is hematopoietic stem cell transplantation (HSCT), which is not widely utilized due to significant costs and risks associated with the procedure and limited number of suitable well-matched donors. As such, the current course of treatments are aimed at avoiding sudden attacks of pain, reliving symptoms and preventing complications, which are costly over the course of a lifetime of a patient. Accordingly, there is a need in developing new treatments for sickle cell disease and for related diseases and conditions that would benefit from the modulation of blood-based proteins, such as hemoglobin.

Hemoglobin (Hb) is a protein found in red blood cells that delivers oxygen from the lung to various tissues and organs throughout the body. Oxygen release from hemoglobin is accomplished through conformational changes under allosteric regulation. The tense (T) state refers to the when hemoglobin is in the deoxygenated state and it is not bound to oxygen. The relaxed (R) state refers to when hemoglobin is in the oxygenated state and it is bound to oxygen.

Sickle-Cell Disease

Sickle-cell disease (SCD) is a group of chronic, inherited blood disorders that is attributed to an abnormality in hemoglobin. A mutation in the beta chain of hemoglobin, causes deoxygenated hemoglobin to be more susceptible to polymerization, which results in the formation of rigid polymers that change the shape of hemoglobin from the normal, flexible disc to a rigid, crescent, or sickle. Accordingly, hemoglobin S (HbS) refers to the sickle hemoglobin. Sickled-shaped hemoglobin cells are likely to stick to vessel walls, causing a blockage that impedes the blood flow and prevents oxygen from reaching nearby tissues. Maintaining hemoglobin in the oxygenated state has been implicated in delaying the polymerization of deoxygenated hemoglobin.

The lack of tissue oxygen results in attacks of sudden, severe pain, also known as pain crisis. Such attacks occur without warning and often require hospitalization for effective treatment. In addition, as sickle cells do not last as long as normal cells, a person affected with sickle-cell disease usually has a lower number of red bloods cells than normal, resulting in an anemia Moreover, sickle-cell disease over a lifetime also results in organ damage, including but not limited to the spleen, brain, eyes, lungs, liver, heart, kidneys, joins, bones and/or skin.

Sickle cell disease is a life-long disease and the severity of the illness varies from person to person. Since the only cure to sickle-cell disease is hematopoietic stem cell transplantation (HSCT), which is not a viable option for most due to the significant costs and risks associated with procedure and limited number of suitable well-matched donors, the current treatment options for sickle cell disease are aimed at avoiding crises, reliving symptoms and preventing complications. Accordingly, there exists a need in developing new methods for treating for sickle cell disease and for related diseases and conditions that would benefit from the modulation of blood-based proteins, such as hemoglobin.

In one aspect, provided herein are compounds and compositions that allosterically modulate blood-based proteins. In some aspects, the blood-based proteins are hemoglobin, abnormal hemoglobin and/or sickle hemoglobin.

In one aspect, provided herein are compounds and compositions that conformationally modulate blood-based proteins. In some aspects, the blood-based proteins are hemoglobin, abnormal hemoglobin and/or sickle hemoglobin.

In one aspect, provided herein are compounds and compositions that increase the oxygen affinity of blood-based proteins. In some aspects, the blood-based proteins are hemoglobin, abnormal hemoglobin and/or sickle hemoglobin. In some embodiments, the increase in affinity for oxygen is achieved from maintaining hemoglobin in the oxygenated state, or R state. In some embodiments, the increase in affinity for oxygen is achieved from preventing and/or inhibiting the polymerization of deoxygenated hemoglobin.

In one aspect, provided herein are compounds and compositions that are useful for treating diseases or conditions characterized by oxygen deficiency. In some embodiments, the diseases or conditions include sickle cell disease and disorders and conditions that are associated with sickle cell disease.

Types of Sickle-Cell Diseases

As sickle-cell disease is a genetic blood disorder, the specific types of sickle cell disease are classified according to the genes inherited by the patient. Hemoglobin SS disease (HbSS) is the most common type of sickle cell disease, and occurs when the two copies of the sickle cell gene, hemoglobin S, are inherited, one from parent. In some instances, hemoglobin SS is also known as sickle cell anemia. Hemoglobin SS is the most severe form of sickle cell disease. Hemoglobin SC disease (HbSC) refers to when one copy to the hemoglobin S gene is inherited and when one copy of the hemoglobin C gene, a gene for abnormal hemoglobin known as "C", is inherited. Individuals with hemoglobin SC disease have symptoms, such as anemia, that are milder than individuals with hemoglobin SS disease.

Hemoglobin SB+ (beta) thalassemia refers to when one copy of the sickle cell gene is inherited and one gene for beta thalassemia, which is another type of anemia, is inherited from the other parent. The "+" refers to one type of beta thalassemia. Those with hemoglobin SB+(beta) thalassemia have a milder form of sickle cell disease. Hemoglobin SB-zero (Beta) thalassemia refers to the when the other type of beta thalassemia, "0", is inherited with a copy of the sickle cell gene. Those with beta-zero thalassemia have a more severe form of sickle-cell disease.

Other rare forms of sickle cell diseases include those wherein one copy of the sickle cell gene is inherited and one copy of an abnormal hemoglobin gene, such as "D", "E", or "O" is inherited (HbSD, HbSE and HbSO). The severity of these rarer forms of sickle-cell disease varies.

In some embodiments, the compounds disclosed herein and compositions thereof are useful for the treatment of sickle-cell disease. In some embodiments, the sickle-cell disease is hemoglobin SS, hemoglobin SC, hemoglobin SB+(beta) thalassemia, or hemoglobin SB-zero (beta) thalassemia. In some embodiments, the sickle-cell disease is a disease resulting from when one copy of the sickle cell gene is inherited from parent and a copy of an abnormal hemoglobin gene selected from "D", "E", or "O" is inherited from the other parent.

Hypoxemic Pulmonary Disorders

Provided herein in one aspect are compounds and compositions thereof that are useful for the treatment of diseases or conditions that would benefit from cellular and/or tissue oxygenation. Such diseases or conditions that would benefit from cellular and/or tissue oxygenation include disorders or conditions characterized by failure of the lung to supply adequate oxygen to blood, resulting in hypoxia. Other disorders that could benefit from cellular and/or tissue oxygenation include disorders or conditions characterized by failure of the lung to supply adequate oxygen to blood, resulting in hypoxia. An example of such a disorder is hypoxemic pulmonary disorder. Examples of hypoxemic pulmonary disorders include but are not limited to idiopathic pulmonary fibrosis (IPF), acute respiratory distress syndrome (ARDS), and chronic obstructive pulmonary disease (COPD). Idiopathic pulmonary fibrosis (IPF) is a chronic and ultimately fatal disease that causes the formation of scar tissue, or fibrosis, in the lungs, which leads to progressive decline in lung function. Acute respiratory distress syndrome (ARDS) is serious life threatening condition that occurs in critically ill patients, wherein fluid builds up in the air sacs of the lungs and prevents enough oxygen from being delivered from the lungs to the blood. Acute respiratory distress syndrome is caused by any major indirect or direct injury to the lungs. Common causes include but are not limited to sepsis, inhalation of harmful substances, severe pneumonia, head injuries, and chest injuries. Chronic obstructive pulmonary disease (COPD) is a type of obstructive lung disease characterized by long-term poor airflow. The main symptoms include shortness of breath and cough with sputum production. COPD is a progressive disease, meaning it typically worsens over time. Eventually everyday activities, such as walking up stairs, become difficult.

In some embodiments, the compounds disclosed herein and compositions thereof are useful in the treatment of disorders or conditions characterized by failure of the lung to supply adequate oxygen to blood. In some embodiments, the compounds disclosed herein and compositions thereof are useful in the treatment of hypoxemic pulmonary disorders. In some embodiments, the compounds disclosed herein and compositions thereof are useful in the treatment of idiopathic pulmonary fibrosis (IPF). In some embodiments, the compounds disclosed herein and compositions thereof are useful in the treatment of acute respiratory distress syndrome (ARDS). In some embodiments, the compounds disclosed herein and compositions thereof are useful in the treatment of chronic obstructive pulmonary disease (COPD).

Mitochondrial Diseases

Mitochondria are ancient organelles that are essential for normal physiology and health. The respiratory chain (RC) is crucial to mitochondrial function and generates approximately 90% of cellular ATP via oxidative phosphorylation. In the oxidative step, four large protein complexes transfer electrons from NADH (the reduced form of nicotinamide adenine dinucleotide) or FADH (the reduced form of flavin adenine dinucleotide) to oxygen while generating a proton gradient. Approximately 90% of the oxygen we breathe is utilized as a substrate for the RC. In the phosphorylation step, the proton gradient is dissipated by a fifth and final complex to generate ATP. Numerous additional chemical reactions and transport processes are intimately coupled to the redox and proton pumping activities of the RC.

Defects in the mitochondrial respiratory chain (RC) underlie a spectrum of human conditions, ranging from devastating inborn errors of metabolism to aging. Genetic or small-molecule activation of the hypoxia response has been shown to be protective against mitochondrial toxicity in cultured cells and zebrafish models. Chronic hypoxia leads to a marked improvement in survival, body weight, body temperature, behavior, neuropathology, and disease biomarkers in a genetic mouse model of Leigh syndrome, the most common pediatric manifestation of mitochondrial disease.

Other Diseases or Conditions

In some embodiments, other disorders or conditions that benefit from administration of any one of the compounds disclosed herein or compositions thereof include cancer, hypertensive disorders, pulmonary disorder, strokes, high altitude sickness, ulcers, pressure sores, deep vein thrombosis, pulmonary embolism, vision loss, Alzheimer's disease, and inflammatory diseases such as Inflammatory bowel disease (IBD).

Additional therapeutic uses of the compounds disclosed herein or compositions thereof also include wound healing and sensitizing hypoxic tumor cells resistant to standard chemotherapy and/or radiotherapy due to low levels of oxygen in the cell.

Compounds

In one aspect, presented herein are compounds of Formula (I), or a pharmaceutically acceptable salt or solvate thereof:

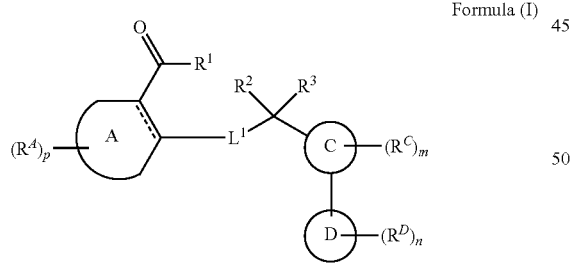

Formula (I)

wherein,
$R^1$ is H or D;
$L^1$ is X or —C($R^7$)($R^8$)—;
X is —O—, —S—, —S(O)—, —S($O_2$)— or —$NR^4$—;
$R^7$ and $R^8$ are each independently H, D, substituted or unsubstituted $C_1$-$C_6$alkyl, or substituted or unsubstituted $C_1$-$C_6$deuteroalkyl;
$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

$R^2$ is H or D;
$R^3$ is H or D;
ring A is a bicyclic heterocycle or a bicyclic carbocycle, provided that ring A is not indazolyl; ring C is a monocyclic heterocycle or a monocyclic carbocycle;
ring D is a monocyclic heterocycle, bicyclic heterocycle, monocyclic carbocycle, or a bicyclic carbocycle;
each $R^A$, $R^C$, and $R^D$ are independently H, D, halogen, —CN, —OH, —OD, —$OR^5$, —$SR^5$, —S(=O)$R^6$, —$NO_2$, —N($R^5$)$_2$, —S(=O)$_2R^6$, —NHS(=O)$_2R^6$, —S(=O)$_2$N($R^5$)$_2$, —C(=O)$R^6$, —OC(=O)$R^6$, —$CO_2R^5$, —$OCO_2R^6$, —C(=O)N(R)$_2$, —OC(=O)N(R)$_2$, —$NR^5$C(=O)N(R)$_2$, —$NR^5$C(=O)$R^6$, —$NR^5$C(=O)$OR^6$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl, wherein a hydrogen atom on a substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl is optionally replaced with at least one D;
each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl, wherein a hydrogen atom on a substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl is optionally replaced with at least one D;
or two $R^5$ on the same N atom are taken together with the N atom to which they are attached to form a N-containing heterocycloalkyl;
each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
p is 0, 1, 2 or 3;
m is 0, 1, 2 or 3; and
n is 0, 1, 2 or 3.

In some embodiments, ring A is a bicyclic heterocycle that is a 8-, 9- or 10-membered bicyclic heterocycle. In some embodiments, ring A is a bicyclic heterocycle that has 1-4 N atoms, 0-1 O atoms, and 0-1 S atoms in the bicyclic ring. In some embodiments, ring A is a bicyclic heterocycle that has 0-4 N atoms, 1 O atom or 1 S atom in the bicyclic ring.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is a bicyclic heterocycle that is indolinyl, isoindolinyl, indolinonyl, 1,2,3,4-tetrahydroquinolinyl, 1,2,3,4-tetrahydroisoquinolinyl, 3,4-dihydro-2(1H)-quinolinonyl, dihydrobenzofuranyl, dihydroisobenzofuran, dihydrobenzo[b]thiophenyl, or dihydrobenzo[c]thiophenyl.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, indolyl, benzimidazolyl, benzotriazolyl, benzoxazolyl, benzisoxazolyl, benzofuranyl, benzothienyl, benzothiazolyl, or purinyl.

In some embodiments,

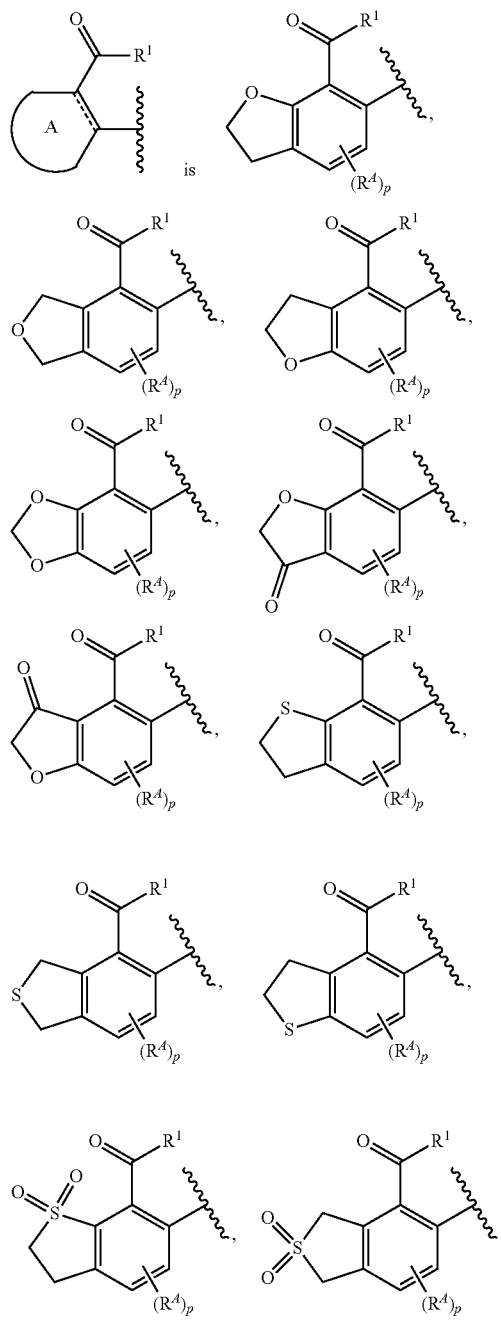

is

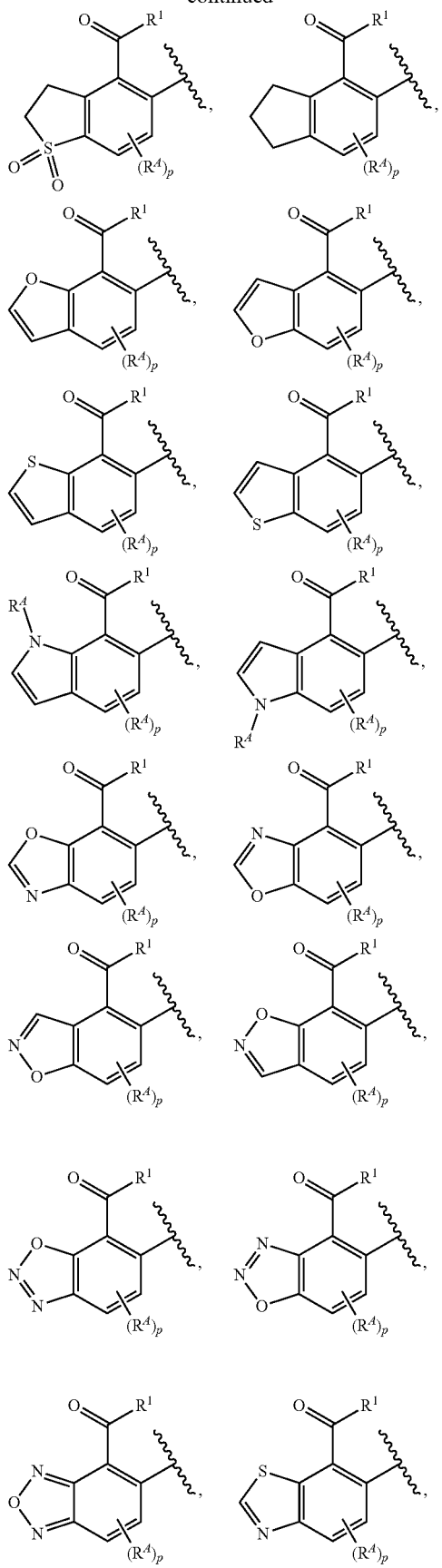

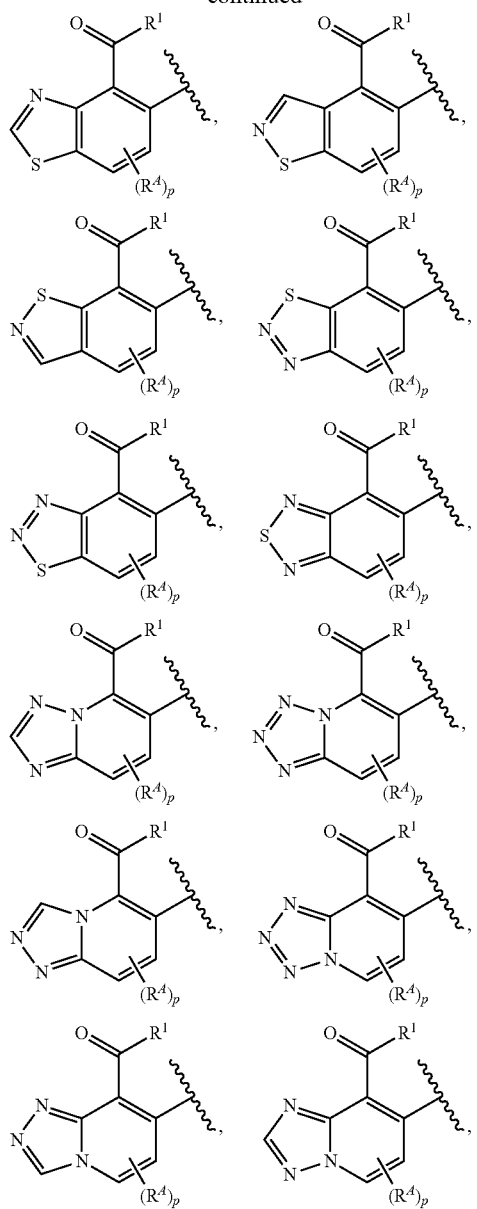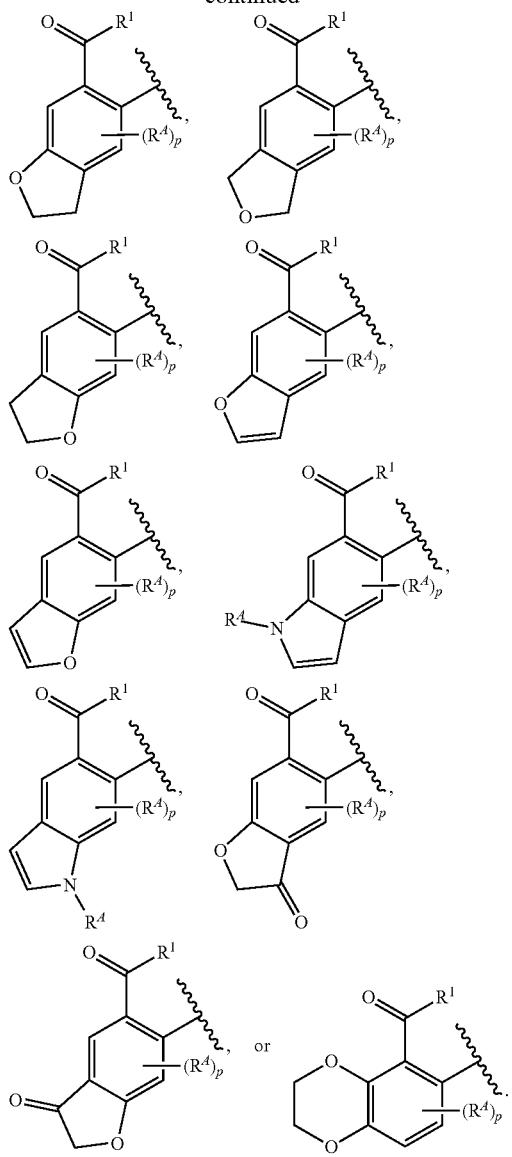
In some embodiments,
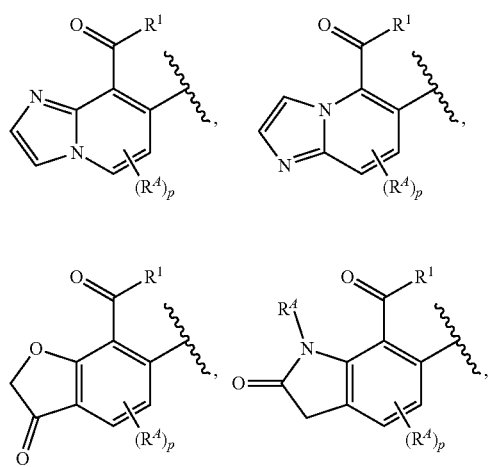

-continued

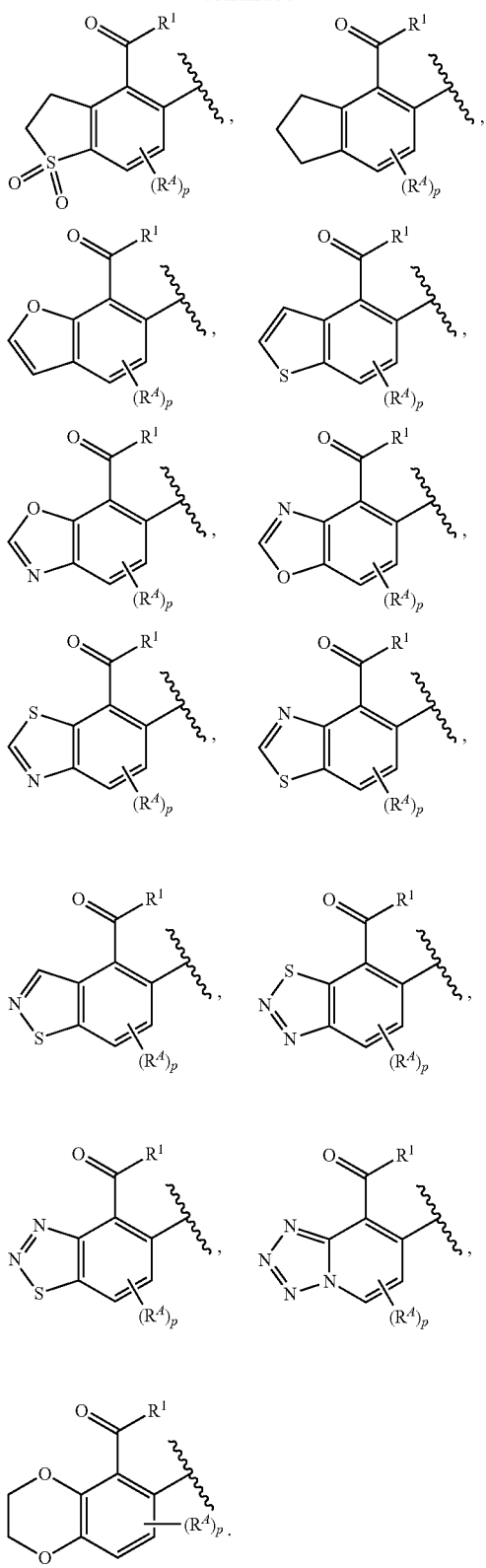

In some embodiments, ring A is a bicyclic carbocycle that is naphthyl, indanyl, or indenyl.

In some embodiments, L¹ is X; and X is O or S. In some embodiments, X is O.

In some embodiments, the groups

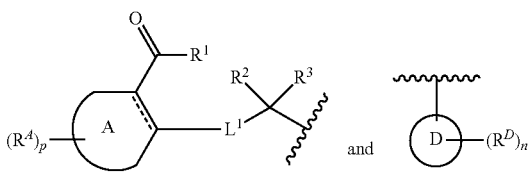

are on adjacent atoms of ring C.

In some embodiments, ring C is a monocyclic heterocycle. In some embodiments, ring C is a monocyclic heterocycle with 1-3 N atoms in the ring. In some embodiments, ring C is a monocyclic 6-membered heterocycle with 1-3 N atoms in the ring. In some embodiments, ring C is a monocyclic 6-membered heterocycle that is pyridinyl, pyrimidinyl, pyrazinyl, or triazinyl In some embodiments,

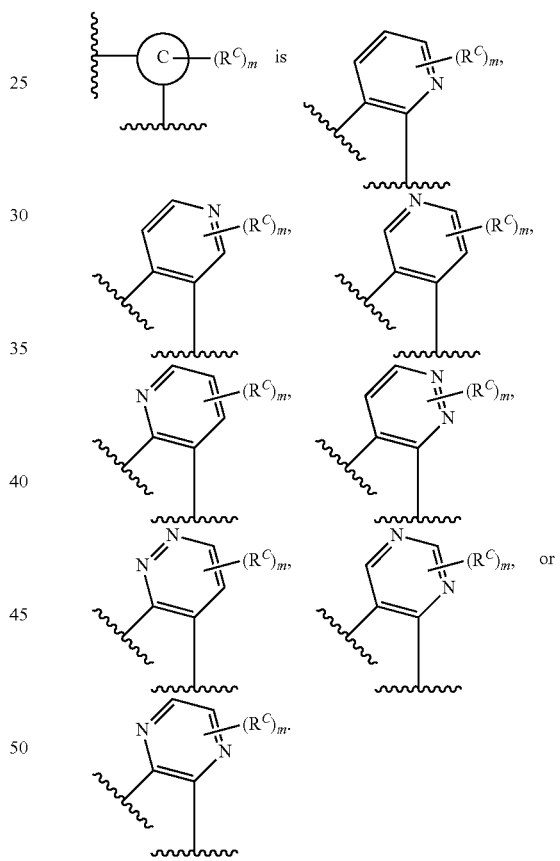

In some embodiments,

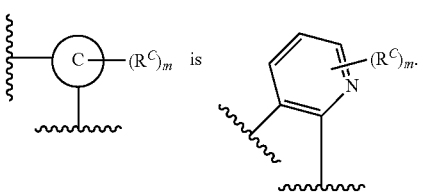

In some embodiments, ring C is a monocyclic 6-membered heterocycle that is

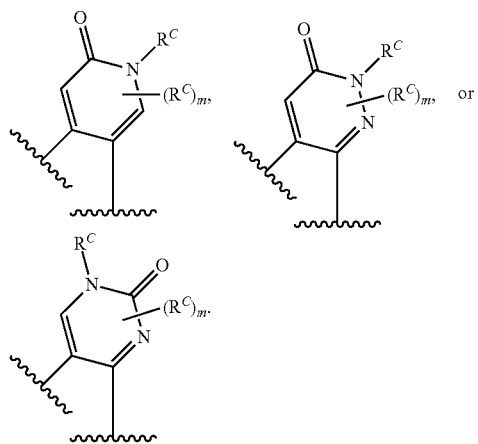

In some embodiments, ring C is phenyl.
In some embodiments,

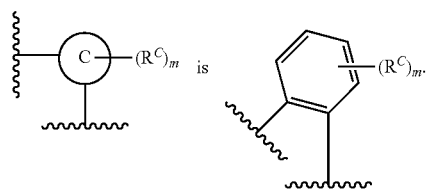

In some embodiments, the compound of Formula (I) has the structure of Formula (Ia), or a pharmaceutically acceptable salt or solvate thereof:

(Formula Ia)

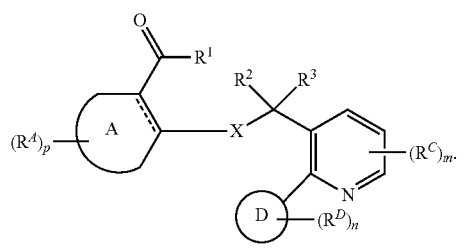

In some embodiments, ring D is a monocyclic heterocycle. In some embodiments, ring D is a monocyclic N-containing heterocycle. In some embodiments, ring D is a monocyclic 5-membered N-containing heterocycle or a monocyclic 6-membered N-containing heterocycle.

In some embodiments, ring D is a monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, thiadiazolyl pyridinyl, pyrimidinyl, pyrazinyl, or triazinyl.

In some embodiments, ring D is a 5-membered monocyclic N-containing heterocycle.

In some embodiments, ring D is a 5-membered monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

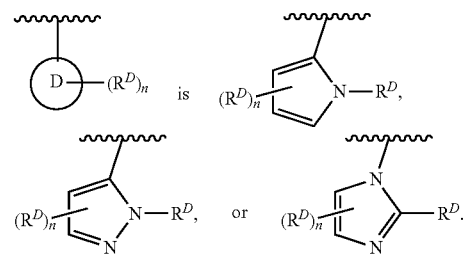

In some embodiments,

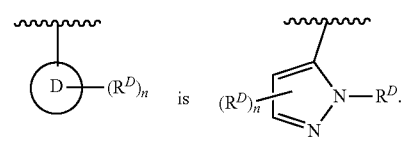

In some embodiments,

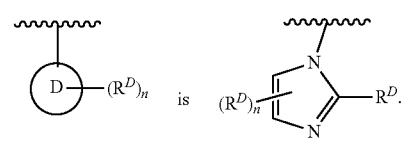

In some embodiments,

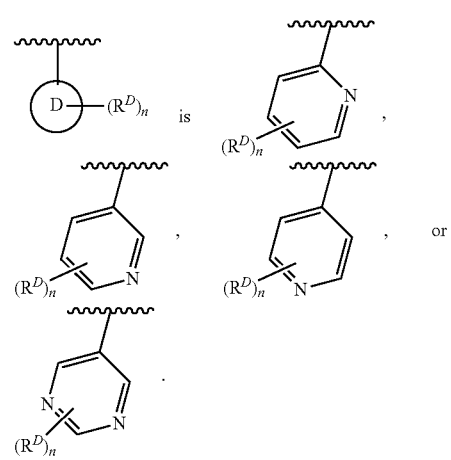

In some embodiments, ring D is a monocyclic heterocycle that is a β-lactam, γ-lactam, δ-lactam or ε-lactam.

In some embodiments,

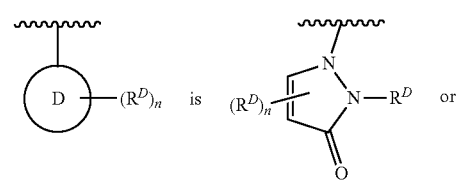

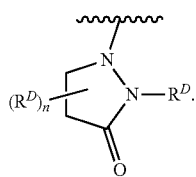

In some embodiments, ring D is a bicyclic heterocycle. In some embodiments, ring D is a bicyclic heterocycle that is a fused bicyclic heterocycle, bridged bicyclic heterocycle, or spiro bicyclic heterocycle.

In some embodiments,

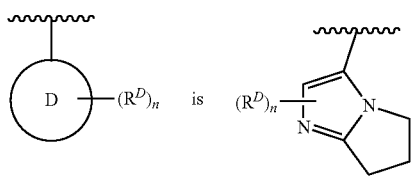

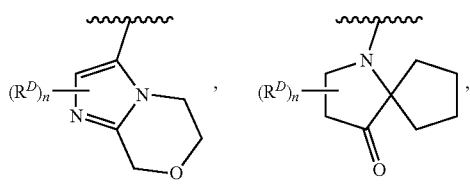

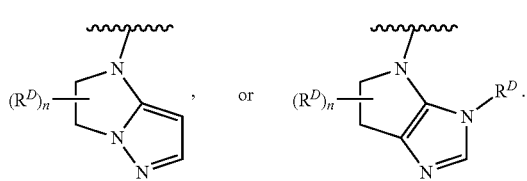

In some embodiments, the compound of Formula (I) has a structure of Formula (Ib), or pharmaceutically acceptable salt or solvate thereof:

Formula (Ib)

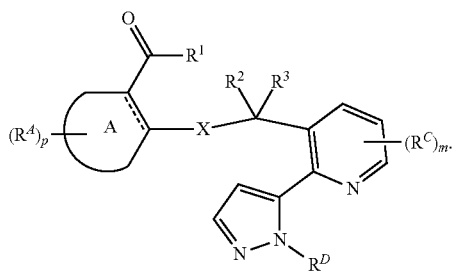

In some embodiments, the compound of Formula (I) has a structure of Formula (Ic), or pharmaceutically acceptable salt or solvate thereof:

Formula (Ic)

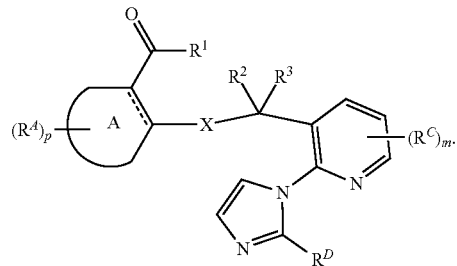

In some embodiments, $R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

Also provided herein in another aspect are compounds of Formula (II), or a pharmaceutically acceptable salt or solvate thereof:

Formula (II)

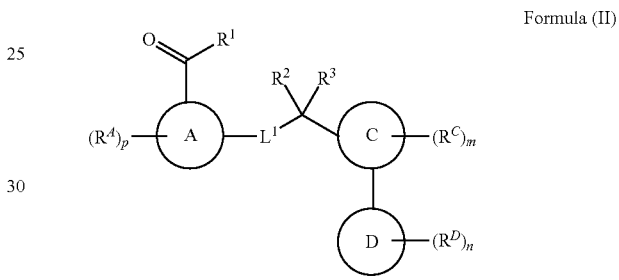

wherein,
$R^1$ is H or D;
$L^1$ is X or —C($R^7$)($R^8$)—;
X is —O—, —S—, —S(O)—, —S(O$_2$)— or —NR$^4$—;
$R^7$ and $R^8$ are each independently H, D, substituted or unsubstituted $C_1$-$C_6$alkyl, or substituted or unsubstituted $C_1$-$C_6$deuteroalkyl;
$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
$R^2$ is H, D, substituted or unsubstituted $C_1$-$C_6$alkyl, or substituted or unsubstituted $C_1$-$C_6$deuteroalkyl;
$R^3$ is D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
or $R^2$ and $R^3$ together with the carbon that they are attached to form a substituted or unsubstituted $C_3$-$C_6$cycloalkyl or a substituted or unsubstituted $C_2$-$C_8$heterocycloalkyl;
or $R^7$ and $R^3$ are taken together with the carbons that they are attached to form a substituted or unsubstituted $C_3$-$C_6$cycloalkyl or a substituted or unsubstituted $C_2$-$C_8$heterocycloalkyl;
or $R^3$ and $R^C$ are taken together with the carbons that they are attached to form a substituted or unsubstituted $C_3$-$C_6$cycloalkyl or a substituted or unsubstituted $C_2$-$C_8$heterocycloalkyl;
or $R^3$ and $R^A$ are taken together with the carbons that they are attached to form a substituted or unsubstituted $C_3$-$C_6$cycloalkyl or a substituted or unsubstituted $C_2$-$C_8$heterocycloalkyl;

ring A is a monocyclic carbocycle, monocyclic heterocycle, bicyclic carbocycle, or bicyclic heterocycle;

ring C is a monocyclic heterocycle or a monocyclic carbocycle;

ring D is a monocyclic heterocycle, bicyclic heterocycle, monocyclic carbocycle, or a bicyclic carbocycle;

each $R^A$, $R^C$, and $R^D$ is independently H, D, halogen, —CN, —OH, —OR$^5$, —SR$^5$, —S(=O)R$^6$, —NO$_2$, —N(R$^5$)$_2$, —S(=O)$_2$R$^6$, —NHS(=O)$_2$R$^6$, —S(=O)$_2$N(R$^5$)$_2$, —C(=O)R$^6$, —OC(=O)R, —CO$_2$R$^5$, —OCO$_2$R$^6$, —C(=O)N(R$^5$)$_2$, —OC(=O)N(R)$_2$, —NR$^5$C(=O)N(R)$_2$, —NR$^5$C(=O)R$^6$, —NR$^5$C(=O)OR$^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;

each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

or two $R^5$ on the same N atom are taken together with the N atom to which they are attached to form a N-containing heterocycloalkyl;

each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

p is 0, 1, 2 or 3;

m is 0, 1, 2 or 3; and n is 0, 1, 2 or 3.

Also provided herein in another aspect are compounds of Formula (II'), or a pharmaceutically acceptable salt or solvate thereof:

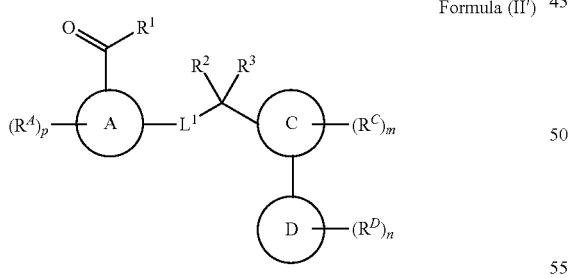

Formula (II')

wherein, $R^1$ is H or D;

$L^1$ is X or —C(R$^7$)(R$^8$)—;

X is —O—, —S—, —S(O)—, —S(O$_2$)— or —NR$^4$—;

$R^7$ and $R^8$ are each independently H, D, substituted or unsubstituted $C_1$-$C_6$alkyl, or substituted or unsubstituted $C_1$-$C_6$deuteroalkyl;

$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

$R^2$ is H, D, substituted or unsubstituted $C_1$-$C_6$alkyl, or substituted or unsubstituted $C_1$-$C_6$deuteroalkyl;

$R^3$ is D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

or $R^2$ and $R^3$ together with the carbon that they are attached to form a substituted or unsubstituted $C_3$-$C_6$cycloalkyl or a substituted or unsubstituted $C_2$-$C_8$heterocycloalkyl;

or $R^7$ and $R^3$ are taken together with the carbons that they are attached to form a substituted or unsubstituted $C_3$-$C_6$cycloalkyl or a substituted or unsubstituted $C_2$-$C_8$heterocycloalkyl; ring A is a monocyclic carbocycle, monocyclic heterocycle, bicyclic carbocycle, or bicyclic heterocycle;

ring C is a monocyclic heterocycle or a monocyclic carbocycle;

ring D is a monocyclic heterocycle, bicyclic heterocycle, monocyclic carbocycle, or a bicyclic carbocycle;

each $R^A$, $R^C$, and $R^D$ is independently H, D, halogen, —CN, —OH, —OR$^5$, —SR$^5$, —S(=O)R$^6$, —NO$_2$, —N(R$^5$)$_2$, —S(=O)$_2$R$^6$, —NHS(=O)$_2$R$^6$, —S(=O)$_2$N(R)$_2$, —C(=O)R$^6$, —OC(=O)R$^6$, —CO$_2$R$^5$, —OCO$_2$R$^6$, —C(=O)N(R)$_2$, —OC(=O)N(R)$_2$, —NR$^5$C(=O)N(R)$_2$, —NR$^5$C(=O)R$^6$, —NR$^5$C(=O)OR$^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;

each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

or two $R^5$ on the same N atom are taken together with the N atom to which they are attached to form a N-containing heterocycloalkyl;

each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

p is 0, 1, 2 or 3;

m is 0, 1, 2 or 3; and n is 0, 1, 2 or 3.

In some embodiments, the groups

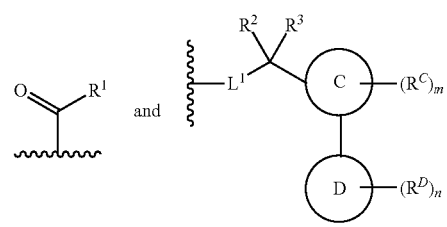

are on adjacent atoms of ring A.

In some embodiments, ring A is phenyl.

In some embodiments,

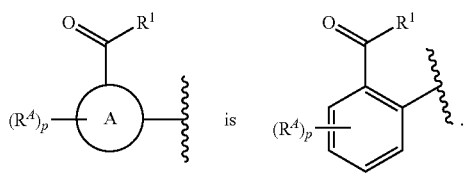

is

In some embodiments, ring A is a monocyclic heterocycle that is a monocyclic heteroaryl. In some embodiments, ring A is a monocyclic heterocycle with 1-3 N atoms in the ring. In some embodiments, ring A is a monocyclic 6-membered heterocycle with 1-3 N atoms in the ring. In some embodiments, ring A is a monocyclic 6-membered heterocycle that is pyridinyl, pyrimidinyl, pyrazinyl, or triazinyl. In some embodiments, ring A is pyridinyl.

In some embodiments,

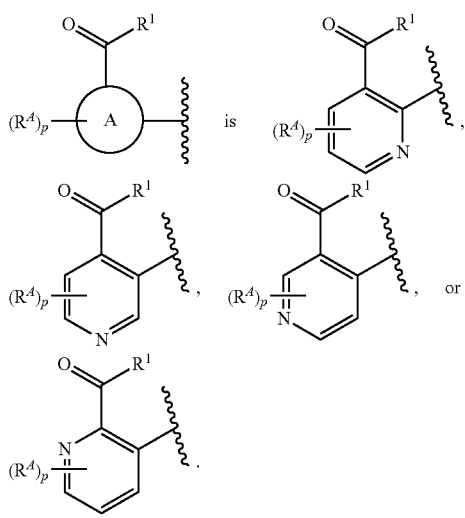

In some embodiments, ring A is a bicyclic heterocycle that is a 8-, 9- or 10-membered bicyclic heterocycle. In some embodiments, ring A is a bicyclic heterocycle that has 1-4 N atoms, 0-1 O atoms, and 0-1 S atoms in the bicyclic ring. In some embodiments, ring A is a bicyclic heterocycle that has 0-4 N atoms, 1 O atom or 1 S atom in the bicyclic ring.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is a bicyclic heterocycle that is indolinyl, isoindolinyl, indolinonyl, 1,2,3,4-tetrahydroquinolinyl, 1,2,3,4-tetrahydroisoquinolinyl, 3,4-dihydro-2 (1H)-quinolinonyl, dihydrobenzofuranyl, dihydroisobenzofuran, dihydrobenzo[b]thiophenyl, or dihydrobenzo[c]thiophenyl.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, indolyl, benzimidazolyl, benzotriazolyl, benzoxazolyl, benzisoxazolyl, benzofuranyl, benzothienyl, benzothiazolyl, or purinyl.

In some embodiments,

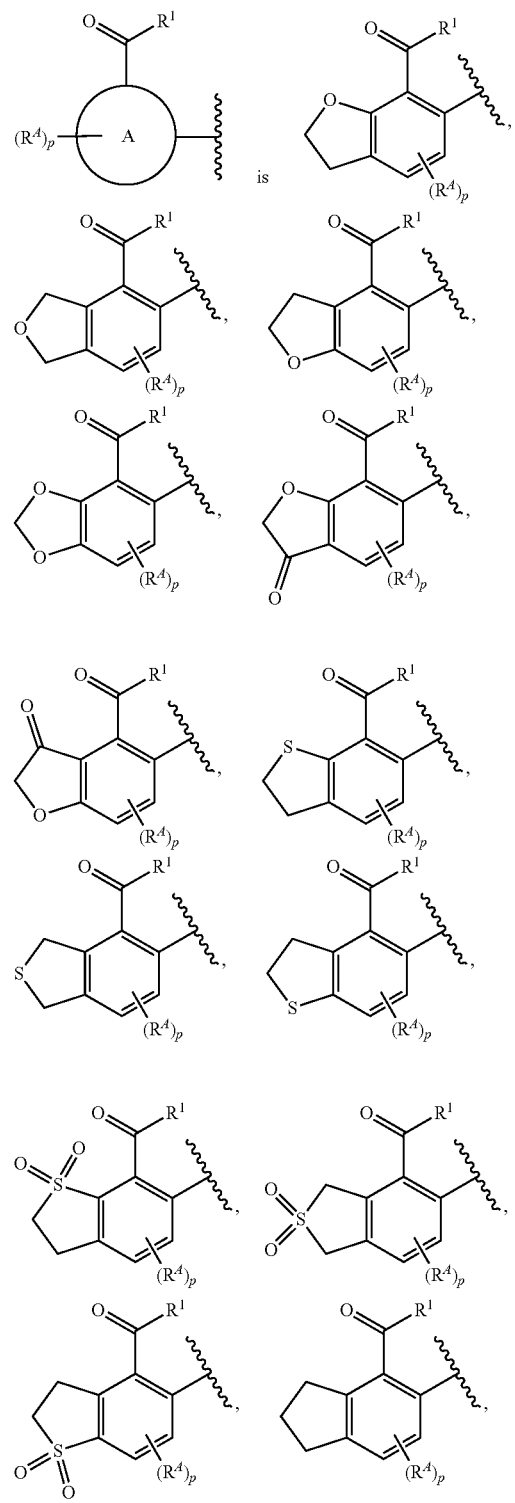

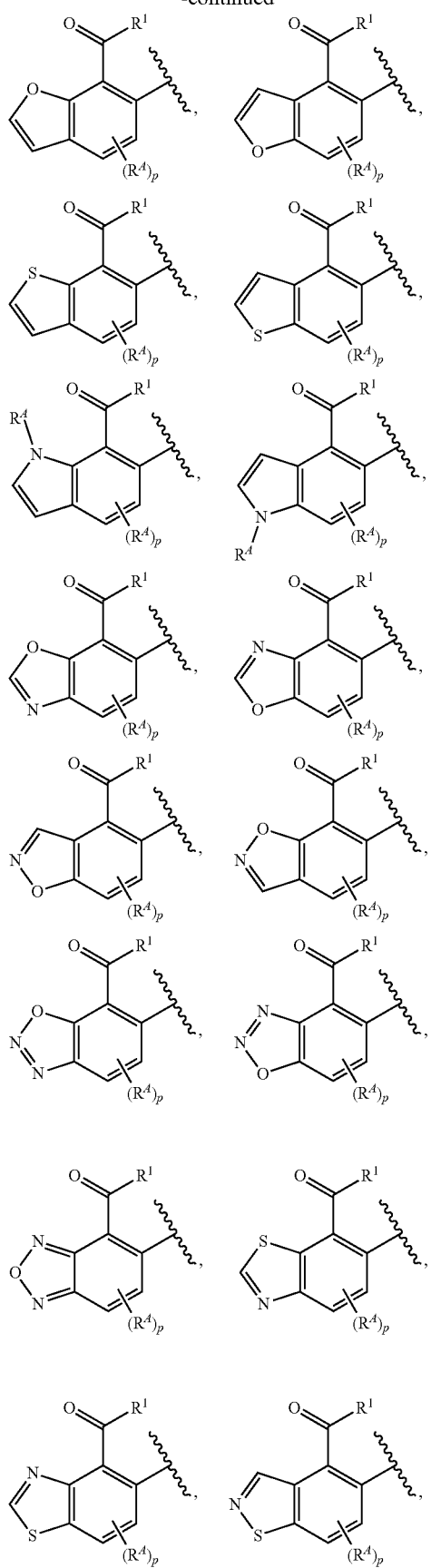
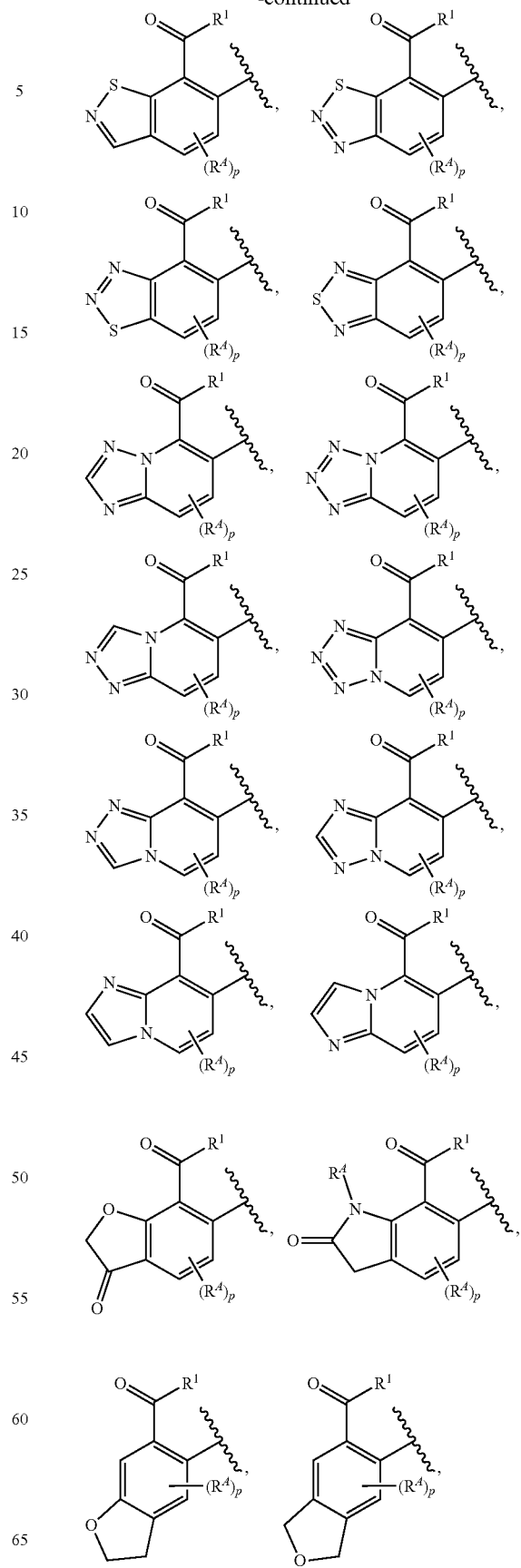

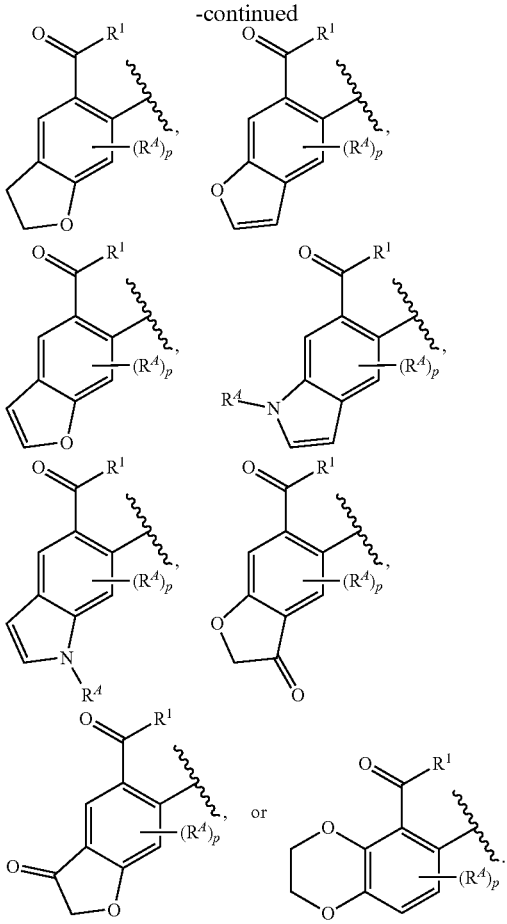

In some embodiments, ring A is a bicyclic carbocycle that is naphthyl, indanyl, or indenyl.

In some embodiments, $L^1$ is X; and X is —O— or —S—. In some embodiments, X is —O—.

In some embodiments, $R^2$ is H or D; and $R^3$ is substituted or unsubstituted $C_1$-$C_3$alkyl, substituted or unsubstituted $C_1$-$C_3$fluoroalkyl, or substituted or unsubstituted $C_1$-$C_3$heteroalkyl. In some embodiments, $R^2$ is H; and $R^3$ is substituted or unsubstituted $C_1$-$C_3$alkyl, substituted or unsubstituted $C_1$-$C_3$fluoroalkyl, or substituted or unsubstituted $C_1$-$C_3$heteroalkyl. In some embodiments, $R^2$ and $R^3$ are each substituted or unsubstituted $C_1$-$C_3$alkyl. In some embodiments, $R^2$ and $R^3$ together with the carbon that they are attached to form a substituted or unsubstituted $C_3$-$C_6$cycloalkyl or a substituted or unsubstituted $C_2$-$C_8$heterocycloalkyl.

In some embodiments,

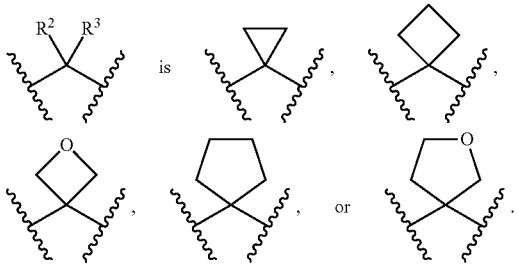

In some embodiments, the groups

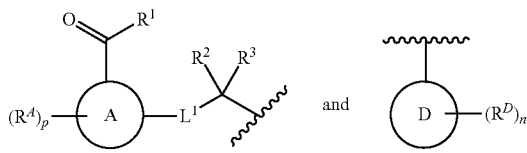

are on adjacent atoms of ring C.

In some embodiments, ring C is a monocyclic heterocycle. In some embodiments, ring C is a monocyclic heterocycle with 1-3 N atoms in the ring. In some embodiments, ring C is a monocyclic 6-membered heterocycle with 1-3 N atoms in the ring. In some embodiments, ring C is a monocyclic 6-membered heterocycle that is pyridinyl, pyrimidinyl, pyrazinyl, or triazinyl In some embodiments,

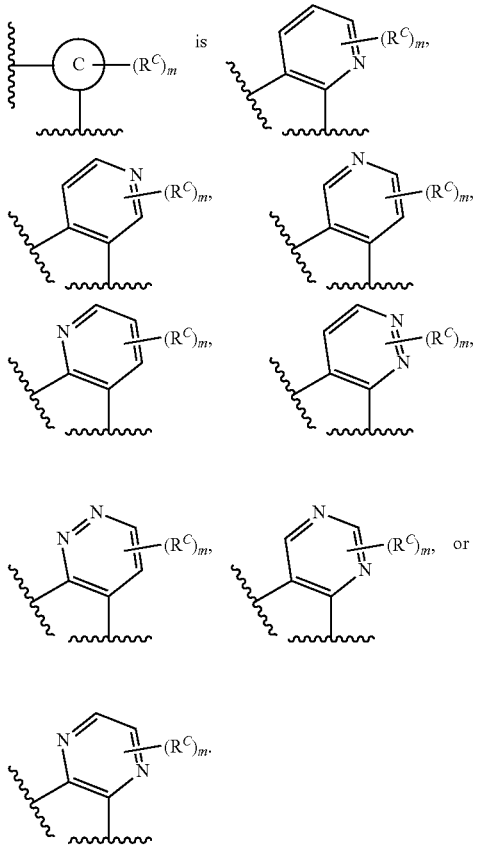

In some embodiments,

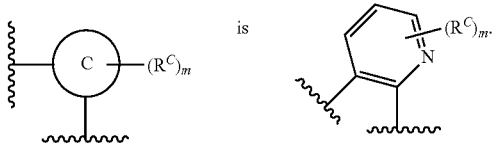

In some embodiments, ring C is a monocyclic 6-membered heterocycle that is

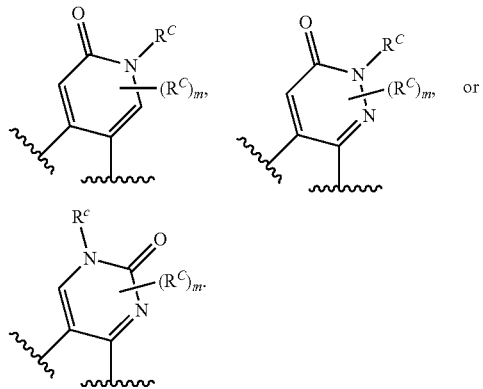

In some embodiments, ring C is phenyl.

In some embodiments is

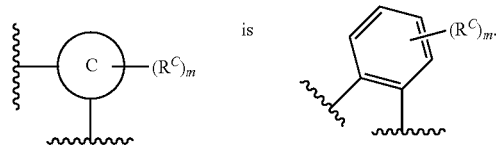

In some embodiments, the compound of Formula (II) has the structure of Formula (IIa), or a pharmaceutically acceptable salt or solvate thereof:

Formula (IIa)

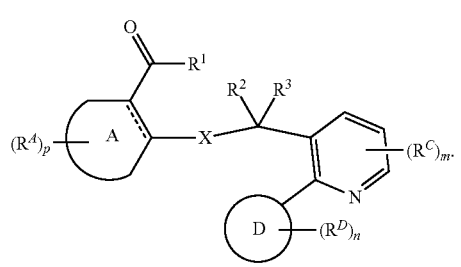

In some embodiments, ring D is a monocyclic heterocycle. In some embodiments, ring D is a monocyclic N-containing heterocycle. In some embodiments, ring D is a monocyclic 5-membered N-containing heterocycle or a monocyclic 6-membered N-containing heterocycle. In some embodiments, ring D is a monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, thiadiazolyl pyridinyl, pyrimidinyl, pyrazinyl, or triazinyl. In some embodiments, ring D is a 5-membered monocyclic N-containing heterocycle. In some embodiments, ring D is a 5-membered monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

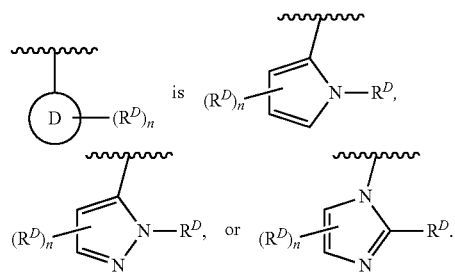

In some embodiments,

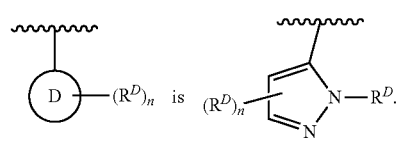

In some embodiments,

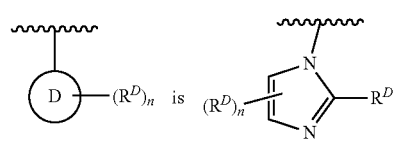

In some embodiments,

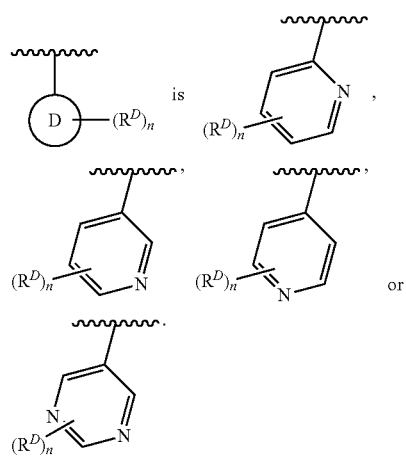

In some embodiments, ring D is a monocyclic heterocycle that is a β-lactam, γ-lactam, δ-lactam or ε-lactam.

In some embodiments,

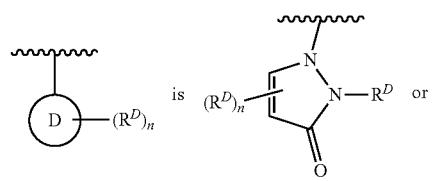

-continued

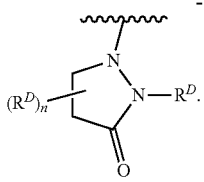

In some embodiments, ring D is a bicyclic heterocycle. In some embodiments, ring D is a bicyclic heterocycle that is a fused bicyclic heterocycle, bridged bicyclic heterocycle, or spiro bicyclic heterocycle.

In some embodiments,

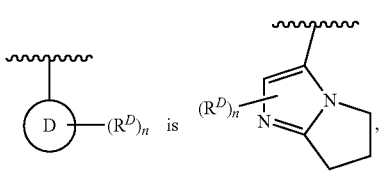

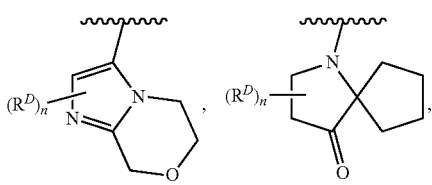

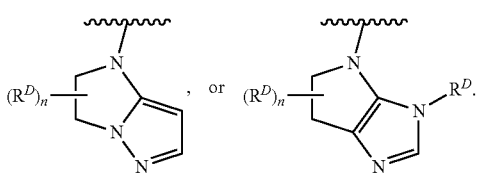

In some embodiments, the compound of Formula (II) has a structure of Formula (IIb), or pharmaceutically acceptable salt or solvate thereof:

Formula (IIb)

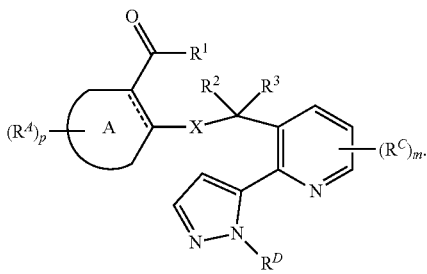

In some embodiments, the compound of Formula (II) has a structure of Formula (IIc), or pharmaceutically acceptable salt or solvate thereof:

Formula (IIc)

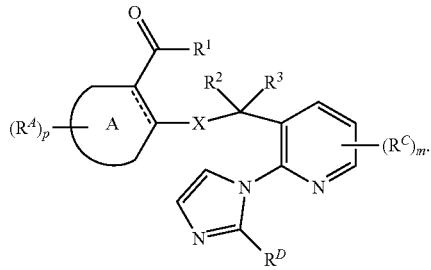

In some embodiments, $R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

In another aspect, presented herein are compounds of Formula (III), or a pharmaceutically acceptable salt or solvate thereof:

Formula (III)

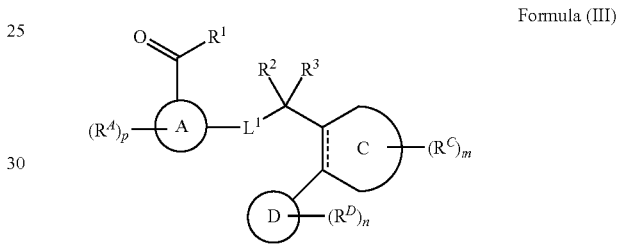

wherein, $R^1$ is H or D;

$L^1$ is X or —C($R^7$)($R^8$)—;

X is —O—, —S—, —S(O)—, —S(O$_2$)— or —NR$^4$—;

$R^7$ and $R^8$ are each independently H, D, substituted or unsubstituted $C_1$-$C_6$alkyl, or substituted or unsubstituted $C_1$-$C_6$deuteroalkyl;

$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;

$R^2$ is H or D;

$R^3$ is H or D;

ring A is phenyl or a monocyclic heterocycle;

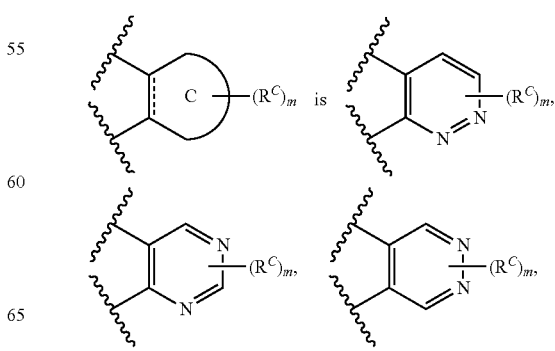

-continued

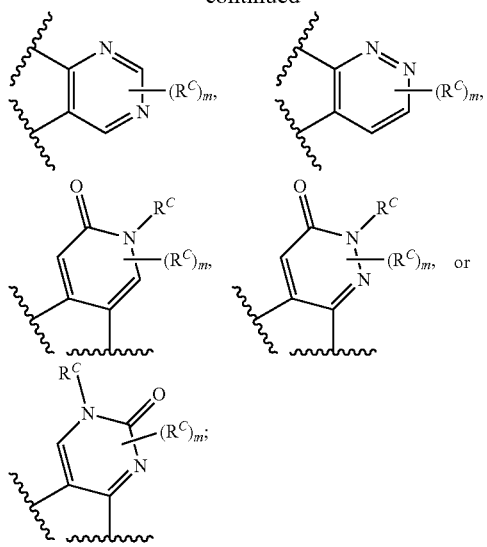

ring D is a monocyclic heterocycle, bicyclic heterocycle, monocyclic carbocycle, or a bicyclic carbocycle;
each $R^A$, $R^C$, and $R^D$ are independently H, D, halogen, —CN, —OH, —$OR^5$, —$SR^5$, —S(=O)$R^6$, —$NO_2$, —N($R^5$)$_2$, —S(=O)$_2R^6$, —NHS(=O)$_2R^6$, —S(=O)$_2$N(R)$_2$, —C(=O)$R^6$, —OC(=O)$R^6$, —$CO_2R^5$, —$OCO_2R^6$, —C(=O)N(R)$_2$, —OC(=O)N(R)$_2$, —$NR^5$C(=O)N(R)$_2$, —$NR^5$C(=O)$R^6$, —$NR^5$C(=O)O$R^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;
each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
or two $R^5$ on the same N atom are taken together with the N atom to which they are attached to form a N-containing heterocycloalkyl;
each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
p is 0, 1, 2 or 3;
m is 0, 1, 2 or 3; and n is 0, 1, 2 or 3.
In some embodiments, the groups

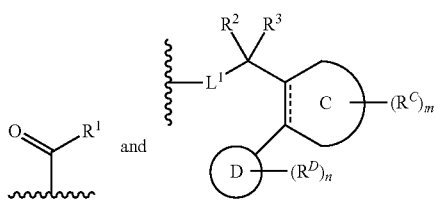

are on adjacent atoms of ring A.
In some embodiments, ring A is phenyl.
In some embodiments is

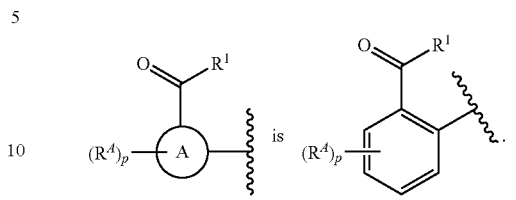

In some embodiments, ring A is a monocyclic heterocyle that is a monocyclic heteroaryl. In some embodiments, ring A is a monocyclic 6-membered heterocycle that is pyridinyl, pyrimidinyl, pyrazinyl, or triazinyl.
In some embodiments,

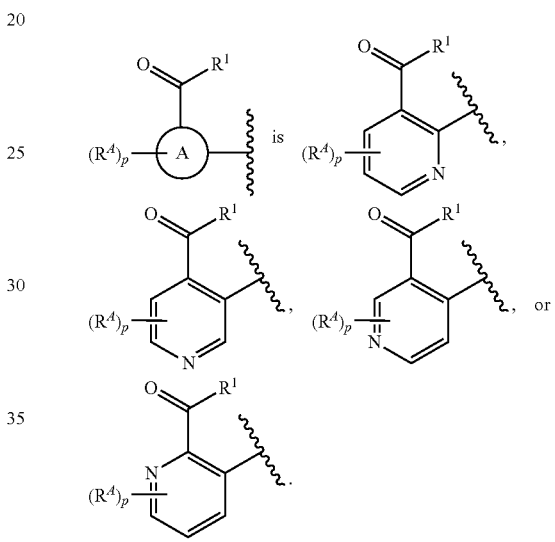

In some embodiments, $L^1$ is X; and X is —O— or —S—.
In some embodiments, X is —O—.
In some embodiments, ring D is a monocyclic heterocycle. In some embodiments, ring D is a monocyclic N-containing heterocycle. In some embodiments, ring D is a monocyclic 5-membered N-containing heterocycle or a monocyclic 6-membered N-containing heterocycle. In some embodiments, ring D is a monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, thiadiazolyl pyridinyl, pyrimidinyl, pyrazinyl, or triazinyl. In some embodiments, ring D is a 5-membered monocyclic N-containing heterocycle. In some embodiments, ring D is a 5-membered monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, or thiadiazolyl.
In some embodiments,

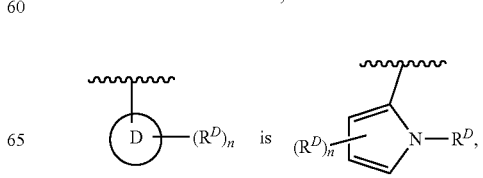

-continued

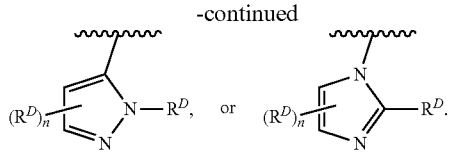

In some embodiments,

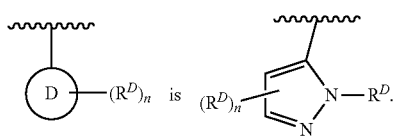

In some embodiments,

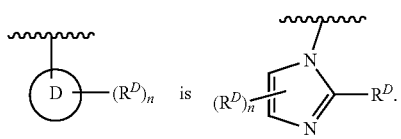

In some embodiments,

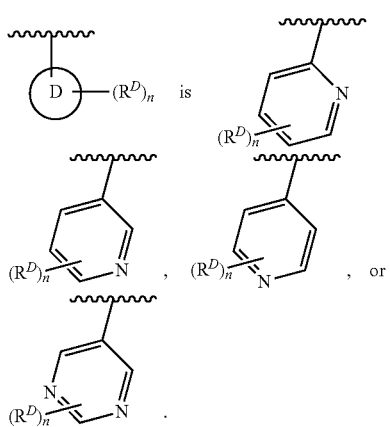

In some embodiments, ring D is a monocyclic heterocycle that is a β-lactam, γ-lactam, δ-lactam or ε-lactam.

In some embodiments,

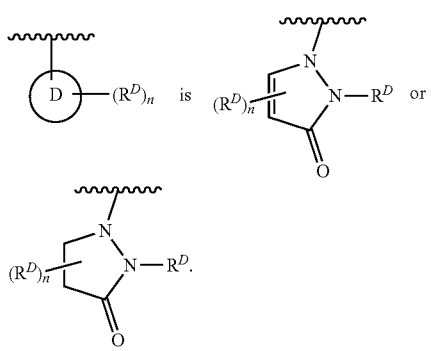

In some embodiments, ring D is a bicyclic heterocycle. In some embodiments, ring D is a bicyclic heterocycle that is a fused bicyclic heterocycle, bridged bicyclic heterocycle, or spiro bicyclic heterocycle.

In some embodiments,

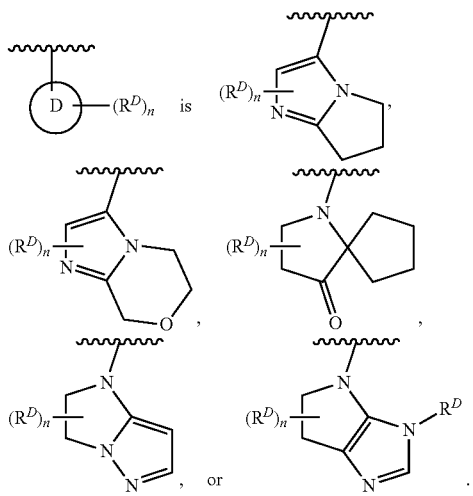

In some embodiments, the compound of Formula (III) has a structure of Formula (IIIa), or pharmaceutically acceptable salt or solvate thereof:

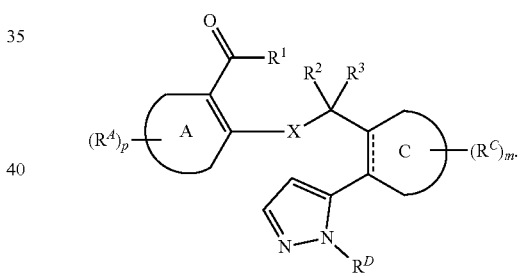

Formula (IIIa)

In some embodiments, the compound of Formula (III) has a structure of Formula (IIIb), or pharmaceutically acceptable salt or solvate thereof:

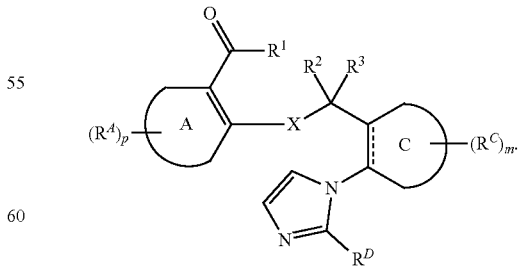

Formula (IIIb)

In some embodiments, $R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

In another aspect, presented herein are compounds of Formula (IV), or a pharmaceutically acceptable salt or solvate thereof:

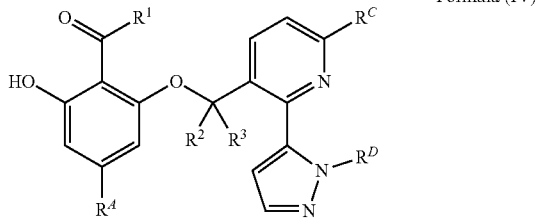

Formula (IV)

wherein, $R^1$ is H or D;
$R^2$ is H or D;
$R^3$ is H or D;
$R^A$ is H, D, or F;
$R^C$ is H, D, or F; and
$R^D$ is H, D, $C_1$-$C_6$alkyl, or $C_1$-$C_6$deuteroalkyl;
provided that when $R^D$ is H or $C_1$-$C_6$alkyl then at least one of $R^1$, $R^2$, $R^3$, $R^A$, and $R^C$ is D.

In some embodiments, $R^D$ is $C_1$-$C_6$deuteroalkyl. In some embodiments, $R^D$ is —CH(CD$_3$)$_2$.
In some embodiments, $R^1$ is D.
In some embodiments, $R^2$ is D; and $R^3$ is D.
In some embodiments, $R^A$ is H or F. In some embodiments, $R^A$ is F.
In some embodiments, $R^C$ is H or F. In some embodiments, $R^C$ is F.

In another aspect, presented herein are compounds of Formula (V), or a pharmaceutically acceptable salt or solvate thereof:

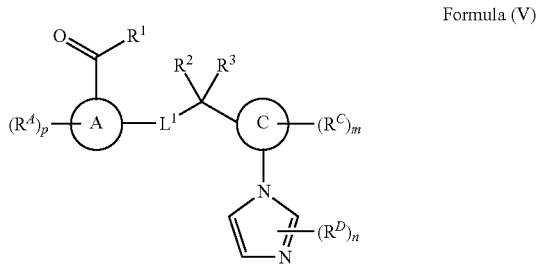

Formula (V)

wherein, $R^1$ is H or D;
$L^1$ is X or —C($R^7$)($R^8$)—;
X is —O—, —S—, —S(O)—, —S(O$_2$)— or —NR$^4$—;
$R^7$ and $R^8$ are each independently H, D, substituted or unsubstituted $C_1$-$C_6$alkyl, or substituted or unsubstituted $C_1$-$C_6$deuteroalkyl;
$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
$R^2$ is H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
$R^3$ is H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
or $R^2$ and $R^3$ together with the carbon that they are attached to form a substituted or unsubstituted $C_3$-$C_6$cycloalkyl or a substituted or unsubstituted $C_2$-$C_8$eterocycloalkyl;
ring A is a monocyclic carbocycle, monocyclic heterocycle, bicyclic carbocycle, or bicyclic heterocycle;
ring C is a monocyclic heterocycle or a monocyclic carbocycle;
each $R^A$, $R^C$, and $R^D$ is independently H, D, halogen, —CN, —OH, —OR$^5$, —SR$^5$, —S(=O)R$^6$, —NO$_2$, —N(R$^5$)$_2$, —S(=O)$_2$R$^6$, —NHS(=O)$_2$R$^6$, —S(=O)$_2$N(R)$_2$, —C(=O)R$^6$, —OC(=O)R$^6$, —CO$_2$R$^5$, —OCO$_2$R$^6$, —C(=O)N(R)$_2$, —OC(=O)N(R)$_2$, —NR$^5$C(=O)N(R)$_2$, —NR$^5$C(=O)R$^6$, —NR$^5$C(=O)OR$^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;
each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
or two $R^5$ on the same N atom are taken together with the N atom to which they are attached to form a N-containing heterocycloalkyl;
each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
p is 0, 1, 2 or 3;
m is 0, 1, 2 or 3; and
n is 0, 1, 2 or 3.
In some embodiments, the groups

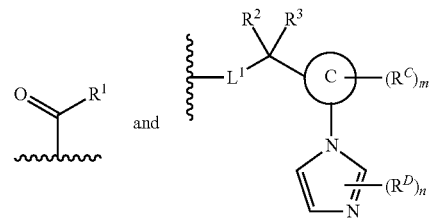

are on adjacent atoms of ring A.
In some embodiments, ring A is phenyl.
In some embodiments,

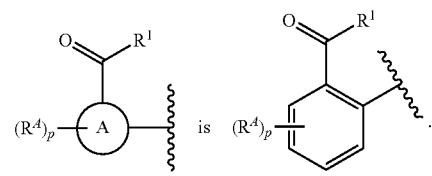

.

In some embodiments, ring A is a monocyclic heterocycle that is a monocyclic heteroaryl.

In some embodiments, ring A is a monocyclic heterocycle with 1-3 N atoms in the ring.

In some embodiments, ring A is a monocyclic 6-membered heterocycle with 1-3 N atoms in the ring.

In some embodiments, ring A is a monocyclic 6-membered heterocycle that is pyridinyl, pyrimidinyl, pyrazinyl, or triazinyl In some embodiments, ring A is pyridinyl.

In some embodiments,

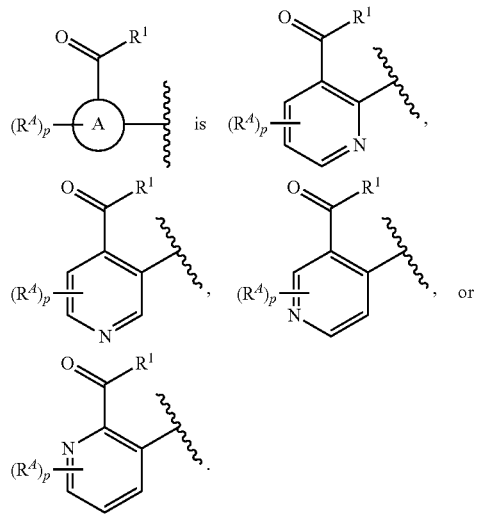

In some embodiments, ring A is a bicyclic heterocycle that is a 8-, 9- or 10-membered bicyclic heterocycle.

In some embodiments, ring A is a bicyclic heterocycle that has 1-4 N atoms, 0-1 O atoms, and 0-1 S atoms in the bicyclic ring.

In some embodiments, ring A is a bicyclic heterocycle that has 0-4 N atoms, 1 O atom, or 1 S atom in the bicyclic ring.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is a bicyclic heterocycle that is indolinyl, isoindolinyl, indolinonyl, 1,2,3,4-tetrahydroquinolinyl, 1,2,3,4-tetrahydroisoquinolinyl, 3,4-dihydro-2(1H)-quinolinonyl, dihydrobenzofuranyl, dihydroisobenzofuran, dihydrobenzo[b]thiophenyl, or dihydrobenzo[c]thiophenyl.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, indolyl, benzimidazolyl, benzotriazolyl, benzoxazolyl, benzisoxazolyl, benzofuranyl, benzothienyl, benzothiazolyl, or purinyl.

In some embodiments,

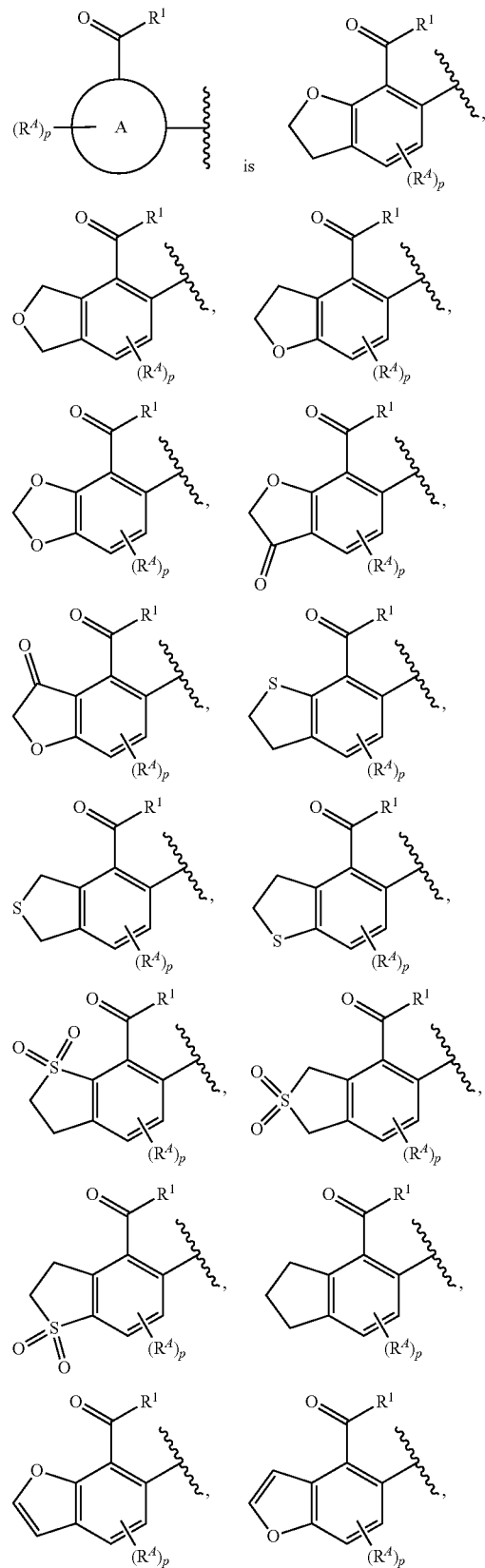

-continued
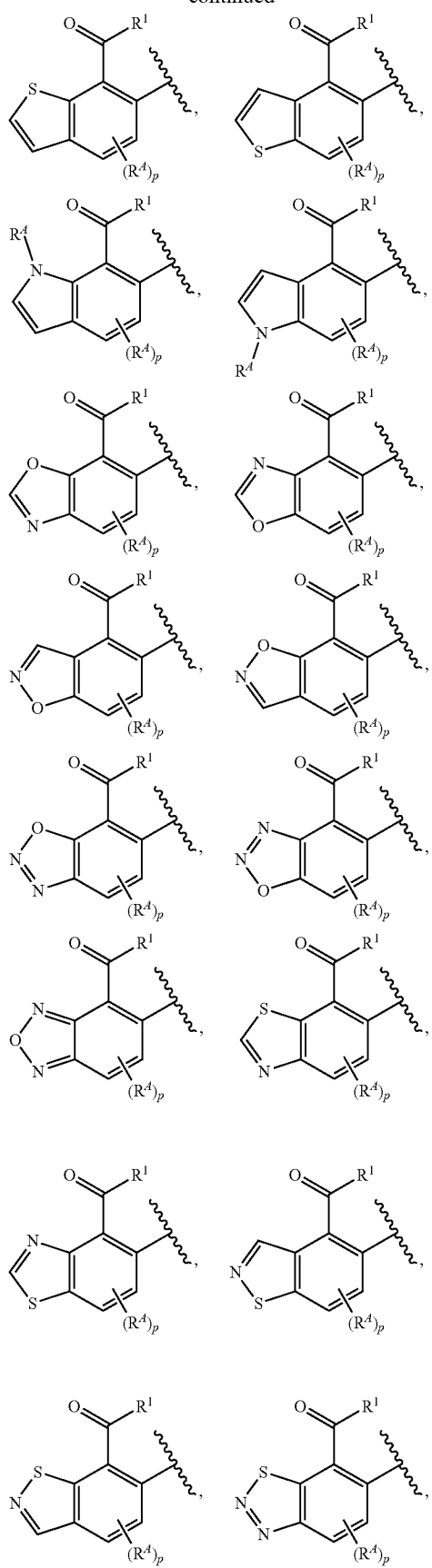
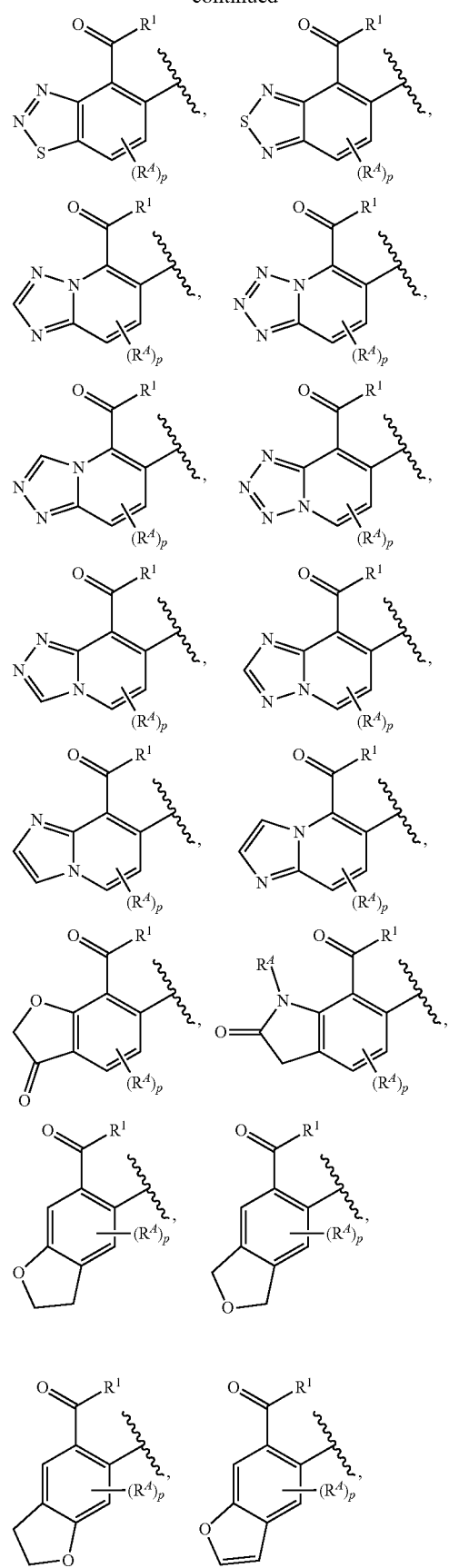

-continued

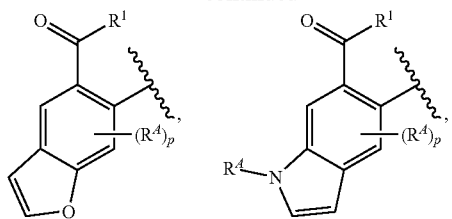

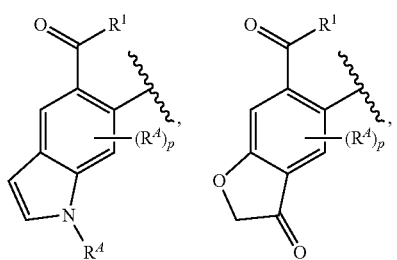

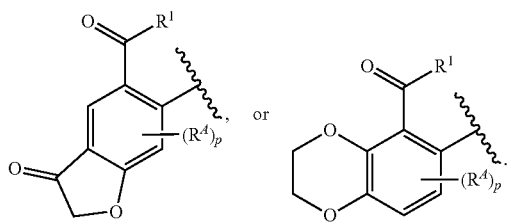

In some embodiments, ring A is a bicyclic carbocycle that is naphthyl, indanyl, or indenyl.

In some embodiments, $L^1$ is X; and X is —O— or —S—.

In some embodiments, X is —O—.

In some embodiments, $R^2$ is H; and $R^3$ is H. In some embodiments, $R^2$ is D; and $R^3$ is D.

In some embodiments, $R^2$ is H; and $R^3$ is substituted or unsubstituted $C_1$-$C_3$alkyl, substituted or unsubstituted $C_1$-$C_3$fluoroalkyl, or substituted or unsubstituted $C_1$-$C_3$heteroalkyl.

In some embodiments, $R^2$ and $R^3$ are each substituted or unsubstituted $C_1$-$C_3$alkyl.

In some embodiments, $R^2$ and $R^3$ together with the carbon that they are attached to form a substituted or unsubstituted $C_3$-$C_6$cycloalkyl or a substituted or unsubstituted $C_2$-$C_8$eterocycloalkyl.

In some embodiments,

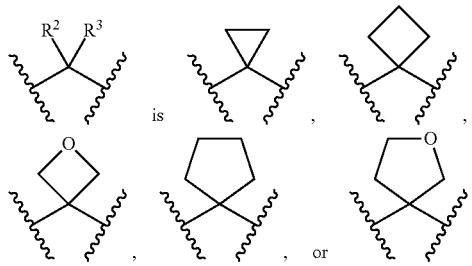

In some embodiments, the groups

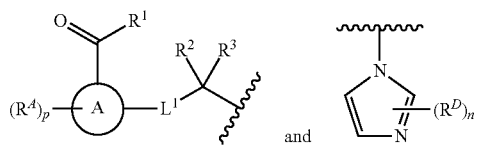

are on adjacent atoms of ring C.

In some embodiments, ring C is a monocyclic heterocycle.

In some embodiments, ring C is a monocyclic heterocycle with 1-3 N atoms in the ring.

In some embodiments, ring C is a monocyclic 6-membered heterocycle with 1-3 N atoms in the ring.

In some embodiments, ring C is a monocyclic 6-membered heterocycle that is pyridinyl, pyrimidinyl, pyrazinyl, or triazinyl In some embodiments,

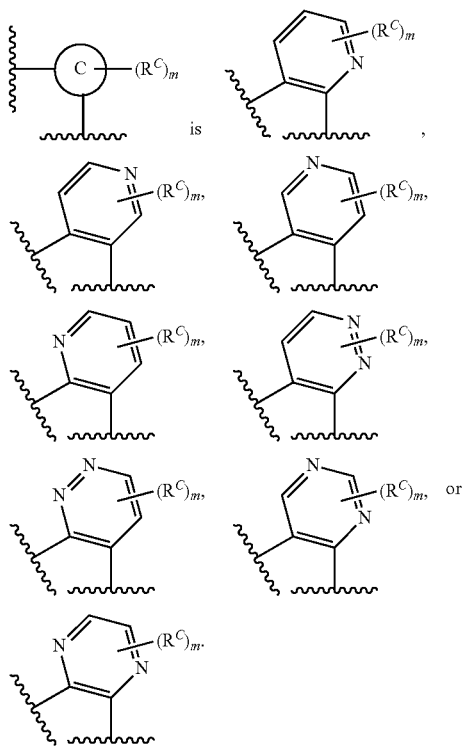

In some embodiments,

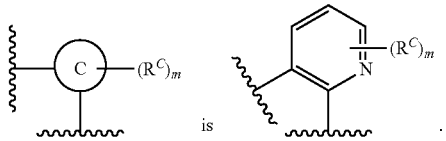

In some embodiments, ring C is a monocyclic 6-membered heterocycle that is

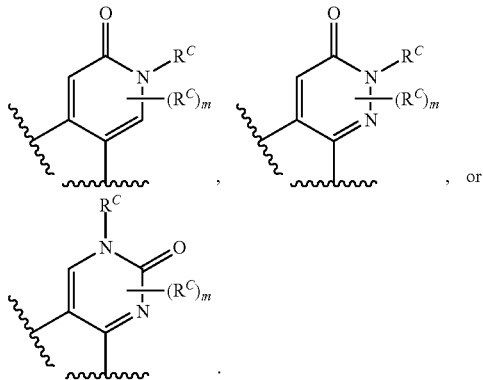

, or

In some embodiments, ring C is phenyl.
In some embodiments,

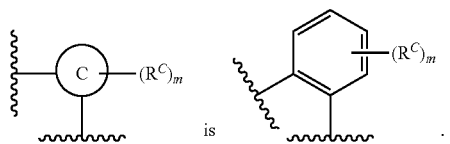

is

In some embodiments, the compound of Formula (V) has the structure of Formula (Va), or a pharmaceutically acceptable salt or solvate thereof:

(Formula Va)

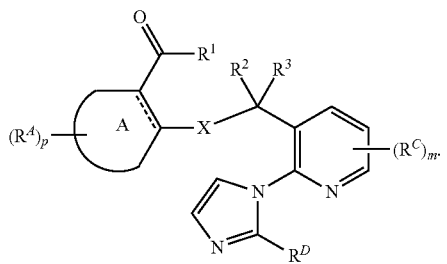

In some embodiments, $R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

In another aspect, presented herein are compounds of Formula (VI), or a pharmaceutically acceptable salt or solvate thereof:

Formula (VI)

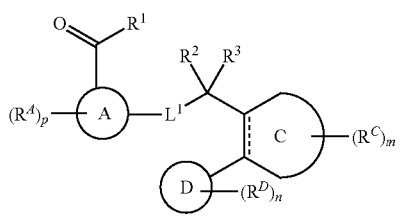

wherein,
$R^1$ is H or D;
$L^1$ is X or —C($R^7$)($R^8$)—;
X is —O—, —S—, —S(O)—, —S($O_2$)— or —$NR^4$—;
$R^7$ and $R^8$ are each independently H, D, substituted or unsubstituted $C_1$-$C_6$alkyl, or substituted or unsubstituted $C_1$-$C_6$deuteroalkyl;
$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
$R^2$ is H or D;
$R^3$ is H or D;
ring A is phenyl or a monocyclic heterocycle;

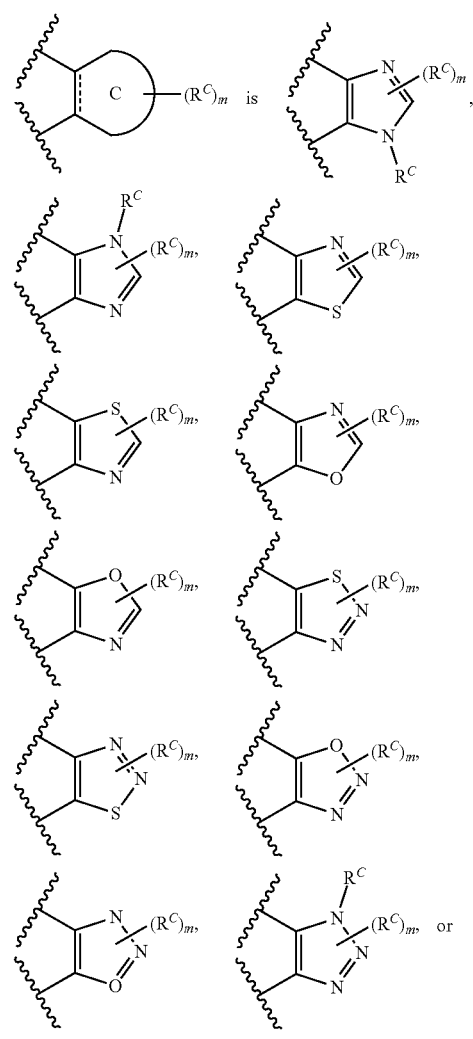

ring D is a monocyclic heterocycle, bicyclic heterocycle, monocyclic carbocycle, or a bicyclic carbocycle;
each $R^A$, $R^C$, and $R^D$ are independently H, D, halogen, —CN, —OH, —$OR^5$, —$SR^5$, —S(=O)$R^6$, —$NO_2$, —N(R$^5$)$_2$, —S(=O)$_2$R$^6$, —NHS(=O)$_2$R$^6$, —S(=O)$_2$N(R$^5$)$_2$, —C(=O)R$^6$, —OC(=O)R$^6$, —CO$_2$R$^5$, —OCO$_2$R$^6$, —C(=O)N(R)$_2$, —OC(=O)N(R)$_2$, —NR$^5$C(=O)N(R)$_2$, —NR$^5$C(=O)R$^6$, —NR$^5$C(=O)OR$^6$, substituted or unsubstituted C$_1$-C$_6$alkyl, substituted or unsubstituted C$_1$-C$_6$deuteroalkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted aryl, or substituted or unsubstituted heteroaryl;

each R$^5$ is independently H, D, substituted or unsubstituted C$_1$-C$_6$alkyl, substituted or unsubstituted C$_1$-C$_6$deuteroalkyl, substituted or unsubstituted C$_1$-C$_6$fluoroalkyl, substituted or unsubstituted C$_3$-C$_6$cycloalkyl, substituted or unsubstituted aryl, or substituted or unsubstituted heteroaryl;

or two R$^5$ on the same N atom are taken together with the N atom to which they are attached to form a N-containing heterocycloalkyl;

each R$^6$ is independently substituted or unsubstituted C$_1$-C$_6$alkyl, substituted or unsubstituted C$_1$-C$_6$deuteroalkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted aryl, or substituted or unsubstituted heteroaryl;

p is 0, 1, 2 or 3;
m is 0, 1, 2 or 3; and
n is 0, 1, 2 or 3.

In some embodiments, the groups

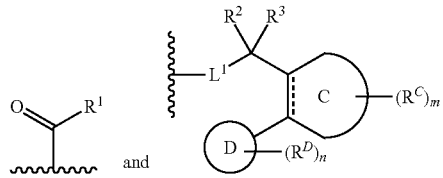

are on adjacent atoms of ring A.
In some embodiments, ring A is phenyl.
In some embodiments

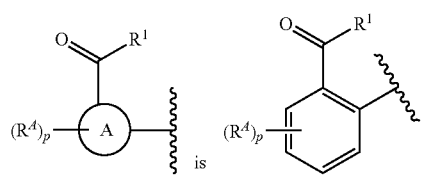

In some embodiments, ring A is a monocyclic heterocyle that is a monocyclic heteroaryl. In some embodiments, ring A is a monocyclic 6-membered heterocycle that is pyridinyl, pyrimidinyl, pyrazinyl, or triazinyl.

In some embodiments,

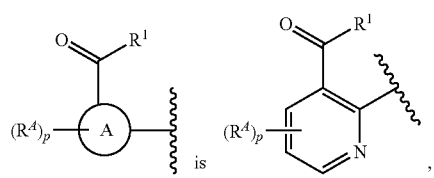

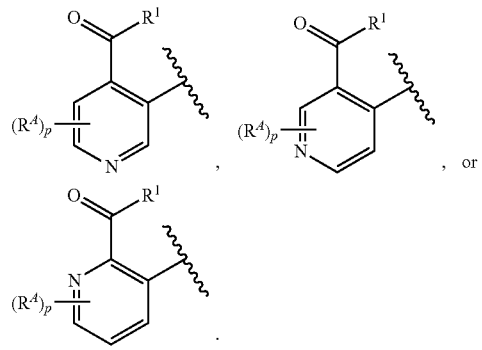

In some embodiments, L$^1$ is X; and X is —O— or —S—.
In some embodiments, X is —O—.

In some embodiments, ring D is a monocyclic heterocycle. In some embodiments, ring D is a monocyclic N-containing heterocycle. In some embodiments, ring D is a monocyclic 5-membered N-containing heterocycle or a monocyclic 6-membered N-containing heterocycle. In some embodiments, ring D is a monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, thiadiazolyl pyridinyl, pyrimidinyl, pyrazinyl, or triazinyl. In some embodiments, ring D is a 5-membered monocyclic N-containing heterocycle. In some embodiments, ring D is a 5-membered monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

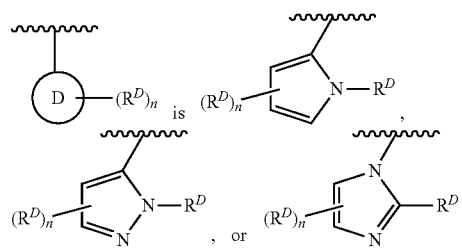

In some embodiments,

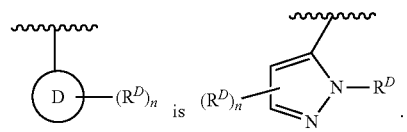

In some embodiments,

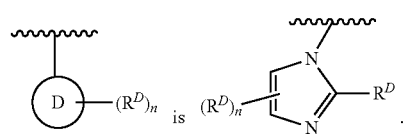

In some embodiments,

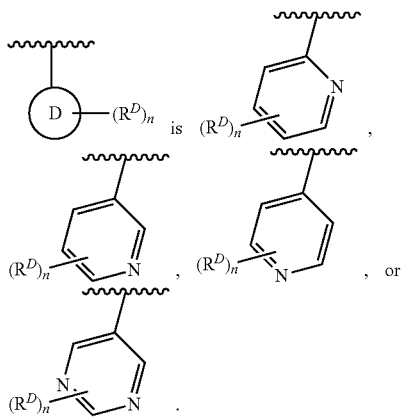

In some embodiments, ring D is a bicyclic heterocycle. In some embodiments, ring D is a bicyclic heterocycle that is a fused bicyclic heterocycle, bridged bicyclic heterocycle, or spiro bicyclic heterocycle.

In some embodiments, the compound of Formula (VI) has a structure of Formula (VIa), or pharmaceutically acceptable salt or solvate thereof:

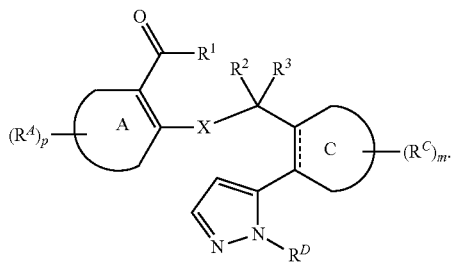

Formula (VIa)

In some embodiments, the compound of Formula (VI) has a structure of Formula (VIb), or pharmaceutically acceptable salt or solvate thereof:

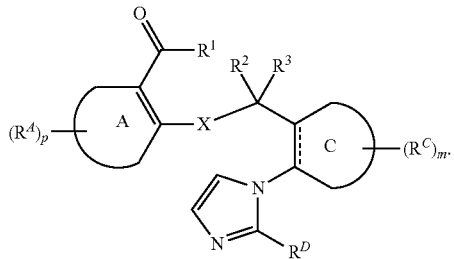

Formula (VIb)

In some embodiments, $R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

Also provided herein in another aspect are compounds of Formula (VII), or a pharmaceutically acceptable salt or solvate thereof:

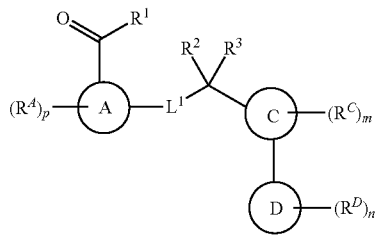

Formula (VII)

wherein,
R is H or D;
$L^1$ is X;
X is —S—, —S(O)—, or —S(O$_2$)—;
$R^7$ and $R^8$ are each independently H, D, substituted or unsubstituted $C_1$-$C_6$alkyl, or substituted or unsubstituted $C_1$-$C_6$deuteroalkyl;
$R^4$ is hydrogen, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
$R^2$ is H, D, substituted or unsubstituted $C_1$-$C_6$alkyl, or substituted or unsubstituted $C_1$-$C_6$deuteroalkyl;
$R^3$ is H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
or $R^2$ and $R^3$ together with the carbon that they are attached to form a substituted or unsubstituted $C_3$-$C_6$cycloalkyl or a substituted or unsubstituted $C_2$-$C_8$eterocycloalkyl;
or $R^7$ and $R^3$ are taken together with the carbons that they are attached to form a substituted or unsubstituted $C_3$-$C_6$cycloalkyl or a substituted or unsubstituted $C_2$-$C_8$eterocycloalkyl; ring A is a monocyclic carbocycle, monocyclic heterocycle, bicyclic carbocycle, or bicyclic heterocycle;
ring C is a monocyclic heterocycle or a monocyclic carbocycle;
ring D is a monocyclic heterocycle, bicyclic heterocycle, monocyclic carbocycle, or a bicyclic carbocycle;
each $R^A$, $R^C$, and $R^D$ is independently H, D, halogen, —CN, —OH, —OR$^5$, —SR$^5$, —S(=O)R$^6$, —NO$_2$, —N(R$^5$)$_2$, —S(=O)$_2$R$^6$, —NHS(=O)$_2$R$^6$, —S(=O)$_2$N(R)$_2$, —C(=O)R$^6$, —OC(=O)R$^6$, —CO$_2$R$^5$, —OCO$_2$R$^6$, —C(=O)N(R)$_2$, —OC(=O)N(R)$_2$, —NR$^5$C(=O)N(R)$_2$, —NR$^5$C(=O)R$^6$, —NR$^5$C(=O)OR$^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;
each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
or two $R^5$ on the same N atom are taken together with the N atom to which they are attached to form a N-containing heterocycloalkyl;

each $R^6$ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

p is 0, 1, 2 or 3;
m is 0, 1, 2 or 3; and
n is 0, 1, 2 or 3.

In some embodiments, the groups

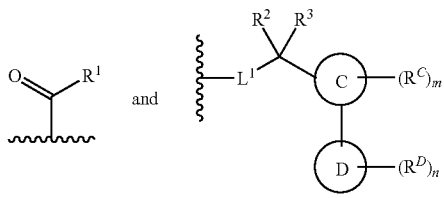

are on adjacent atoms of ring A.

In some embodiments, ring A is phenyl.
In some embodiments,

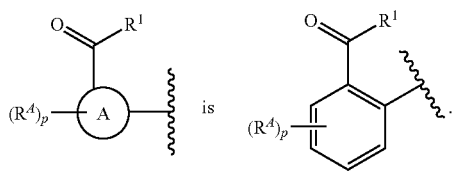

In some embodiments, ring A is a monocyclic heterocycle that is a monocyclic heteroaryl. In some embodiments, ring A is a monocyclic heterocycle with 1-3 N atoms in the ring. In some embodiments, ring A is a monocyclic 6-membered heterocycle with 1-3 N atoms in the ring. In some embodiments, ring A is a monocyclic 6-membered heterocycle that is pyridinyl, pyrimidinyl, pyrazinyl, or triazinyl. In some embodiments, ring A is pyridinyl.

In some embodiments,

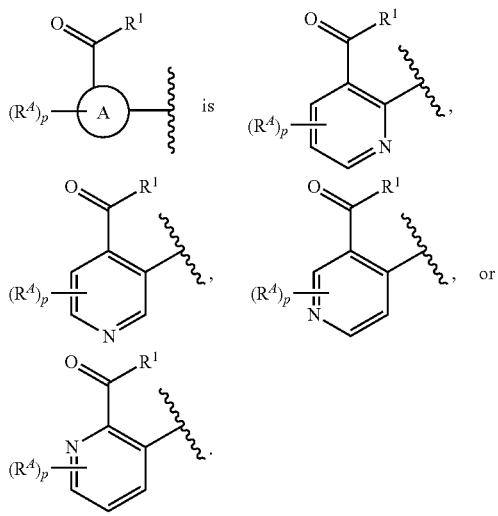

In some embodiments, ring A is a bicyclic heterocycle that is a 8-, 9- or 10-membered bicyclic heterocycle. In some embodiments, ring A is a bicyclic heterocycle that has 1-4 N atoms, 0-1 O atoms, and 0-1 S atoms in the bicyclic ring. In some embodiments, ring A is a bicyclic heterocycle that has 0-4 N atoms, 1 O atom or 1 S atom in the bicyclic ring.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is a bicyclic heterocycle that is indolinyl, isoindolinyl, indolinonyl, 1,2,3,4-tetrahydroquinolinyl, 1,2,3,4-tetrahydroisoquinolinyl, 3,4-dihydro-2 (1H)-quinolinonyl, dihydrobenzofuranyl, dihydroisobenzofuran, dihydrobenzo[b]thiophenyl, or dihydrobenzo[c] thiophenyl.

In some embodiments, ring A is a bicyclic heterocycle that is quinolinyl, isoquinolinyl, cinnolinyl, phthalazinyl, quinazolinyl, quinoxalinyl, naphthyridinyl, pteridinyl, indolizinyl, indolyl, benzimidazolyl, benzotriazolyl, benzoxazolyl, benzisoxazolyl, benzofuranyl, benzothienyl, benzothiazolyl, or purinyl.

In some embodiments,

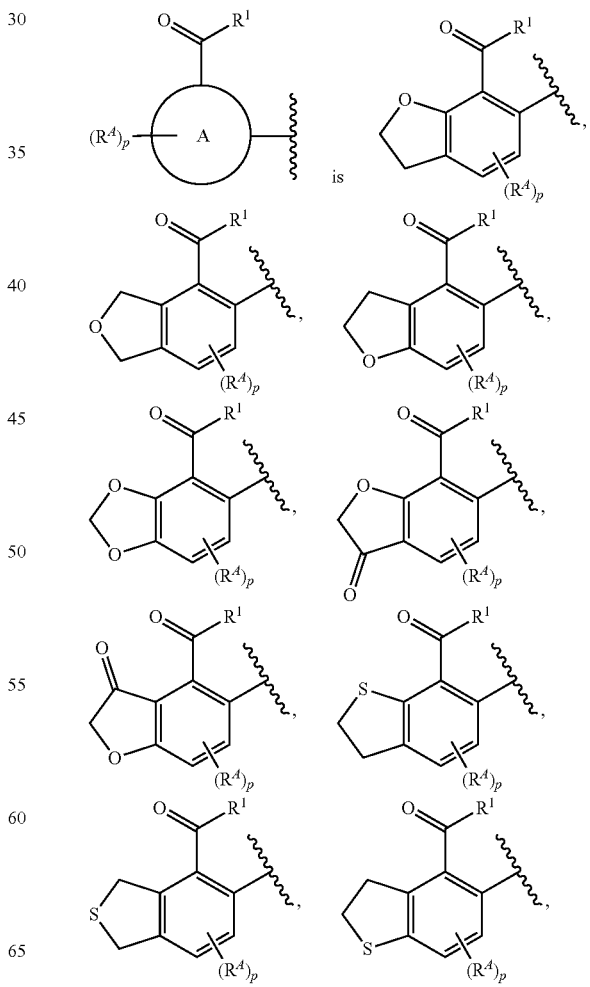

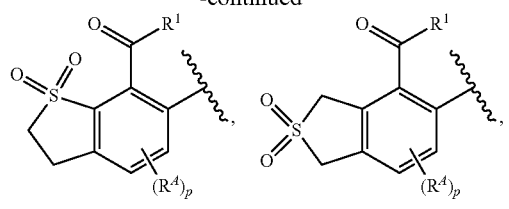
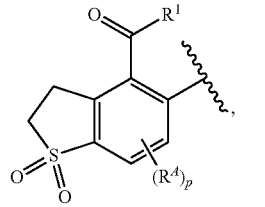
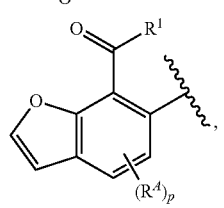
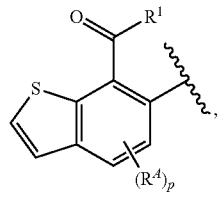
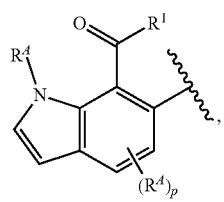
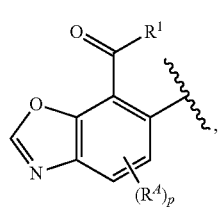
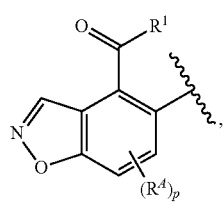
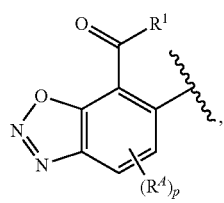
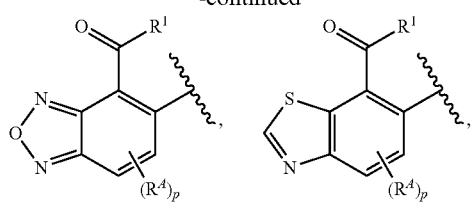
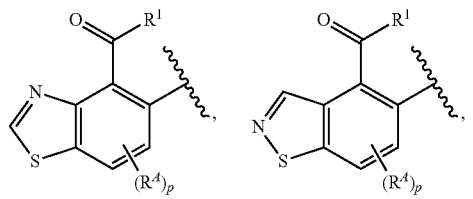
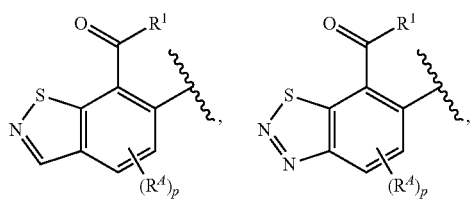
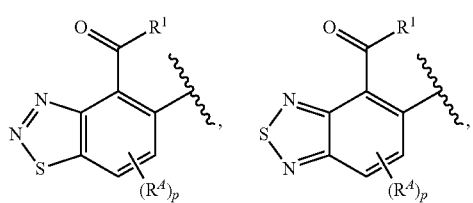
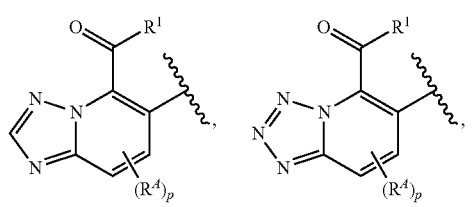
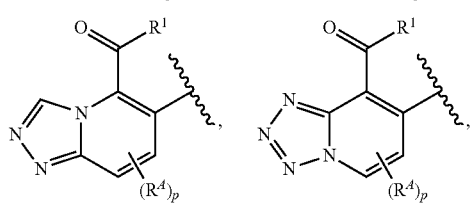
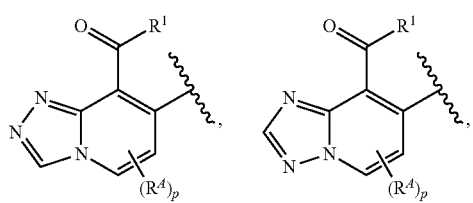
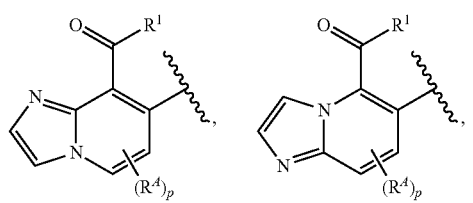

-continued

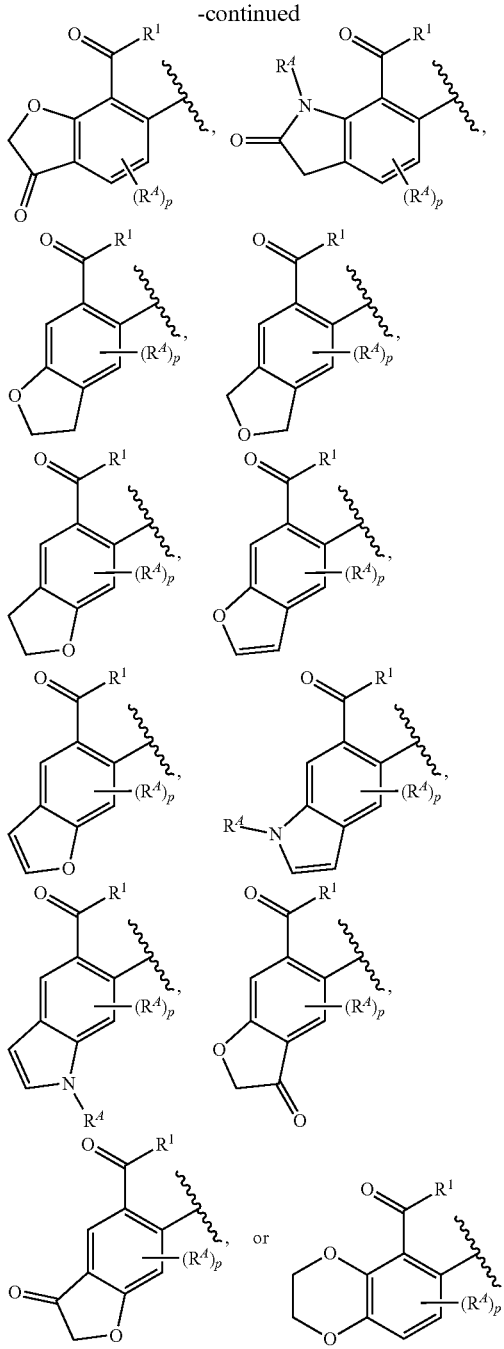

In some embodiments, ring A is a bicyclic carbocycle that is naphthyl, indanyl, or indenyl In some embodiments, $L^1$ is X; and X is —S—.

In some embodiments, $R^2$ is H or D; and $R^3$ is substituted or unsubstituted $C_1$-$C_3$alkyl, substituted or unsubstituted $C_1$-$C_3$fluoroalkyl, or substituted or unsubstituted $C_1$-$C_3$heteroalkyl. In some embodiments, $R^2$ is H; and $R^3$ is substituted or unsubstituted $C_1$-$C_3$alkyl, substituted or unsubstituted $C_1$-$C_3$fluoroalkyl, or substituted or unsubstituted $C_1$-$C_3$heteroalkyl. In some embodiments, $R^2$ and $R^3$ are each substituted or unsubstituted $C_1$-$C_3$alkyl. In some embodiments, $R^2$ and $R^3$ together with the carbon that they are attached to form a substituted or unsubstituted $C_3$-$C_6$cycloalkyl or a substituted or unsubstituted $C_2$-$C_8$heterocycloalkyl.

In some embodiments,

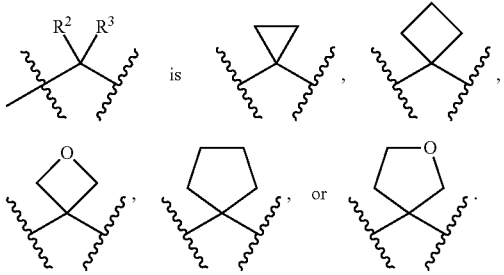

In some embodiments, the groups

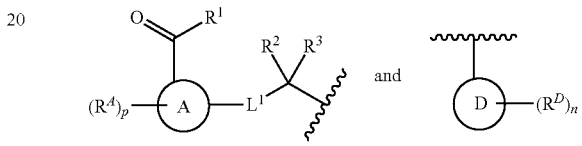

are on adjacent atoms of ring C.

In some embodiments, ring C is a monocyclic heterocycle. In some embodiments, ring C is a monocyclic heterocycle with 1-3 N atoms in the ring. In some embodiments, ring C is a monocyclic 6-membered heterocycle with 1-3 N atoms in the ring. In some embodiments, ring C is a monocyclic 6-membered heterocycle that is pyridinyl, pyrimidinyl, pyrazinyl, or triazinyl In some embodiments,

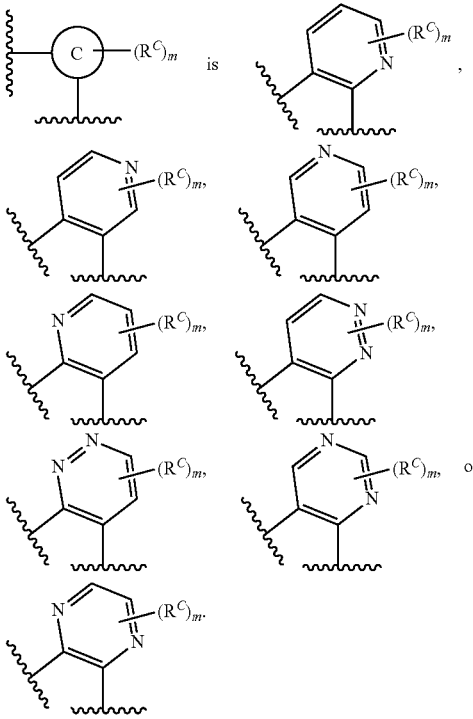

In some embodiments,

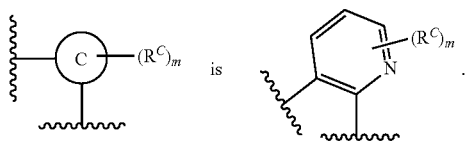

In some embodiments, ring C is a monocyclic 6-membered heterocycle that is

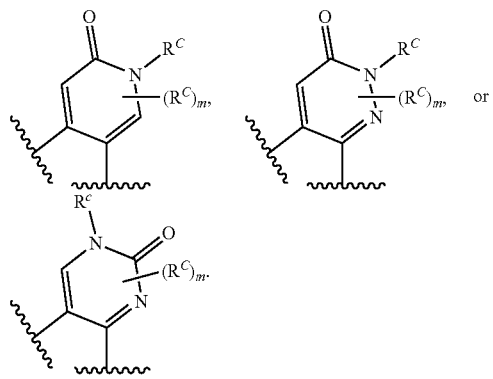

In some embodiments, ring C is phenyl.
In some embodiments,

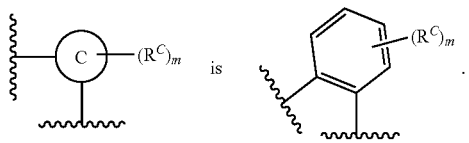

In some embodiments, the compound of Formula (VII) has the structure of Formula (VIIa), or a pharmaceutically acceptable salt or solvate thereof:

Formula (VIIa)

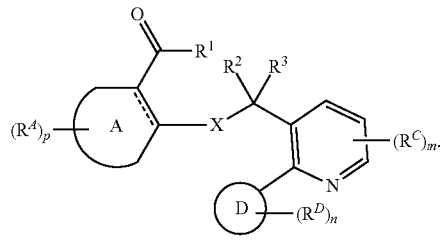

In some embodiments, ring D is a monocyclic heterocycle. In some embodiments, ring D is a monocyclic N-containing heterocycle. In some embodiments, ring D is a monocyclic 5-membered N-containing heterocycle or a monocyclic 6-membered N-containing heterocycle. In some embodiments, ring D is a monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, thiadiazolyl pyridinyl, pyrimidinyl, pyrazinyl, or triazinyl. In some embodiments, ring D is a 5-membered monocyclic N-containing heterocycle. In some embodiments, ring D is a 5-membered monocyclic N-containing heterocycle that is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

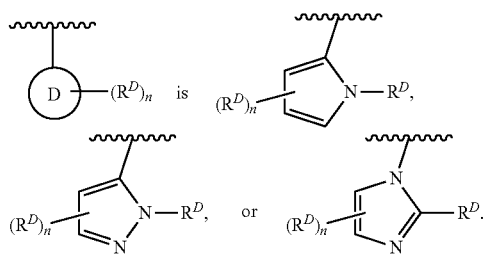

In some embodiments,

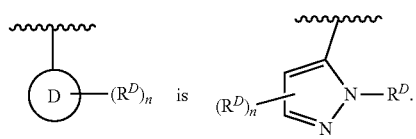

In some embodiments,

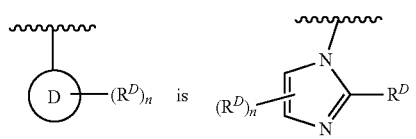

In some embodiments,

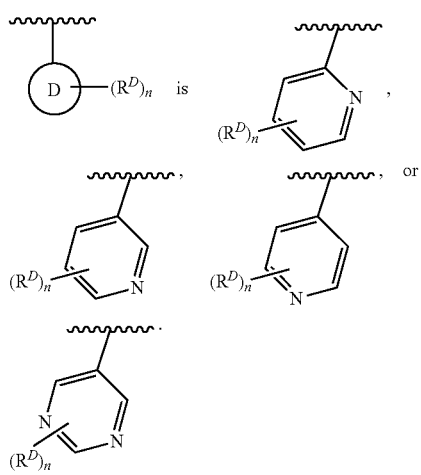

In some embodiments, ring D is a monocyclic heterocycle that is a β-lactam, γ-lactam, δ-lactam or ε-lactam.

In some embodiments, ring D is a bicyclic heterocycle. In some embodiments, ring D is a bicyclic heterocycle that is a fused bicyclic heterocycle, bridged bicyclic heterocycle, or spiro bicyclic heterocycle.

In some embodiments, the compound of Formula (VII) has a structure of Formula (VIIb), or pharmaceutically acceptable salt or solvate thereof:

Formula (VIIb)

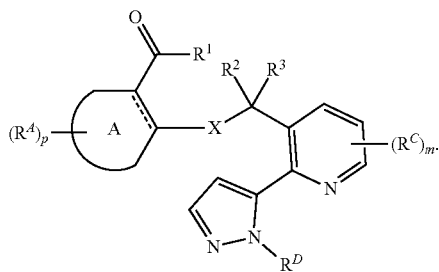

Formula (VIIc)

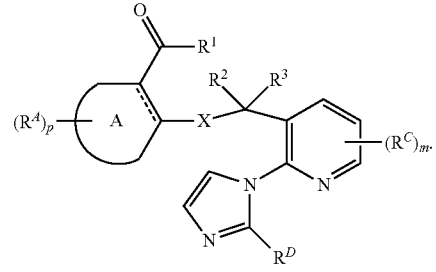

In some embodiments, the compound of Formula (VII) has a structure of Formula (VIIc), or pharmaceutically acceptable salt or solvate thereof:

In some embodiments, $R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

In some embodiments, the compound of the present disclosure, or the pharmaceutically acceptable salt thereof, is selected from:

| Ex. | Name | Structure |
|---|---|---|
| 2 | 5-((2-(1-isopropyl-1H-pyrazol-5-yl)pyridin-3-yl)methoxy)-2,3-dihydrobenzofuran-4-carbaldehyde | 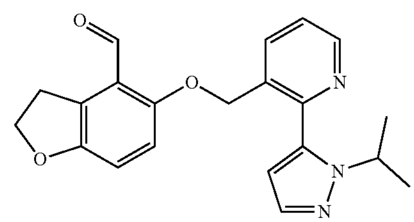 [SMILES: CC(C)n1nccc1-c1ncccc1COc1ccc2c(c1C=O)CCO2] |
| 3 | 5-((2-(1-isopropyl-1H-pyrazol-5-yl)pyridin-3-yl)methoxy)-2,3-dihydrobenzofuran-6-carbaldehyde | 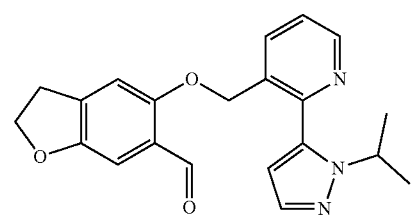 [SMILES: CC(C)n1nccc1-c1ncccc1COc1cc2c(cc1C=O)OCC2] |
| 4 | 6-((2-(1-isopropyl-1H-pyrazol-5-yl)pyridin-3-yl)methoxy)-2,3-dihydrobenzofuran-7-carbaldehyde | 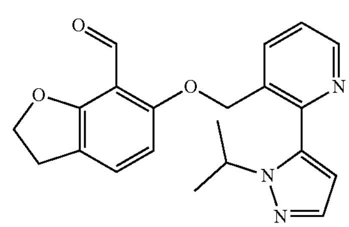 [SMILES: CC(C)n1nccc1-c1ncccc1COc1ccc2c(c1C=O)OCC2] |
| 5 | 6-((2-(1-isopropyl-1H-pyrazol-5-yl)pyridin-3-yl)methoxy)benzofuran-7-carbaldehyde | 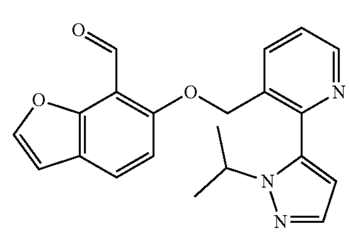 [SMILES: CC(C)n1nccc1-c1ncccc1COc1ccc2ccoc2c1C=O] |

-continued

| Ex. | Name | Structure |
|---|---|---|
| 6 | 5-((2-(1-isopropyl-1H-pyrazol-5-yl)pyridin-3-yl)methoxy)benzo[d][1,3]dioxole-4-carbaldehyde | 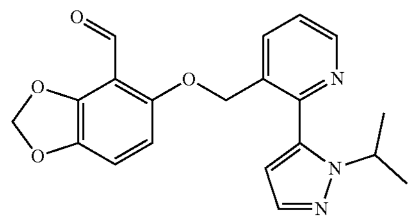 [SMILES: CC(C)n1nccc1-c1ncccc1COc1ccc2c(c1C=O)OCO2] |
| 7 | 6-((2-(1-isopropyl-1H-pyrazol-5-yl)pyridin-3-yl)methoxy)-2,3-dihydrobenzo[b][1,4]dioxine-5-carbaldehyde | 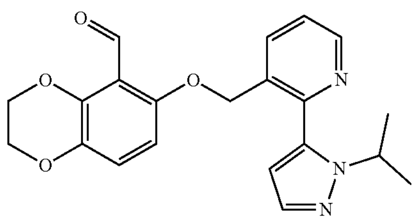 [SMILES: CC(C)n1nccc1-c1ncccc1COc1ccc2c(c1C=O)OCCO2] |
| 8 | 2,2-difluoro-5-((2-(1-isopropyl-1H-pyrazol-5-yl)pyridin-3-yl)methoxy)benzo[d][1,3]dioxole-4-carbaldehyde | 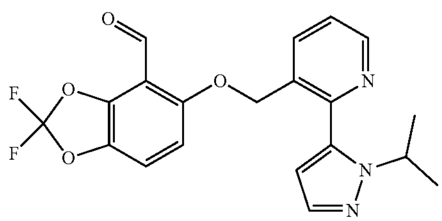 [SMILES: CC(C)n1nccc1-c1ncccc1COc1ccc2c(c1C=O)OC(F)(F)O2] |
| 9 | 2,2-difluoro-3-hydroxy-5-((2-(1-isopropyl-1H-pyrazol-5-yl)pyridin-3-yl)methoxy)-2,3-dihydrobenzofuran-4-carbaldehyde | 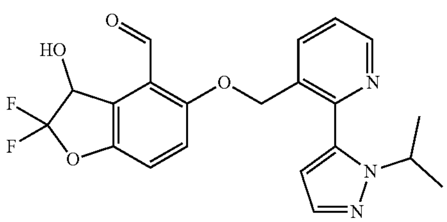 [SMILES: CC(C)n1nccc1-c1ncccc1COc1ccc2c(c1C=O)C(O)C(F)(F)O2] |
| 10 | 2,2-difluoro-3-hydroxy-5-((2-(1-isopropyl-1H-pyrazol-5-yl)pyridin-3-yl)methoxy)-2,3-dihydro-1H-indene-4-carbaldehyde | 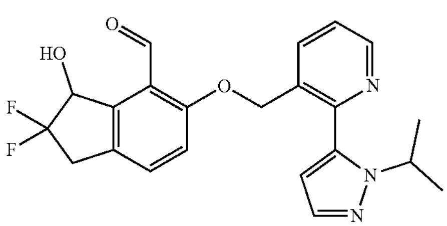 [SMILES: CC(C)n1nccc1-c1ncccc1COc1ccc2c(c1C=O)C(O)C(F)(F)C2] |
| 11 | 5-((2-(1-isopropyl-1H-pyrazol-5-yl)pyridin-3-yl)methoxy)benzo[d]isothiazole-4-carbaldehyde | 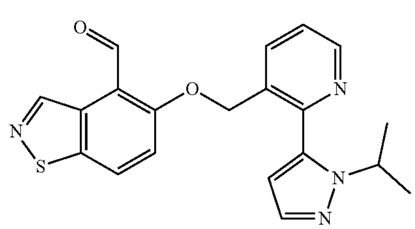 [SMILES: CC(C)n1nccc1-c1ncccc1COc1ccc2sncc2c1C=O] |
| 12 | 6-((2-(1-isopropyl-1H-pyrazol-5-yl)pyridin-3-yl)methoxy)benzo[d]thiazole-7-carbaldehyde | 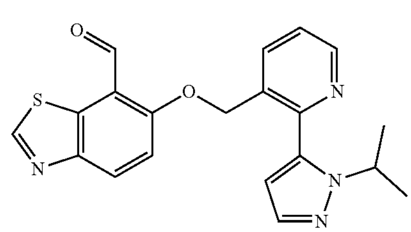 [SMILES: CC(C)n1nccc1-c1ncccc1COc1ccc2ncsc2c1C=O] |

-continued

| Ex. | Name | Structure |
|---|---|---|
| 13 | 7-((2-(1-isopropyl-1H-pyrazol-5-yl)pyridin-3-yl)methoxy)tetrazolo[1,5-a]pyridine-8-carbaldehyde | 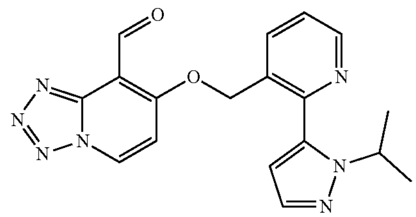 [SMILES: CC(C)n1nccc1-c1ncccc1COc1ccn2nnnc2c1C=O] |
| 14 | 5-((2-(1-isopropyl-1H-pyrazol-5-yl)pyridin-3-yl)methoxy)benzo[d]oxazole-4-carbaldehyde | 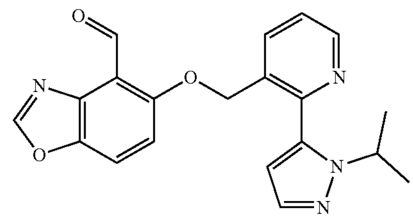 |
| 15 | 6-((2-(1-isopropyl-1H-pyrazol-5-yl)pyridin-3-yl)methoxy)benzo[d]oxazole-7-carbaldehyde | 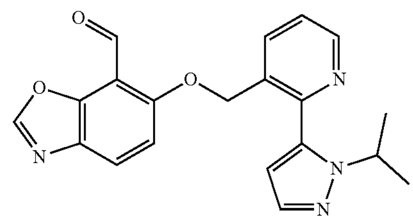 |
| 16 | 5-((2-(1-isopropyl-1H-pyrazol-5-yl)pyridin-3-yl)methoxy)benzo[d]thiazole-4-carbaldehyde | 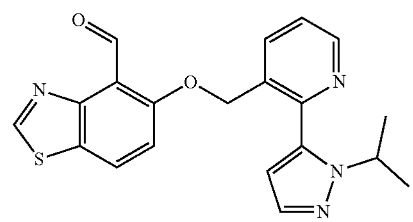 [SMILES: CC(C)n1nccc1-c1ncccc1COc1ccc2scnc2c1C=O] |
| 17 | 5-((2-(1-isopropyl-1H-pyrazol-5-yl)pyridin-3-yl)methoxy)benzo[d][1,2,3]thiadiazole-4-carbaldehyde | 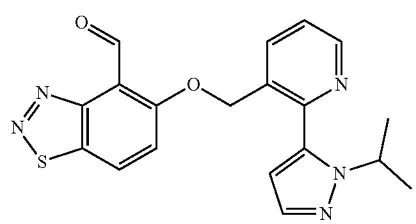 [SMILES: CC(C)n1nccc1-c1ncccc1COc1ccc2snnc2c1C=O] |
| 18 | 6-((2-(1-isopropyl-1H-pyrazol-5-yl)pyridin-3-yl)methoxy)benzo[d][1,2,3]thiadiazole-7-carbaldehyde | 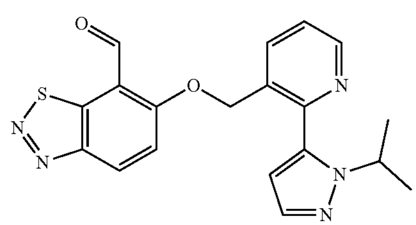 [SMILES: CC(C)n1nccc1-c1ncccc1COc1ccc2nnsc2c1C=O] |
| 19 | 6-((2-(1-isopropyl-1H-pyrazol-5-yl)pyridin-3-yl)methoxy)quinazoline-5-carbaldehyde | 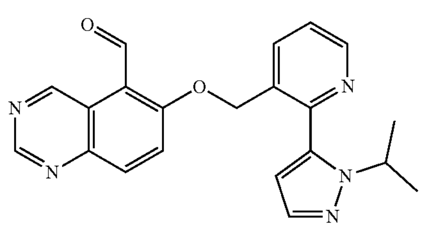 [SMILES: CC(C)n1nccc1-c1ncccc1COc1ccc2ncncc2c1C=O] |

-continued

| Ex. | Name | Structure |
|---|---|---|
| 20 | 5-((2-(1-isopropyl-1H-pyrazol-5-yl)pyridin-3-yl)methoxy)benzo[b]thiophene-4-carbaldehyde | 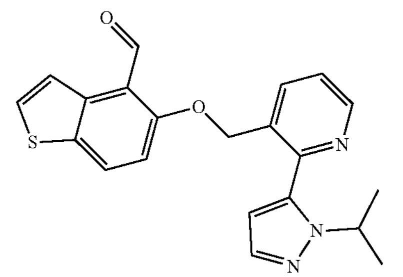 [SMILES: CC(C)n1nccc1-c1ncccc1COc1ccc2sccc2c1C=O] |
| 21 | 5-((2-(1-isopropyl-1H-pyrazol-5-yl)pyridin-3-yl)methoxy)-2,3-dihydrobenzo[b]thiophene-4-carbaldehyde 1,1-dioxide | 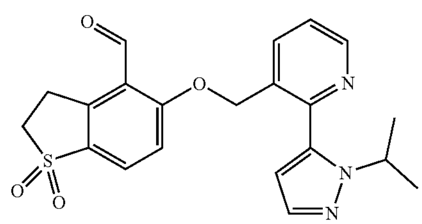 [SMILES: CC(C)n1nccc1-c1ncccc1COc1ccc2c(c1C=O)CCS2(=O)=O] |
| 22 | 6-((2-(4-fluoro-1-isopropyl-1H-pyrazol-5-yl)pyridin-3-yl)methoxy)benzo[d]oxazole-7-carbaldehyde | 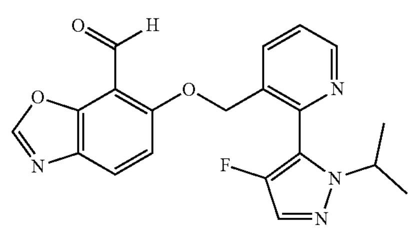 [SMILES: CC(C)n1ncc(F)c1-c1ncccc1COc1ccc2ncoc2c1C=O] |
| 23 | 2-hydroxy-6-(((2-(1-isopropyl-1H-pyrazol-5-yl)pyridin-3-yl)methyl)thio)benzaldehyde | 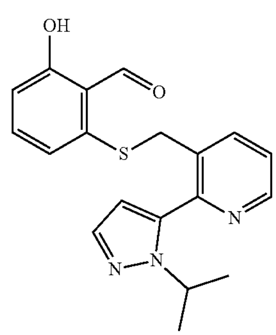 [SMILES: CC(C)n1nccc1-c1ncccc1CSc1cccc(O)c1C=O] |
| 24 | | 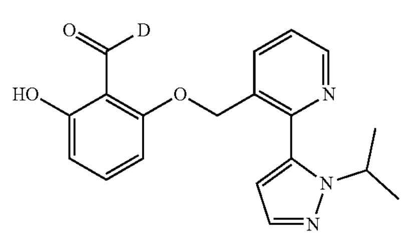 [SMILES: [2H]C(=O)c1c(O)cccc1OCc1cccnc1-c1ccnn1C(C)C] |
| 25 | 2-((2-(4-fluoro-1-isopropyl-1H-pyrazol-5-yl)pyridin-3-yl)methoxy-d2)-6-hydroxybenzaldehyde | 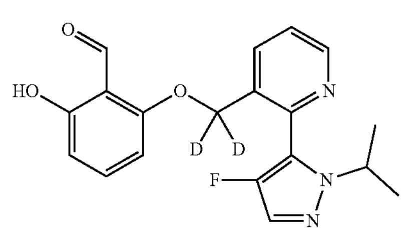 [SMILES: [2H]C([2H])(Oc1cccc(O)c1C=O)c1cccnc1-c1c(F)cnn1C(C)C] |

| Ex. | Name |
|---|---|
| 26 | 4-fluoro-2-((2-(4-fluoro-1-isopropyl-1H-pyrazol-5-yl)pyridin-3-yl)methoxy-d2)-6-hydroxybenzaldehyde |
| 27b | 4-fluoro-2-hydroxy-6-((2-(1-isopropyl-1H-pyrazol-5-yl)pyridin-3-yl)methoxy-d2)benzaldehyde |
| 27 | 4-fluoro-2-hydroxy-6-((2-(1-isopropyl-1H-pyrazol-5-yl)pyridin-3-yl)methoxy-d2)benzaldehyde hydrochloric acid |
| 28 | 6-((2-(1-isopropyl-1H-pyrazol-5-yl)pyridin-3-yl)methoxy-d2)benzo[d]oxazole-7-carbaldehyde |
| 29e | 2-hydroxy-6-((2-(2-isopropyl-1H-imidazol-1-yl)pyridin-3-yl)methoxy-d2)benzaldehyde |
| 29 | 2-hydroxy-6-((2-(2-isopropyl-1H-imidazol-1-yl)pyridin-3-yl)methoxy-d2)benzaldehyde hydrochloric acid |

| Ex. | Name | Structure |
|---|---|---|
| 30 | 2-hydroxy-6-((2-(1-(propan-2-yl-1,1,1,3,3,3-d6)-1H-pyrazol-5-yl)pyridin-3-yl)methoxy)benzaldehyde | 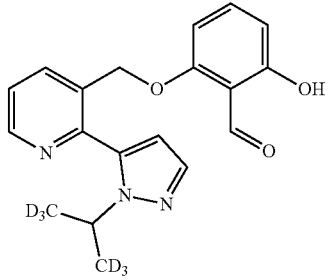 [SMILES: [2H]C([2H])([2H])C(n1nccc1-c1ncccc1COc1cccc(O)c1C=O)C([2H])([2H])[2H]] |
| 31 | 4-fluoro-2-hydroxy-6-((2-(1-(propan-2-yl-1,1,1,3,3,3-d6)-1H-pyrazol-5-yl)pyridin-3-yl)methoxy)benzaldehyde | 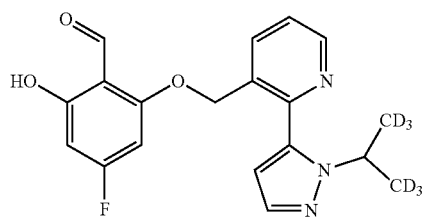 [SMILES: [2H]C([2H])([2H])C(n1nccc1-c1ncccc1COc1cc(F)cc(O)c1C=O)C([2H])([2H])[2H]] |
| 32 | 2-((2-(4-fluoro-1-(propan-2-yl-1,1,1,3,3,3-d6)-1H-pyrazol-5-yl)pyridin-3-yl)methoxy)-6-hydroxybenzaldehyde | 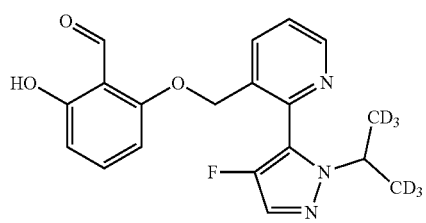 [SMILES: [2H]C([2H])([2H])C(n1ncc(F)c1-c1ncccc1COc1cccc(O)c1C=O)C([2H])([2H])[2H]] |
| 33 | 6-((2-(1-(propan-2-yl-1,1,1,3,3,3-d6)-1H-pyrazol-5-yl)pyridin-3-yl)methoxy)benzo[d]oxazole-7-carbaldehyde | 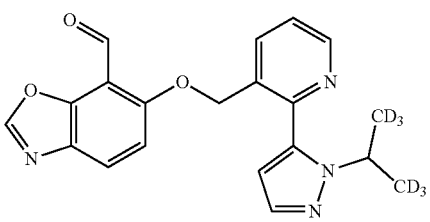 [SMILES: [2H]C([2H])([2H])C(n1nccc1-c1ncccc1COc1ccc2ncoc2c1C=O)C([2H])([2H])[2H]] |
| 34 | 4-fluoro-2-((4-(4-fluoro-1-(propan-2-yl-1,1,1,3,3,3-d6)-1H-pyrazol-5-yl)pyrimidin-5-yl)methoxy)-6-hydroxybenzaldehyde | 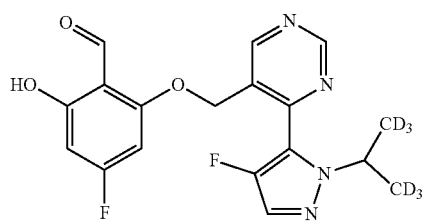 [SMILES: [2H]C([2H])([2H])C(n1ncc(F)c1-c1ncncc1COc1cc(F)cc(O)c1C=O)C([2H])([2H])[2H]] |
| 35 | 2-((4-(4-fluoro-1-(propan-2-yl-1,1,1,3,3,3-d6)-1H-pyrazol-5-yl)pyrimidin-5-yl)methoxy)-6-hydroxybenzaldehyde | 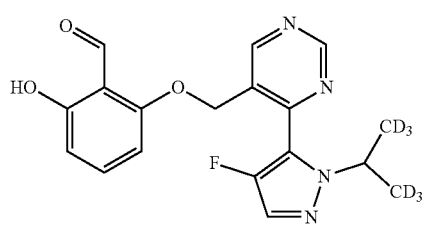 [SMILES: [2H]C([2H])([2H])C(n1ncc(F)c1-c1ncncc1COc1cccc(O)c1C=O)C([2H])([2H])[2H]] |

-continued

| Ex. | Name | Structure |
|---|---|---|
| 36 | 4-fluoro-2-hydroxy-6-((4-(1-(propan-2-yl-1,1,1,3,3,3-d6)-1H-pyrazol-5-yl)pyrimidin-5-yl)methoxy)benzaldehyde | 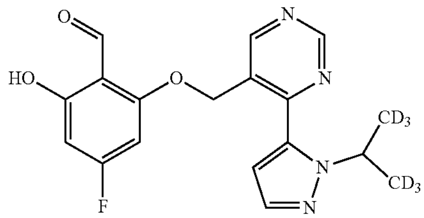 [SMILES: [2H]C([2H])([2H])C(n1nccc1-c1ncncc1COc1cc(F)cc(O)c1C=O)C([2H])([2H])[2H]] |
| 37 | 2-hydroxy-6-((4-(1-(propan-2-yl-1,1,1,3,3,3-d6)-1H-pyrazol-5-yl)pyrimidin-5-yl)methoxy)benzaldehyde | 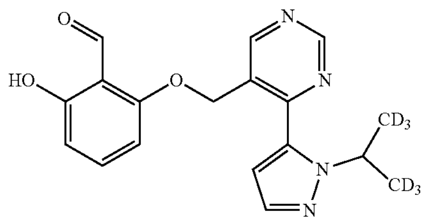 [SMILES: [2H]C([2H])([2H])C(n1nccc1-c1ncncc1COc1cccc(O)c1C=O)C([2H])([2H])[2H]] |
| 38 | 2-hydroxy-6-((4-(1-isopropyl-1H-pyrazol-5-yl)pyrimidin-5-yl)methoxy-d2)benzaldehyde | 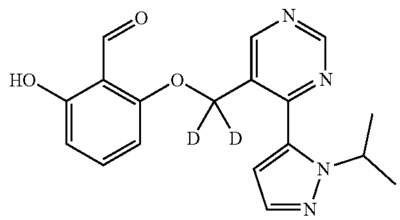 [SMILES: [2H]C([2H])(Oc1cccc(O)c1C=O)c1cncnc1-c1ccnn1C(C)C] |
| 39 | 4-fluoro-2-hydroxy-6-((4-(1-isopropyl-1H-pyrazol-5-yl)pyrimidin-5-yl)methoxy-d2)benzaldehyde | 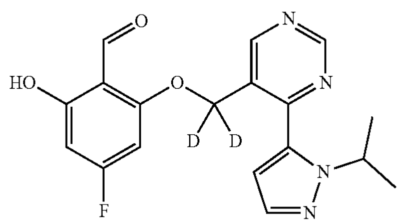 [SMILES: [2H]C([2H])(Oc1cc(F)cc(O)c1C=O)c1cncnc1-c1ccnn1C(C)C] |
| 40 | 3-fluoro-2-hydroxy-6-((4-(1-isopropyl-1H-pyrazol-5-yl)pyrimidin-5-yl)methoxy-d2)benzaldehyde | 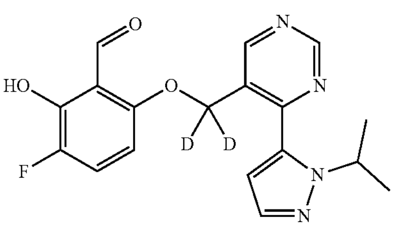 [SMILES: [2H]C([2H])(Oc1ccc(F)c(O)c1C=O)c1cncnc1-c1ccnn1C(C)C] |
| 41 | 2-((4-(4-fluoro-1-isopropyl-1H-pyrazol-5-yl)pyrimidin-5-yl)methoxy-d2)-6-hydroxybenzaldehyde | 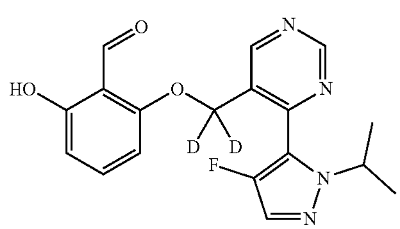 [SMILES: [2H]C([2H])(Oc1cccc(O)c1C=O)c1cncnc1-c1c(F)cnn1C(C)C] |
| 42 | 2-hydroxy-6-((4-(2-isopropyl-1H-imidazol-1-yl)pyrimidin-5-yl)methoxy-d2)benzaldehyde | 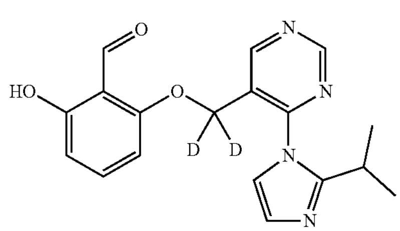 [SMILES: [2H]C([2H])(Oc1cccc(O)c1C=O)c1cncnc1-n1ccnc1C(C)C] |

-continued

| Ex. | Name | Structure |
|-----|------|-----------|
| 43 | 6-((4-(2-isopropyl-1H-imidazol-1-yl)pyrimidin-5-yl)methoxy-d2)benzo[d]oxazole-7-carbaldehyde | 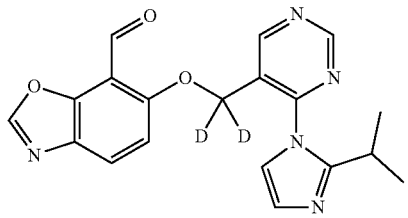 [SMILES: [2H]C([2H])(Oc1ccc2ncoc2c1C=O)c1cncnc1-n1ccnc1C(C)C] |
| 44 | 4-fluoro-2-hydroxy-6-((4-(2-isopropyl-1H-imidazol-1-yl)pyrimidin-5-yl)methoxy-d2)benzaldehyde | 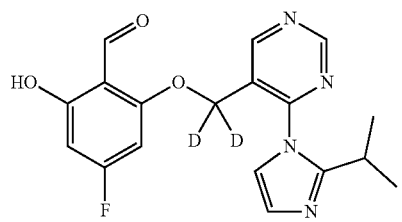 [SMILES: [2H]C([2H])(Oc1cc(F)cc(O)c1C=O)c1cncnc1-n1ccnc1C(C)C] |
| 45 | 2-((2-(2-cyclopropyl-1H-imidazol-1-yl)pyridin-3-yl)methoxy-d2)-6-hydroxybenzaldehyde | 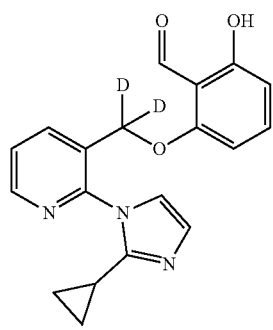 [SMILES: [2H]C([2H])(Oc1cccc(O)c1C=O)c1cccnc1-n1ccnc1C1CC1] |
| 46 | 2-hydroxy-6-((3-(1-isopropyl-1H-pyrazol-5-yl)pyridin-2-yl)methoxy-d2)benzaldehyde | 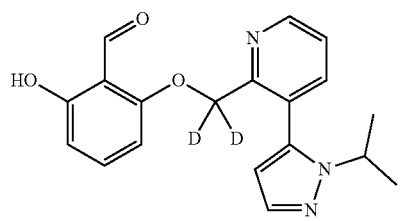 [SMILES: [2H]C([2H])(Oc1cccc(O)c1C=O)c1ncccc1-c1ccnn1C(C)C] |
| 47 | 4-fluoro-2-hydroxy-6-((3-(1-isopropyl-1H-pyrazol-5-yl)pyridin-2-yl)methoxy-d2)benzaldehyde | 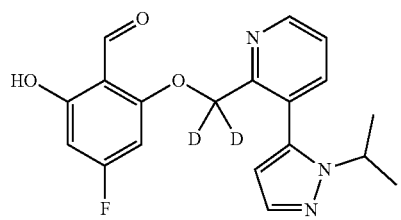 [SMILES: [2H]C([2H])(Oc1cc(F)cc(O)c1C=O)c1ncccc1-c1ccnn1C(C)C] |
| 48 | 2-hydroxy-6-((2-(1-(propan-2-yl-2-d)-1H-pyrazol-5-yl)pyridin-3-yl)methoxy)benzaldehyde | 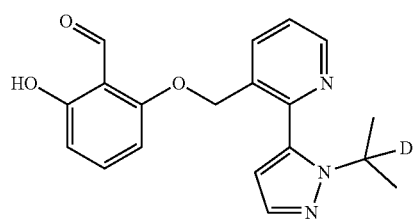 [SMILES: [2H]C(C)(C)n1nccc1-c1ncccc1COc1cccc(O)c1C=O] |

-continued

| Ex. | Name | Structure |
|---|---|---|
| 49 | 2-hydroxy-6-((6-methyl-2-(1-(propan-2-yl-2-d)-1H-pyrazol-5-yl)pyridin-3-yl)methoxy)benzaldehyde | 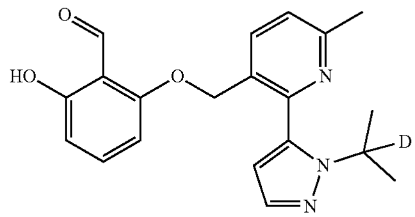 [SMILES: [2H]C(C)(C)n1nccc1-c1nc(C)ccc1COc1cccc(O)c1C=O] |
| 50 | 2-hydroxy-6-((4-(1-(propan-2-yl-2-d)-1H-pyrazol-5-yl)pyrimidin-5-yl)methoxy)benzaldehyde | 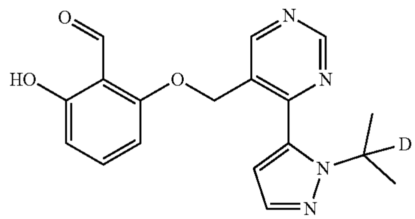 [SMILES: [2H]C(C)(C)n1nccc1-c1ncncc1COc1cccc(O)c1C=O] |
| 51 | 2-hydroxy-6-((3-(1-(propan-2-yl-2-d)-1H-pyrazol-5-yl)pyrazin-2-yl)methoxy)benzaldehyde | 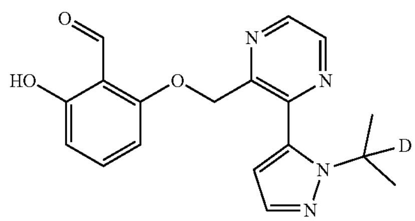 [SMILES: [2H]C(C)(C)n1nccc1-c1nccnc1COc1cccc(O)c1C=O] |
| 53 | 6-((4-(1-isopropyl-1H-pyrazol-5-yl)pyrimidin-5-yl)methoxy)benzo[d]thiazole-7-carbaldehyde | 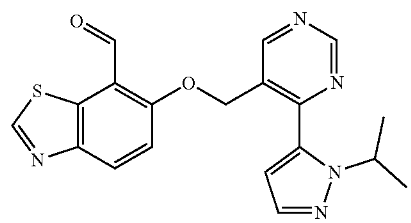 [SMILES: CC(C)n1nccc1-c1ncncc1COc1ccc2ncsc2c1C=O] |
| 54 | 6-((4-(1-isopropyl-1H-pyrazol-5-yl)pyrimidin-5-yl)methoxy)benzo[d]oxazole-7-carbaldehyde | 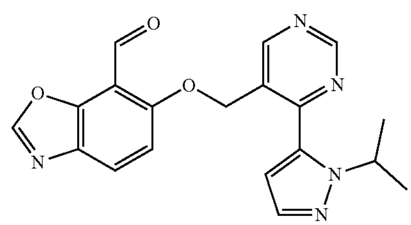 [SMILES: CC(C)n1nccc1-c1ncncc1COc1ccc2ncoc2c1C=O] |
| 55 | 7-((4-(1-isopropyl-1H-pyrazol-5-yl)pyrimidin-5-yl)methoxy)quinoline-8-carbaldehyde | 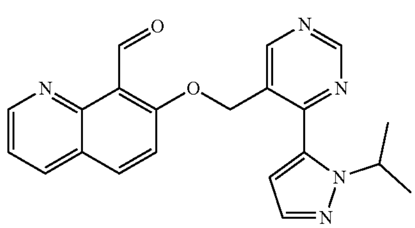 [SMILES: CC(C)n1nccc1-c1ncncc1COc1ccc2cccnc2c1C=O] |
| 56 | 7-((4-(1-isopropyl-1H-pyrazol-5-yl)pyrimidin-5-yl)methoxy)quinoline-8-carbaldehyde | 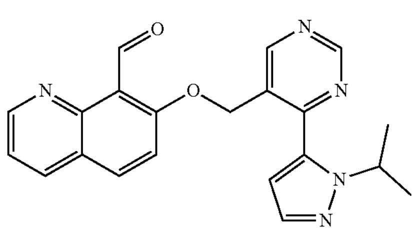 [SMILES: CC(C)n1nccc1-c1ncncc1COc1ccc2cccnc2c1C=O] |

-continued

| Ex. | Name | Structure |
|---|---|---|
| 57 | 2-((4-(4-fluoro-1-isopropyl-1H-pyrazol-5-yl)pyrimidin-5-yl)methoxy)-6-hydroxybenzaldehyde | 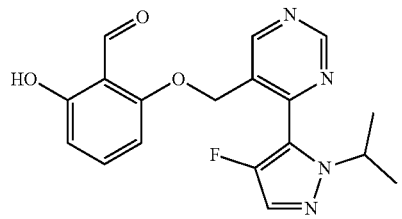 [SMILES: CC(C)n1ncc(F)c1-c1ncncc1COc1cccc(O)c1C=O] |
| 58 | 6-((3-(1-isopropyl-1H-pyrazol-5-yl)pyridin-2-yl)methoxy)benzo[d]oxazole-7-carbaldehyde | 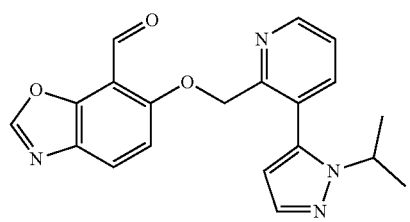 [SMILES: CC(C)n1nccc1-c1cccnc1COc1ccc2ncoc2c1C=O] |
| 59 | 2-hydroxy-6-((3-(1-isopropyl-1H-pyrazol-5-yl)-1-methyl-6-oxo-1,6-dihydropyridazin-4-yl)methoxy)benzaldehyde | 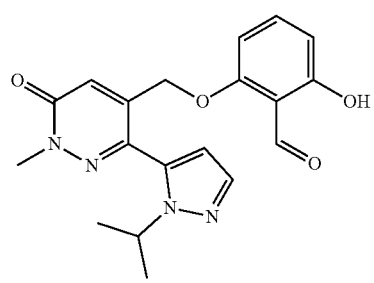 [SMILES: CC(C)n1nccc1-c1nn(C)c(=O)cc1COc1cccc(O)c1C=O] |
| 60 | 2-hydroxy-6-((5-(1-isopropyl-1H-pyrazol-5-yl)-1-methyl-2-oxo-1,2-dihydropyridin-4-yl)methoxy)benzaldehyde | 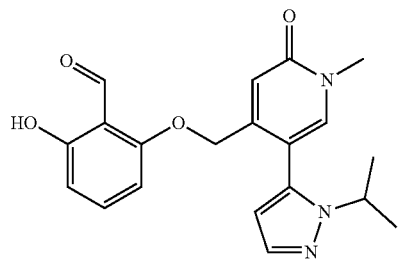 [SMILES: CC(C)n1nccc1-c1cn(C)c(=O)cc1COc1cccc(O)c1C=O] |
| 61g | 2-hydroxy-6-((4-(1-isopropyl-1H-pyrazol-5-yl)-2,3-dihydrofuro[3,2-c]pyridin-3-yl)oxy)benzaldehyde | 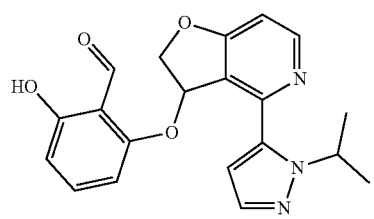 [SMILES: CC(C)n1nccc1-c1nccc2c1C(Oc1cccc(O)c1C=O)CO2] |
| 61h | 6-hydroxy-2-(4-hydroxy-2-(1-isopropyl-1H-pyrazol-5-yl)pyridin-3-yl)-2,3-dihydrobenzofuran-7-carbaldehyde | 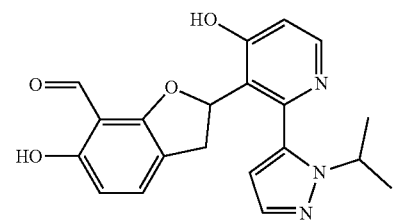 [SMILES: CC(C)n1nccc1-c1nccc(O)c1C1Cc2ccc(O)c(C=O)c2O1] |

| Ex. | Name | Structure |
|---|---|---|
| 62a | (R)-2-hydroxy-6-((4-(1-isopropyl-1H-pyrazol-5-yl)-2,3-dihydrofuro[3,2-c]pyridin-3-yl)oxy)benzaldehyde | 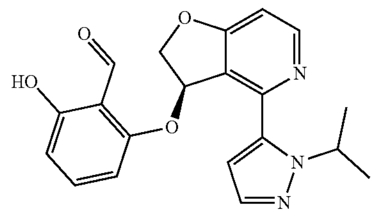 [SMILES: CC(C)n1nccc1-c1nccc2c1[C@@H](Oc1cccc(O)c1C=O)CO2] |
| 62b | (S)-2-hydroxy-6-((4-(1-isopropyl-1H-pyrazol-5-yl)-2,3-dihydrofuro[3,2-c]pyridin-3-yl)oxy)benzaldehyde | 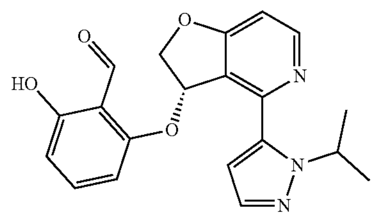 [SMILES: CC(C)n1nccc1-c1nccc2c1[C@H](Oc1cccc(O)c1C=O)CO2] |
| 63 | 2-hydroxy-6-((5-(1-isopropyl-1H-pyrazol-5-yl)-1-methyl-1H-imidazol-4-yl)methoxy)benzaldehyde | 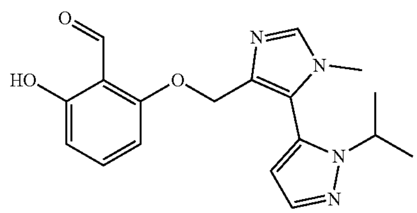 [SMILES: CC(C)n1nccc1-c1c(COc2cccc(O)c2C=O)ncn1C] |
| 64 | 2-hydroxy-6-((5-(1-isopropyl-1H-pyrazol-5-yl)thiazol-4-yl)methoxy)benzaldehyde | 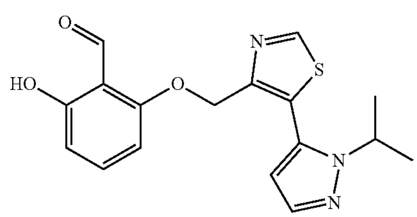 [SMILES: CC(C)n1nccc1-c1scnc1COc1cccc(O)c1C=O] |
| 65 | 2-hydroxy-6-((4-(1-isopropyl-1H-pyrazol-5-yl)thiazol-5-yl)methoxy)benzaldehyde | 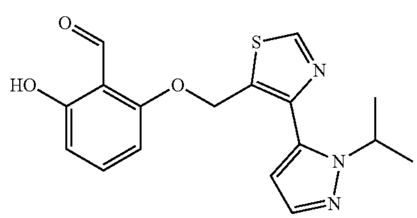 [SMILES: CC(C)n1nccc1-c1ncsc1COc1cccc(O)c1C=O] |
| 66 | 2-hydroxy-6-((5-(1-isopropyl-1H-pyrazol-5-yl)oxazol-4-yl)methoxy)benzaldehyde | 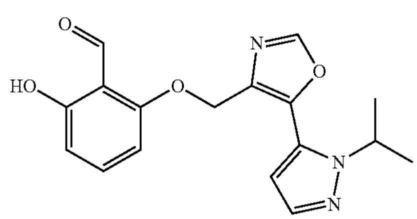 [SMILES: CC(C)n1nccc1-c1ocnc1COc1cccc(O)c1C=O] |
| 67 | 2-hydroxy-6-((4-(1-isopropyl-1H-pyrazol-5-yl)oxazol-5-yl)methoxy)benzaldehyde | 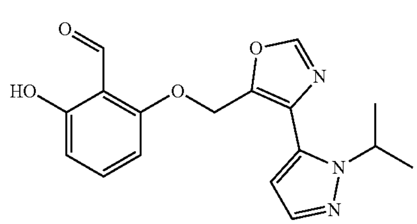 [SMILES: CC(C)n1nccc1-c1ncoc1COc1cccc(O)c1C=O] |

| Ex. | Name | Structure |
|---|---|---|
| 68 | 2-hydroxy-6-((5-(1-isopropyl-1H-pyrazol-5-yl)-2-methyloxazol-4-yl)methoxy)benzaldehyde | 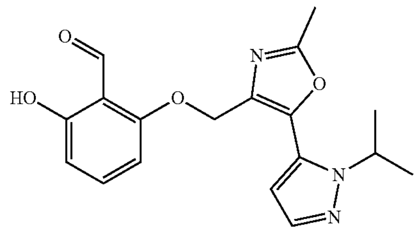 [SMILES: Cc1nc(COc2cccc(O)c2C=O)c(-c2ccnn2C(C)C)o1] |
| 69 | 2-hydroxy-6-((4-(1-isopropyl-1H-pyrazol-5-yl)-1-methyl-1H-imidazol-5-yl)methoxy)benzaldehyde | 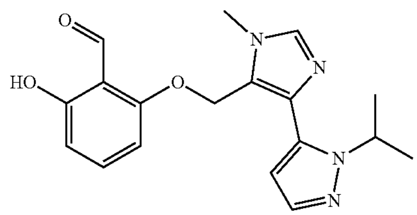 [SMILES: CC(C)n1nccc1-c1ncn(C)c1COc1cccc(O)c1C=O] |
| 70 | 2-hydroxy-6-((4-(1-isopropyl-1H-pyrazol-5-yl)-2-methylthiazol-5-yl)methoxy)benzaldehyde | 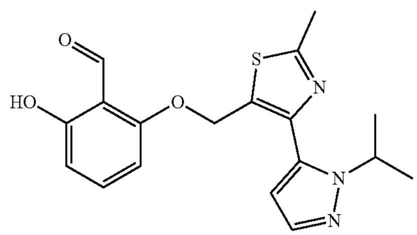 [SMILES: Cc1nc(-c2ccnn2C(C)C)c(COc2cccc(O)c2C=O)s1] |
| 71 | 2-((4-(5-fluoro-2-isopropyl-1H-imidazol-1-yl)pyrimidin-5-yl)methoxy-d2)-6-hydroxybenzaldehyde | 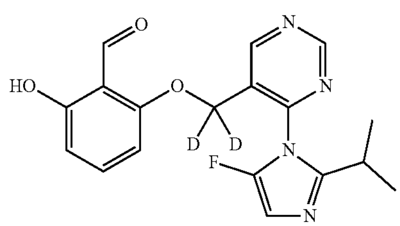 [SMILES: [2H]C([2H])(Oc1cccc(O)c1C=O)c1cncnc1-n1c(F)cnc1C(C)C] |
| 72 | 2-hydroxy-6-((3-(2-isopropyl-1H-imidazol-1-yl)pyrazin-2-yl)methoxy-d2)benzaldehyde | 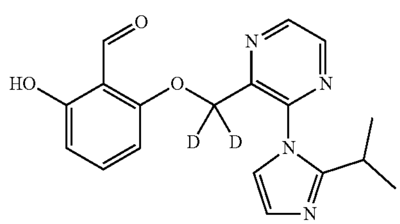 [SMILES: [2H]C([2H])(Oc1cccc(O)c1C=O)c1nccnc1-n1ccnc1C(C)C] |
| 73 | 2-formyl-3-((4-(1-isopropyl-1H-pyrazol-5-yl)pyrimidin-5-yl)methoxy-d2)phenyl dihydrogen phosphate | 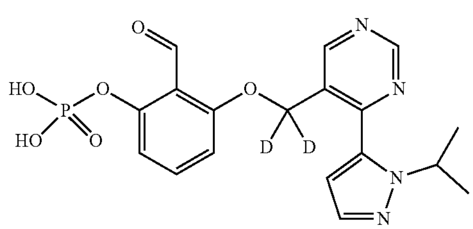 [SMILES: [2H]C([2H])(Oc1cccc(OP(=O)(O)O)c1C=O)c1cncnc1-c1ccnn1C(C)C] |
| 74 | 2-((4-fluoro-2-(1-isopropyl-1H-pyrazol-5-yl)pyridin-3-yl)methoxy)-6-hydroxybenzaldehyde | 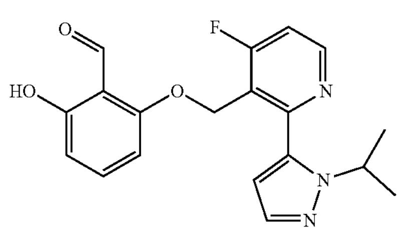 [SMILES: CC(C)n1nccc1-c1nccc(F)c1COc1cccc(O)c1C=O] |

| Ex. | Name | Structure |
|---|---|---|
| 75 | 2-((4-fluoro-2-(1-isopropyl-1H-pyrazol-5-yl)pyridin-3-yl)methoxy-d2)-6-hydroxybenzaldehyde | 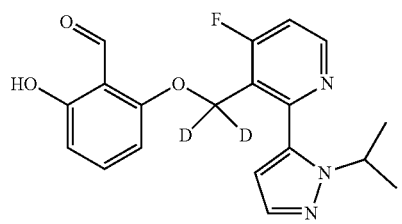 [SMILES: [2H]C([2H])(Oc1cccc(O)c1C=O)c1c(F)ccnc1-c1ccnn1C(C)C] |
In some embodiments, the compound of the present disclosure, or the pharmaceutically acceptable salt thereof, is selected from:
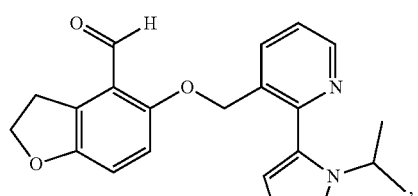,
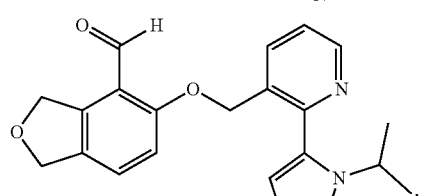,
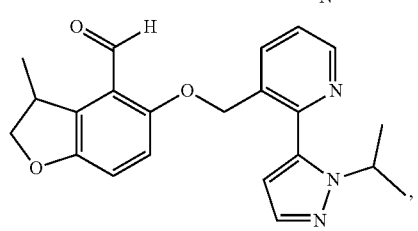,
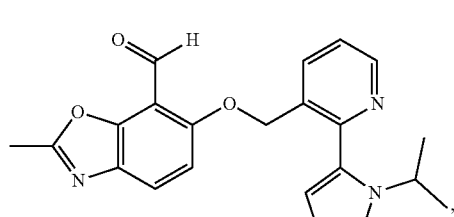,
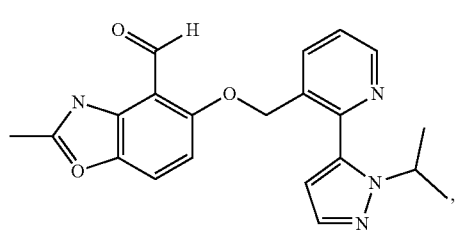,
-continued
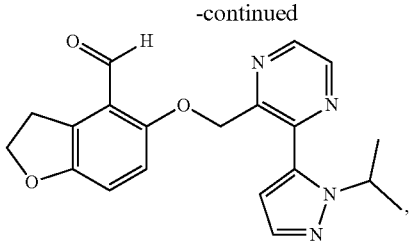,
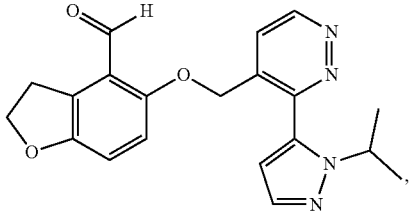,
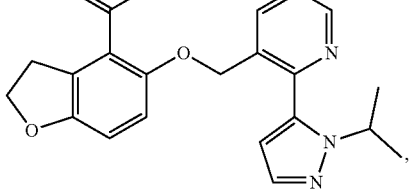,
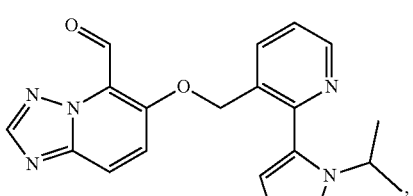,
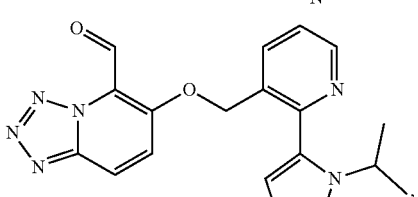,
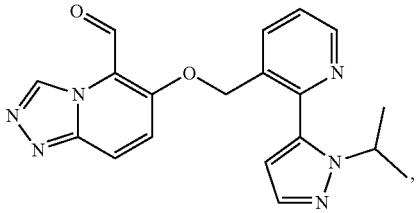, 87
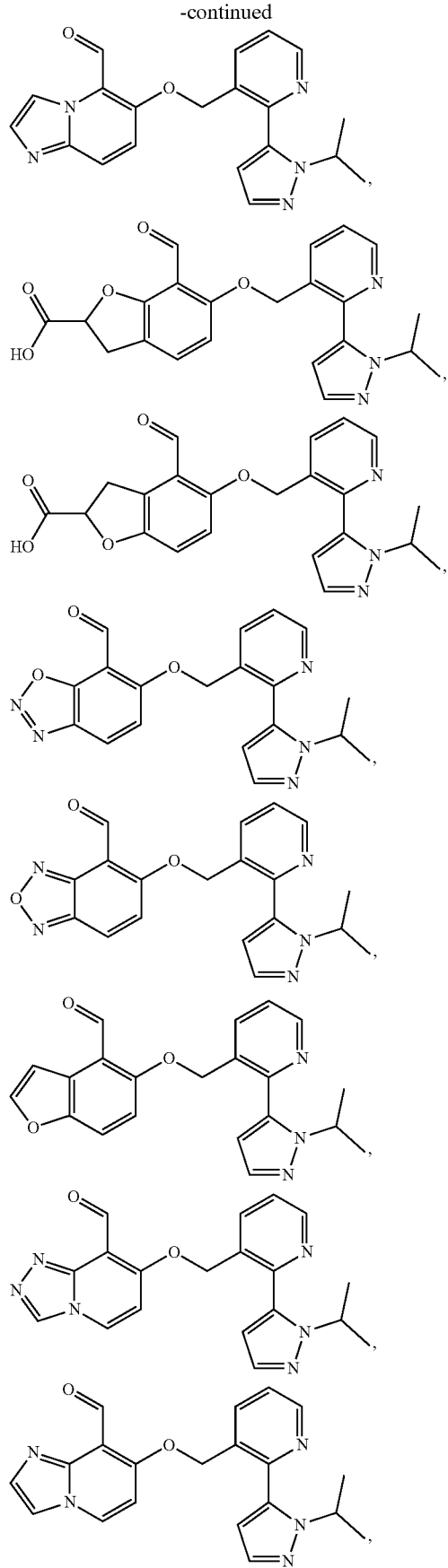
88
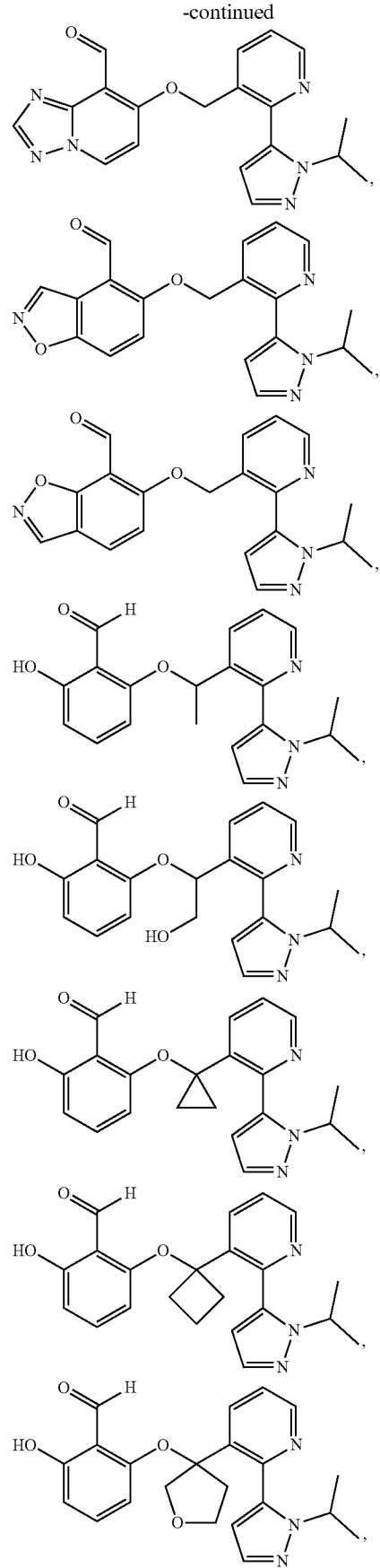

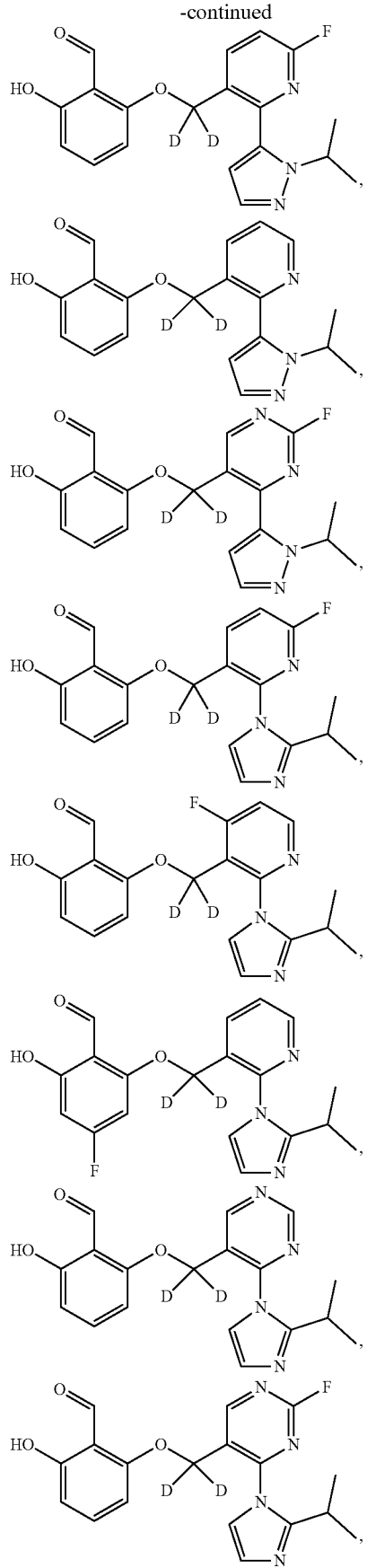
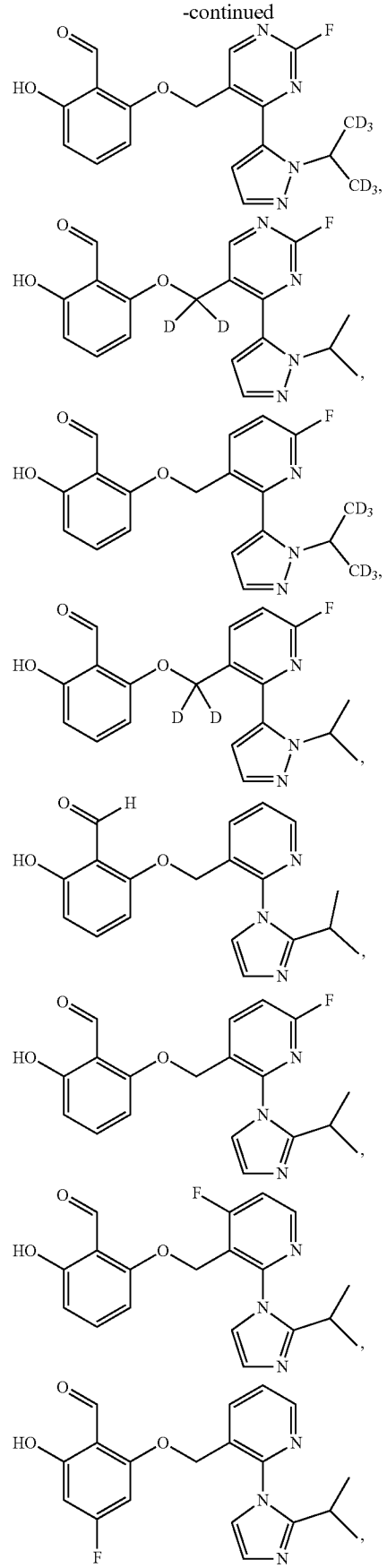

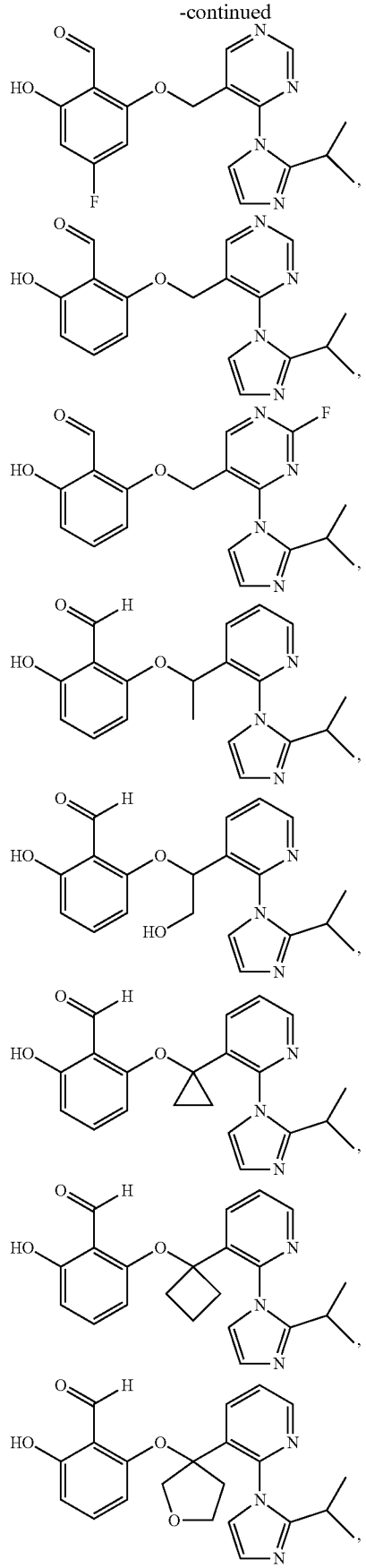
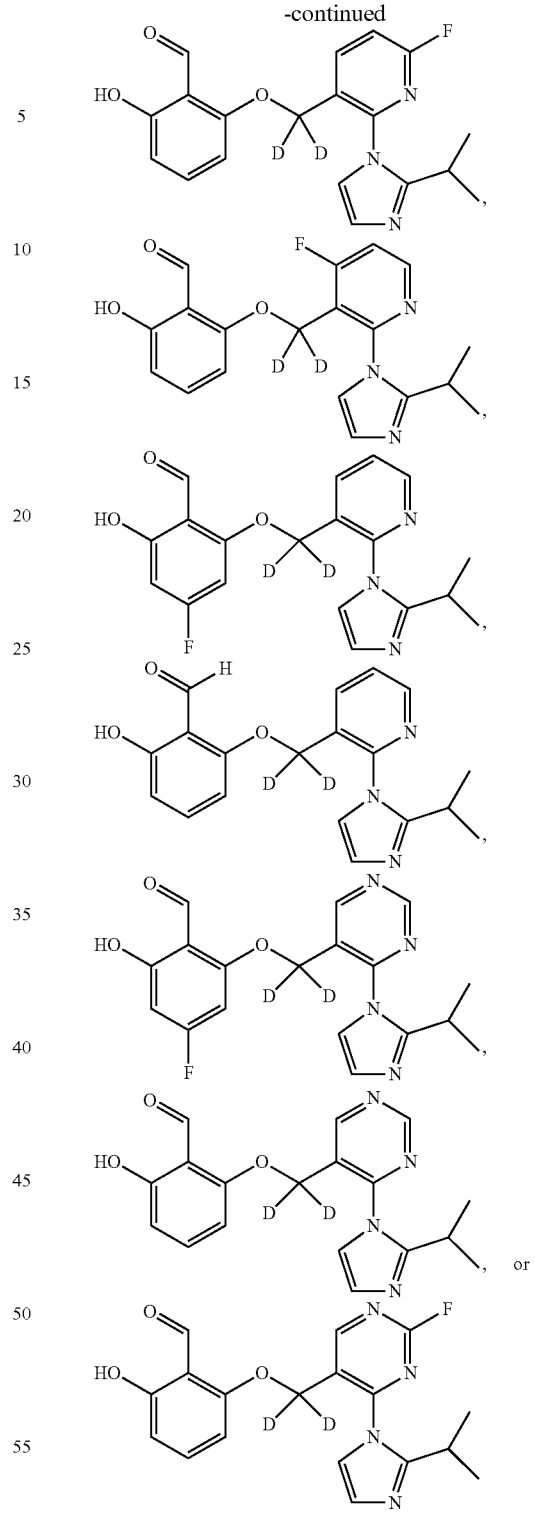

Further Forms of Compounds

In one aspect, compounds described herein possess one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In some embodiments, the active entity is a phenolic compound as described herein. A further example of a prodrug might be a short peptide (polyaminoacids) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like.

Prodrug forms of the herein described compounds, wherein the prodrug is metabolized in vivo to produce a compound of Formula (I), (II), (II'), (III), (IV), (V), (VI), or (VII), as set forth herein are included within the scope of the claims. In some cases, some of the herein-described compounds may be a prodrug for another derivative or active compound.

In some embodiments, sites on the aromatic ring portion of compounds described herein are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2$H, $^3$H, $^{13}$C, $^{14}$C, $^{15}$N, $^{18}$O, $^{17}$O, $^{35}$S, $^{8}$F, $^{36}$Cl. In one aspect, isotopically-labeled compounds described herein, for example those into which radioactive isotopes such as $^3$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms that are present in the compounds described herein is replaced with one or more deuterium atoms.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein with acids. Pharmaceutically acceptable salts are also obtained by reacting a compound described herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a maleic acid salt, a fumaric acid salt, a trifluoroacetic acid salt, a tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

Synthesis of Compounds

Compounds described herein are synthesized using standard synthetic techniques or using methods known in the art in combination with methods described herein. In additions, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999). General methods for the preparation of compounds can be modified by the use of appropriate reagents and conditions for the introduction of the various moieties found in the formulae as provided herein.

In some embodiments, the compounds described herein are prepared as outlined in the following Schemes.

In some embodiments, a compound, such as 1-1, is prepared according to the route as shown in Scheme 1.

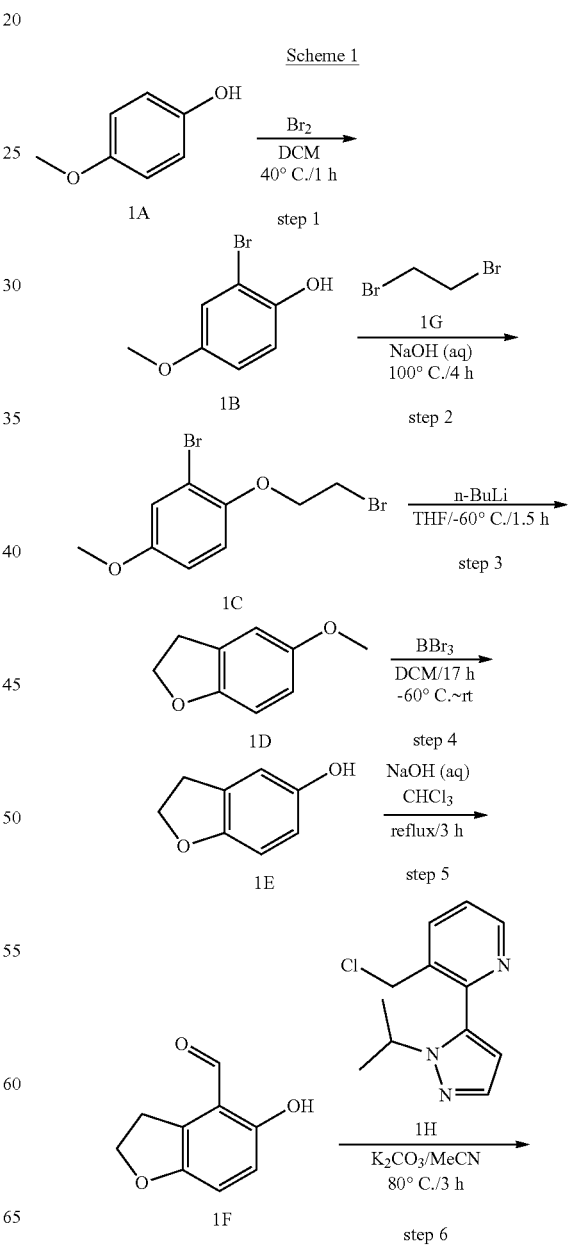

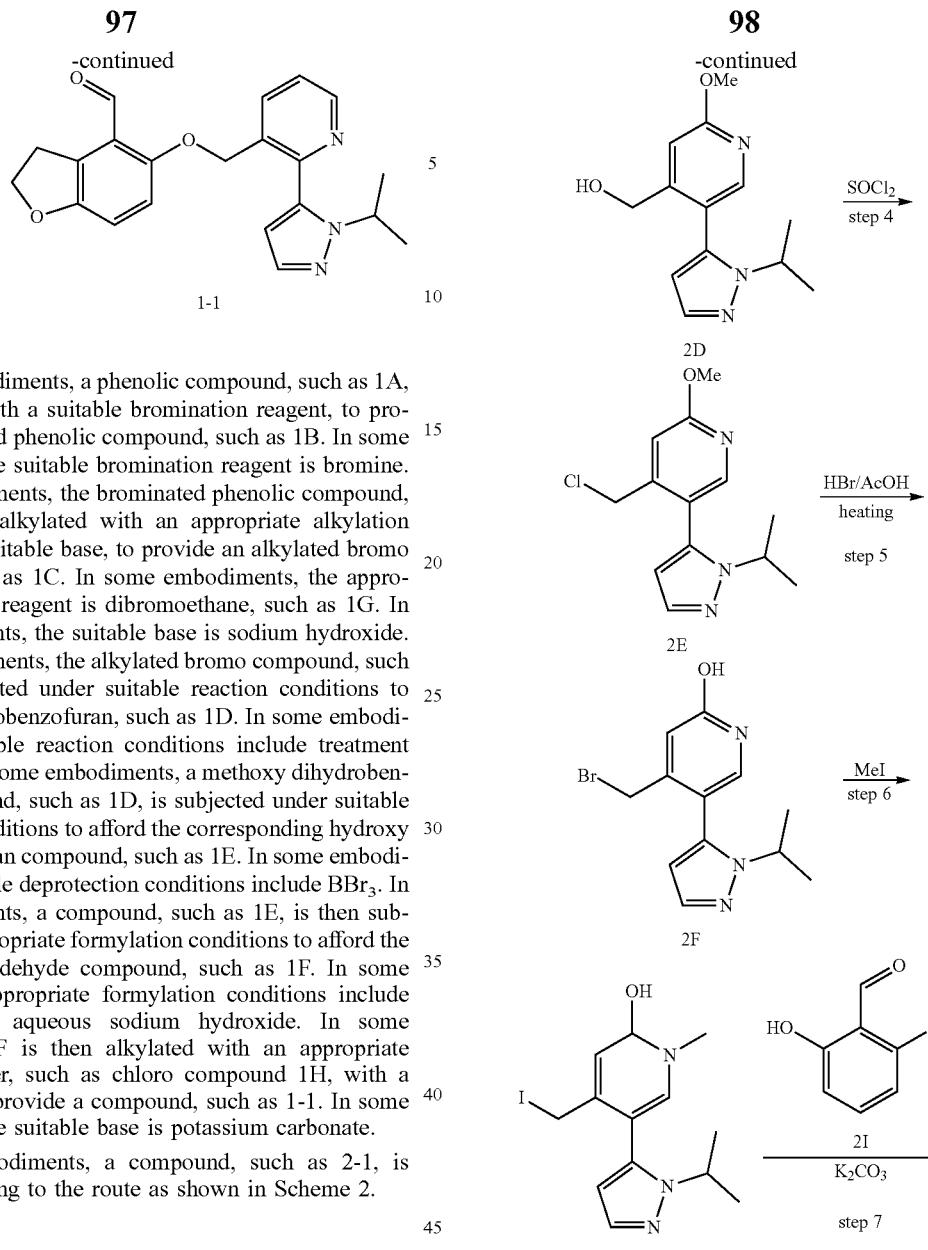

In some embodiments, a phenolic compound, such as 1A, is brominated with a suitable bromination reagent, to provide a brominated phenolic compound, such as 1B. In some embodiments, the suitable bromination reagent is bromine. In some embodiments, the brominated phenolic compound, such as 1B, is alkylated with an appropriate alkylation reagent with a suitable base, to provide an alkylated bromo compound, such as 1C. In some embodiments, the appropriate alkylation reagent is dibromoethane, such as 1G. In some embodiments, the suitable base is sodium hydroxide. In some embodiments, the alkylated bromo compound, such as 1C, is subjected under suitable reaction conditions to provide a dihydrobenzofuran, such as 1D. In some embodiments, the suitable reaction conditions include treatment with n-BuLi. In some embodiments, a methoxy dihydrobenzofuran compound, such as 1D, is subjected under suitable deprotection conditions to afford the corresponding hydroxy dihydrobenzofuran compound, such as 1E. In some embodiments, the suitable deprotection conditions include BBr$_3$. In some embodiments, a compound, such as 1E, is then subjected under appropriate formylation conditions to afford the corresponding aldehyde compound, such as 1F. In some embodiments, appropriate formylation conditions include chloroform and aqueous sodium hydroxide. In some embodiments, 1F is then alkylated with an appropriate alkylation partner, such as chloro compound 1H, with a suitable base to provide a compound, such as 1-1. In some embodiments, the suitable base is potassium carbonate.

In some embodiments, a compound, such as 2-1, is prepared according to the route as shown in Scheme 2.

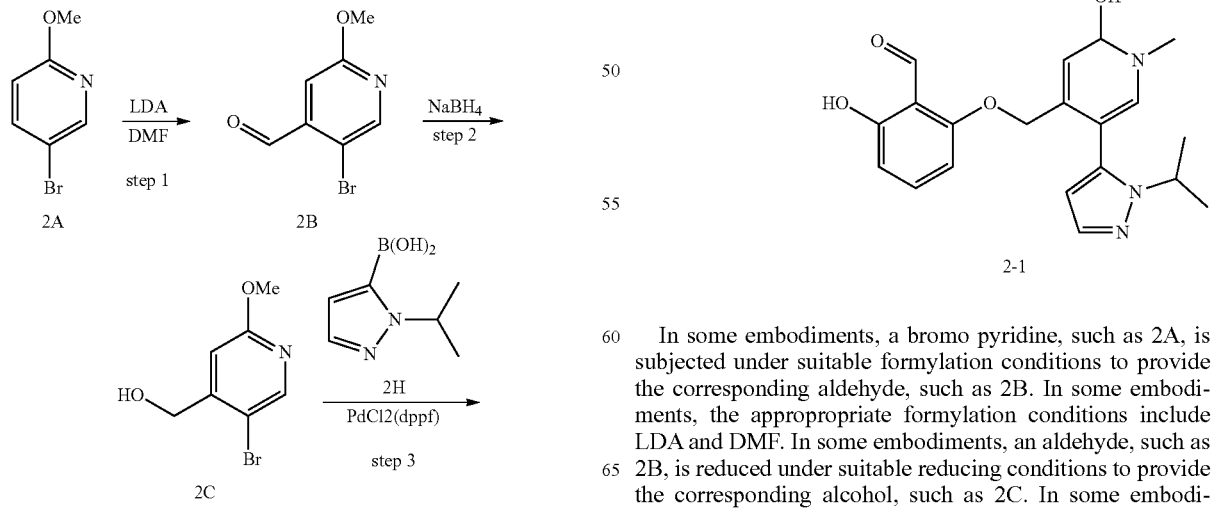

In some embodiments, a bromo pyridine, such as 2A, is subjected under suitable formylation conditions to provide the corresponding aldehyde, such as 2B. In some embodiments, the appropriate formylation conditions include LDA and DMF. In some embodiments, an aldehyde, such as 2B, is reduced under suitable reducing conditions to provide the corresponding alcohol, such as 2C. In some embodiments, the suitable reducing conditions include NaBH$_4$. In some embodiments, bromo pyridine, such as 2C, is then subjected under suitable palladium cross-coupling conditions with a suitable coupling partner, such as the boronic acid 2H to provide the corresponding coupled product, such as 2D. In some embodiments, suitable palladium-catalyzed cross coupling conditions include Pd(dppf)Cl$_2$. In some embodiments, an alcohol, such as 2D, is subjected under the appropriate chlorination conditions to provide the corresponding chloro compound, such as 2E. In some embodiments, the appropriate chlorination reagent is SOCl$_2$. In some embodiment, the chloro compound, such as 2E, is converted to the corresponding bromo compound, such as compound 2F, with treatment under appropriate bromination conditions. In some embodiments, the appropriate bromination conditions include HBr and acetic acetic. In some embodiments, the bromo hydroxypyridine, such as 2F, is subjected under appropriate conditions to provide an iodo methylpyridine, such as 2G. In some embodiments, the appropriate conditions include treatment with MeI. In some embodiments, iodo methylpyridine is alkylated with an appropriate dihydroxybenzene, such as 2I, with a suitable base to provide 2-1. In some embodiments, the suitable base is K$_2$CO$_3$.

In some embodiments, a compound, such as 3-1, is prepared according to the route as shown in Scheme 3.

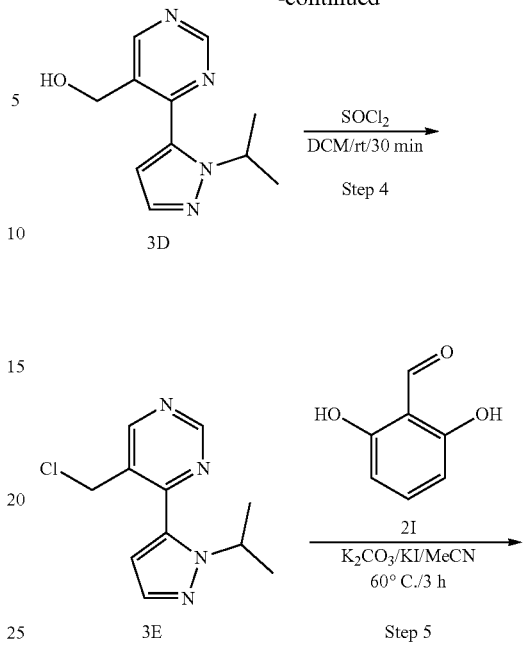

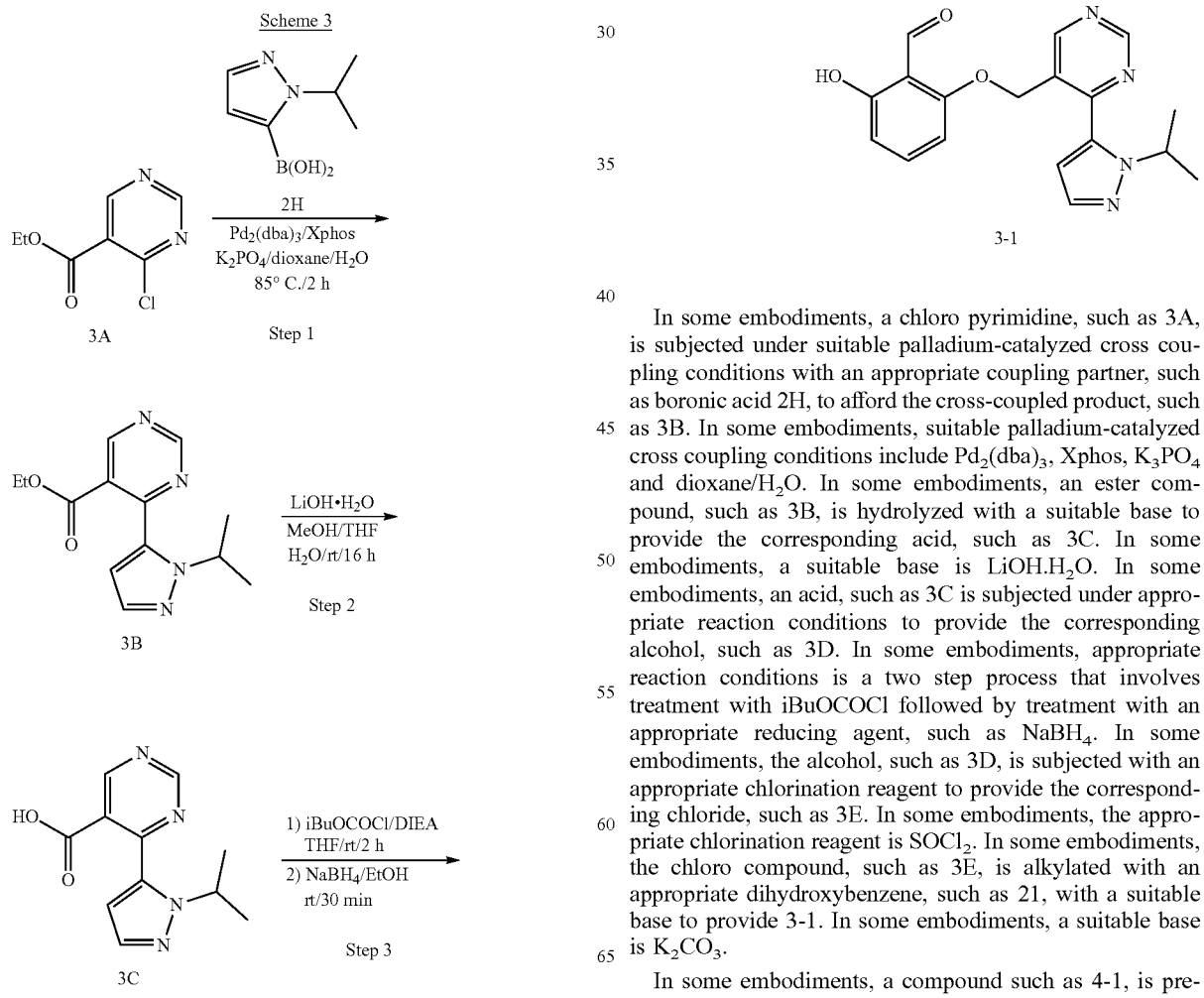

In some embodiments, a chloro pyrimidine, such as 3A, is subjected under suitable palladium-catalyzed cross coupling conditions with an appropriate coupling partner, such as boronic acid 2H, to afford the cross-coupled product, such as 3B. In some embodiments, suitable palladium-catalyzed cross coupling conditions include Pd$_2$(dba)$_3$, Xphos, K$_3$PO$_4$ and dioxane/H$_2$O. In some embodiments, an ester compound, such as 3B, is hydrolyzed with a suitable base to provide the corresponding acid, such as 3C. In some embodiments, a suitable base is LiOH.H$_2$O. In some embodiments, an acid, such as 3C is subjected under appropriate reaction conditions to provide the corresponding alcohol, such as 3D. In some embodiments, appropriate reaction conditions is a two step process that involves treatment with iBuOCOCl followed by treatment with an appropriate reducing agent, such as NaBH$_4$. In some embodiments, the alcohol, such as 3D, is subjected with an appropriate chlorination reagent to provide the corresponding chloride, such as 3E. In some embodiments, the appropriate chlorination reagent is SOCl$_2$. In some embodiments, the chloro compound, such as 3E, is alkylated with an appropriate dihydroxybenzene, such as 2I, with a suitable base to provide 3-1. In some embodiments, a suitable base is K$_2$CO$_3$.

In some embodiments, a compound such as 4-1, is prepared according to the route as shown in Scheme 4.

Scheme 4

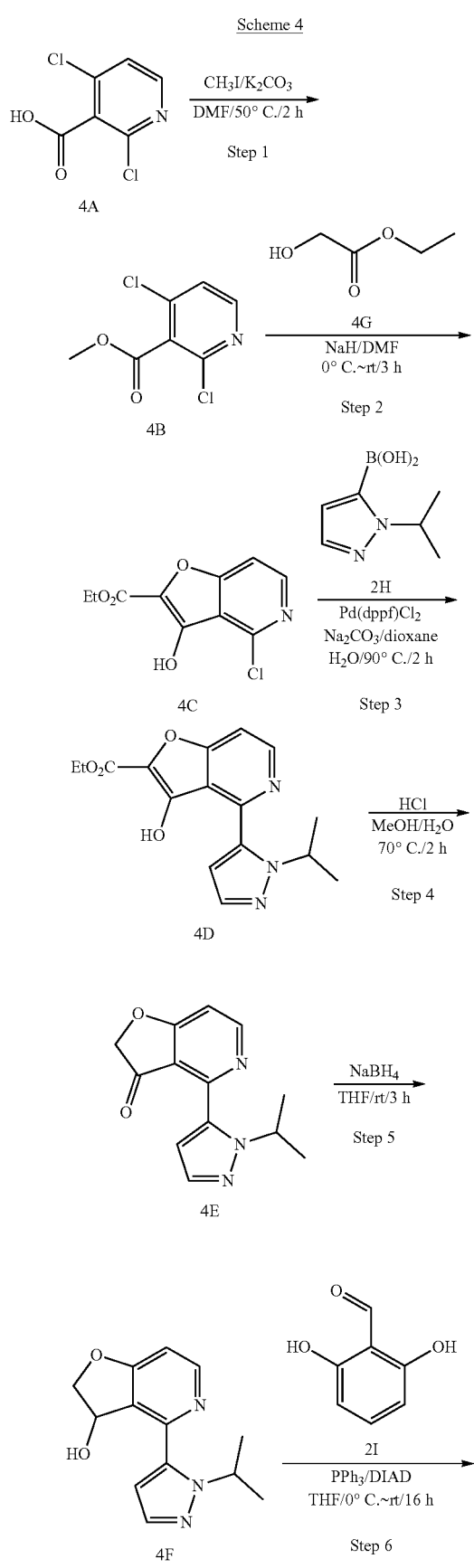

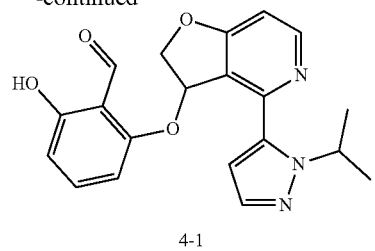

4-1

In some embodiments, an acid, such as 4A, is subjected under suitable reaction conditions to provide the corresponding methyl ester, such as 4B. In some embodiments, suitable reaction conditions include MeI and $K_2CO_3$. In some embodiments, a pyridine, such as 4B, is subjected under the appropriate reaction conditions and reagents to provide the corresponding furopyridine, such as 4C. In some embodiments, the appropriate reaction conditions is alkylation with ethyl 2-hydroxyacetate followed by treatment with a suitable base to promote cyclization. In some embodiments, the suitable base is NaH. In some embodiments, a furopyridine, such as 4C, is subjected to suitable palladium-catalyzed cross coupling conditions with an appropriate boronic acid, such as boronic acid 2H, to provide the corresponding cross-coupled product, such as 4D. In some embodiments, suitable palladium-catalyzed cross coupling conditions include $Pd(dppf)Cl_2$, $Na_2CO_3$ and dioxane/$H_2O$. In some embodiments, a compound, such as 4D, is subjected under suitable reaction conditions to provide a compound, such as 4E. In some embodiments, suitable reaction conditions include treatment with HCl in MeOH/$H_2O$. In some embodiments, a compound, such as 4E, is subjected to a suitable reducing agent to provide the corresponding hydroxyl compound, such as 4F. In some embodiments, a suitable reducing agent is $NaBH_4$. In some embodiments, the hydroxy compound, such as 4F, is alkylated with an appropriate dihydroxybenzene, such as 21, with suitable reaction conditions to provide 4-1. In some embodiments, suitable reaction conditions include $PPh_3$ and DIAD.

In one aspect, compounds described herein are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl moiety may be branched or straight chain. The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, and the like. In some embodiments, 1 or more hydrogen atoms of an alkyl are replaced with 1 or more deuterium atoms.

The term "alkylene" refers to a divalent alkyl radical. Any of the above mentioned monovalent alkyl groups may be an alkylene by abstraction of a second hydrogen atom from the alkyl. Typical alkylene groups include, but are not limited to, —CH$_2$—, —CH(CH$_3$)—, —C(CH$_3$)$_2$—, —CH$_2$CH$_2$—, —CH$_2$CH$_2$CH$_2$— and the like.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x and y are selected from the group x=1, y=1 and x=2, y=0.

The term "aromatic" refers to a planar ring having a delocalized π-electron system containing 4n+2π electrons, where n is an integer. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a C$_6$-C$_{10}$aryl. Depending on the structure, an aryl group can be a monoradical or a diradical (i.e., an arylene group). In some embodiments, 1 or more hydrogen atoms of an aryl are replaced with 1 or more deuterium atoms The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a C$_3$-C$_6$cycloalkyl.

The term "halo" or, alternatively, "halogen" or "halide" means fluoro (F), chloro (Cl), bromo (Br) or iodo (I). In some embodiments, halogen is F or Cl. In some embodiments, halogen is F.

The term "fluoroalkyl" refers to an alkyl in which one or more hydrogen atoms are replaced by a fluorine atom. In one aspect, a fluoroalkyl is a C$_1$-C$_6$fluoroalkyl. In some embodiments, a fluoroalkyl is a monofluoroalkyl, wherein one hydrogen atom of the alkyl is replaced by a fluorine atom. In some embodiments, a fluoroalkyl is a difluoroalkyl, wherein two hydrogen atoms of the alkyl are replaced by a fluorine atom. In some embodiments, a fluoroalkyl is a trifluoroalkyl, wherein three hydrogen atom of the alkyl are replaced by a fluorine atom. In some embodiments, a fluoroalkyl is a monofluoroalkyl, difluoroalkyl, or trifluoroalkyl. In some embodiments, a monofluoroalkyl is —CH$_2$F, —CHF$_2$, —CF$_3$, —CHFCH$_3$, —CH$_2$CH$_2$F, —CH$_2$CHF$_2$, —CH$_2$CF$_3$, —CH$_2$CH$_2$CF$_3$, —CH$_2$CH$_2$CH$_2$CF$_3$, —CHCH$_3$CF$_3$, —CH(CF$_3$)$_2$, or —CF(CH$_3$)$_2$.

The term "heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. In one aspect, a heteroalkyl is a C$_1$-C$_6$heteroalkyl. In some embodiments, a heteroalkyl is a C$_1$-C$_4$heteroalkyl. In some embodiments, a heteroalkyl is an alkyl group in which one or more skeletal atoms of the alkyl is oxygen (e.g. a hydroxyalkyl or an alkoxyalkyl).

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached (or C-linked) or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

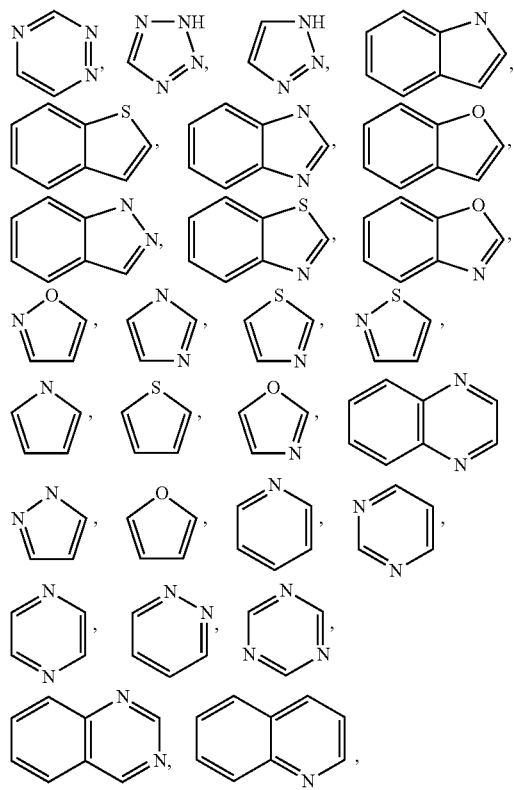

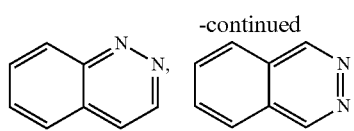

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group can be a monoradical or a diradical (i.e., a heteroarylene group).

A "heterocycloalkyl" or "heteroalicyclic" group refers to a cycloalkyl group wherein at least one of the carbon atoms of the cycloalkyl is replaced with nitrogen (unsubstituted or substituted, e.g. —NH—, —NR$^3$—), oxygen (—O—), or sulfur (e.g. —S—, —S(=O)— or —S(=O)$_2$—). The radicals may be fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkyl, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formula (I), (II), (II'), (III), (IV), (V), (VI), or (VII), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader. In some embodiment, a modulator is an agonist.

The term "allosterically modulate" as used herein, means to interact with a target either directly or indirectly induce a conformational change that alters the activity of the target, including, by way of example only, to enhance the activity of the target, to inhibit the activity of the target, to limit the activity of the target, or to extend the activity of the target.

The term "antagonist" as used herein, refers to a small-molecule agent that binds to a target and subsequently decreases the agonist induced transcriptional activity of the target.

The term "agonist" as used herein, refers to a small-molecule agent that binds to a target and subsequently increases target transcriptional activity in the absence of a known agonist.

The term "inverse agonist" as used herein, refers to a small-molecule agent that binds to a target and subsequently decreases the basal level of target transcriptional activity that is present in the absence of a known agonist.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, Liver, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), (II'), (III), (IV), (V), (VI), or (VII), or a pharmaceutically acceptable salt thereof, and a co-agent, are both administered to a patient simultaneously in the form of a single entity or dosage. The term "non-fixed combination" means that the active ingredients, e.g. a compound of Formula (I), (II), (II'), (III), (IV), (V), (VI), or (VII), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (II), (II'), (III), (IV), (V), (VI), or (VII), or a pharmaceutically acceptable salt thereof, and at least one pharmaceutically acceptable inactive ingredient. In some embodiments, the compounds described herein are administered as pharmaceutical compositions in which a compound of Formula (I), (II), (II'), (III), (IV), (V), (VI), or (VII), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (II), (II'), (III), (IV), (V), (VI), or (VII), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (II), (II'), (III), (IV), (V), (VI), or (VII), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (II), (II'), (III), (IV), (V), (VI), or (VII), as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), (II), (II'), (III), (IV), (V), (VI), or (VII), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound of Formula (I), (II), (II'), (III), (IV), (V), (VI), or (VII), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula (I), (II), (II'), (III), (IV), (V), (VI), or (VII), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula (I), (II), (II'), (III), (IV), (V), (VI), or (VII), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (II), (II'), (III), (IV), (V), (VI), or (VII), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine.

In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multi-particulate) each containing the formulation described herein. The first group of particles provides a substantially immediate dose of the active compound upon ingestion by a mammal.

The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula (I), (II), (II'), (III), (IV), (V), (VI), or (VII), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), (II), (II'), (III), (IV), (V), (VI), or (VII), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formula (I), (II), (II'), (III), (IV), (V), (VI), or (VII), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula (I), (II), (II'), (III), (IV), (V), (VI), or (VII), or a pharmaceutically acceptable salt thereof, are prepared as transdermal dosage forms. In one embodiment, the transdermal formulations described herein include at least three components: (1) a formulation of a compound of Formula (I), (II), (II'), (III), (IV), (V), (VI), or (VII), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (II), (II'), (III), (IV), (V), (VI), or (VII), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Methods of Dosing and Treatment Regimens

In one embodiment, the compounds of Formula (I), (II), (II'), (III), (IV), (V), (VI), or (VII), or a pharmaceutically acceptable salt thereof, are used in the preparation of medicaments for the treatment of diseases or conditions described herein in a mammal. Methods for treating any of the diseases or conditions described herein in a mammal in need of such treatment, involves administration of pharmaceutical compositions that include at least one compound of Formula (I), (II), (II'), (III), (IV), (V), (VI), or (VII), or a pharmaceutically acceptable salt thereof, or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition.

Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (II), (II'), (III), (IV), (V), (VI), or (VII), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), (II), (II'), (III), (IV), (V), (VI), or (VII), or a pharmaceutically acceptable salt thereof, described herein are from about 0.01 to about 20 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Method of Treatment

Described herein are methods of treating a disease or condition in a subject comprising administering a compound disclosed herein to the subject.

In some embodiments, the disease or condition treated with the compounds described herein is associated with oxygen deficiency. In some embodiments, the disease or condition is selected from sickle-cell disease, cancer, a pulmonary condition, stroke, high altitude sickness, an ulcer, a pressure sore, Alzheimer's disease, acute respiratory disease syndrome, a wound, and inflammatory diseases such as inflammatory bowel disease (IBD). In some embodiments, the disease or condition is sickle-cell disease. In some embodiments, the frequency of sickle-cell crisis in the subject is reduced as compared to a subject being administered the first therapeutic agent alone. In some embodiments, the sickle-cell crisis is selected from a vaso-occlusive crisis, an aplastic crisis, a sequestration crisis, haemolytic crisis, and any combinations thereof. In some embodiments, the subject experiences sickle-cell disease complications. In some embodiments, the sickle-cell disease complications experienced by the subject are reduced as compared to a subject being administered the first therapeutic agent alone. In some embodiments, the sickle-cell disease complication is selected from stroke, anemia, bacterial infections, cholelithiasis, cholecystitis, avascular necrosis, osteomyelitis, acute papillary necrosis in the kidneys, pulmonary hypertension, and any combinations thereof.

In some embodiments, the disease or condition treated with the compounds described herein is a mitochondrial disease. In some embodiments, the mitochondrial disease is selected from mitochondrial myopathy, Leber's hereditary optic neuropathy (LHON), Leigh syndrome, neuropathy/ataxia/retinitis pigmentosa (NARP), myoneurogenic gastrointestinal encephalopathy (MNGIE), myoclonic epilepsy with ragged red fibers (MERRF), mitochondrial myopathy/encephalomyopathy/lactic acidosis/stroke-like symptoms (MELAS), mitochondrial neurogastrointestinal encephalomyopathy (MNGIE), and any combination thereof. In some embodiments, the mitochondrial disease is Leigh syndrome.

In some embodiments, the disease or condition treated with the compounds described herein is a hypoxemic pulmonary disorder.

In some embodiments, the hypoxemic pulmonary disorder is selected from idiopathic pulmonary fibrosis (IPF), acute respiratory distress syndrome (ARDS), Chronic obstructive pulmonary disease (COPD), and any combination thereof. In some embodiments, the hypoxemic pulmonary disorder is idiopathic pulmonary fibrosis (IPF).

Combination Treatments

In certain instances, it is appropriate to administer at least one compound of Formula (I), (II), (II'), (III), (IV), (V), (VI), or (VII), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (II), (II'), (III), (IV), (V), (VI), or (VII), or a pharmaceutically acceptable salt thereof, is co-administered with a second therapeutic agent, wherein the compound of Formula (I), (II), (II'), (III), (IV), (V), (VI), or (VII), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (II), (II'), (III), (IV), (V), (VI), or (VII), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), (II), (II'), (III), (IV), (V), (VI), or (VII), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), (II), (II'), (III), (IV), (V), (VI), or (VII), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms.

In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compounds described herein are administered before the second therapeutic agent. In some embodiments, the compounds described herein are administered after the second therapeutic agent. In some embodiments, the compounds described herein are administered every day and the second therapeutic agent is administered every day. In some embodiments, the compounds described herein are administered every day and the second therapeutic agent is administered once a week. In some embodiments, the compounds described herein are administered every day and the second therapeutic agent is administered once every two weeks. In some embodiments, the compounds described herein are administered every day and the second therapeutic agent is administered once every three weeks. In some embodiments, the compounds described herein are administered every day and the second therapeutic agent is administered once every four weeks.

Exemplary Agents for Use in Combination Therapy

In some embodiments, methods for treatment of the diseases or disorders described herein, comprises administration to a mammal a compound of Formula (I), (II), (II'), (III), (IV), (V), (VI), or (VII), or a pharmaceutically acceptable salt thereof, in combination with oxygen therapy.

In some embodiments, methods for treatment of the diseases or disorders described herein, comprises administration to a mammal a compound of Formula (I), (II), (II'), (III), (IV), (V), (VI), or (VII), or a pharmaceutically acceptable salt thereof, in combination with at least one additional therapeutic agent.

In some embodiments, a compound of Formula (I), (II), (II'), (III), (IV), (V), (VI), or (VII), or a pharmaceutically acceptable salt thereof, in combination with hydroxyurea or derivatives thereof.

In one aspect, a compound of Formula (I), (II), (II'), (III), (IV), (V), (VI), or (VII), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), (II), (II'), (III), (IV), (V), (VI), or (VII), or a pharmaceutically acceptable salt thereof, is used in combination with anti-emetic agents to treat nausea or emesis, which may result from the use of a compound of Formula (I), (II), (II'), (III), (IV), (V), (VI), or (VII), or a pharmaceutically acceptable salt thereof.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, proclorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, *Cannabis*, marinol, dronabinol), and others (such as, but not limited to, trimethobenzamide; ginger, emetrol, propofol).

In some embodiments, a compound of Formula (I), (II), (II'), (III), (IV), (V), (VI), or (VII), or a pharmaceutically acceptable salt thereof, is used in combination with an agent useful in the treatment of anemia. Such an anemia treatment agent is, for example, a continuous erythropoiesis receptor activator (such as epoetin-α).

In some embodiments, a compound of Formula (I), (II), (II'), (III), (IV), (V), (VI), or (VII), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), (II), (II'), (III), (IV), (V), (VI), or (VII), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

P-Selectin Inhibitors

The adherence of sickle red blood cells (RBCs) to the vascular endothelium is thought to contribute to painful vaso-occlusion in sickle cell disease. Sickle cell adherence involves several receptor-mediated processes and may be potentiated by the up-regulated expression of adhesion molecules on activated endothelial cells. Recent results showed that thrombin rapidly increases the adhesivity of endothelial cells for sickle erythrocytes. Studies of the possible interaction of erythrocytes with P-selectin revealed that either P-selectin blocking monoclonal antibodies or sialyl Lewis tetrasaccharide inhibits the enhanced adherence of normal and sickle cells to thrombin-treated endothelial cells. Both RBC types also adhere to immobilized recombinant P-selectin. Pretreating erythrocytes with sialidase reduces their adherence to activated endothelial cells and to immobilized recombinant P-selectin. In some embodiments, the up-regulation of P-selectin in endothelial cells and platelets contributes to the cell-cell interactions that are involved in the pathogenesis of vaso-occlusion and sickle cell-related pain crises.

In some embodiments, a compound of Formula (I), (II), (II'), (III), (IV), (V), (VI), or (VII), or a pharmaceutically acceptable salt thereof, is administered with a P-selectin inhibitor. In some embodiments, the P-selectin inhibitor is selected from crizanlizumab, PSI-697 (2-(4-chlorobenzyl)-3-hydroxy-7,8,9,10-tetrahydrobenzo[h] quinoline-4-carboxylic acid), rivipansel, and any combinations thereof. In some embodiments, the P-selectin inhibitor is crizanlizumab.

Metformin

Metformin has been found to have relevant therapeutic significance in SCD, including enhancement of nitric oxide bioavailability, induction of fetal hemoglobin synthesis, attenuation of the inflammatory phenotype and beneficial effects in ischemia/reperfusion injury. In some embodiments, a compound of Formula (I), (II), (II'), (III), (IV), (V), (VI), or (VII), or a pharmaceutically acceptable salt thereof, is administered with metformin.

L-Glutamine

Increased oxidant stress plays a major part in the pathophysiology of sickle cell disease. It can lead to disturbance of cell membranes, exposure of adhesion molecules and damage to the contents of the sickle red blood cells (sRBC). It has been found that enhancement of nicotinamide adenine dinucleotide (NAD) in sRBC was achieved by supplementation with a precursor of NAD, L-glutamine. In some embodiments, a compound of Formula (I), (II), (II'), (III), (IV), (V), (VI), or (VII), or a pharmaceutically acceptable salt thereof, is administered with L-glutamine.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Example 1: General Procedure for Synthesis of Key Intermediate Example 1

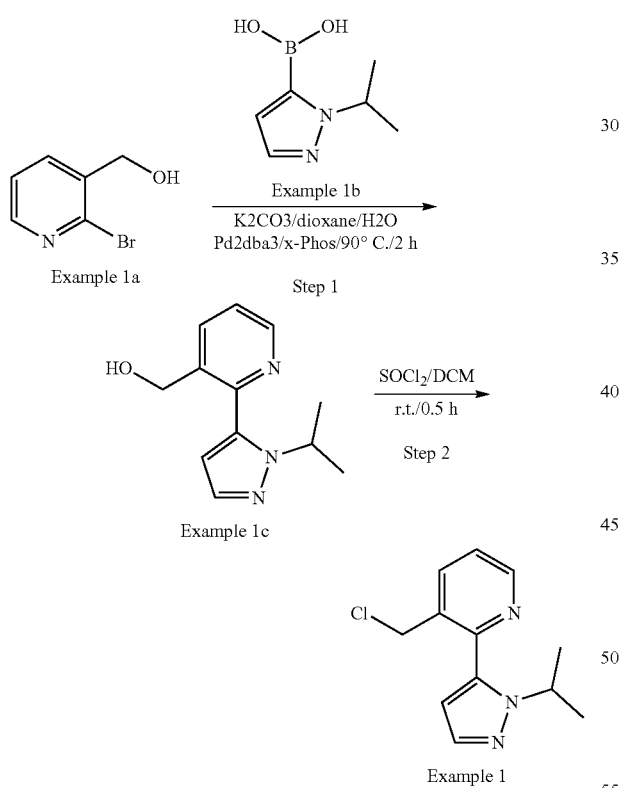

Step 1: Example 1c

To a solution of Example 1a (30 g, 0.159 mol, 1 eq.) in dioxane/water (300 mL/30 mL) was added Example 1b (30 g, 1.2 mol, 1.5 eq.), $K_3PO_4$ (101 g, 0.477 mol, 2.5 eq), $Pd_2(dba)_3$ (3.0 g) and 2-dicyclohexylphosphino-2',4',6'-triisopropylbiphenyl (3 g) under $N_2$ protection and then heated to 90° C. for 2 hrs. After cooled to room temperature, the solvent was removed under reduced pressure; The residue was extracted with EtOAc (200 mL*2). The combined organic phase was washed with brine, dried over $Na_2SO_4$, filtrated and concentrated under reduced pressure to give the crude product which was further purified by silica gel chromatography to give the pure product (Example 1c, 30 g, yield 88%) as yellow oil. MS $[M+1]^+=218$.

Step 2: Example 1

To a solution of Example 1c (20 mg) in DCM (200 mL) was added thionyl chloride (5 mL) and stirred at r.t for 0.5 h. After the reaction was completed, the solvent was removed under reduced pressure to give the desired product (Example 1, 20 g, yield 90%) as white solid.

Example 2: General Procedure for Synthesis of Example 2

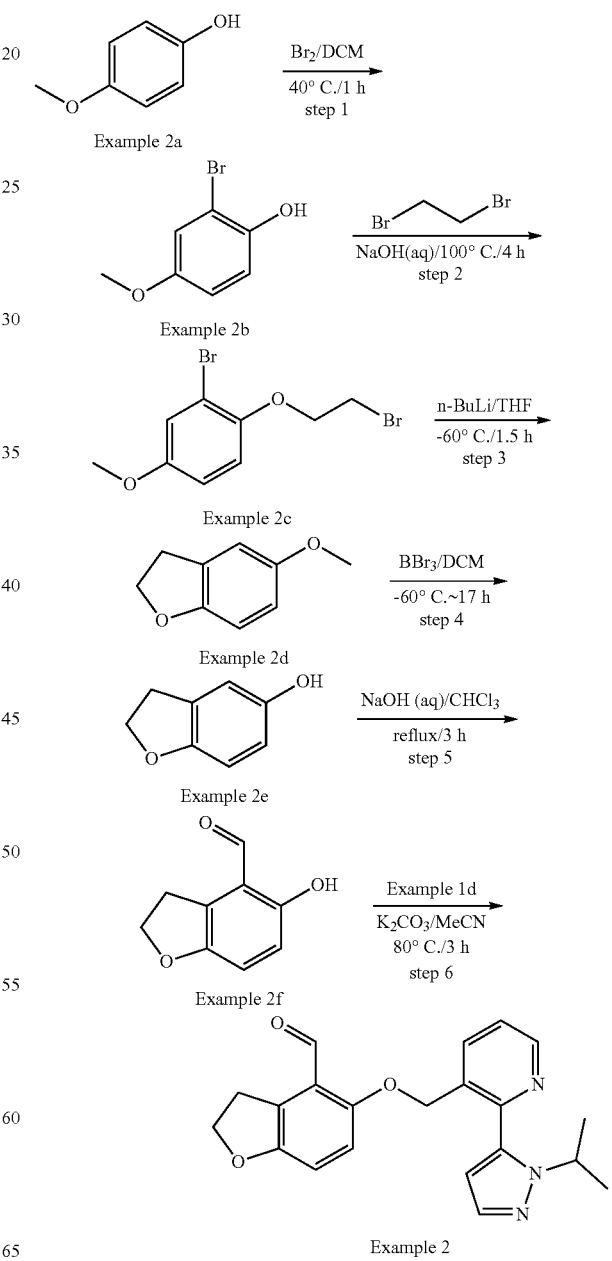

Step 1: Example 2b

To a solution of Example 2a (51.2 g, 0.41 mol) in DCM (0.5 L) cooled in an ice bath was added Br$_2$ (66 g, 0.41 mol) dropwise. After addition, the resulting solution was stirred at 40° C. for 1 h. The reaction mixture was washed with water (400 mL*3), NaHCO$_3$ (200 mL) and brine, dried over Na$_2$SO$_4$ and concentrated to give the desired product (Example 2b, 86.1 g, yield 100%) as colorless oil, which was used in the next step without further purification.

Step 2: Example 2c

A solution of Example 2b (86.1 g, 0.41 mol) in 1,2-dibromoethane (306.5 g, 1.64 mol) at room temperature was treated with aqueous NaOH (41 g in 170 mL of water). The reaction mixture was stirred for 4 h at 100° C. After cooling, DCM (100 mL) and water (100 mL) were added to reaction mixture, and the organic layer was separated and washed with brine (200 mL), dried over MgSO$_4$, filtrated and concentrated under reduced pressure to give the residue which was further purified by silica gel chromatography, eluting with 10% of EtOAc in Petroleum Ether, to give the desired product (Example 2c, 98.1 g, yield 75%) as white solid.

Step 3: Example 2d

A solution of Example 2c (98.1 g, 0.32 mol) in THF (1.0 L) was treated with n-BuLi (152 mL, 0.38 mol) and stirred at −60° C. for 1.5 h. The reaction mixture was warmed to room temperature and diluted with EtOAc (200 mL). The combined organic phase was washed with brine (200 mL), dried over MgSO$_4$, filtrated, and concentrated under reduced pressure to give the desired product (Example 2d, 43.1 g, yield 91%) as yellow solid, which was used to the next step without further purification.

$^1$H NMR (400 MHz, CDCl$_3$) δ 6.78 (d, J=2.2 Hz, 1H), 6.69 (d, J=8.6 Hz, 1H), 6.64 (dd, J=8.6, 2.5 Hz, 1H), 4.53 (t, J=8.6 Hz, 2H), 3.17 (t, J=8.6 Hz, 2H).

Step 4: Example 2e

To a solution of Example 2d (43.1 g, 0.29 mol) in DCM (800 mL) at −60° C. was added BBr$_3$ (215 mL, 1M in DCM) dropwise. The reaction mixture was allowed to stir at room temperature for 17 h. The reaction mixture was quenched slowly with MeOH (200 mL), and basified with NaHCO$_3$ to pH-8. The organic layer was separated, dried over Na$_2$SO$_4$, filtrated and concentrated under reduced pressure. The residue was purified by silica gel chromatography, eluting with 10% of EtOAc in Petroleum Ether, to give the desired product (Example 2e, 14.8 g, yield 38%) as white solid.

$^1$H NMR (400 MHz, DMSO) δ 8.76 (s, 1H), 6.59 (d, J=8.5 Hz, 1H), 6.51 (d, J=2.8 Hz, 1H), 6.46 (dd, J=8.5, 2.9 Hz, 1H), 3.60 (t, J=7.6 Hz, 2H), 2.96 (t, J=7.6 Hz, 2H).

Step 5: Example 2f

A mixture of Example 2e (9.0 g, 0.07 mol), chloroform (16.7 g), water (28 mL) and NaOH (22.6 g) was refluxed for 3 h. The reaction mixture was cooled to ambient temperature, diluted with DCM (100 mL) and washed with water. The organic layer was dried over MgSO$_4$, filtrated and concentrated under reduced pressure. The residue was purified by flash chromatography, eluting with 10% of EtOAc in Petroleum Ether, to give the desired product (Example 2f, 80 mg, yield 7%) as light yellow solid.

$^1$H NMR (400 MHz, CDCl$_3$) δ 10.68 (s, 1H), 10.03 (s, 1H), 7.00 (d, J=8.8 Hz, 1H), 6.76 (d, J=8.8 Hz, 1H), 4.66 (t, J=8.8 Hz, 2H), 3.49 (t, J=8.7 Hz, 2H).

Step 6: Example 2

A mixture of Example 2f (80 mg, 0.49 mmol) and K$_2$CO$_3$ (135 mg, 0.97 mmol) in DMF (3 mL) was stirred at room temperature for 5 min. To this mixture was added Example 1d (115 mg, 0.49 mmol). The resulting mixture was heated at 80° C. for 3 h and then cooled, which was then extracted with EtOAc (20 mL*2). The combined organic phase was washed with brine, dried over Na$_2$SO$_4$, concentrated under reduced pressure. The residue was purified by silica gel chromatography, eluting with 10% of EtOAc in Petroleum Ether, to give the desired product (Example 2, 35 mg, yield 20%) as yellow solid. MS [M+1]$^+$=364.2

$^1$H NMR (400 MHz, Chloroform-d) δ 10.53 (s, 1H), 8.76 (d, J=3.9 Hz, 1H), 8.09 (d, J=7.7 Hz, 1H), 7.64 (s, 1H), 7.48 (dd, J=7.6, 4.7 Hz, 1H), 6.90 (d, J=8.7 Hz, 1H), 6.63 (d, J=8.7 Hz, 1H), 6.40 (s, 1H), 5.02 (s, 2H), 4.66-4.57 (m, 3H), 3.51 (dd, J=15.1, 6.3 Hz, 2H), 1.49 (d, J=6.6 Hz, 6H).

Example 3: General Procedure for Synthesis of Example 3

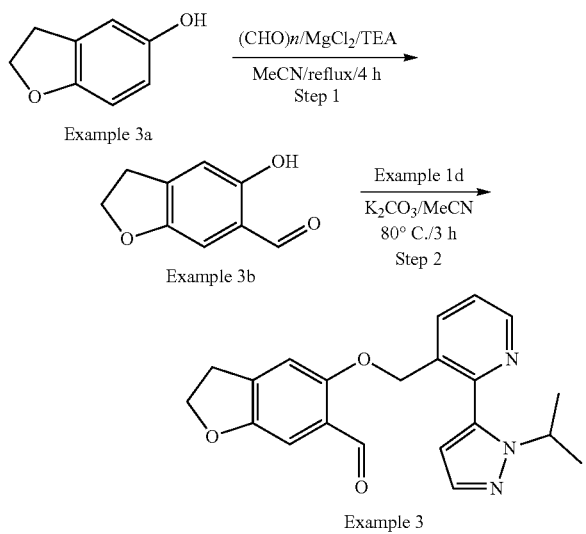

Step 1: Example 3b

A slurry of Example 3a (2.1 g, 0.015 mol) and acetonitrile (100 mL) were added to a three-necked bottle, to which paraformaldehyde (3.2 g, 0.11 mol), anhydrous magnesium chloride (2.2 g, 0.023 mol) and triethylamine (6.2 g, 0.062 mol) were added in this order with stirring at room temperature. After refluxing for 4 h, the reaction solution was poured into ice water, which was acidified with aqueous HCl solution to a pH of 5. After extraction with EtOAc (50 mL*2), combined organic phase was dried over MgSO$_4$ and concentrated under reduced pressure. The residue was purified by silica gel chromatography, eluting with 12% of EtOAc in Petroleum Ether, to give the desired product (Example 3b, 450 mg, yield 18%) as yellow solid.

$^1$H NMR (400 MHz, CDCl$_3$) δ 10.97 (s, 1H), 9.77 (s, 1H), 6.86 (s, 2H), 4.58 (t, J=8.6 Hz, 2H), 3.25 (t, J=8.6 Hz, 2H).

Step 2: Example 3

A mixture of Example 3b (178 mg, 1.08 mmol) and K$_2$CO$_3$ (299 mg, 2.16 mmol) in DMF (3 mL) was stirred at room temperature for 5 min. To this mixture was added Example 1d (255 mg, 1.08 mmol). The resulting mixture was heated at 80° C. for 3 h and then cooled, which was then extracted with EtOAc (20 mL*2). The combined organic phase was washed with brine, dried over Na$_2$SO$_4$, concentrated under reduced pressure. The residue was purified by silica gel chromatography, eluting with 10% of EtOAc in Petroleum Ether, to give the desired product (Example 3, 147 mg, yield 37%) as yellow solid. MS [M+1]=364.2

$^1$H NMR (400 MHz, Chloroform-d) δ 10.38 (s, 1H), 8.74 (d, J=3.3 Hz, 1H), 8.07 (d, J=7.5 Hz, 1H), 7.62 (s, 1H), 7.45 (dd, J=7.1, 4.2 Hz, 1H), 7.20 (s, 1H), 6.75 (s, 1H), 6.38 (s, 1H), 5.03 (s, 2H), 4.64 (dd, J=12.9, 6.5 Hz, 1H), 4.57 (t, J=8.6 Hz, 2H), 3.22 (t, J=8.6 Hz, 2H), 1.47 (d, J=6.5 Hz, 6H).

Example 4: General Procedure for Synthesis of Example 4

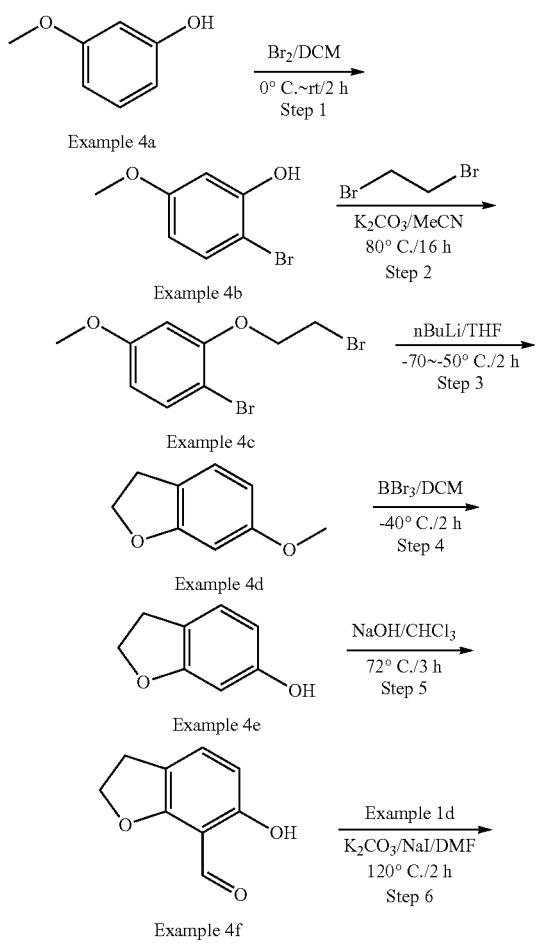

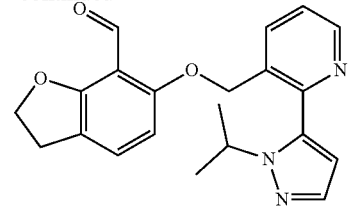

Example 4

Step 1: Example 4b

To a solution of Example 4a (24.8 g, 0.2 mol, 1.0 eq.) in DCM (20 mL) was added Br$_2$ (30.4 g, 0.19 mol, 0.95 eq.) in an ice bath. The mixture was then warmed to room temperature and stirred for another 2 h. The reaction was quenched by adding 40 mL of NaHCO$_3$ (aq. 15%), and then extracted with DCM (20 mL*2). The combined organic phase was dried over Na$_2$SO$_4$, concentrated under reduced pressure to give the desired product (Example 4b, 34.5 g, crude yield 85%) as colorless oil without further purification.

Step 2: Example 4c

A mixture of Example 4b (20.3 g, 0.1 mol), BrCH$_2$CH$_2$Br (22.5 g, 0.12 mol) and potassium carbonate (27.6 g, 0.2 mol) was stirred in acetonitrile (300 mL) at 80° C. for 16 h. The solvent was then removed, the residue was further purified by silica gel chromatography, eluting with 20%-50% of EtOAc in Petroleum Ether, to give the desired product (Example 4c, 16.1 g, yield 52%) as yellow oil.

Step 3: Example 4d

To a solution of Example 4c (3.1 g, 10.0 mmol, 1.0 eq.) in THF (40 mL) was added 1.6 M n-BuLi (6.8 mL, 11.0 mmol, 1.1 eq.) at −70° C. The mixture was stirred at −70° C. for 30 min, and then warmed to −50° C. and stirred for another 1.5 h. The reaction was quenched by adding 30 mL of water and extracted with EtOAc (35 mL*2). The combined organic phase was washed with brine, dried over Na$_2$SO$_4$, and concentrated under reduced pressure to give the desired product (Example 4d, 1.1 g, crude yield 71%) as yellow oil. MS [M+1]$^+$=151.2

Step 4: Example 4e

To a solution of Example 4d (1.1 g, 7.1 mmol) in DCM (22 mL) was added 10 mL of BBr$_3$/DCM (1.0 M, 10.0 mmol) dropwise at −40° C. The reaction mixture was stirred at the same temperature for 2 h. TLC showed the starting material was consumed completely. The reaction was quenched by adding 20 mL of methanol carefully, and the solvent was then removed under reduced pressure. The residue was further purified by silica gel chromatography, eluting with 15%-45% of EtOAc in Petroleum Ether, to give the desired product (Example 4e, 0.52 g, yield 79%) as yellow solid.

Step 5: Example 4f

To a solution of Example 4e (1.36 g, 10.0 mmol, 1.0 eq.) in NaOH (12 mL, aq. 25%) was added chloroform (2.4 g, 20.2 mmol, 2.0 eq.). The mixture was stirred at 72° C. for 3 h. The mixture was then neutralized by 6 M HCl (15 mL*2), and extracted with EtOAc (15 mL*2). The combined organic phase was concentrated under reduced pressure, the residue was purified by silica gel chromatography, eluting with 10%-25% of EtOAc in Petroleum Ether, to give the desired product (Example 4f, 72 mg, yield 4%) as light yellow oil.

Step 6: Example 4

A mixture of Example 4f (72 mg, 0.47 mmol), Example 1d (0.14 g, 0.58 mmol), potassium carbonate (140 mg, 0.98 mmol) and NaI (20 mg) was stirred at 120° C. for 2 h. The reaction was quenched by adding 20 mL of water, extracted with EtOAc (35 mL*2). The combined organic phase was washed with brine, dried over $Na_2SO_4$, and concentrated under reduced pressure. The residue was further purified by prep-HPLC (water/MeOH=90%-20%), to give the desired product (Example 4.10 mg, yield 6%) as white solid. MS $[M+1]^+$=364.2.

$^1$H NMR (400 MHz, $CDCl_3$) δ 10.41 (s, 1H), 8.84 (dd, J=5.0, 1.7 Hz, 1H), 8.43 (dd, J=8.0, 1.7 Hz, 1H), 7.80 (d, J=2.0 Hz, 1H), 7.66 (dd, J=8.0, 5.0 Hz, 1H), 6.46 (d, J=2.0 Hz, 1H), 6.25 (d, J=8.2 Hz, 1H), 4.98 (s, 2H), 4.77 (t, J=8.7 Hz, 2H), 4.43 (p, J=6.6 Hz, 1H), 3.16 (t, J=8.7 Hz, 2H), 1.46 (d, J=6.6 Hz, 6H).

Example 5: General Procedure for Synthesis of Example 5

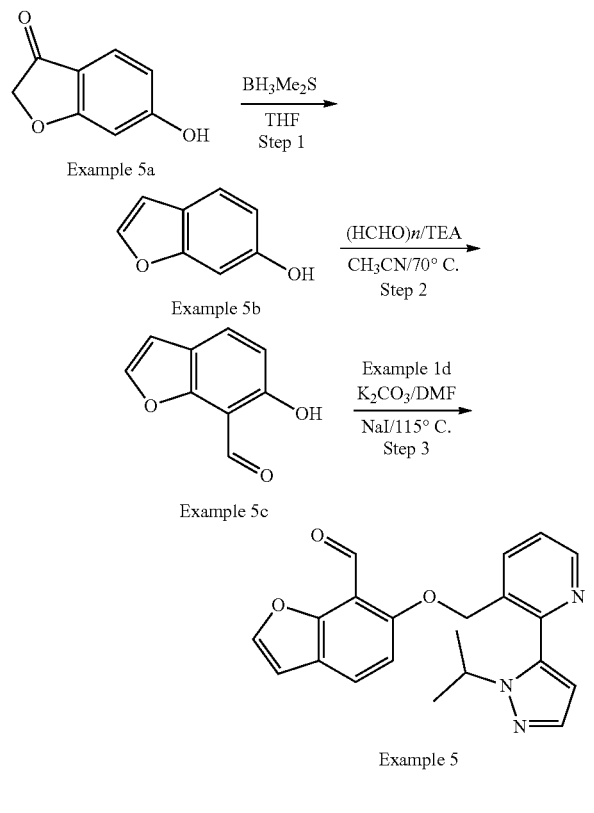

Step 1: Example 5b

To a solution of Example 5a (1.5 g, 10.0 mol, 1.0 eq) in THF (20 mL) was added 5 mL $BH_3Me_2S$ (10M, 0.5 mol, 5 eq) at ice temperature (0° C.), the mixture was then turned to room temperature and stirred for another 16 hrs. The reaction was quenched by adding 40 mL of methanol. The solvent was then removed, and the residue was further purified by flash chromatography, eluting with 40%-70% of EtOAc in Petroleum Ether, to give the desired product (Example 5b, 0.26 g, crude yield 21%) as yellow solid. MS $[M+1]^+$=135.1

Step 2: Example 5c

To a suspension of Example 5b (0.26 g, 1.9 mmol, 1 eq.), triethylamine (0.65 g, 6.5 mmol, 3.4 eq.), and magnesium dichloride (0.29 g, 3.1 mmol, 1.6 eq.) in acetonitrile (25 mL) was added paraformaldehyde (0.36 g, 13 mmol, 6.8 eq.) portionwise. The resulting mixture was refluxed for 3.5 hours at which time TLC revealed that all the starting material was consumed. The reaction mixture was acidified with 6 N HCl, concentrated and extracted with ether (3*15 mL). The ether extracts were washed with water, brine, dried over $Na_2SO_4$ and concentrated under reduced pressure to give the desired product (Example 5c, 0.22 g, crude yield 65%) as yellow oil.

Step 3: Example 5

A mixture of Example 5c (70 mg, 0.47 mmol), Example 1d (0.14 g, 0.58 mmol), potassium carbonate (140 mg, 0.98 mmol) and NaI (20 mg) was stirred at 120° C. for 2 hrs, the reaction was quenched by adding 20 mL of water, extracted with EtOAc (35 mL*2). The combined organic phase was washed with brine, dried over $Na_2SO_4$, and concentrated under reduced pressure to give yellow oil, which was further purified by prep-HPLC (water/MeOH=90%-20%) to give the desired product (Example 5, 45 mg, yield 26%) as white solid. MS $[M+1]^+$=362.2.

$^1$H NMR (400 MHz, $CDCl_3$) δ 10.69 (s, 1H), 8.76 (dd, J=4.9, 1.7 Hz, 1H), 8.18 (dd, J=7.9, 1.6 Hz, 1H), 7.75-7.69 (m, 2H), 7.64 (d, J=1.8 Hz, 1H), 7.48 (dd, J=7.9, 4.8 Hz, 1H), 6.82 (d, J=8.7 Hz, 1H), 6.74 (d, J=2.2 Hz, 1H), 6.41 (d, J=1.9 Hz, 1H), 5.16 (s, 2H), 4.60-4.64 (m, 1H), 1.49 (d, J=6.6 Hz, 6H).

Example 6: General Procedure for Synthesis of Example 6

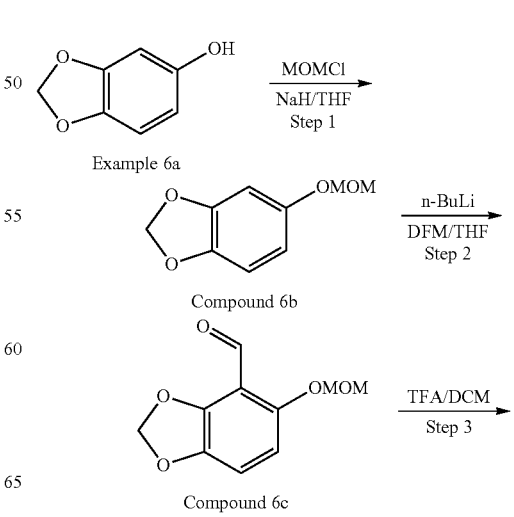

-continued

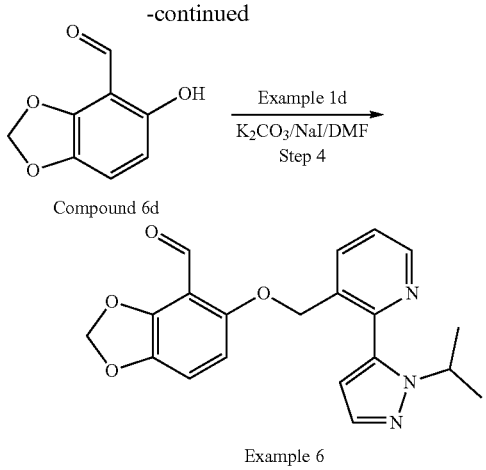

Compound 6d

Example 6

Step 1: Example 6b

To a solution of Example 6a (6.1 g, 44.2 mmol) in THF (60 mL) was added NaH partially (60%, 2.6 g, 66.3 mmol) at 0° C., the mixture was stirred at 0° C. for 1 h, and then MOM-Cl (4.2 g, 53.1 mmol) was added slowly at 0° C. After adding over, the reaction was then turned to room temperature and stirred for another 1 hr. The reaction was quenched by adding 90 mL water and extracted with EtOAc (100 mL*2). The combined organic phase was washed with brine, dried over $Na_2SO_4$, and concentrated under residued pressure to give 10.1 g of yellow oil, which was further purified by silica gel chromatography to give the desired product (Example 6b, 4.2 g, crude yield 52%) as colorless oil. MS $[M+13]^+=195.1$.

Step 2: Example 6c

To a solution of Example 6b (2.2 g, 12.1 mmol) in 30 mL of anhydrous THF was added 1.5 g TMEA at −65° C., then 6.3 mL of n-BuLi was added slowly maintaining the temperature below −60° C. The mixture was stirred at −65° C. for further 30 minutes, followed by adding 1 mL of DMF slowly and stirred for another 1 hr. The reaction was then quenched by adding 10 mL of water, extracted with EA (20 mL*2). The combined organic phase was dried over $MgSO_4$, concentrated under reduced pressure to give the desired product (Example 6c, 2.1 g, crude yield 82%) as yellow solid. MS $[M+1]^+=211.1$.

$^1$H NMR (400 MHz, $CDCl_3$) δ 10.38 (s, 1H), 6.89 (d, J=8.6 Hz, 1H), 6.60 (d, J=8.6 Hz, 1H), 6.09 (s, 2H), 5.20 (s, 2H), 3.50 (s, 3H).

Step 3: Example 6d

To a solution of Example 6c (0.81 g, 3.8 mmol) in DCM (30 mL) was added TFA (0.8 mL), the mixture was stirred at 0° C. for 1 hr, then it was turned to r.t and stirred for another 2 hrs. The solvent was then removed under reduced pressure to give the desired product (Example 6d, 0.4 g, yield 58%) as yellow solid.

Step 4: Example 6

A mixture of Example 6d (190 mg, 1.1 mmol), Example 1d (0.24 g, 1.0 mmol), potassium carbonate (470 mg, 3.4 mmol) and NaI (100 mg) was stirred in DMF (20 mL) at 120° C. for 2 hrs; the reaction was quenched by adding water (20 mL), extracted with EtOAc (35 mL*2). The combined organic phase was washed with brine, dried over $Na_2SO_4$, and concentrated under reduced pressure to give brown oil (0.43 g), which was further purified by silica gel chromatography, eluting with 45%-75% of EtOAc in Petroleum Ether, to give the desired product (Example 6, 0.07 g, yield 18%) as yellow solid. MS $[M+1]^+=366.1$.

$^1$H NMR (400 MHz, $CDCl_3$) δ 10.39 (s, 1H), 8.73 (dd, J=4.8, 1.9 Hz, 1H), 8.04 (dd, J=7.9, 1.9 Hz, 1H), 7.60 (d, J=1.9 Hz, 1H), 7.42 (dd, J=7.9, 4.7 Hz, 1H), 6.86 (d, J=8.5 Hz, 1H), 6.35 (d, J=1.9 Hz, 1H), 6.22 (d, J=8.6 Hz, 1H), 6.10 (s, 2H), 5.01 (s, 2H), 4.66-4.58 (m, 1H), 1.46 (d, J=6.6 Hz, 6H).

Example 7: General Procedure for Synthesis of Example 7

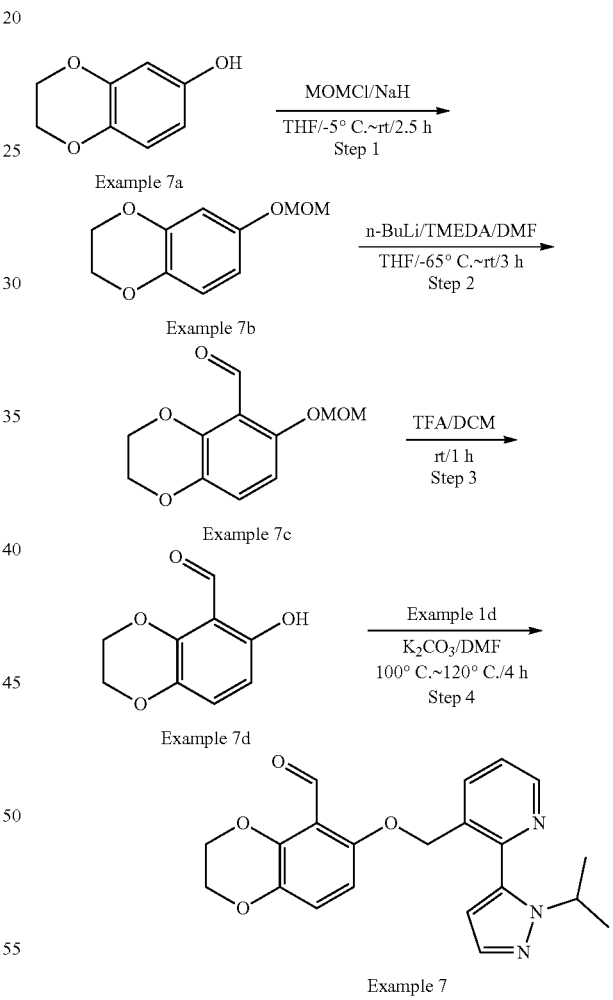

Step 1: Example 7b

To a solution of Example 7a (500 mg, 3.29 mmol, 1.0 eq) in THF (10 mL) was cooled to −10~0° C. and added NaH (210 mg, 5.26 mmol, 1.6 eq) under $N_2$. The mixture was stirred at −10~0° C. for 30 min, and then MOMCl (397 mg, 4.93 mmol, 1.5 eq) was added dropwise. The resulting mixture was stirred at RT for 2 h. The reaction mixture was extracted with EA (30 mL) and H₂O. The organic layer was dried over Na₂SO₄ and concentrated under reduced pressure. The residue was purified by flash column chromatography, eluting with 25% of EtOAc in Petroleum Ether, to give the desired product (Example 7b, 320 mg, yield 50%) as colorless oil. MS [M+1]$^+$=197.1

Step 2: Example 7c

To a solution of Example 7b (320 mg, 1.63 mmol, 1.0 eq) in THF (8 mL) was added TMEDA (208 mg, 1.79 mmol, 1.1 eq) and cooled to −65° C. under N₂. n-BuLi (0.8 mL, 2.12 mmol, 1.3 eq, 2.5 M) was added dropwise and the mixture was stirred for 30 min at this temperature. Then DMF (133 mg, 1.79 mmol, 1.1 eq) was added, and the resulting mixture was stirred at −65° C. for 1 h, warmed to RT for 1 h. The reaction mixture was extracted with EA (30 mL) and H₂O. The organic layer was dried over Na₂SO₄ and concentrated under reduced pressure. The residue was purified by flash column chromatography, eluting with 33% of EtOAc in Petroleum Ether, to give the desired product (Example 7c, 170 mg, yield 46%) as yellow oil. MS [M+1]$^+$=225.0

Step 3: Example 7d

To a solution of Example 7c (170 mg, 0.76 mmol, 1.0 eq) in DCM (5 mL) was added TFA (0.2 mL). The mixture was stirred at RT for 1 h. The reaction mixture was concentrated under reduced pressure to give the desired product (Example 7d, 140 mg), which was used for next step without future purification. MS [M+1]$^+$=181.1

Step 4: Example 7

To a solution of Example 7d (70 mg, 0.39 mmol, 1.0 eq) in DMF (2 mL) was added 5 (82 mg, 0.35 mmol, 0.9 eq), K₂CO₃ (161 mg, 1.17 mmol, 3.0 eq) and NaI (17 mg, 0.12 mmol, 0.3 eq). The mixture was stirred at 100° C. for 2 h. Then the mixture was heated to 120° C., for 2 hrs. The reaction mixture was extracted with EA (20 mL) and H₂O. The organic layer was dried over Na₂SO₄ and concentrated under reduced pressure. The residue was purified by Pre-HPLC to give the desired product (Example 7, 22 mg, yield 15%) as white solid. MS [M+1]$^+$=380.2

$^1$H NMR (400 MHz, DMSO-d₆) δ 10.25 (s, 1H), 8.70 (dd, J=4.8, 1.7 Hz, 1H), 8.18 (dd, J=7.9, 1.7 Hz, 1H), 7.57-7.48 (m, 2H), 7.06 (d, J=9.0 Hz, 1H), 6.56-6.49 (m, 2H), 5.04 (s, 2H), 4.60 (p, J=6.6 Hz, 1H), 4.30-4.28 (m, 2H), 4.22-4.19 (m, 2H), 1.32 (d, J=6.5 Hz, 6H).

Example 8: General Procedure for Synthesis of Example 8

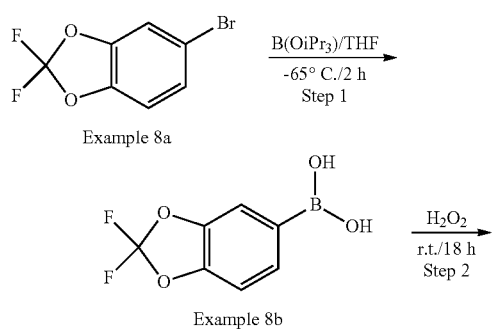

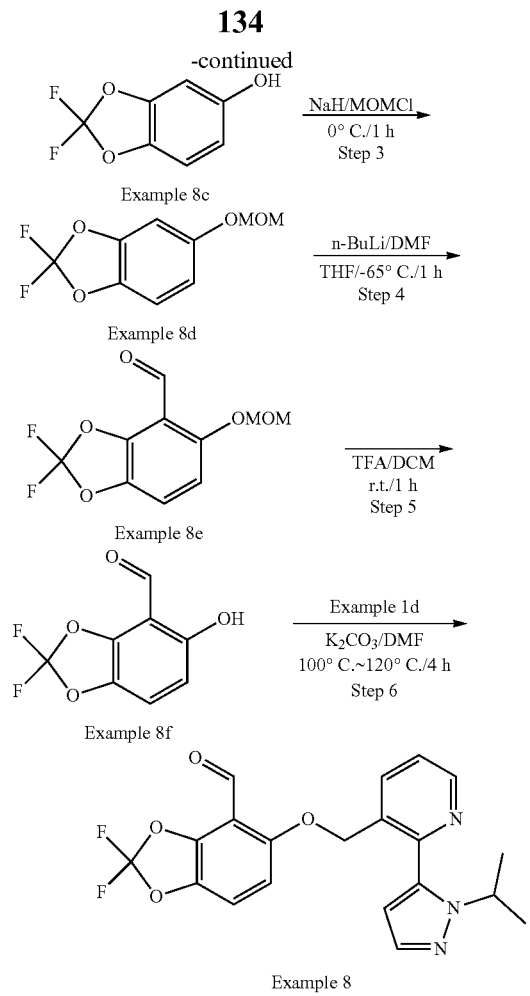

Step 1: Example 8b

Example 8a (15.7 g, 0.066 mol), B(OiPr)₃ (18.7 g, 0.099 mol), was dissolved in THF (300 mL), the mixture was cooled to −65° C. under N₂, n-BuLi (32 mL, 0.079 mol) was added dropwise. After addition, the reaction mixture was stirred at −60° C. for 1 h, then warmed to r.t., NH₄Cl (200 mL) and EA (200 mL) was added, the mixture was acidified to pH 2-3 by adding HCl (3 N). The organic phase was separated, washed with water, brine and dried over Na₂SO₄, filtrated and concentrated under reduced pressure to give the desired product (Example 8b, 16 g, yield 100%) as white solid.

Step 2: Example 8c

Example 8b (11.7 g, 0.058 mol) was dissolved in a solution of THF (200 mL) and H₂O₂ (100 mL) the resulting mixture was stirred at r.t. over night. TLC showed Example 8b was consumed, EA (200 mL) was added successively the mixture was stirred at r.t for 1 h, the organic layer was separated, washed with sat Na₂SO₃ (200 mL*5), dried over Na₂SO₄, filtrated and concentrated under reduced pressure to give the desired product (Example 8c, 8.6 g, yield 86%) as yellow oil. MS [M+1]$^+$=175

$^1$H NMR (400 MHz, DMSO-d₆) δ 9.76 (s, 1H), 7.10 (dd, J=12.3, 7.8 Hz, 1H), 6.80-6.70 (m, 1H), 6.57-6.44 (m, 1H)

Step 3: Example 8d

Example 8c (3.3 g, 0.019 mol) was dissolved in THF (35 mL), the mixture was cooled to 0° C., NaH (910 mg, 0.023 mol) was added in three batches. After addition the reaction mixture was stirred at r.t. for 1 h, and then cooled to 0° C., MOMCl (1.74 g, 0.021 mol) was added, dropwise, the reaction mixture was stirred at r.t. for 1 h. The reaction was quenched by adding water (10 mL), and then extracted with EA (50 mL*2). The combined organic phase was washed with water, brine, dried over $Na_2SO_4$, filtrated and concentrated under reduced pressure to give the desired product (Example 8d, 3.4 g, yield 82%) as yellow oil.

Step 4: Example 8e

Example 8d (3.4 g, 15.6 mmol), DMF (1.7 g, 23.4 mmol) was dissolved in THF (70 mL), the mixture was cooled to −65° C. under $N_2$, n-BuLi (7.5 mL, 18.7 mmol) was added dropwise. After addition, the reaction mixture was stirred at −60° C. for 1 h. Then warmed to r.t., $NH_4Cl$ (50 mL) and EA (200 mL) were added. The mixture was acidified to pH 2-3 by adding HCl (3N), the organic phase was separated, washed with water, brine, dried over $Na_2SO_4$, filtrated and concentrated under reduced pressure to give 3.4 g crude product, which was purified by flash column chromatography, eluting with 10% of EtOAc in Petroleum Ether, to give the desired product (Example 8e, 875 mg, yield 22.8%) as yellow oil.

$^1$H NMR (400 MHz, $CDCl_3$-d) δ 10.39 (s, 1H), 7.17 (d, J=8.9 Hz, 1H), 6.93 (d, J=8.9 Hz, 1H), 5.26 (s, 2H), 3.52 (s, 3H).

Step 5: Example 8f

Example 8e (875 mg, 3.56 mmol) was dissolved in DCM (10 mL), TFA (3 mL) was added, the mixture was stirred at r.t. for 1 h. TLC showed Compound 33 was consumed. The mixture was concentrated under reduced pressure to give the desired product (Example 8f, 800 mg, yield 100%) as yellow oil, which was used for the next step without further purification.

Step 6: Example 8

Example 8f (800 mg, 3.96 mmol), Compound 1d (933 mg, 3.96 mmol), $K_2CO_3$ (1.6 g, 11.9 mmol) and KI (80 mg, 0.48 mmol) was added to DMF (20 mL), the mixture was stirred for 3 hrs under $N_2$ at 110° C. The residue was extracted with EtOAc (50 mL*2). The combined organic phase was washed with brine, dried over $Na_2SO_4$, filtrated and concentrated under reduced pressure to give the crude product which was further purified by silica gel chromatography to give the pure produce (Example 8, 600 mg, yield 100%) as yellow oil. MS $[M+1]^+=402$ $^1$H NMR (400 MHz, $CDCl_3$-d)) δ 11.91 (s, 1H), 10.39 (s, 1H), 7.51-7.36 (m, 3H), 7.19 (dd, J=5.9, 3.5 Hz, 1H), 6.59 (dd, J=8.3, 5.2 Hz, 2H), 5.73 (s, 2H), 1.84 (s, 6H).

Example 9: General Procedure for Synthesis of Example 9

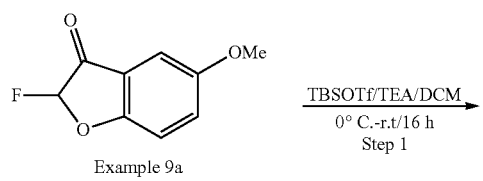

Example 9a

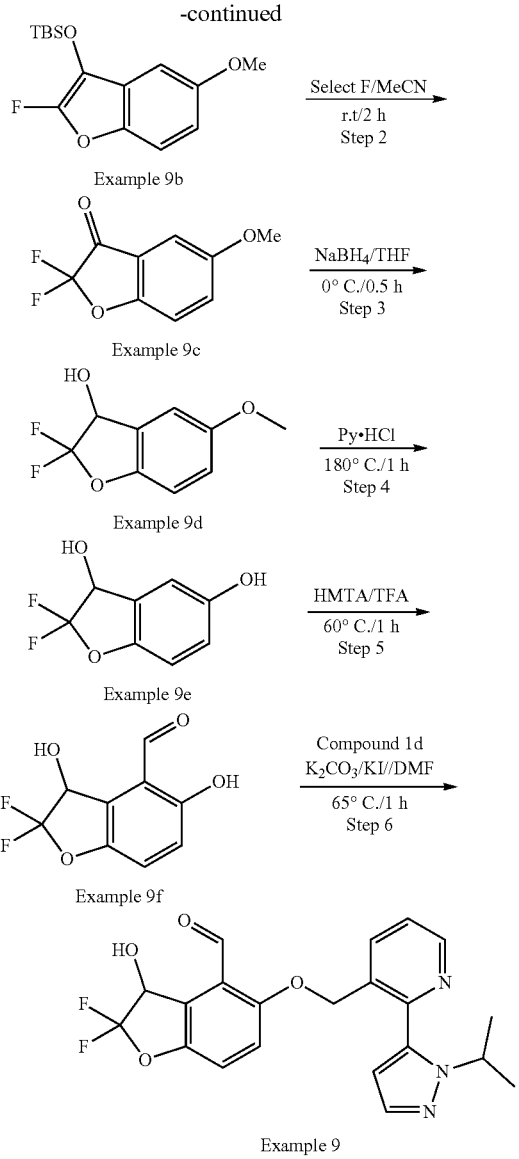

Step 1: Example 9b

To a solution of Example 9a (330 mg, 1.8 mmol, 1.0 eq) in DCM (13 mL) was added TEA (1.5 mL, 10.9 mmol, 6.0 eq) and then cooled to 0° C. under $N_2$ protection. Then TBSOTf (1.44 g, 5.5 mmol, 3.0 eq) was added dropwise and slowly warmed to r.t for 16 hrs. (Detected by TLC PE:EA=10:1). After the reaction was completed, the resulting mixture was diluted with DCM (20 mL), washed with sat. $NaHCO_3$, water and brine, dried over $Na_2SO_4$, concentrated under reduced pressure to give the desired product (Example 9b, 540 mg, yield 100%) as brown oil, which was used for the next step without further purification. MS $[M+1]^+=297$

Step 2: Example 9c

To a solution of Example 9b (540 mg, 1.8 mmol, 1.0 eq) in acetonitrile (22 mL) was added Select F (1.6 g, 4.6 mmol, 2.5 eq) and stirred at r.t. for 2 hrs. (Detected by TLC PE:EA=15:1). After the reaction was completed, the resulting mixture was concentrated under reduced pressure. The residue was extracted with DCM (100 mL), then washed with water (20 mL*2) and brine (20 mL), dried over Na₂SO₄, then concentrated under reduced pressure to give the desired product (Example 9c, 770 mg, yield 100%) as yellow oil, which was used for the next step without further purification. MS [M+1]=201

Step 3: Example 9d

To a solution of Example 9c (770 mg, 3.9 mmol, 1.0 eq) in dry THF (30 mL) was added sodium borohydride (292 mg, 7.7 mmol, 2.0 eq) at 0° C. and stirred for 0.5 hr. (Detected by TLC PE:EA=5:1). After the reaction was completed, the resulting mixture was quenched by adding sat. NH₄Cl (30 mL), extracted with EtOAc (100 mL). The combined organic phase was washed with brine (20 mL), dried over Na₂SO₄, concentrated under reduced pressure. The residue was purified by Prep-TLC to give the desired product (Example 9d, 350 mg, yield 45%) as yellow oil. MS [M+1]⁺=203

Step 4: Example 9e

To a mixture of Example 9d (300 mg, 1.5 mmol, 1.0 eq) and pyridine hydrochloride (6.9 g, 59.4 mmol, 40.0 eq) was heated to 180° C. and stirred for 1 hr under N₂ protection. (Detected by TLC PE/EA=3/1 and LCMS). After the reaction cooled to r.t., water (20 mL) was added to the resulting mixture and extracted with EA (80 mL). The combined organic phase was washed with brine, dried with Na₂SO₄, concentrated under reduced pressure to give the desired product (Example 9e, 417 mg, yield 100%), which was used for the next step without further purification. MS [M+1] =189

Step 5: Example 9f

To a solution of Example 9e (417 mg, 2.2 mmol, 1.0 eq) in TFA was added HMTA (1.2 g, 8.9 mmol, 4.0 eq) under N₂ protection and heated to 60° C. and stirred for 1 hr. (Detected by TLC PE/EA=5/1). After the reaction cooled to r.t., the solvent was removed under reduced pressure and the residue was diluted with EtOAc (10 mL), washed with sat. NaHCO₃ (30 mL) and brine (10 mL), dried over Na₂SO₄. Then concentrated under reduced pressure and purified by Prep-TLC to give the product (Example 9f, 42 mg, yield 9%). MS [M+1]⁺=217

Step 6: Example 9

To a mixture of Example 9f (37 mg, 0.17 mmol, 1.0 eq), Example 1d (45 mg, 0.18 mmol, 1.1 eq), potassium carbonate (94.5 mg, 0.68 mmol, 4.0 eq) and sodium iodide (2.5 mg, 0.017 mmol, 0.1 eq) in DMF (5 mL) was heated to 65° C. and stirred for 1 hr. After the reaction cooled to r.t., the solvent was removed under reduced pressure. The residue was diluted with EtOAc (25 mL), filtrated and concentrated under reduced pressure. The residue was purified by Prep-HPLC to give the desired product (Example 9, 14 mg, yield 20%) as white solid. MS [M+1]⁺=416.

¹H NMR (400 MHz, CDCl₃-d) δ 10.46 (s, 1H), 8.76 (dd, J=4.8, 1.7 Hz, 1H), 7.97 (dd, J=7.9, 1.7 Hz, 1H), 7.60 (d, J=1.8 Hz, 1H), 7.43 (dd, J=7.9, 4.8 Hz, 1H), 7.17 (m, 1H), 6.91 (d, J=9.0 Hz, 1H), 6.34 (d, J=1.9 Hz, 1H), 5.52 (dt, J=13.0, 3.5 Hz, 1H), 5.10 (s, 2H), 4.65 (p, J=6.6 Hz, 1H), 4.32 (s, 1H), 1.47 (d, J=6.6 Hz, 6H).

Example 10: General Procedure for Synthesis of Example 10

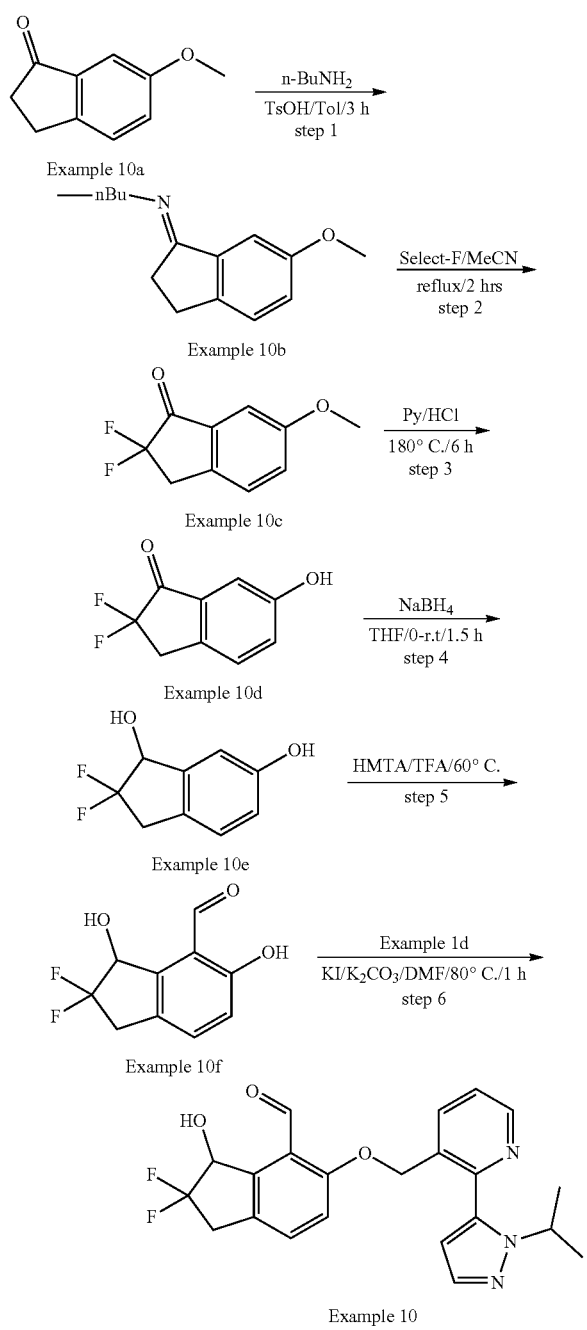

Step 1: Example 10b

A mixture of Example 10a (65 g, 0.4 mol) and butan-1-amine (100 g, 1.2 mol), TsOH (2 g, 0.01 mol) was stirred at 110° C. in toluene (600 mL) for 3 hrs. The reaction was quenched by water (1 L), and then extracted with EA (2 L), the organic phase was combined and concentrated to give the desired product (Example 10b, 100 g, yield 100%) as yellow oil. LCMS [M+1]$^+$=218.1

Step 2: Example 10c

A mixture of Example 10b (100 g, 0.5 mol) and select-F (358 g, 1 mol) was stirred at 80° C. in CH$_3$CN (600 mL) for 2 hrs. The reaction was quenched with water (2 L), the residue was extracted with EtOAc (2000 mL*2). The combined organic phase was washed with brine, dried over Na$_2$SO$_4$, filtrated and concentrated under reduced pressure to give the crude product which was further purified by silica gel chromatography to give the pure product (Example 10c, 60 g, yield 61%) as yellow oil. LCMS [M+1]$^+$=199.1

Step 3: Example 10d

A mixture of Example 10c (50 g, 0.4 mol) and Py/HCl (350 g, 4 mol) was stirred at 180° C. for 6 hrs. The reaction was quenched with water (2 L), then extracted with EA (2 L) combined the organic phase, washed with brine, dried with Na$_2$SO$_4$. The organic filtrate was concentrated in vacuum to give a brownish oil, purified by flash column chromatography (PE:EA=2:1) to give the desired product (Example 10d, 25 g, yield 34%) as yellow solid.

Step 4: Example 10e

To a solution of Example 10d (5 g, 0.027 mol, 1.0 eq) in THF (30 mL) was added NaBH$_4$ (2 g, 5.66 mmol, 2.0 eq) at ice temperature (0° C.), the mixture was then turned to room temperature and stirred for another 1.5 h. The reaction was quenched with water (20 mL), The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product (Example 10e, 5 g, yield 100%) as a yellow solid.

Step 5: Example 10f

To a mixture of Example 10e (1 g, 5 mmol) in TFA (10 mL) was added HMTA (3 g, 21 mmol), the mixture was stirred at 60° C. for 1 hr. The solvent was then removed under reduce pressure, the residue was further purified by silica gel chromatography (PE:EA=3:1) to give the desired product (Example 10f, 200 mg, yield 18%) as a white solid.

Step 6: Example 10

A mixture of Example 10f (500 mg, 2.33 mmol), Example 1d (500 mg, 1.84 mmol), potassium carbonate (1.3 g, 9.42 mmol) and KI (18 mg, 0.11 mmol) was stirred in DMF (8 mL) at 80° C. for 1 hrs, the reaction was quenched by water (12 mL), the reaction mixture was then extracted with EA (40 mL), the organic phase was combined and concentrated under reduced pressure to give 500 mg yellow oil as crude product, which was further purified by prep-HPLC to give the desired product Example 10 (230 mg, yield 6%) as a white solid. LCMS [M+1]$^+$=414.1.

$^1$H NMR (400 MHz, CDCl$_3$-d) δ 10.49 (s, 1H), 8.76 (dd, J=4.8, 1.7 Hz, 1H), 7.98 (dd, J=7.9, 1.7 Hz, 1H), 7.60 (d, J=2.0 Hz, 1H), 7.47-7.38 (m, 2H), 6.89 (d, J=8.5 Hz, 1H), 6.36-6.32 (m, 1H), 5.33 (dd, J=15.1, 2.9 Hz, 1H), 5.12 (s, 3H), 4.70-4.58 (m, 1H), 3.51-3.40 (m, 1H), 3.31 (dd, J=16.3, 7.7 Hz, 1H), 1.47 (d, J=6.7 Hz, 6H).

Example 11: General Procedure for Synthesis of Example 11

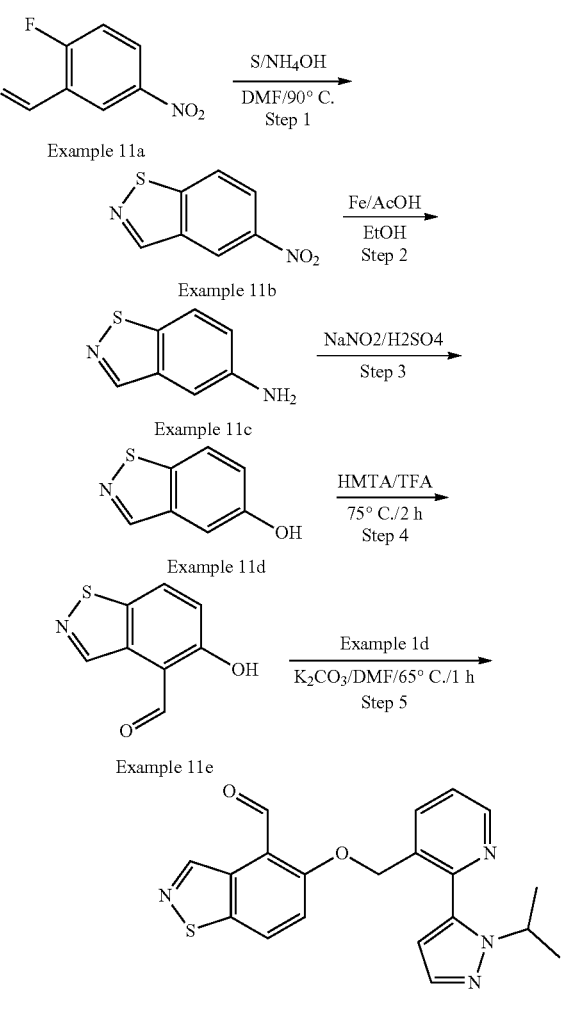

Step 1: Example 11b

To a solution of Example 11a (3.38 g, 20 mmol, 1.0 eq.) in DMF (12.25 mL) was treated with sulfur (672 mg, 21 mmol, 1.05 eq.) and NH$_4$OH (12.25 mL) at r.t., then heated at 90° C. for 3 hrs. TLC indicated the consumption of Example 11a and new spot generated, the mixture was added ice water, the precipitate was filtrate to afford the crude product (Example 11b, yield 100%), which was used for next step without further purification.

Step 2: Example 11c

To a solution of crude Example 11b in EtOH (20 mL) was added with iron powder (986 mg, 17.6 mmol, 3.2 eq.) and HCl (1 mL) in one batch, heated to reflux. TLC indicated the fully consumption of Example 11b. The mixture then firstly filtrated; the residue was extracted with EtOAc (50 mL*2).

The combined organic phase was washed with brine, dried over $Na_2SO_4$, filtrated and concentrated under reduced pressure to give the crude product which was further purified by silica gel chromatography to give the pure product (Example 1c, 1.85 g, yield 61.7%) as a yellow solid. LCMS $[M+H]^+=151.1$ Step 3: Example 11d $H_2SO_4$ added into water, then Example 11c (700 mg, 4.67 mmol) was added, heated to 90° C. for 2 hrs, afterwards cooled to 0° C., $NaNO_2$ solution (338 mg, 4.9 mmol, 1.05 eq.) was added to the previous mixture dropwise, then stirred at r.t. for a while, added this mixture to a mixture of water/$H_2SO_4$ (36 mL/3 mL) at 90° C. dropwise, then stirred for 2 hrs. The mixture then was hot filtrated; the residue was extracted with EtOAc (50 mL*2). The combined organic phase was washed with brine, dried over $Na_2SO_4$, filtrated and concentrated under reduced pressure to give the crude product which was further purified by silica gel chromatography to give the pure product (Example 1 d, 400 mg, yield 57%) as a white solid.

$^1$H NMR (400 MHz, DMSO-$d_6$) δ 9.80 (s, 1H), 8.91 (d, J=0.9 Hz, 1H), 7.97 (d, J=8.8 Hz, 1H), 7.44 (d, J=2.3 Hz, 1H), 7.11 (dd, J=8.8, 2.3 Hz, 1H). LCMS $[M+H]^+=152.1$.

Step 4: Example 11e

To a solution of Example 11d (18 mg, 0.12 mmol) in trifluoroacetic acid (1.0 mL) was added hexamethylenetetramine (34 mg, 0.24 mmol), the resulting mixture was refluxed at 80° C. for about 3 h. The reaction mixture was then cooled and poured into ice-water, and extracted with ethyl acetate. The organic layers were combined, dried over $Na_2SO_4$, filtered and concentrated under reduced pressure to give the crude desired product (Example 11e, 5 mg, yield 70%) as a yellow solid.

$^1$H NMR (400 MHz, $CDCl_3$-d) δ 12.00 (s, 1H), 10.67 (s, 1H), 9.29 (d, J=1.0 Hz, 1H), 8.08 (dd, J=9.0, 1.0 Hz, 1H), 7.24 (d, J=9.2 Hz, 1H). LCMS $[M+H]^+=180.1$

Step 5: Example 11

A mixture of Example 11e (66 mg, 0.368 mmol) and $K_2CO_3$ (200 mg, 1.44 mmol) in DMF (5 mL) was added Example 1d (120 mg, 0.44 mmol) at r.t. The mixture was heated at 65° C. for 1 h. Cooled to r.t., added HCl (2N) to pH=7, the residue was extracted with EtOAc (200 mL*2). The combined organic phase was washed with brine, dried over $Na_2SO_4$, filtrated and concentrated under reduced pressure to give the crude product which was further purified by silica gel chromatography to give the pure product Example 11 (65 mg, yield 46.7%) as white solid. LCMS $[M+H]^+=379.1$ $^1$H NMR (400 MHz, $CDCl_3$-d) δ 10.75 (s, 1H), 9.81 (d, J=1.0 Hz, 1H), 8.77 (dd, J=4.7, 1.7 Hz, 1H), 8.10 (dd, J=9.0, 1.0 Hz, 1H), 8.04 (dd, J=7.8, 1.7 Hz, 1H), 7.61 (d, J=1.8 Hz, 1H), 7.45 (dd, J=7.9, 4.8 Hz, 1H), 7.19 (d, J=9.0 Hz, 1H), 6.38 (d, J=1.9 Hz, 1H), 5.25 (s, 2H), 4.66 (p, J=6.6 Hz, 1H), 1.48 (d, J=6.6 Hz, 6H).

Example 12: General Procedure for Synthesis of Example 12

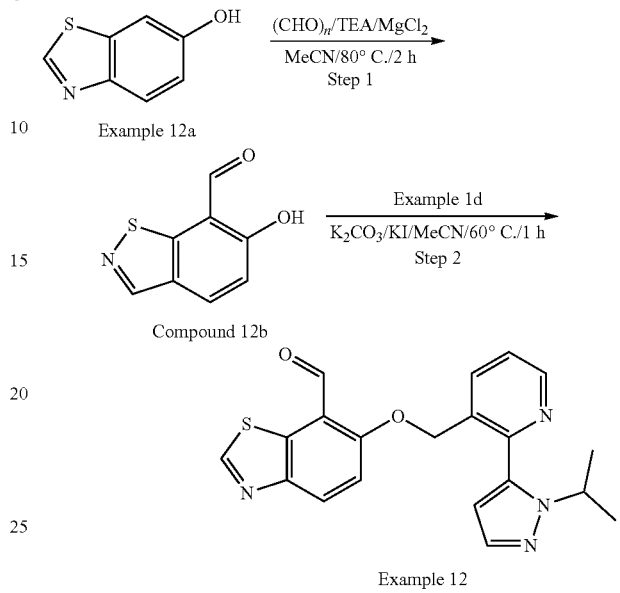

Step 1: Example 12b

Slurry of Example 12a (560 mg, 3.74 mmol) and acetonitrile (5 mL) was added to a three-necked bottle, to which paraformaldehyde (753 mg, 25.05 mmol), anhydrous magnesium chloride (532 mg, 5.59 mmol) and triethylamine (1.39 g, 13.8 mmol) were added in this order with stirring at room temperature. After refluxing for 2 hours, the reaction solution was poured into ice water, which was adjusted with aqueous HCl solution to a pH of 5, the residue was extracted with EtOAc (200 mL*2). The combined organic phase was washed with brine, dried over $Na_2SO_4$, filtrated and concentrated under reduced pressure to give the crude product which was further purified by silica gel chromatography to give the pure product (Example 12b, 200 mg, yield 53%). LCMS $[M+1]^+=180$ Step 2: Example 12

To a solution of Example 12b (150 mg, 0.586 mmol, 1.0 eq) in acetonitrile (4 mL) was added Example 1d (238 mg, 0.879 mmol, 1.5 eq), potassium carbonate (202 mg, 1.465 mmol, 2.5 eq) and potassium iodide (2 mg), then heated to 60° C. for 4 hrs. After cooled to room temperature, water (5 mL) was added to the mixture, the residue was extracted with EtOAc (200 mL*2). The combined organic phase was washed with brine, dried over $Na_2SO_4$, filtrated and concentrated under reduced pressure to give the crude product which was further purified by silica gel chromatography to give the pure product Example 12 (100 mg, yield 70%) as white solid. LCMS [M+1]=379

$^1$H NMR (400 MHz, $CDCl_3$-d) δ 10.69 (s, 1H), 9.03 (s, 1H), 8.77 (dd, J=4.8, 1.7 Hz, 1H), 8.28 (d, J=9.0 Hz, 1H), 8.04 (dd, J=7.9, 1.7 Hz, 1H), 7.61 (d, J=1.8 Hz, 1H), 7.44 (dd, J=7.9, 4.8 Hz, 1H), 7.13 (d, J=9.0 Hz, 1H), 6.39 (d, J=1.9 Hz, 1H), 5.26 (s, 2H), 4.68 (p, J=6.6 Hz, 1H), 1.49 (d, J=6.6 Hz, 6H).

Example 13: General Procedure for Synthesis of Example 13

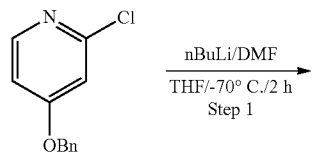

Example 13a

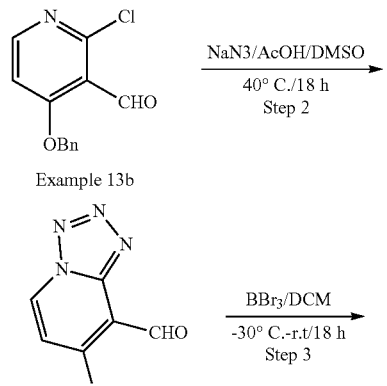

Example 13b

Example 13c

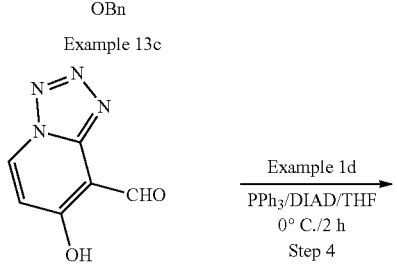

Example 13d

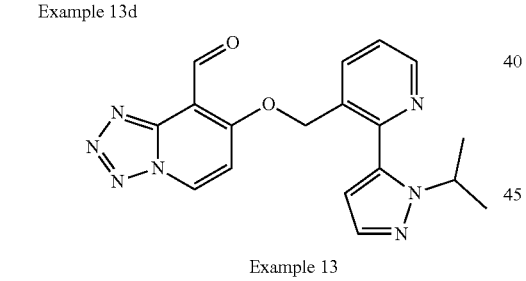

Example 13

Step 1: Example 13b

To a solution of Example 13a (7.9 g, 36.1 mmol) in anhydrous THF (80 mL) at −70° C. was added n-BuLi (16 mL 39.7 mmol) dropwise under the protection of nitrogen. After it was stirred at −70° C. for about 10 mins, dry DMF (4.0 g, 54.1 mmol) was added. The reaction was stirred at −40° C. for another 1 h, which was followed by quenched with NH$_4$Cl aqueous solution (40 mL 20%); the residue was extracted with EtOAc (100 mL*2). The combined organic phase was washed with brine, dried over Na$_2$SO$_4$, filtrated and concentrated under reduced pressure to give the crude product which was further purified by silica gel chromatography to give the pure product (Example 13b, 3 g, 12.1 mmol, yield 34%) as yellow oil.

Step 2: Example 13c

To a solution of Example 13b (3.0 g, 12.2 mmol) in DMSO (60 mL) was added NaN$_3$ (2.4 g 36.9 mmol) slowly, after that acetic acid (12 mL) and water (24 mL) was added with the protection of nitrogen. The reaction mixture was stirred at 40° C. overnight. Slightly yellow solid (Example 13c, 1.1 g, 4.3 mmol, yield 35%) was successfully obtained by filtration, which was directly used in the next step. LCMS [M+H]$^+$=255.1

Step 3: Example 13d

To a solution of Example 13c (0.60 g, 2.36 mmol) in DCM (20 mL) was added BBr$_3$/DCM (10 mL 1M) at −30° C. for 20 mins, the mixture was then allowed to stirred at room temperature for another 16 hrs. LCMS showed the reaction was completed. The reaction was then quenched by adding methanol (20 mL), the solvent was removed under vacuum and the residue was purified by column chromatography (DCM/MeOH=5/1) to give the desired product (Example 13d, 0.37 g, 2.26 mmol, yield 96%) as yellow solid which was used for the next step directly. LCMS [M+1]$^+$=165.1

Step 4: Example 13

To a solution of Example 13d (116 mg, 0.71 mmol), Example 1d (153 mg, 0.71 mmol), PPh$_3$ (0.37 g, 1.42 mmol) in THF (30 mL) was added DIAD (214 mg, 1.1 mmol) at 0° C. under the protection of nitrogen. The reaction was stirred at 0° C. for 2 hrs, TLC showed the reaction was completed, the solvent was then removed and the residue was then purified by prep HPLC to give Example 13 (75 mg, 0.21 mmol, yield 21.0%) as white solid.

MS [M+1]$^+$=364.1

$^1$H NMR (400 MHz, DMSO-d$_6$) δ 9.82 (s, 1H), 8.81 (d, J=8.0 Hz, 1H), 8.65 (dd, J=4.9, 1.3 Hz, 1H), 7.57 (m, 2H), 7.39 (dd, J=8.0, 4.9 Hz, 1H), 6.58 (m, 2H), 6.21 (s, 2H), 4.61-4.49 (m, 1H), 1.40 (d, J=6.6 Hz, 6H).

Example 14: General Procedure for Synthesis of Example 14

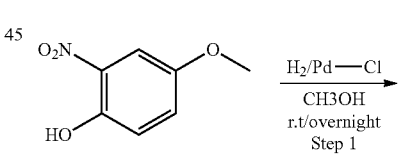

Example 14a

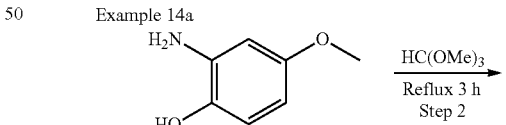

Example 14b

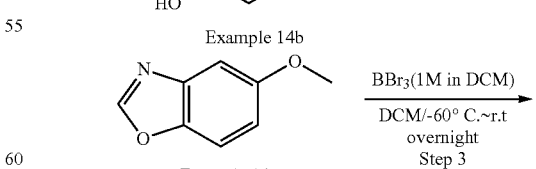

Example 14c

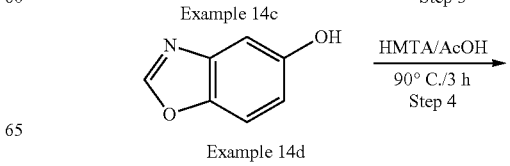

Example 14d

-continued

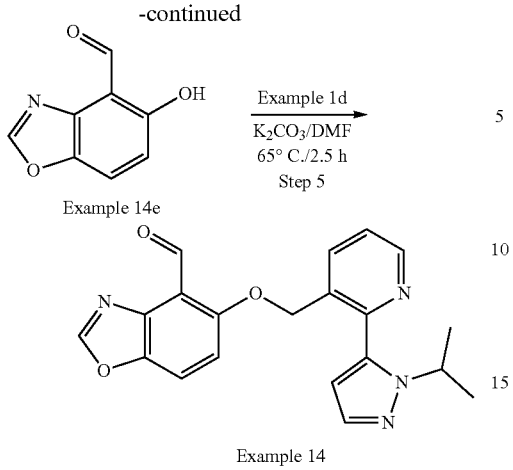

Step 1: Example 14b

A mixture of Example 14a (10 g, 59.1 mmol) and Pd/C (1 g 10%) was stirred under the hydrogen balloon in MeOH (500 mL) at r.t for 16 hrs. After the reaction (detected by TLC and LCMS) was completed, the black suspension was filtered through celite, and then concentrated at 45° C. under reduced pressure to give the desired product (Example 14b, 7 g, yield 85%) as brown solid. LCMS $[M+1]^+=140$

Step 2: Example 14c

To a solution of Example 14b (6 g, 43.1 mmol) in trimethylorthoformate (96 mL, 906 mmol) was heated to reflux for 3 hrs. After cooled to r.t, removed the solvent under reduced pressure, then purified by flash column chromatography (EA/PE=0-15%) to give the product (Example 14c, 5 g, yield 78%) as yellow solid. LCMS $[M+1]^+=150$

Step 3: Example 14d

To a solution of Example 14c (5 g, 33.6 mmol) in DCM (250 mL) was cooled to −60° C., then $BBr_3$ in DCM (42 g, 168 mmol, 150 mL) was added dropwise below −50° C. under $N_2$ protection and keep for 1.5 h. Then slowly warm to r.t. for 24 hrs. The reaction was quenched with MeOH (80 mL) at −50° C., then extracted with DCM (500 mL), washed with sat. $NaHCO_3$, water and brine, the organic layer was dried over $Na_2SO_4$, filtered, and the filtrate was then concentrated at 40° C. under reduced pressure to give the crude product (Example 14d, 1.7 g, yield 38%) as yellow solid. LCMS $[M+1]^+=136$

Step 4: Example 14e

To a mixture of Example 14d (500 mg, 3.7 mmol), hexamethylenetetramine (2.1 g, 14.8 mmol) and AcOH (100 mL) was heated to 90° C. under $N_2$ protection for 3 hrs. After the reaction was cooled to r.t, DCM (100 mL) was added, washed with water, brine, sat. $NaHCO_3$ and brine, dried over $Na_2SO_4$, filtered and the filtrate was then concentrated and purified by flash column chromatography to give the product (Example 14e, 80 mg, yield 13%) as yellow solid. LCMS $[M+1]^+=164$

Step 5: Example 14

To a mixture of Example 14e (60 mg, 0.37 mmol), Example 1d (95.4 mg, 0.4 mmol) and $K_2CO_3$ (203 mg, 1.47 mmol) in DMF (5 mL) was heated to 65° C. under $N_2$ protection for 2.5 hrs. After the reaction completed, poured into ice water (20 mL), the residue was extracted with EtOAc (20 mL*2). The combined organic phase was washed with brine, dried over $Na_2SO_4$, filtrated and concentrated under reduced pressure to give the crude product which was further purified by prep-HPLC to give the desired product Example 14 (51 mg, yield 38%) as white solid. LCMS $[M+1]^+=363$ $^1H$ NMR (400 MHz, $CDCl_3$-d) δ 10.79 (s, 1H), 8.75 (d, J=4.6 Hz, 1H), 8.25 (m, 2H), 7.74 (d, J=8.9 Hz, 1H), 7.63 (d, J=1.4 Hz, 1H), 7.49 (dd, J=7.9, 4.6 Hz, 1H), 6.95 (d, J=8.9 Hz, 1H), 6.40 (s, 1H), 5.16 (s, 2H), 4.62 (p, J=6.6 Hz, 1H), 1.48 (d, J=6.6 Hz, 6H).

Example 15: General Procedure for Synthesis of Example 15

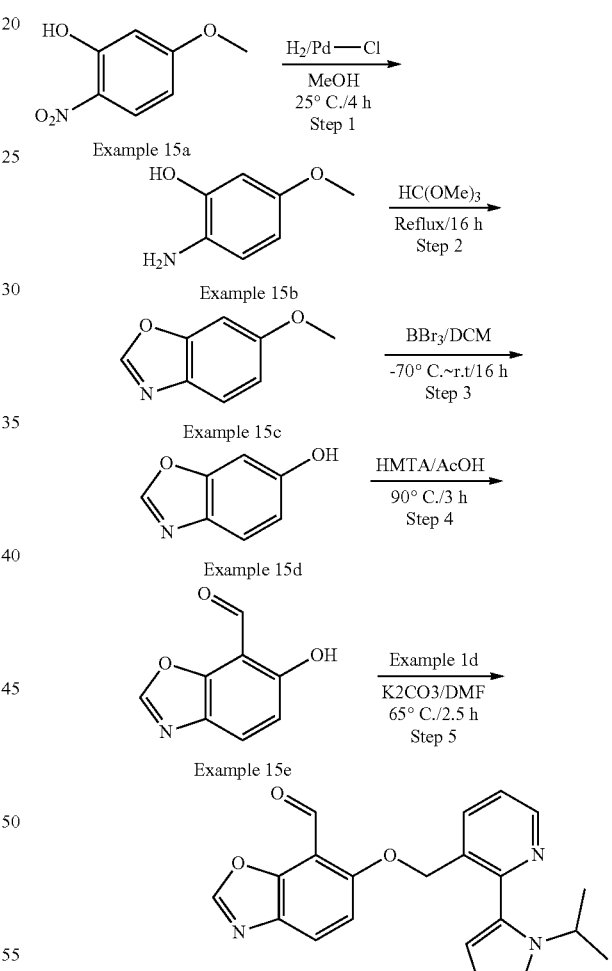

Step 1: Example 15b

A mixture of Example 15a (40 g, 230 mmol), Pd/C (4.0 g, 10%) was stirred under the hydrogen balloon (15 psi) in MeOH (600 mL) at 25° C. for 16 hrs. After the reaction (detected by TLC) was completed, the black suspension was filtered through celite, then concentrated at 45° C. under reduced pressure to give the desired product (Example 15b, 31.5 g, yield 95.7%) as brown solid. LCMS [M+1]⁺=140

Step 2: Example

To a solution of Example 15b (21.5 g, 154.5 mmol) in trimethylorthoformate (200 mL) was heated to reflux for 16 hrs. After cooled to r.t, the residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product (Example 15c, 14.0 g, yield 60.8%) as yellow solid. LCMS [M+1]⁺=150

Step 3: Example 15d

To a solution of Example 15c (4.0 g, 26.81 mmol) in DCM (100 mL) was cooled to −70° C., then the solution of BBr$_3$ (7.5 mL, 80.45 mmol) was added dropwise below −60° C. under N$_2$ protection and keep for 30 min, then slowly warmed to r.t for 16 hrs. (Detected by TLC PE:EA=3:1) The reaction was quenched with MeOH (15 mL) at −50° C. and diluted with H$_2$O (100 mL) and separated, then extracted with DCM (300 mL), combined the organic phase, and washed with sat. NaHCO$_3$ (450 mL), brine (300 mL), dried with Na$_2$SO$_4$, filtered and concentrated at 40° C. under reduced pressure, the residue was purified by silica gel chromatography (eluted with DCM/MeOH=20/1) to give the desired product (Example 15d, 1.0 g, yield 27.6%) as yellow solid. LCMS [M+1]⁺=136

Step 4: Example 15e

To a mixture of Example 15d (1.0 g, 7.4 mmol) in AcOH (30 mL) was added HMTA (4.15 g, 29.6 mmol) at room temperature, the reaction mixture was heated to 80° C. under N$_2$ protection for 2 hrs. After the reaction cooled to r.t., EtOAc (50 mL) was added to the mixture, then washed with water (30 mL*3), sat. NaHCO$_3$ (30 mL*3) and brine (30 mL*3), dried over Na$_2$SO$_4$, filtrated and concentrated under reduced pressure to give the crude product which was further purified by silica gel chromatography to give the pure product (Example 15e, 40 mg, yield 3.33%) as a yellow solid. LCMS [M+1]⁺=164

Step 5: Example 15

To a suspension of Example 15e (40 mg, 0.24 mmol), Example 1d (57 mg, 0.24 mmol) and K2CO3 (135 mg, 0.98 mmol) in DMF (5 mL) was heated to 60° C. and stirred for 1.5 hrs under N$_2$. (Detected by LCMS) After the reaction completed, poured into ice water (20 mL), extracted with EtOAc (20 mL*3) and combined, washed with water, brine and dried with Na$_2$SO$_4$, filtered and the filtrate was concentrated, the residue was purified by prep-HPLC to afford the product Example 15 (25 mg, yield 28%) as yellowy solid. LCMS [M+1]⁺=363.

$^1$H NMR (400 MHz, CDCl$_3$-d) δ 10.60 (s, 1H), 8.77 (s, 1H), 8.15 (s, 1H), 8.07 (s, 1H), 7.92 (d, J=7.1 Hz, 1H), 7.61 (s, 1H), 7.45 (s, 1H), 6.95 (d, J=8.1 Hz, 1H), 6.38 (s, 1H), 5.21 (s, 2H), 4.66 (s, 1H), 1.48 (d, J=5.3 Hz, 6H).

Example 16: General Procedure for Synthesis of Example 16

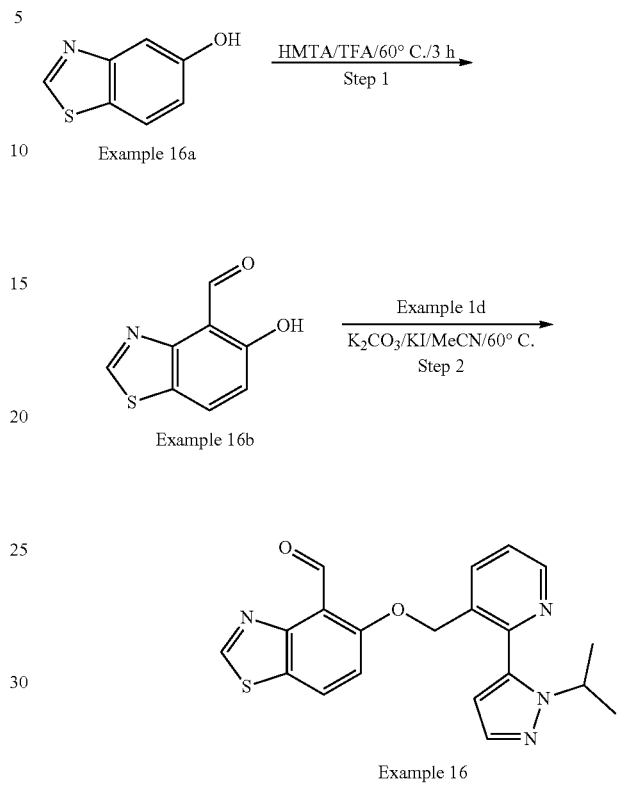

To a mixture of Example 16a (800 mg, 5.29 mmol) in TFA (10 mL) was added HMTA (2.9 g, 21.19 mmol), the mixture was stirred at 60° C. for 4 hr, and then turned to room temperature for another 6 hrs. The residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product (Example 16b, 80 mg, yield 10%) white solid. LCMS [M+1]=180

Step 2: Example 16

To a solution of Example 16b (50 mg, 0.21 mmol, 1.0 eq) in acetonitrile (1 mL) was added Example 1d (45 mg, 0.25 mmol, 1.2 eq), potassium carbonate (72 mg, 0.5 mmol, 2.5 eq) and potassium iodide (1 mg), then heated to 60° C. for 4 hrs. After cooled to room temperature, water (2 mL) was added to the mixture, then extracted with EA (10 mL*2) and combined the organic phase, washed with brine, dried with (Na$_2$SO$_4$), filtered and concentrated under reduced pressure to give a crude product (80 mg) which was further purified by Prep-HPLC to give the desired product Example 16 (20 mg, yield 50%) as white solid. LCMS [M+1]=379

$^1$H NMR (400 MHz, CDCl$_3$-d) δ 11.08 (s, 1H), 9.20 (s, 1H), 8.72 (s, 1H), 8.34 (d, J=7.9 Hz, 1H), 8.08 (d, J=9.0 Hz, 1H), 7.63 (s, 1H), 7.50-7.43 (m, 1H), 7.08 (d, J=8.9 Hz, 1H), 6.39 (s, 1H), 5.20 (s, 2H), 4.67-4.59 (m, 1H), 1.48 (s, 3H), 1.46 (s, 3H).

Example 17: General Procedure for Synthesis of Example 17

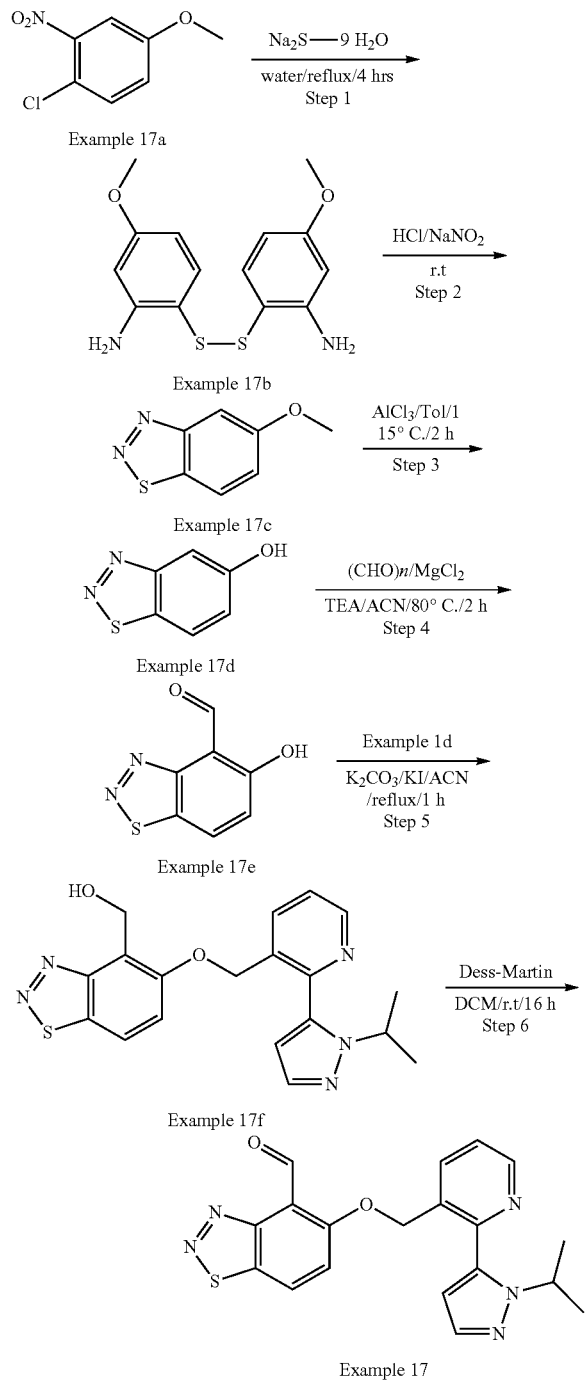

Step 1: Example 17b

To a solution of Na₂S (44.6 g, 0.18 mol) in Water (120 mL), then Example 17a (11.6 g, 0.062 mol) was added, the mixture was stirred at 100° C. for 1 h, then cooled to r.t., AcOH (50 mL) was added and extracted with EA (100 mL*2), the organic layer was washed with brine (200 mL), dried over Na₂SO₄, and concentrated, the residue was puri- fied by flash column chromatography to afford the desired product (Example 17b, 11.2 g, yield 100%) as yellow solid.

Step 2: Example 17c

To a mixture of Example 17b (11.2 g, 0.062 mol) in water (20 mL) was added aqueous 0.2 N hydrochloric acid (850 mL, 0.13 mol) slowly at r.t., sodium nitrite (6.5 g, 0.094 mol) was then added slowly at r.t., the reaction was stirred at r.t. for 30 min. The residue was extracted with EtOAc (200 mL*2). The combined organic phase was washed with brine, dried over Na₂SO₄, filtrated and concentrated under reduced pressure to give the crude product which was further purified by silica gel chromatography to give the pure product (Example 17c, 2.4 g, yield 22%) as colorless solid.

Step 3: Example 17d

To a solution of Example 17c (460 mg, 2.77 mmol) in toluene (10 mL) was added AlCl₃ (1.1 g, 8.31 mmol) at r.t., the reaction mixture was heated to 115° C. for 2 hours. After cooled to r.t, water (50 mL) and EA (50 mL) were added, the mixture was stirred at r.t. for 20 min, the organic layer was washed with water (20 mL*2) brine (20 mL), dried over Na₂SO₄ and concentrated, purified by flash column chromatography to afford the desired product (Example 17d, 350 mg, yield 83%) as yellow solid.

Step 4: Example 17e

A slurry of Example 17d (230 mg 1.51 mmol) and acetonitrile (3 mL) were added to a three-necked bottle, to which paraformaldehyde (304 mg 10.14 mmol), anhydrous magnesium chloride (532 mg 5.59 mmol) and triethylamine (229 mg 2.27 mmol) were added in this order with stirring at room temperature. After refluxing for 2 hours, the reaction solution was poured into ice water, which was adjusted with aqueous HCl solution to a pH of 5, the residue was extracted with EtOAc (20 mL*2). The combined organic phase was washed with brine, dried over Na₂SO₄, filtrated and con- centrated under reduced pressure to give the crude product which was further purified by silica gel chromatography to give the pure product (PE:ethyl acetate=5:1) to give the product (Example 17e, 200 mg, yield 73%). LCMS [M+1]⁺=181

Step 5: Example 17f

A slurry of Example 17e (200 mg, 1.11 mmol), Example 1d (300 mg, 1.11 mmol), K₂CO₃ (306 mg, 2.02 mmol), KI (18 mg, 0.11 mmol) were suspended in acetonitrile (2.2 mL), the mixture was heated to reflux for 1 hr, then cooled to r.t, EA (50 mL) was added, filtered and concentrated under reduced pressure, the residue was purified by flash column chromatography (PE:EA=2:1) to give the desired product (Example 17f, 130 mg, yield 64%) as white solid. LCMS [M+1]⁺=381

Step 6: Example 17

A solution of Example 17f (100 mg, 0.26 mmol) in DCM (2.6 mL), was treated with Dess-martin (557 mg, 1.31 mmol), then stirred at r.t. under N₂ overnight. LCMS detected Example 17f was consumed and TM was formed, filtered and concentrated to give 160 mg crude as a colorless oil, purified by Prep-HPLC Example 17 (54 mg, yield 55%) was obtained as yellow solid. LCMS [M+1]⁺=380

$^1$H NMR (400 MHz, DMSO-d$_6$) δ 10.90 (s, 1H), 8.74 (dd, J=4.7, 1.5 Hz, 1H), 8.65 (d, J=9.1 Hz, 1H), 8.30 (dd, J=7.9, 1.3 Hz, 1H), 7.79 (d, J=9.2 Hz, 1H), 7.57 (dd, J=7.8, 4.8 Hz, 1H), 7.51 (d, J=1.7 Hz, 1H), 6.58 (d, J=1.8 Hz, 1H), 5.39 (s, 2H), 4.64 (dd, J=13.2, 6.6 Hz, 1H), 1.33 (d, J=6.6 Hz, 6H).

Example 18: General Procedure for Synthesis of Example 18

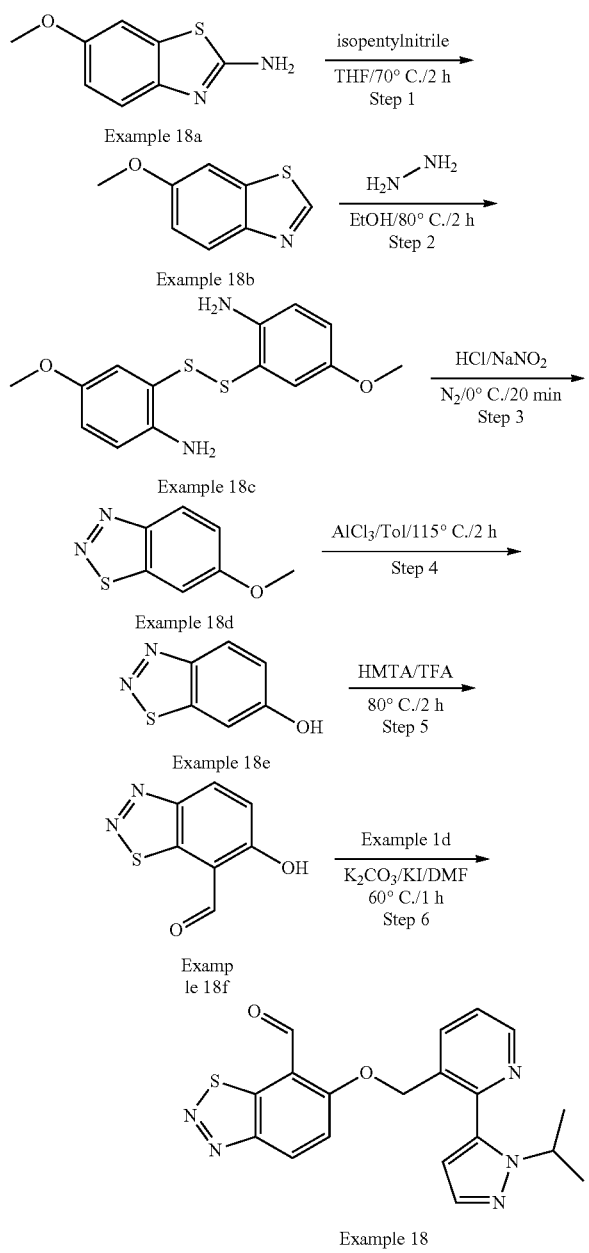

Step 1: Example 18b

To a solution of Example 18a (11.7 g, 0.065 mol) in THF (100 mL), then isopentylnitrite (15.2 g, 0.13 mol) was added under nitrogen, the mixture was stirred at 70° C. for 2 h. Then water (500 mL) was added, extracted with EA (500 mL*2), the organic layer was washed with brine (200 mL), dried over Na$_2$SO$_4$, filtered and the filtrate was concentrated, purified by flash column chromatography to give the desired product (Example 18b, 10.2 g, yield 95%) as colorless oil. LCMS [M+1]$^+$=166

Step 2: Example 18c

A solution of Example 18b (10.2 g, 0.062 mol) in ethanol (10 mL) was treated with hydrazine monohydrate (31 g, 0.62 mol). The reaction mixture was stirred for 3 hrs at 80° C. and concentrated to give a crude product (Example 18c, 10 g, yield 90%) as yellow solid. LCMS [M+1]$^+$=309

Step 3: Example 18d

To a mixture of Example 18c (10 g, 0.065 mol) in water (20 mL) was added aqueous 0.5 N hydrochloric acid (258 mL, 0.13 mol) slowly at r.t., sodium nitrite (827 mg, 12.0 mmol) was then added slowly at r.t., and the reaction was stirred at r.t for 30 min. The residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product (Example 18d, 2.1 g, yield 19%) as colorless solid. LCMS [M+1]$^+$=167

Step 4: Example 18e

To a solution of Example 18d (444 mg, 2.67 mmol) in Tol (10 mL) was added AlCl$_3$ (1.1 g, 8.02 mmol) at r.t. After addition, the reaction mixture was heated to 115° C. for 2 h. Water (50 mL) and EA (50 mL) were added, the organic layer was washed with water (20 mL*2), brine (20 mL), dried over Na$_2$SO$_4$, filtered and concentrated, purified by flash column chromatography to give the desired product (Example 18e, 370 mg, yield 91%) as yellow solid. LCMS [M+1]$^+$=153

Step 5: Example 18f

Example 18e (320 mg, 2.11 mol) in TFA (10 mL) was added HMTA (590 mg, 4.21 mmol), the reaction mixture was allowed stirred at 80° C. for 2 h. TLC showed SM was consumed, then concentrated to give (Example 18f, 300 mg, yield 78%) as yellow solid. LCMS [M+1]$^+$=181 $^1$H NMR (400 MHz, DMSO-d$_6$) δ 10.20 (s, 1H), 8.31 (d, J=9.3 Hz, 1H), 6.92 (d, J=9.3 Hz, 1H).

Step 6: Example 18

A slurry of Example 18f (300 mg, 1.67 mmol), Example 1d (452 mg, 1.67 mmol), K$_2$CO$_3$ (690 mg, 5.0 mmol), KI (28 mg, 0.17 mmol) were suspended in acetonitrile (10 mL), the mixture was heated to reflux for 1 hr, then cooled to r.t., EA (50 mL) was added, filtered and concentrated under reduced pressure, the residue was purified by flash column chromatography (PE:EA=2:1) to give 220 mg crude product, which was further purified by Prep-HPLC to obtain Example 18 (15 mg, yield 3%). LCMS [M+1]$^+$=380

$^1$H NMR (400 MHz, DMSO-d$_6$) δ 10.40 (s, 1H), 9.00 (d, J=9.2 Hz, 1H), 8.75 (d, J=3.6 Hz, 1H), 8.28 (d, J=7.4 Hz, 1H), 7.71 (d, J=9.2 Hz, 1H), 7.56 (dd, J=7.8, 4.8 Hz, 1H), 7.51 (d, J=1.1 Hz, 1H), 6.58 (d, J=1.4 Hz, 1H), 5.52 (s, 2H), 4.66-4.60 (m, 1H), 1.32 (d, J=6.5 Hz, 6H).

Example 19: General Procedure for Synthesis of Example 19

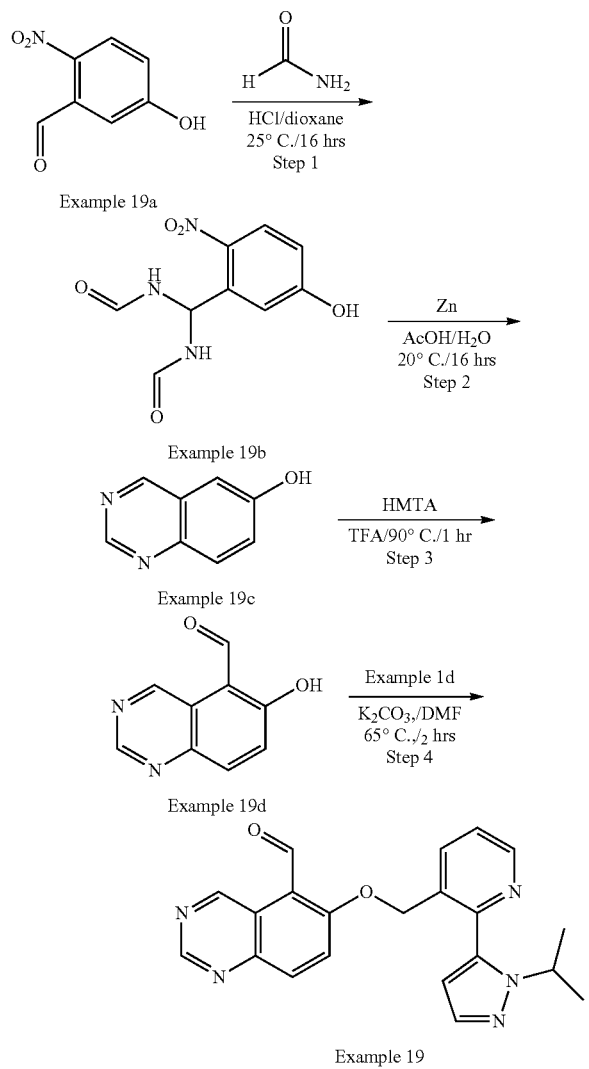

To a solution of Example 19a (20 g, 120 mmol) in formamide (80 mL) was added HCl (100 mL, 4.0M in Dioxane) at 25° C., the solid was dissolved and the reaction mixture was stirred for 16 hrs at 25° C. LCMS showed the starting material was consumed completely, ice-water was added and adjusted to pH 4 with 30% NaOH solution and filtered, and the filter cake was washed with $H_2O$ and dried in vacuum to afford the product (Example 19b, 26.75 g, yield 93.4%) as yellow solid. LCMS $[M+1]^+=240$

Step 2: Example 19c

To a suspension of Example 19b (21.75 g, 91 mmol) and Zn (68.43 g, 1.04 mol) in ice water (450 mL) was added AcOH (87.36 g, 1.45 mol) slowly at 20° C., the yellow suspension was stirred for 30 min, Zn (26.77 g, 409.5 mmol) was added and the suspension was stirred at 20° C. for 16 hrs. LCMS showed the starting material was consumed completely, the reaction mixture was filtered and the filter cake was washed with $H_2O$ (50 mL*2) and the filtrate was concentrated. The residue was dissolved in $H_2O$ and adjusted to pH 5 with sat. aq. $NaHCO_3$ and extracted with (DCM/i-PrOH=3/1 200 mL*6) to afford the product (Example 19c, 11.7 g, yield 88%) as yellow solid. LCMS $[M+1]^+=147$

Step 3: Example 19d

To a yellow solution of Example 19c (500 mg, 3.42 mmol) dissolved in TFA (20 mL) was added HMTA (1.92 g, 13.7 mmol) at room temperature under $N_2$, the yellow reaction mixture was stirred at 90° C. for 1 hr. TLC (DCM/MeOH=10/1) showed the starting material was consumed completely, the reaction mixture was cooled to room temperature and diluted with EtOAc (30 mL) and washed with $H_2O$ (20 mL*3), brine (20 mL), dried over $Na_2SO_4$, filtered and concentrated. The residue was purified by flash-column chromatography eluted with EA/PE (50%-100%) to afford the product (Example 19d, 60 mg, yield 10%) as yellow solid. LCMS $[M+1]^+=175$

Step 4: Example 19

A mixture of Example 19d (60 mg, 0.34 mmol), Example 1d (81 mg, 0.34 mmol) and $K_2CO_3$ (94 mg, 0.68 mmol) in DMF (2 mL) was heated to 65° C. for 2 h. LCMS showed the starting material was consumed completely, the reaction mixture was cooled to room temperature and filtered, the filter cake was washed with EA (10 mL*3), the filtrate was concentrated and purified by prep-HPLC to afford Example 19 (12 mg, yield 10%) as white solid. LCMS $[M+1]^+=374$ $^1$H NMR (400 MHz, CDCl3-d) δ 10.53 (s, 1H), 10.38 (s, 1H), 9.26 (s, 1H), 8.75 (s, 1H), 8.32 (d, J=8 MHz, 1H), 8.24 (d, J=8 MHz, 1H), 8.06 (d, J=8 MHz, 1H), 7.58-7.52 (m, 2H), 6.56 (s, 1H), 5.49 (s, 2H), 4.67-4.6 (m, 1H), 1.3 (d, J=4.0 MHz, 6H).

Example 20: General Procedure for Synthesis of Example 20

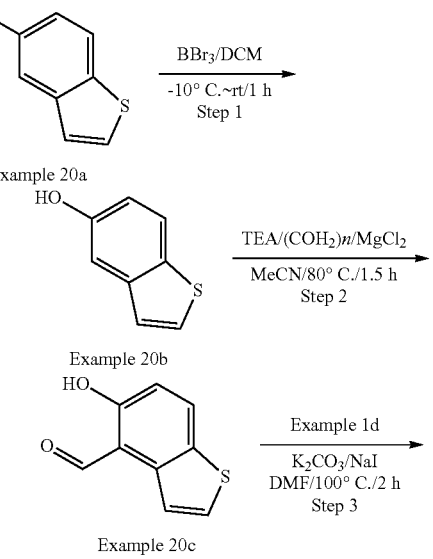

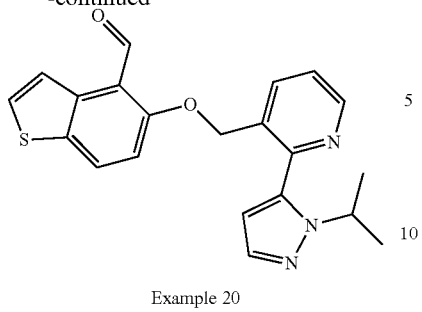

Example 20

Step 1: Example 20b

To a solution of Example 20a (1.5 g, 9.14 mmol, 1.0 eq) in DCM (20 mL) was added dropwise BBr₃ (36.6 ml, 36.6 mmol, 4.0 eq, 1M in DCM) at −10° C. under N₂. The mixture was stirred at this temperature for 30 min, and then warmed to r.t. for 1 h. The reaction was quenched with MeOH at −5° C. The mixture was extracted with DCM (50 mL) and water. The organic layer was washed with aq. NaHCO₃, dried over Na₂SO₄ and concentrated. The residue was purified by flash column chromatography (PE:EA=4:1) to give the desired product (Example 20b, 1 g, yield 73%, as a yellow solid).

MS [M+1]⁺=151.0

Step 2: Example 20c

To a solution of Example 20b (50 mg, 0.33 mmol, 1.0 eq) in MeCN (2 mL) was added TEA (114 mg, 1.13 mmol, 3.4 eq), (CH₂O) (68 mg, 2.27 mmol, 6.8 eq) and MgCl₂ (51 mg, 0.53 mmol, 1.6 eq). The mixture was stirred at 80° C. for 1.5 h. The reaction mixture was acidified by 0.5M HCl to pH=5-6, and extracted with EA (20 mL). The organic layer was dried Na₂SO₄ and concentrated. The residue was purified by Pre-TLC (PE:EA=3:1) to give the product (Example 20c, 10 mg, yield 17%) as a yellow solid. LCMS [M+1]⁺=179.0

Step 3: Example 20

To a solution of Example 20c (10 mg, 0.056 mmol, 1.0 eq) in DMF (1 mL) was added Example 1d (13 mg, 0.056 mmol, 1.0 eq), K₂CO₃ (23 mg, 0.17 mmol, 3.0 eq) and NaI (2 mg, 0.017 mmol, 0.3 eq). The mixture was stirred at 100° C. for 2 h. The reaction mixture was extracted with EA (10 mL) and H₂O. The organic layer was dried over Na₂O₄ and concentrated. The residue was purified by Pre-HPLC to give the product Example 20 (10 mg, yield 47%) as a white solid. LCMS [M+1]⁺=378.1 ¹H NMR (400 MHz, CDCl₃-d) δ 10.77 (s, 1H), 8.75 (dd, J=4.8, 1.7 Hz, 1H), 8.41 (dd, J=5.5, 0.8 Hz, 1H), 8.05 (dd, J=7.9, 1.7 Hz, 1H), 7.99 (dd, J=8.9, 0.8 Hz, 1H), 7.71 (d, J=5.5 Hz, 1H), 7.61 (d, J=1.9 Hz, 1H), 7.43 (dd, J=7.9, 4.8 Hz, 1H), 6.95 (d, J=8.9 Hz, 1H), 6.39 (d, J=1.9 Hz, 1H), 5.19 (s, 2H), 4.66 (p, J=6.6 Hz, 1H), 1.48 (d, J=6.6 Hz, 6H).

Example 21: General Procedure for Synthesis of Example 21

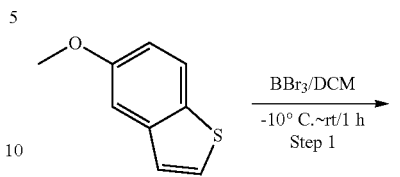

Example 21a

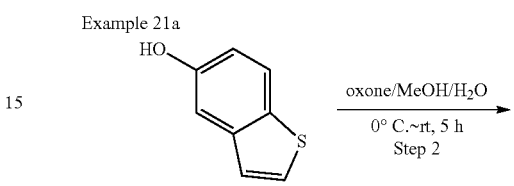

Example 21b

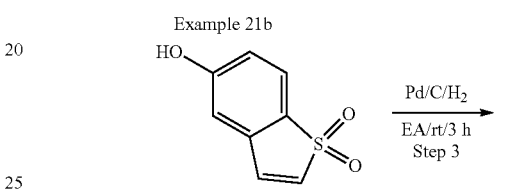

Example 21c

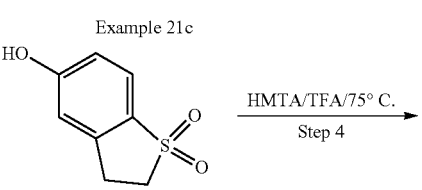

Example 21d

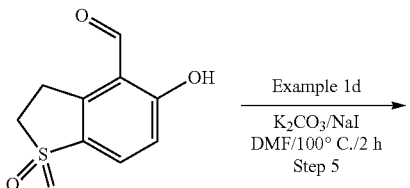

Example 21e

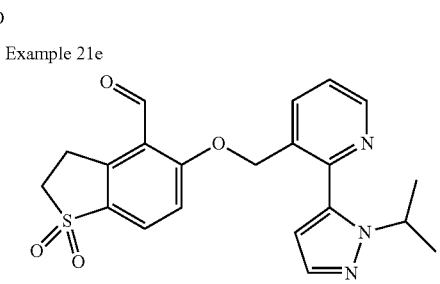

Example 21

Step 1: Example 21b

To a solution of Example 21a (1.5 g, 9.14 mmol, 1.0 eq) in DCM (20 mL) was added dropwise BBr₃ (36.6 ml, 36.6 mmol, 4.0 eq, 1M in DCM) at −10° C. under N₂. The mixture was stirred at this temperature for 30 min, and then warmed to r.t. for 1 h. The reaction was quenched with MeOH at −10° C. The residue was extracted with DCM (50 mL*2). The combined organic phase was washed with brine, dried over Na₂SO₄, filtrated and concentrated under reduced pressure to give the crude product which was further purified by silica gel chromatography to give the pure product (Example 21b, 1 g, yield 73%, as a yellow solid). LCMS [M+1]$^+$=151.0

Step 2: Example 21c

To a solution of oxone (1.8 g, 3.0 mmol, 1.5 eq) in H$_2$O (15 mL) was added dropwise a solution of Example 21b (300 mg, 2.0 mmol, 1.0 eq) in MeOH (15 mL) over 5 minutes under ice-cooling. After stirring at r.t. for 5 hrs, the residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product (Example 21c, 280 mg, yield 77%) as a white solid. LCMS [M+1]$^+$=183.0

Step 3: Example 21d

To a solution of Example 21c (100 mg, 0.55 mmol, 1.0 eq) in EA (10 mL) was added Pd/C (10 mg). The mixture was stirred under H$_2$ balloon at r.t. for 3 h. The reaction mixture was filtered. The filtrate was concentrated to give the crude product (Example 21d, 100 mg, yield 99%) as a white solid. LCMS [M+1]$^+$185.0

Step 4: Example 21e

To a solution of Example 21d (150 mg, 0.82 mmol, 1.0 eq) in TFA (4 mL) was added HMTA (137 mg, 0.98 mmol, 1.2 eq). The mixture was stirred at 75° C. overnight under N$_2$. Added 3M HCl (5 mL) and stirred at r.t. for 30 min. The resulting mixture was extracted with DCM (20 mL) and H$_2$O. The organic layer was dried over Na$_2$SO$_4$ and concentrated. The residue was purified by Pre-TLC (PE:EA=1: 1) to give the product (Example 21e, 23 mg, yield 13%) as a yellow solid. LCMS [M+1]$^+$=213.0

Step 5: Example 21

To a solution of Example 21e (23 mg, 0.11 mmol, 1.0 eq) in DMF (1.5 mL) was added Example 1d (26 mg, 0.11 mmol, 1.0 eq), K$_2$CO$_3$ (45 mg, 0.32 mmol, 3.0 eq) and NaI (5 mg, 0.032 mmol, 0.3 eq). The mixture was stirred at 100° C. for 2 hrs. The residue was extracted with EtOAc (10 mL*2). The combined organic phase was washed with brine, dried over Na$_2$SO$_4$, filtrated and concentrated under reduced pressure to give the crude product which was further purified by Pre-HPLC to give the product Example 21 (3 mg, yield 7%) as a white solid. LCMS [M+1]$^+$=412.1

$^1$H NMR (400 MHz, DMSO-d$_6$) δ 10.32 (s, 1H), 8.74 (dd, J=4.8, 1.7 Hz, 1H), 8.20 (dd, J=7.9, 1.7 Hz, 1H), 8.00 (d, J=8.7 Hz, 1H), 7.58-7.49 (m, 2H), 7.36 (d, J=8.8 Hz, 1H), 6.53 (d, J=1.9 Hz, 1H), 5.34 (s, 2H), 4.63 (p, J=6.5 Hz, 1H), 3.56 (s, 4H), 1.33 (d, J=6.6 Hz, 6H).

Example 22: General Procedure for Synthesis of Example 22

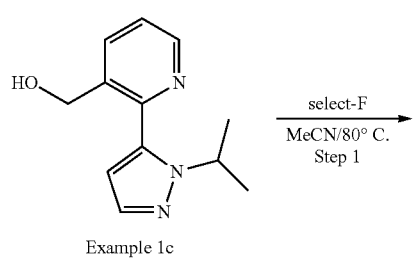

Example 1c

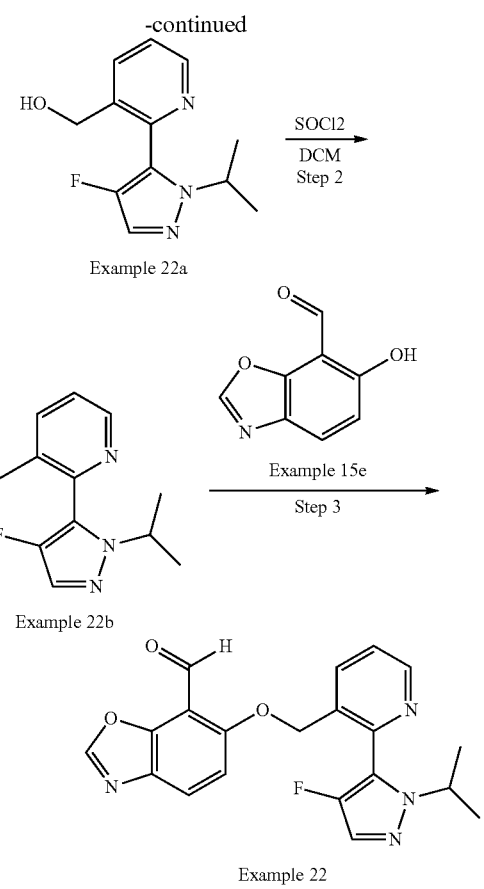

Step 1: Example 22a

A solution of Example 1c (217 mg, 1.0 mmol) in CH$_3$CN (5 mL) was treated with Select Fluor (531 mg, 1.5 mmol) and the reaction mixture was heated at 80° C. for 4 hours. After cooling to room temperature the solution was evaporated and the residue was purified on silica gel using a mixture of (PE:EA=100:30) as eluent to give the desired product (Example 22a, 157 mg, yield 54.7%) as a white solid.

$^1$H NMR (400 MHz, CDCl$_3$) δ 8.60 (dd, J=4.8, 1.7 Hz, 1H), 8.00 (dd, J=7.9, 1.7 Hz, 1H), 7.41-7.33 (m, 2H), 4.60 (s, 2H), 4.41 (p, J=6.6 Hz, 1H), 1.36 (d, J=6.7 Hz, 6H). LCMS [M+H]$^+$=236.1.

Step 2: Example 22b

To Example 22a (157 mg, 0.668 mmol) in DCM (5 mL) was added SOCl$_2$ (0.5 mL) at r.t. The reaction mixture was stirred at r.t. for 0.5 h and concentrated to dryness. The crude solid was suspended in toluene and concentrated to dryness to give the desired product (Example 22b, 165 mg) as yellow solid, which was used for next step without further purification. LCMS [M+H]$^+$=254.1.

Step 3: Example 22

A mixture of δ-hydroxybenzo[d]oxazole-7-carbaldehyde (Example 15e, 82 mg, 0.5 mmol) and K$_2$CO$_3$ (210 mg, 1.5 mmol) in DMF (10 mL) was added Example 22b (145 mg, 0.5 mmol) at r.t. The mixture was heated at 80° C. for 1.5 h, Cooled to r.t. Added water (25 mL) and extracted with EtOAc (50 mL*3). The combined organic layers were washed with brine, dried over Na₂SO₄, concentrated, and purified on silica gel using a mixture of (PE:EA=100:30) as eluent to give the desired product Example 22 (71 mg, yield 37%) as an white solid. LCMS [M+H]⁺=381.1.

¹H NMR (400 MHz, CDCl₃-d) δ 10.60 (s, 1H), 8.77 (dd, J=4.8, 1.7 Hz, 1H), 8.14 (s, 1H), 8.11 (dd, J=8.0, 1.7 Hz, 1H), 7.92 (d, J=8.9 Hz, 1H), 7.47 (dd, J=7.4, 4.7 Hz, 2H), 6.97 (d, J=8.9 Hz, 1H), 5.28 (s, 2H), 4.64 (p, J=6.6 Hz, 1H), 1.45 (d, J=6.6 Hz, 6H).

Example 23: General Procedure for Synthesis of Example 23

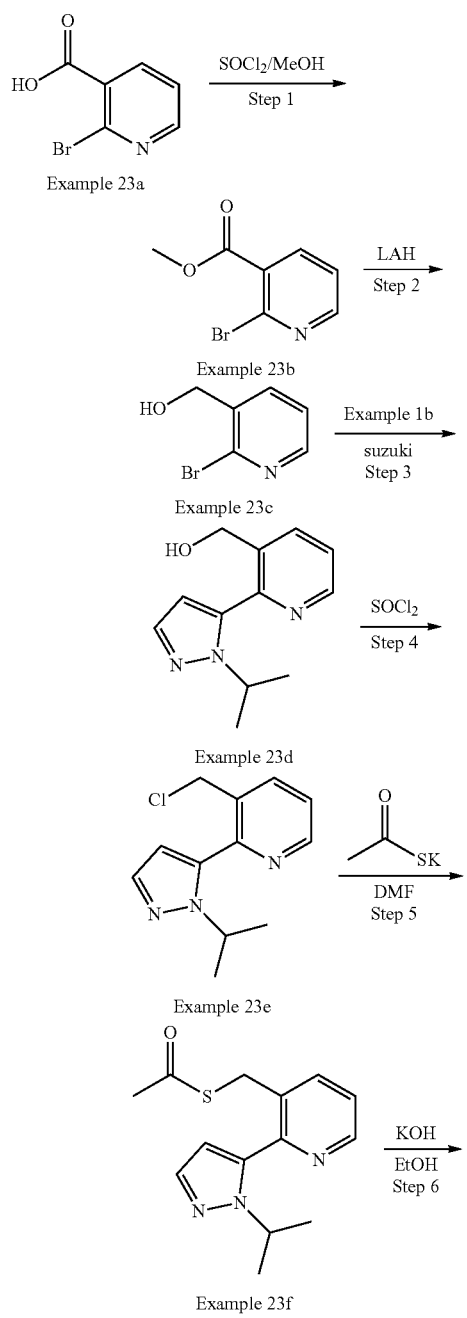

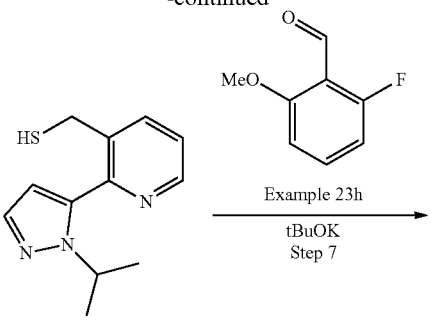

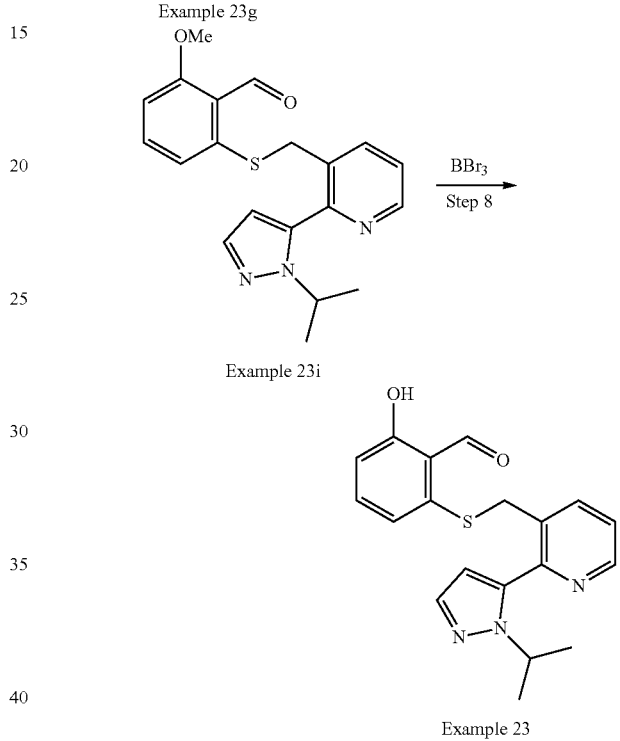

Step 1: Example 23b

A mixture of 2-bromonicotinic acid (Example 23a, 2.0 g, 10.0 mmol) and 12 mL sulfurous dichloride was stirred at 80° C. for 3 hrs, the solvent was then removed under vacuum, followed by adding 40 mL methanol, the mixture was stirred at r.t. for another 2 hrs, the solvent was then removed, washed by water (10 mL), the desired product was successfully obtained (Example 23b, 2.2 g, crude yield 95%) as white solid.

Step 2: Example 23c

To a solution of Example 23b (2.16 g, 10.0 mmol, 1.0 eq) in THF (28 mL) was added LAH (1.11 g, 30.0 mmol, 3.0 eq) at 0° C. for 15 mins, the mixture was stirred at r.t for another 3 hrs, the reaction was then quenched by adding 1.5 mL water, the solid was filtered, the filtrate was combined and purified by silica gel chromatography (PE/EA=2/1) to give the desired product (Example 23c, 1.5 g, crude yield 75%) as white solid. LCMS [M+1]⁺=191.3

Step 3: Example 23d

To a solution of Example 23c (1.5 g, 7.98 mmol) in dioxane/H₂O (8 mL/2 mL) was added (1-isopropyl-1H- pyrazol-5-yl)boronic acid (Example 1b, 1.23 g, 7.98 mmol), PdCl$_2$(dppf) (0.58 g, 0.8 mmol) and NaHCO$_3$ (1.7 g, 20.2 mmol). The resulting solution was stirred at 100° C. for 10 hrs under N$_2$. The reaction mixture was partitioned between EtOAc (30 mL*2) and H$_2$O (20 mL). The combined organic layers were saturated with brine, dried over Na$_2$SO$_4$, filtered and concentrated. The residue was purified by silica gel chromatography, eluting with 50-100% EtOAc in Petroleum Ether, to afford the desired product (Example 23d, 1.01 g, yield 58%) as light brown oil.

Step 4: Example 23e

To a solution of Example 23d (0.92 g, 4.23 mmol) in DCM (18 mL) was added sulfurous dichloride (3 mL), the mixture was then stirred at 40° C. for 2 hrs, TLC showed the start materials consumed completely, the solvent was then removed to give the crude product (Example 23e, 0.89 g, crude yield 89%) as yellow solid. LCMS [M+1]$^+$=236.2

Step 5: Example 23f

To a solution of Example 23e (0.79 g, 3.35 mmol) in DMF (11 mL) was added potassium ethanethioate (1.14 g), the mixture was stirred at 80° C. for 2 hrs, the reaction mixture was then portioned between EA (20 mL) and 15 mL water, the organic phase was then combined and combined, the residue was further purified by silica gel chromatography (PE/EA=23%-55%) to give the desired product (Example 23f, 0.49 g, yield 53%) as slightly yellow oil. LCMS [M+1]$^+$=276.1

Step 6: Example 23g

To a solution of Example 23f (0.49 g, 1.78 mmol) in methanol (10 mL) was added 0.2 g potassium hydroxide and 1.5 mL water, the mixture was stirred at room temperature for 2 hrs, the solvent was then removed, the residue was further purified by silica gel chromatography (PE/EA=1/1) to give the desired product (Example 23g, 304 mg, yield 73%) as slightly yellow solid.

Step 7: Example 23i

A mixture of Example 23g (0.3 g, 1.6 mmol), 2-fluoro-δ-methoxybenzaldehyde (Example 23h, 0.39 g) and potassium 2-methylpropan-2-olate (0.39 g) was stirred at THF under reflux for 2 hrs. The solvent was then removed under vacuum, the residue was further purified by combined-flash (PE/EA=20%-65%) to give the desired product (Example 23i, 220 mg, yield 37%) as slightly yellow solid. LCMS [M+1]$^+$=368.2.

Step 8: Example 23

To a solution of Example 23i (0.17 g, 0.46 mmol) in DCM (8 mL) was added BBr$_3$/DCM (3.5 mL, 1 M) at −40° C. for 30 min, the mixture was then turn to 0° C. and stirred for another 2 hrs. The reaction was quenched by adding 15 mL methanol and the solvent was removed under vacuum, the residue was further purified by prepared-HPLC (MeOH/MeOH=15%-65%) to give the desired product Example 23 (48 mg, yield 30%) slightly yellow oil. LCMS [M+1]$^+$=354.1.

$^1$H NMR (400 MHz, Chloroform-d) δ 12.09 (s, 1H), 10.39 (s, 1H), 8.78 (d, J=4.6 Hz, 1H), 7.86-7.72 (m, 2H), 7.50 (dd, J=8.0, 4.6 Hz, 1H), 7.40 (t, J=8.0 Hz, 1H), 6.92 (d, J=8.5 Hz, 1H), 6.79 (d, J=7.5 Hz, 1H), 6.45 (d, J=2.0 Hz, 1H), 4.44-4.24 (m, 1H), 4.03 (s, 2H), 1.47 (d, J=6.5 Hz, 6H).

Example 24: General Procedure for Synthesis of Example 24

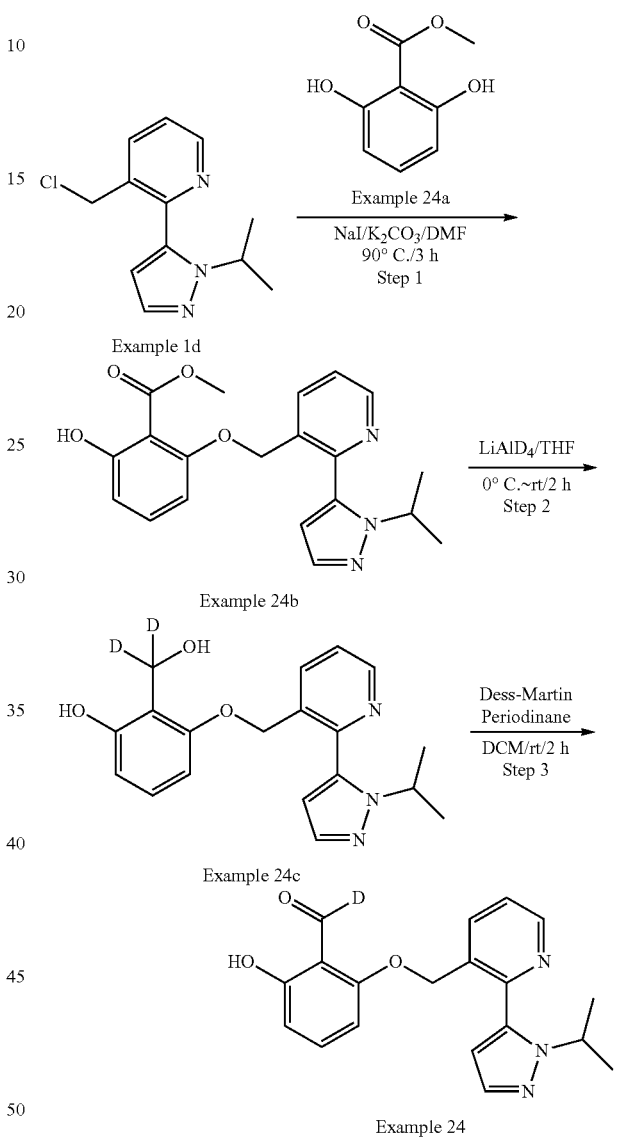

Step 1: Example 24b

A mixture of Example 1d (0.76 g, 2.79 mmol), methyl 2,6-dihydroxybenzoate (Example 24a, 0.57 g, 3.39 mmol), K$_2$CO$_3$ (0.96 g, 6.96 mmol) and NaI (50 mg, 0.33 mmol) in DMF (10 mL) was stirred at 90° C. for 3 h. The reaction was quenched by adding 8 mL of water; the residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product (Example 24b, 0.42 g, yield 41%) as a yellow solid. LCMS [M+1]$^+$=368.2

Step 2: Example 24c

To a solution of Example 24b (0.4 g, 1.1 mmol) in anhydrous THF (14 mL) was added LiAlD$_4$ (160 mg, 3.8 mmol). The mixture was stirred at 0° C. for 1 h, which was then warm to room temperature and stirred for another 1 h. The reaction was quenched by adding 0.2 mL of 20% sodium hydroxide solution, followed by adding 0.2 mL of water. The reaction was then filtered, and the filtrate was concentrated to afford the desired product (Example 24c, 0.3 g, yield 75%) as a light yellow solid.

Step 3: Example 24

A mixture of Example 24c (0.11 g, 0.32 mmol), and Dess-Martin reagent (0.15 g, 0.35 mmol) in DCM (15 mL) was stirred at room temperature for 2 h. The reaction was then quenched by adding 20 mL of sodium bicarbonate solution, and extracted with EtOAc (20 mL*2). The organic phases were combined, washed with brine, dried over Na$_2$SO$_4$, and concentrated under vacuum, which was further purified by silica gel column (Petroleum Ether/EtOAc=20%-50%), to afford Example 24 (10 mg, yield 11%) as a slightly yellow solid. LCMS [M+1]$^+$=339.2.

$^1$H NMR (400 MHz, CDCl$_3$) δ 11.94 (s, 1H), 8.80 (s, 1H), 8.06 (d, J=7.7 Hz, 1H), 7.71 (s, 1H), 7.52 (s, 1H), 7.39 (t, J=8.4 Hz, 1H), 6.59 (d, J=8.5 Hz, 1H), 6.40 (s, 1H), 6.26 (d, J=8.3 Hz, 1H), 5.05 (s, 2H), 4.57 (s, 1H), 1.47 (d, J=6.5 Hz, 6H).

Example 25: General Procedure for Synthesis of Example 25

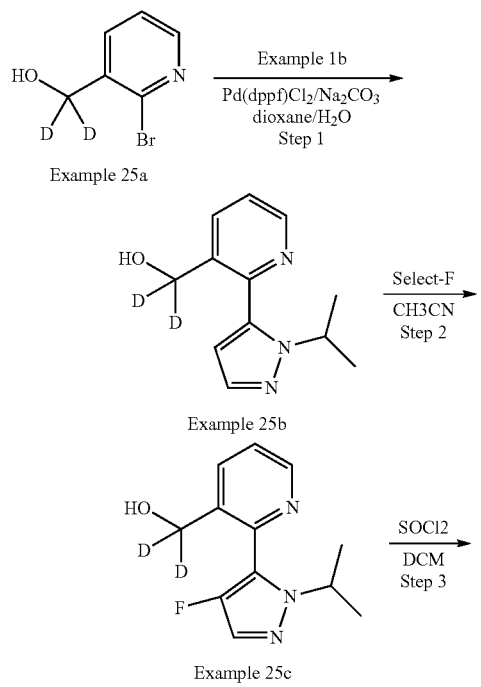

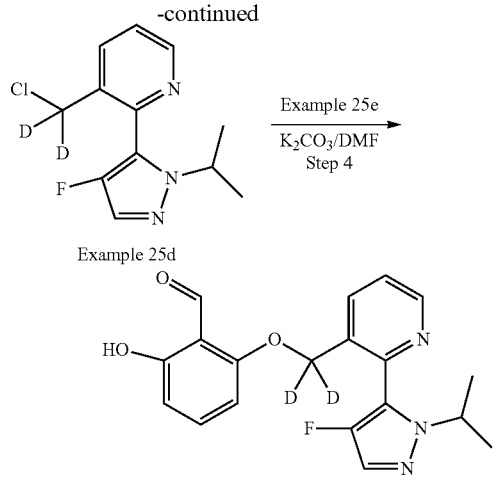

Step 1: Example 25b

To a solution of Example 25a (1.63 g, 8.63 mmol) in dioxin (63 mL) was added (1-isopropyl-1H-pyrazol-5-yl)boronicacid (Example 1b, 2.0 g, 2.94 mmol), 2N Na$_2$CO$_3$ (21.6 mL, 43.15 mmol), Pd(dppf)Cl$_2$ (315 mg, 0.43 mmol) under N$_2$ protection and then heated to 90° C. for 18 hrs. After cooled to room temperature, the solvent was removed under reduced pressure, the residue was extracted with EtOAc (20 mL*2) and combined the organic phase, washed with brine, dried over Na$_2$SO$_4$, filtered and concentrated under reduced pressure to give the crude and further purified by silica chromatography to give the desired product (Example 25b, 800 mg, yield 42.3%) as yellow oil. LCMS [M+1]$^+$=220.1

Step 2: Example 25c

A solution of Example 25b (300 mg, 1.36 mmol) in CH$_3$CN (5 mL) was treated with Selectfluor (728 mg, 2.05 mmol) and the reaction mixture was heated at 80° C. for 3 hours. After cooling to room temperature the solution was evaporated and the residue was purified by silica chromatography using a mixture of (PE:EA=100:30) as eluent to give the product (Example 25c, 150 mg, yield 46.5%). LCMS [M+H]$^+$=238.1.

Step 3: Example 25d

To Example 25c (150 mg, 0.63 mmol) in DCM (5 mL) was added SOCl$_2$ (0.5 mL) at r.t. The reaction mixture was stirred at r.t. for 1 h and concentrated to dryness. The crude solid was suspended in toluene and concentrated to dryness to give the desired product (Example 25d, 165 mg, yield 100%) as yellow solid, which was used for next step without further purification.

Step 4: Example 25

A mixture of 2,6-dihydroxybenzaldehyde (Example 25e, 37 mg, 0.237 mmol) and K$_2$CO$_3$ (75 mg, 0.543 mmol) in DMF (10 mL) was added Example 25d (50 mg, 0.207 mmol) at r.t. The mixture was heated at 60° C. for 2 hrs, then cooled to r.t. Added water (25 mL) and the residue was extracted with EtOAc (10 mL*2). The combined organic phase was washed with brine, dried over Na$_2$SO$_4$, filtrated and concentrated under reduced pressure to give the crude product which was further purified by silica gel chromatography to give the pure product Example 25 (20 mg, yield 11%) as an off-white solid. LCMS [M+H]=358.1.

$^1$H NMR (400 MHz, CDCl$_3$-d) δ 11.92 (s, 1H), 10.36 (s, 1H), 8.76 (dd, J=4.8, 1.7 Hz, 1H), 8.00 (dd, J=8.0, 1.7 Hz, 1H), 7.50-7.41 (m, 2H), 7.36 (t, J=8.4 Hz, 1H), 6.55 (d, J=8.5 Hz, 1H), 6.32-6.23 (m, 1H), 4.63 (p, J=6.6 Hz, 1H), 1.45 (d, J=6.6 Hz, 6H).

Example 26: General Procedure for Synthesis of Example 26

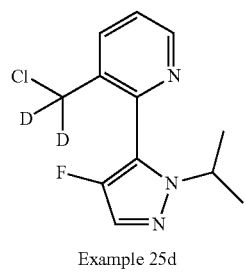

Example 25d

+

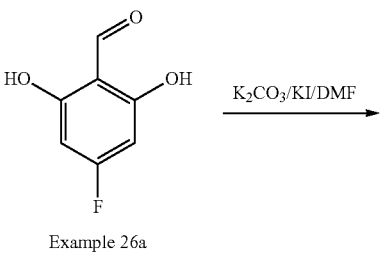

Example 26a

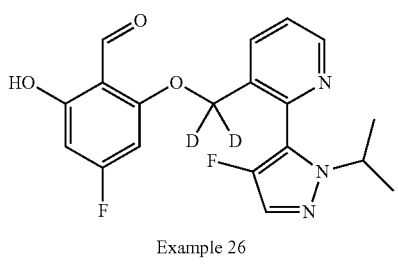

Example 26

Example 26

The Example 25d (226 mg 0.88 mmol), Example 26a (138 mg 0.88 mmol), K$_3$CO$_3$ (244 mg 1.76 mmol), KI (10 mg 0.06 mmol) was suspended in DMF (5 mL), heated to 80° C. for 40 mins, TLC detected the reaction was complete, the filtered was concentrated and purified by doing Prep-HPLC to afford the desired product Example 26 (40 mg) as a white solid. LCMS [M+1]=376

$^1$H NMR (400 MHz, CDCl$_3$) δ 12.28 (d, J=1.1 Hz, 1H), 10.21 (s, 1H), 8.77 (dd, J=4.7, 1.6 Hz, 1H), 7.98 (dd, J=7.9, 1.6 Hz, 1H), 7.50-7.42 (m, 2H), 6.25 (dd, J=10.3, 2.0 Hz, 1H), 6.00 (dd, J=10.6, 2.1 Hz, 1H), 4.65 (dt, J=13.2, 6.6 Hz, 1H), 1.45 (d, J=6.6 Hz, 6H).

Example 27: General Procedure for Synthesis of Example 27b & Example 27

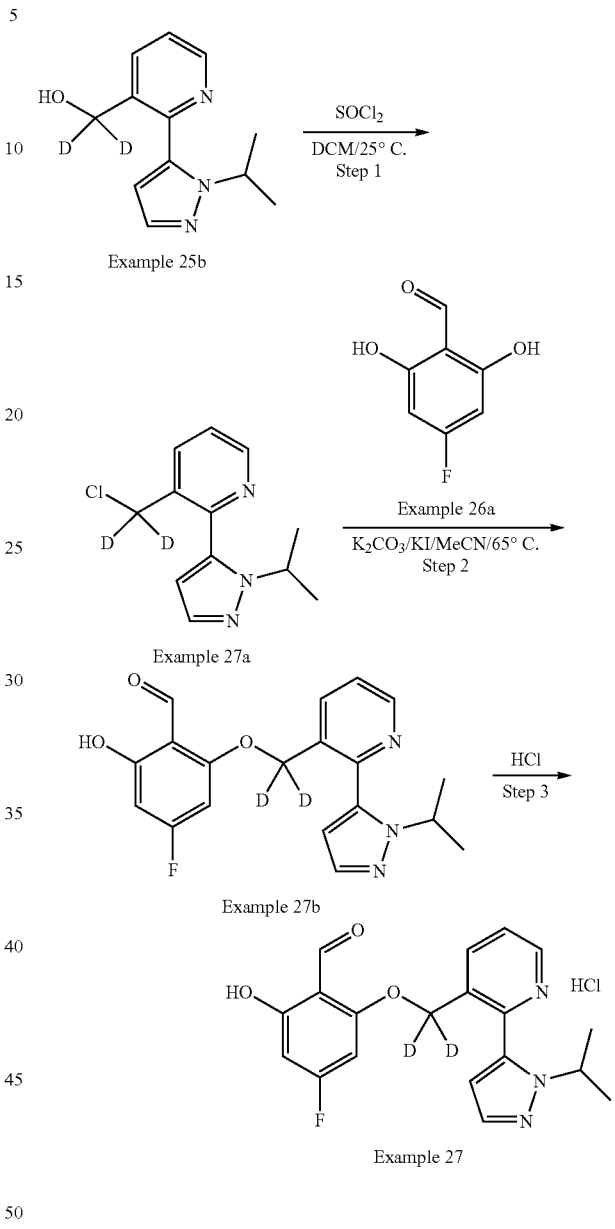

Step 1: Example 27a

To a solution of Example 25b (0.64 g, 2.92 mmol) in dry DCM (15 mL) was added SOCl$_2$ (1.5 mL) at 25° C. for 2 hrs. LCMS showed starting material was consumed completely. The reaction mixture was concentrated under reduced pressure to afford the desired product (Example 27a, 0.6 g, yield 86.6%) as yellow solid. LCMS [M+1]$^+$=238.

Step 2: Example 27b

A suspension of Example 27a (547 mg, 2.31 mmol), 4-fluoro-2,6-dihydroxy benzaldehydein (Example 26a, 300 mg, 1.92 mmol), K$_2$CO$_3$ (1.06 g, 7.69 mmol) and KI (3.2 mg, 0.019 mmol) in MeCN (2 mL) was heated to 65° C. and stirred for 3 hrs. The reaction mixture was filtered and the filter cake was washed with EtOAc (3*10 mL). The combined organic phase was washed with brine, dried over Na$_2$SO$_4$, filtrated and concentrated under reduced pressure to give the crude product which was further purified by silica gel chromatography to give the pure product Example 27b (277 mg) as a white solid. MS [M+1]$^+$=358

$^1$H NMR (400 MHz, Chloroform-d) δ 10.29 (s, 1H), 10.22 (s, 1H), 8.77-8.75 (d, J=6.4 Hz, 1H), 7.95-7.93 (d, J=6.4 Hz, 1H), 7.61 (s, 1H), 7.44-7.41 (q, 1H), 6.32 (s, 1H), 6.32 (d, 1H), 6.0 (d, 1H), 4.66 (m, 1H), 1.48 (d, J=6.4 Hz, 6H).

Step 3: Example 27

Example 27b (1 g) was dissolved in HCl (50 mL), stirred at r.t. for 0.5 h, then concentrated and dried under high vacuum to give Example 27 (1 g) as a yellow solid.

$^1$H NMR (400 MHz, DMSO-d$_6$) δ 12.06 (s, 1H), 10.26 (s, 1H), 10.03 (s, 1H), 8.76 (dd, J=4.9, 1.6 Hz, 1H), 8.26 (d, J=7.7 Hz, 1H), 7.59 (dd, J=8.0, 4.9 Hz, 1H), 7.54 (d, J=1.8 Hz, 1H), 6.58-6.50 (m, 2H), 6.44 (dd, J=10.7, 2.3 Hz, 1H), 4.61 (p, J=6.6 Hz, 1H), 1.33 (d, J=6.6 Hz, 6H).

Example 28: General Procedure for Synthesis of Example 28

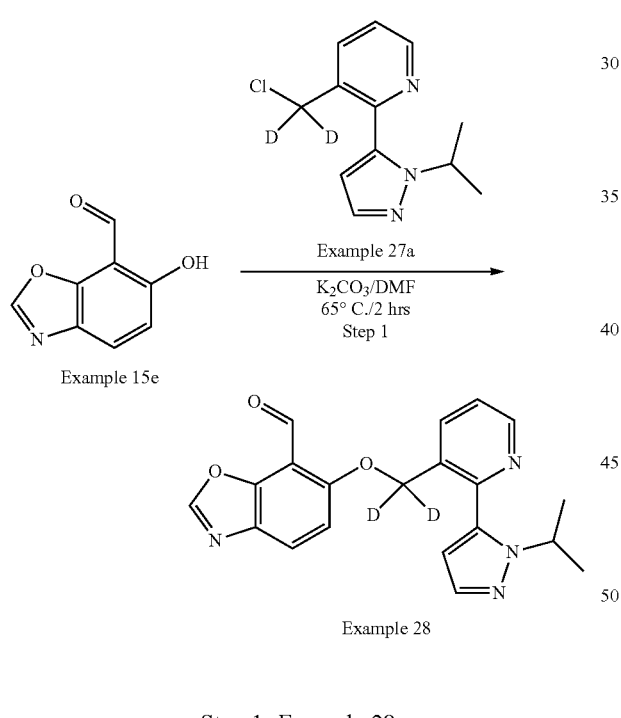

Step 1: Example 28

To a mixture of Example 15e (200 mg, 0.73 mmol) and K$_2$CO$_3$ in DMF was added Example 27a (131 mg, 0.8 mmol) at room temperature and then the reaction mixture was heated to 65° C. and stirred for 2 hrs. The reaction mixture was diluted with water (20 mL) and extracted with EtOAc (15 mL*4). The combined organic layers were washed with brine (25 mL*3), dried over Na$_2$SO$_4$, filtered and concentrated under reduced pressure to give the crude product which was further purified by silica gel chromatography to give the pure product Example 28 (211 mg, yield 79.3%) as a white solid. LCMS [M+1]$^+$=365.

$^1$H NMR (400 MHz, CDCl$_3$-d) δ 10.60 (s, 1H), 8.77 (s, 1H), 8.15 (s, 1H), 8.07-8.05 (d, J=8 Hz, 1H), 7.94-7.91 (d, J=12 Hz, 1H), 7.61 (s, 1H), 7.45-7.43 (m, 1H), 6.96-6.94 (d, J=8 Hz, 1H), 6.38 (s, 1H), 4.72-4.62 (m, 1H), 1.49-1.48 (d, J=4 Hz, 6H).

Example 29: General Procedure for Synthesis of Example 29e & Example 29

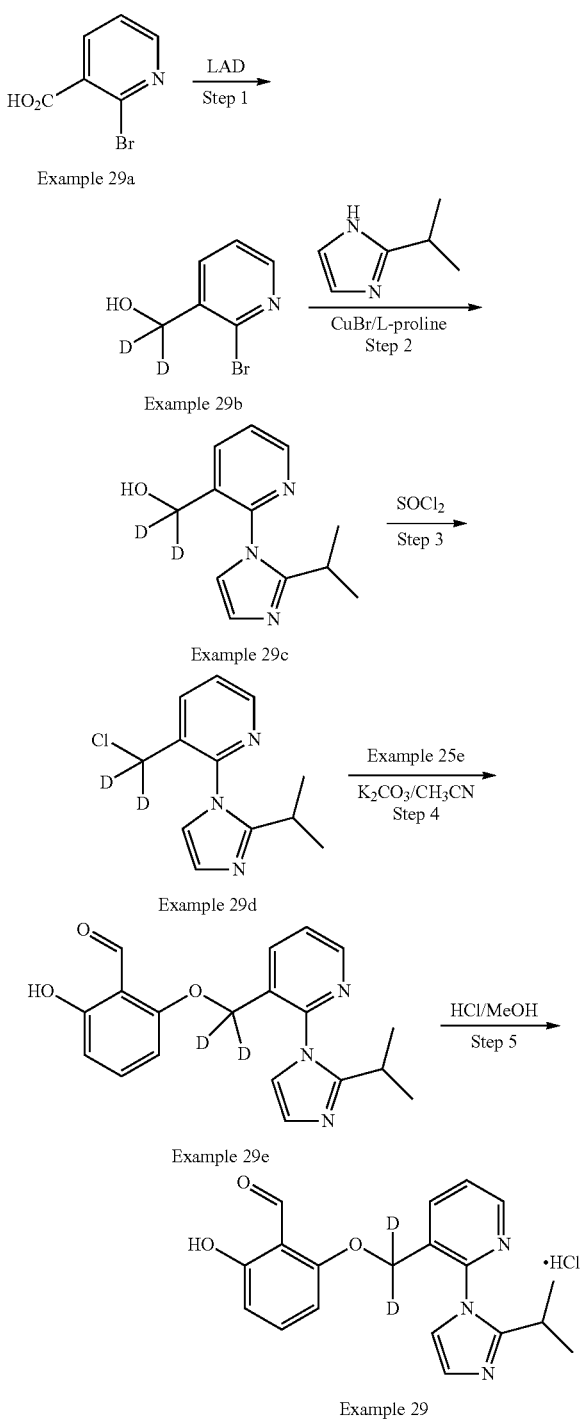

Step 1: Example 29b

To a solution of Example 29a (4.4 g, 22.0 mmol) in THF (90 mL) was added LAD partially (1.8 g, 44.0 mmol) at 0° C., the mixture was stirred at 0° C. for 30 min and then turned to room temperature for another 1 hr. The reaction was quenched by adding 5 mL water slowly at 0° C. and then filtered, washed with EtOAc (40 mL) twice, the filtration was combined, washed with brine, dried over $Na_2SO_4$, and concentrated under vacuum to give 4.5 g yellow oil, which was further purified by combined flash (EA/PE=25%-50%) to afford pure product (Example 29b, 1.3 g, yield 32%) as yellow solid. LCMS $[M+1]^+$=190.1

Step 2: Example 29c

A mixture of Example 29b (1.3 g, 6.8 mmol), 2-isopropyl-1H-imidazole (0.9 g, 8.2 mmol), CuBr (0.14 g, 1.0 mmol), L-proline (0.12 g, 1.0 mmol) and $Cs_2CO_3$ (4.3 g, 13.6 mmol) was stirred in 40 mL toluene under reflux with the protection of nitrogen for 16 hrs. The solvent was then removed under vacuum, the residue was then washed by water (35 mL), extracted with EtOAc (55 mL) twice, the organic phase was combined, washed with brine, dried over $Na_2SO_4$, and concentrated under vacuum to give brown oil, which was further purified by combined-flash (EA/PE=70%-95%) to give the desired product Example 29c (120 mg, yield 9%) as yellow solid. LCMS $[M+1]^+$=220.1

Step 3: Example 29d

To a solution of Example 29c (120 mg, 0.54 mmol) in DCM (12 mL) was added $SOCl_2$ (1.5 mL) at 0° C. for 15 min, the mixture was stirred at r.t for 30 min, concentrated under vacuum to give the desired product (Example 29d, 120 mg, yield 92%) as yellow solid. LCMS $[M+1]^+$=238.1

Step 4: Example 29e

A mixture of Example 29d (120 mg, 0.5 mmol), 2,6-dihydroxybenzaldehyde (Example 5e, 90 mg, 0.65 mmol), 140 mg potassium carbonate (2.0 mmol) and 20 mg NaI was stirred in 20 mL acetonitrile at 75° C. for 2 hrs, the reaction was then quenched by adding 15 mL water, extracted with EtOAc (35 mL) twice, the organic phase was combined, washed with brine, dried over $Na_2SO_4$, and concentrated under vacuum to give brown oil, which was further purified by prep-HPLC ($CH_3CN$/MeOH=60%-95%) to give the desired product Example 29e (24 mg, yield 14%) as slightly yellow solid. LCMS $[M+1]^+$=340.1

$^1$H NMR (400 MHz, CDCl3) δ 11.92 (s, 1H), 10.36 (s, 1H), 8.66-8.64 (m, 1H), 8.08-8.06 (m, 1H), 7.52-7.55 (m, 1H), 7.38 (t, J=8.4 Hz, 1H), 7.12 (d, J=1.6 Hz, 1H), 6.98 (d, J=1.6 Hz, 1H), 6.58 (d, J=8.4 Hz, 1H), 6.22 (d, J=8.4 Hz, 1H), 2.92-2.89 (m, 1H), 1.25 (d, J=6.8 Hz, 6H).

Step 5: Example 29

Example 29e (2.2 g) was dissolved in HCl (50 mL, 2.5M in MeOH), stirred at r.t for 1 h. Then concentrated and dried under high vacuum to give the desired product Example 29 (2.3 g, yield 100%) as a yellow solid. LCMS $[M+1]^+$340

$^1$H NMR (400 MHz, DMSO-$d_6$) δ 15.37 (s, 1H), 11.66 (s, 1H), 10.23 (s, 1H), 8.72 (dd, J=4.7, 1.7 Hz, 1H), 8.49 (dd, J=7.8, 1.6 Hz, 1H), 8.06 (d, J=2.0 Hz, 1H), 7.87-7.83 (m, 2H), 7.49 (t, J=8.4 Hz, 1H), 6.59 (dd, J=13.4, 8.4 Hz, 2H), 3.11-3.04 (m, 1H), 1.28 (d, J=7.0 Hz, 6H).

Example 30: General Procedure for Synthesis of Example 30

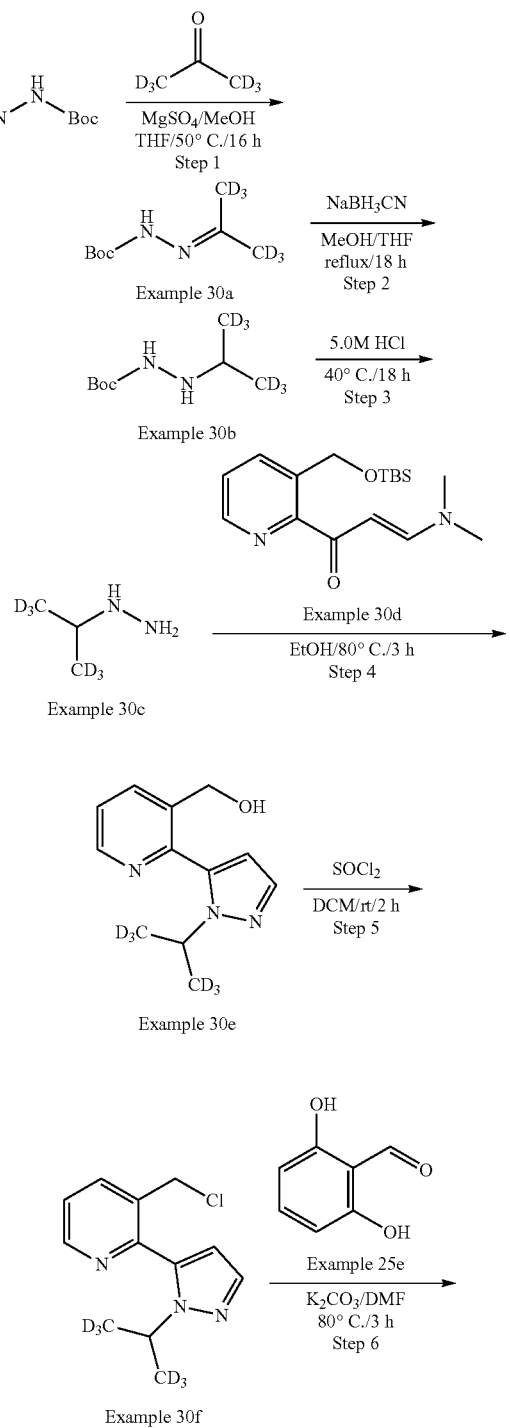

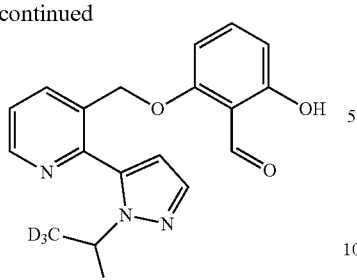

Example 30

Step 1: Example 30a

To a solution of tert-butyl hydrazinecarboxylate (2.64 g, 20 mmol) in THF (25 mL) and MeOH (25 mL) at room temperature under $N_2$ was added acetone-$d_6$ (1.28 g, 20 mmol) and magnesium sulfate (5 g). The resulting suspension was stirred for 16 hrs at 50° C. The reaction mixture was filtered and concentrated in vacuum to give the crude product Example 30a (3.50 g, yield 100%) as a white solid, which was used directly in the next step without further purification. LC-MS [M−56]$^+$=123.2.

Step 2: Example 30b

To a solution of crude Example 30a (3.50 g, 20 mmol) in THF (25 mL) and MeOH (25 mL) were added sodium cyanoborohydride (4.34 g, 69.0 mmol) portionwise, and catalytic amount of acetic acid. The reaction was refluxed under nitrogen for 18 hrs, and then cooled to room temperature. The mixture was concentrated and diluted with a mixture of water (50 mL) and EtOAc (50 mL). The layers were separated and aqueous layer was extracted with EtOAc (50 mL) again. The combined organic layers were washed with brine, dried and concentrated, which was purified on silica gel, using Petroleum Ether/EtOAc=2/1 as eluent, to give the title (Example 30b, 3.40 g, yield 94.4%) as a white solid. LCMS [M−55]$^+$=125.2.

$^1$H NMR (400 MHz, CDCl$_3$) δ 6.24 (s, 1H), 3.63 (s, 1H), 3.12 (s, 1H), 1.46 (s, 9H).

Step 3: Example 30c

To a solution of Example 30b (3.40 g, 19.0 mmol) in MeOH (20 mL) was added HCl (50 mL, 5M in dioxane) and the mixture was stirred at 40° C. for 18 h and then cooled to room temperature. Concentration of the mixture gave the crude product (Example 30c, 2.2 g, yield 100%) as off-white oil, which was used for next step without further purification.

Step 4: Example 30e

To a solution of Example 30d (2.50 g, 7.81 mmol) in EtOH (10 mL) was added Example 30c (1.00 g, 8.60 mmol). The mixture was heated at 80° C. for 3 h and then cooled. HCl (6 N, 2 mL) was added and then mixture was stirred overnight. The mixture was concentrated and diluted with EtOAc (100 mL) and NaHCO$_3$ (sat.) (50 mL). The layers were separated and the aqueous layer was extracted with EtOAc (50 mL×2). The combined organic layers were dried over Na$_2$SO$_4$, concentrated, and purified on silica gel using Petroleum Ether/EtOAc=1/1 as eluent, to give product (Example 30e, 560 mg, yield 32.1%) as a white solid.

Step 5: Example 30f

To a solution of Example 30e (560 mg, 2.5 mmol) in DCM (20 mL) was added SOCl$_2$ (2.0 mL) at room temperature. The reaction mixture was stirred at room temperature for 2 h and concentrated to dryness. The crude solid was suspended in toluene and concentrated to dryness to give product (Example 30f, 700 mg, yield 100%) as an off-white solid, which was used for next step without further purification.

Step 6: Example 30

A mixture of 2,6-dihydroxybenzaldehyde (Example 25e, 348 mg, 2.5 mmol) and K$_2$CO$_3$ (1.73 g, 12.5 mmol) in DMF (25 mL) was stirred at room temperature for 5 min, followed by addition of Example 30f (700 mg, 2.5 mmol). The mixture was heated at 80° C. for 3 h, and then cooled. 2N HCl was added to the mixture until pH reached 7, which was then extracted with EtOAc (50 mL×3). The combined organic layers were washed with brine, dried over Na$_2$SO$_4$, concentrated, and purified on silica gel using a mixture of (Petroleum Ether/EtOAc=100/30) as elution, to give Example 30 (300 mg, yield 35%) as a white solid. LCMS [M+H]$^+$=344.2

$^1$H NMR (400 MHz, CDCl$_3$) δ 11.94 (s, 1H), 10.37 (s, 1H), 8.76 (d, J=3.6 Hz, 1H), 7.99 (d, J=7.3 Hz, 1H), 7.61 (d, J=1.4 Hz, 1H), 7.44 (dd, J=7.8, 4.7 Hz, 1H), 7.38 (t, J=8.4 Hz, 1H), 6.57 (d, J=8.5 Hz, 1H), 6.36 (d, J=1.6 Hz, 1H), 6.27 (d, J=8.2 Hz, 1H), 5.08 (s, 2H), 4.66 (dt, J=13.2, 6.6 Hz, 1H).

Example 31: General Procedure for Synthesis of Example 31

Example 26a

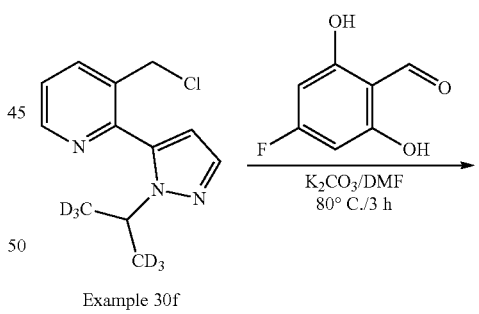

Example 30f

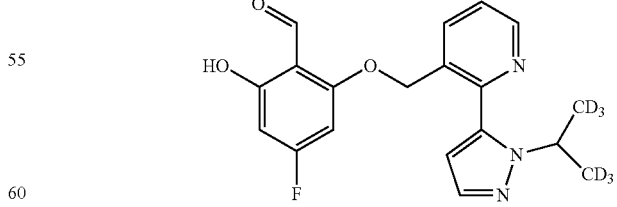

Example 31

A mixture of 4-fluoro-2,6-dihydroxybenzaldehyde (Example 26a, 300 mg, 1.09 mmol) and K$_2$CO$_3$ (452 mg, 3.27 mmol) in DMF (10 mL) was stirred at r.t. for 5 min. To this mixture was added Example 30f (256 mg, 1.64 mmol) at r.t.

The mixture was heated at 60° C. for 2 h, Cooled to r.t. Added 2N HCl to pH=7, and extracted with EtOAc (50 mL*3). The combined organic layers were washed with brine, dried over Na$_2$SO$_4$, concentrated, and purified on silica gel using a mixture of (PE:EA=100:30) as elution to give Example 31 (105 mg, yield 26.7%) as an off-white solid. LCMS [M+H]$^+$=362.1

$^1$H NMR (400 MHz, Chloroform-d) δ 12.29 (s, 1H), 10.22 (s, 1H), 8.76 (dd, J=4.8, 1.7 Hz, 1H), 7.95 (dd, J=7.9, 1.7 Hz, 1H), 7.60 (d, J=1.9 Hz, 1H), 7.43 (dd, J=7.9, 4.8 Hz, 1H), 6.33 (d, J=1.9 Hz, 1H), 6.27 (dd, J=10.3, 2.2 Hz, 1H), 6.00 (dd, J=10.6, 2.2 Hz, 1H), 5.05 (s, 2H), 4.62 (s, 1H), 1.61 (s, 6H).

Example 32: General Procedure for Synthesis of Example 32

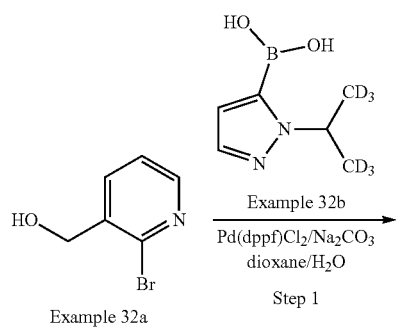

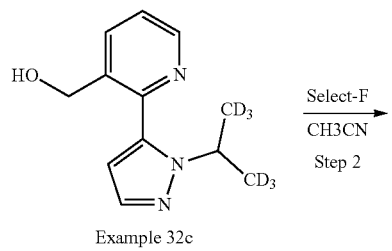

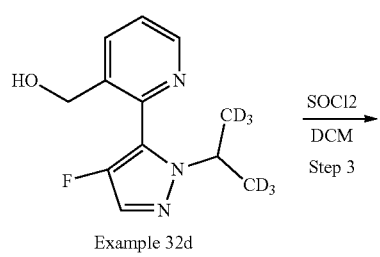

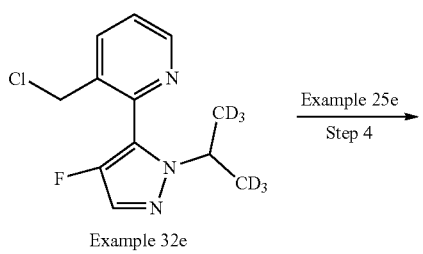

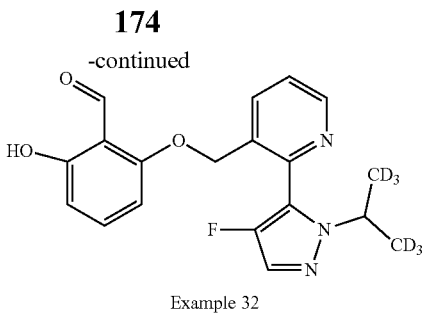

Example 32

Step 1: Example 32c

To a solution of Example 32b (1.63 g, 8.63 mmol, 1 eq) in dioxane (63 mL) was added Example 32a (2.07 g, 12.94 mmol), 2N Na$_2$CO$_3$ (21.6 mL, 43.15 mmol), Pd(dppf)Cl$_2$ (315 mg, 0.43 mmol) under N$_2$ protection and then heated to 90° C. for 18 hrs. After cooled to room temperature, the solvent was removed under reduced pressure, the residue was extracted with EtOAc (20 mL*2) and combined the organic phase, washed with brine, dried over Na$_2$SO$_4$, filtered and concentrated under reduced pressure to give the crude and further purified by silica chromatography to give the desired product Example 32c (800 mg, yield 30%) as yellow oil. LCMS [M+1]$^+$=224.1

Step 2: Example 32d

A solution of Example 32c (102 mg, 1.39 mmol) in CH3CN (5 mL) was treated with Selectfluor. (738 mg, 2.08 mmol) and the reaction mixture was heated at 80° C. for 3 hours. After cooling to room temperature the solution was evaporated and The residue was purified on silica gel using a mixture of (PE:EA=100:30) as eluent to give the desired product (Example 32d, 102 mg, yield 46.5%). LCMS [M+H]$^+$=238.1.

Step 3: Example 32e

To Example 32d (102 mg, 0.42 mmol) in DCM (5 mL) was added SOCl$_2$ (0.5 mL) at r.t. The reaction mixture was stirred at r.t. for 1 h and concentrated to dryness. The crude solid was suspended in toluene and concentrated to dryness to give the desired product (Example 32e, 115 mg) as yellow solid, which was used for next step without further purification. LCMS [M+H]$^+$=260.1.

Step 4: Example 32

A mixture of 2,6-dihydroxybenzaldehyde (Example 25e, 70 mg, 0.5 mmol) and K$_2$CO$_3$ (175 mg, 1.26 mmol) in DMF (5 mL) was added Example 32e (115 mg, 0.42 mmol) at r.t. The mixture was heated at 60° C. for 1 h, Cooled to r.t. Added water (25 mL) and extracted with EtOAc (50 mL*3). The combined organic layers were washed with brine, dried over Na$_2$SO$_4$, concentrated, and purified by Pre-HPLC to give Example 32 (22 mg, yield 14.5%) as white solid. LCMS [M+H]$^+$=362.1.

$^1$H NMR (400 MHz, Chloroform-d) δ 11.92 (s, 1H), 10.36 (s, 1H), 8.76 (dd, J=4.7, 1.7 Hz, 1H), 8.00 (dd, J=7.9, 1.7 Hz, 1H), 7.48-7.42 (m, 2H), 7.36 (t, J=8.4 Hz, 1H), 6.56 (d, J=8.5 Hz, 1H), 6.28 (d, J=8.3 Hz, 1H), 5.16 (s, 2H), 4.59 (s, 1H).

Example 33: General Procedure for Synthesis of Example 33

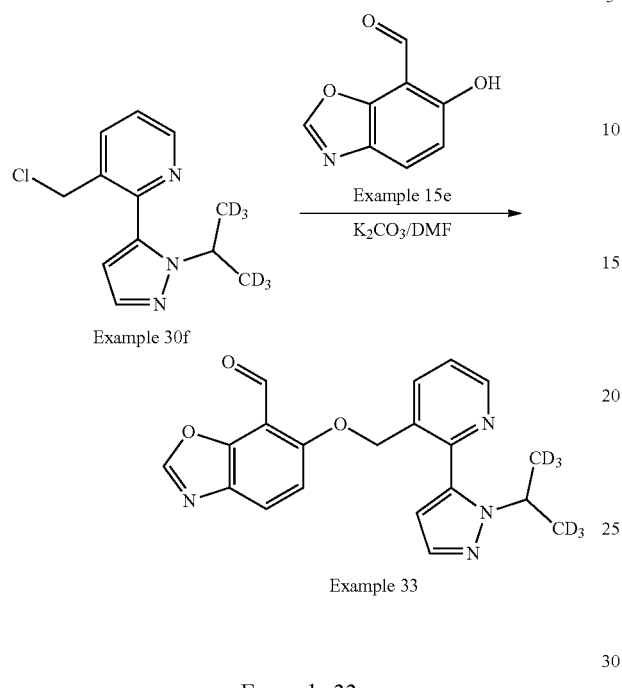

Example 33

Example 33

A mixture of δ-hydroxybenzo[d]oxazole-7-carbaldehyde (Example 15e, 80 mg, 0.49 mmol) and K$_2$CO$_3$ (350 mg, 2.5 mmol) in DMF (5 mL) was added Example 30f (124 mg, 0.44 mmol) at r.t. The mixture was heated at 80° C. for 2 hrs, Cooled to r.t. Added water (25 mL) and extracted with EtOAc (50 mL*3). The combined organic layers were washed with brine, dried over Na$_2$SO$_4$, concentrated, and purified on silica gel using a mixture of (PE:EA=100:30) as elution to give Example 33 (43 mg, yield 27.1%) as an white solid. LCMS [M+H]$^+$=369.1

$^1$H NMR (400 MHz, Chloroform-d) δ10.59 (s, 1H), 8.76 (dd, J=4.8, 1.7 Hz, 1H), 8.14 (s, 1H), 8.06 (dd, J=7.9, 1.7 Hz, 1H), 7.92 (d, J=8.9 Hz, 1H), 7.60 (d, J=1.9 Hz, 1H), 7.44 (dd, J=7.9, 4.8 Hz, 1H), 6.95 (d, J=8.9 Hz, 1H), 6.37 (d, J=1.9 Hz, 1H), 5.20 (s, 2H), 4.62 (s, 1H).

Example 34: General Procedure for Synthesis of Example 34

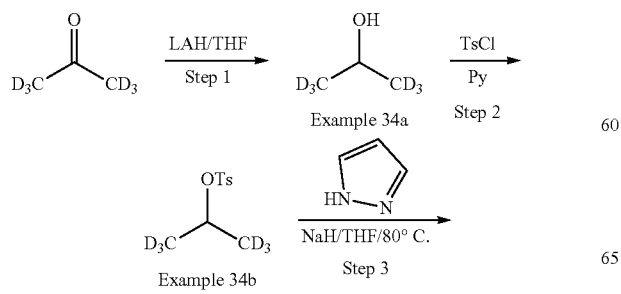

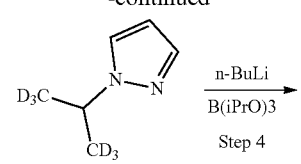

Example 34c

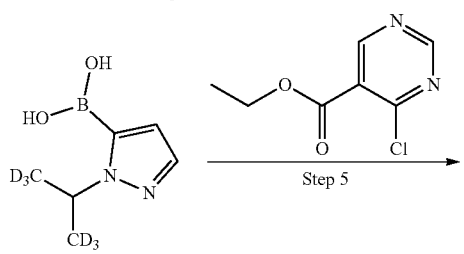

Example 34d

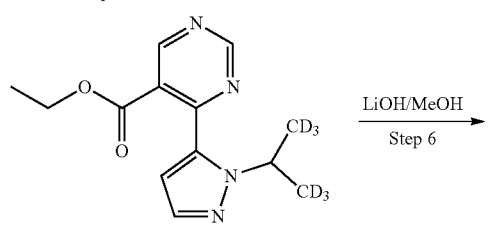

Example 34e

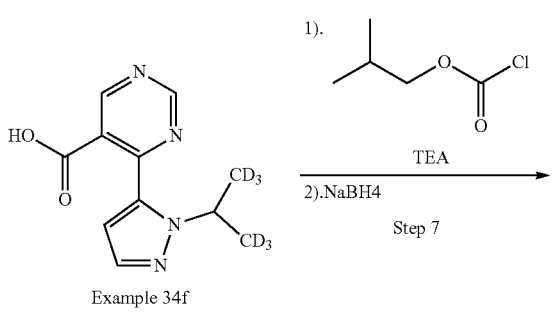

Example 34f

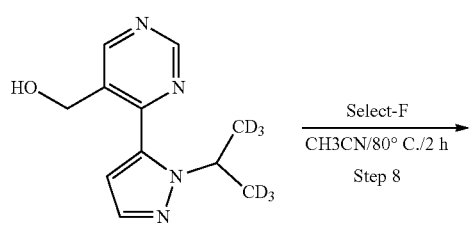

Example 34g

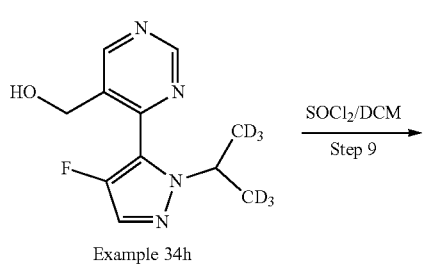

Example 34h

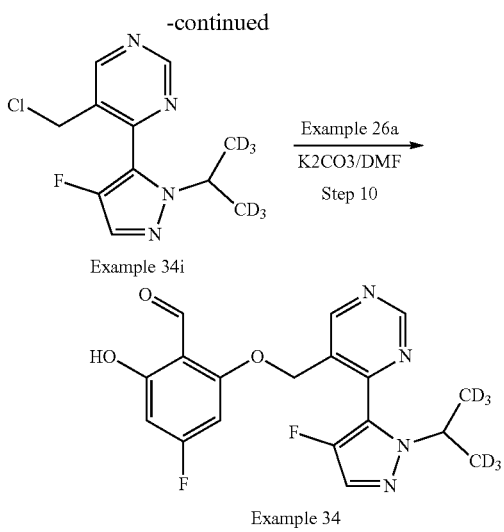

Example 34i

Example 34

Step 1: Example 34a

To a stirred suspension of LiAlH$_4$ (5.0 g, 132 mmol) in diglyme (100 mL) under N$_2$ at 0° C., was slowly added D$_6$-acetone (20 g, 312 mmol). The resulting solution was stirred at 0° C. for 1 h and then diethylene glycol (100 mL) slowly added. The product was distilled from the reaction mixture, and the fraction boiling between 79-105° C. was collected to give the title Example 34a (20.0 g, yield 96%) as colorless oil.

Step 2: Example 34b

Example 34a (20 g, 303 mmol) in Pyridine (100 mL) was added TsCl (63.5 g, 333 mmol) at 0° C. The reaction allowed warmed to r.t. and kept for 18 hrs the reaction liquid was added with water, and extracted with EA (100 mL*3). The combined organic phase was washed with water (200 mL*2), dried over anhydrous sodium sulfate, and concentrated to give a crude product. The crude product was purified by column chromatography to give the Example 34b (50 g, yield 75%) as colorless oil.

Step 3: Example 34c

A mixture of 1H-pyrazole (7.73 g, 113 mmol) in THF (300 mL) was added NaH (60%, 6.78 g, 169.5 mmol) at 0° C., The resulting solution was stirred at 0° C. for 1 h and then Example 34b (25 g, 113 mmol) slowly added. The reaction allowed warmed at 80° C. and kept for 38 hrs. After cooled to r.t., filtered and the product was distilled from the mixture, and the fraction boiling between 95-105° C. was collected under reduced pressure to give the title Example 34c (8.0 g, yield 61%) as colorless oil. LCMS [M+H]$^+$=117.1.

Step 4: Example 34d

To a solution of Example 34c (4.64 g, 40 mmol) in THF (100 mL) at −78° C. was added 2.5M n-BuLi (24 mL, 60 mmol). The solution was stirred at −78° C. for 1 h and Triisopropyl borate (22.5 g, 120 mmol) was added dropwise. The reaction was continued at −78° C. for 0.5 h, then warmed up to r.t. for 18 hrs. The reaction mixture was quenched with brine, adjusted to pH=5-6 with 1N HCl aqueous solution, and extracted with EA (100 mL*3), combined the organic phase, washed with brine, dried over Na$_2$SO$_4$, filtered and concentrated under reduced pressure to give the titled Example 34d (5.2 g, yield 81.25%) as white solid. LCMS [M+H]$^+$=161.1.

Step 5: Example 34e

To a solution of Example 34d (1.5 g, 6.25 mmol) in dioxane (45 mL) was added ethyl 4-chloropyrimidine-5-carboxylate (1.2 g, 6.25 mmol), 2N Na$_2$CO$_3$ (15 mL, 31.25 mmol), Pd(dppf)Cl$_2$ (228 mg, 0.31 mmol) under N$_2$ protection and then heated to 90° C. for 18 hrs. After cooled to room temperature, the solvent was removed under reduced pressure, the residue was extracted with EtOAc (20 mL*2) and combined the organic phase, washed with brine, dried over Na$_2$SO$_4$, filtered and concentrated under reduced pressure to give the crude and further purified by silica chromatography (PE/EA=1:1) to give the desired product Example 34e, (800 mg, yield 48.3%) as yellow oil. MS [M+1]$^+$=267.1

Step 6: Example 34f

To a solution of Example 34e (400 mg, 1.5 mmol) in THF (6 mL) was added 1N LiOH(aq) (3.0 mL, 3.0 mmol) at r.t. for 18 hrs, the reaction was then quenched by 1NHCl to pH=6, and extracted with EA (50 mL*3), The combined organic layers washed with brine, dried over Na$_2$SO$_4$, filtered and concentrated under reduced pressure to give the Example 34f (300 mg, yield 85%) as yellow solid, which was used directly to next step.

Step 7: Example 34g

To a solution of Example 34f (300 mg, 1.25 mmol), Isobutyl chloroformate (205 mg, 1.5 mmol) in THF (20 mL) at 0° C. was added TEA (203 mg, 2.0 mmol), the mixture was stirred at 0° C. for 0.5 hrs, and then NaBH$_4$ (57 mg, 1.5 mmol) in EtOH (1.0 mL) was added at 0° C., which was turned to r.t. for another 30 min. The reaction was then quenched by adding 2 mL water, the residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product Example 34g (120 mg, yield 40%) as white solid. LCMS [M+H]$^+$=225.1.

Step 8: Example 34h

A solution of Example 34g (120 mg, 0.54 mmol) in CH$_3$CN (5 mL) was treated with Selectfluor (287 mg, 0.81 mmol) and the reaction mixture was heated at 80° C. for 3 hours. After cooling to room temperature the solution was evaporated and The residue was purified on silica gel using a mixture of (PE:EA=100:30) as elution to give Example 34h (40 mg, yield 30.5%). LCMS [M+H]$^+$=243.1.

Step 9: Example 34i

To Example 34h (40 mg, 0.165 mmol) in DCM (5 mL) was added SOCl$_2$ (0.3 mL) at r.t. The reaction mixture was stirred at r.t. for 1 h and concentrated to dryness. The crude solid was suspended in toluene and concentrated to dryness to give the crude product (Example 34i, 60 mg) as yellow solid, which was used for next step without further purification.

Step 10: Example 34

A mixture of 4-fluoro-2,6-dihydroxybenzaldehyde (Example 26a, 39 mg, 0.2475 mmol) and K$_2$CO$_3$ (69 mg, 0.495 mmol) in DMF (5 mL) was added Example 34i (50 mg, 0.168 mmol) at r.t. The mixture was heated at 80° C. for 1.5 h, Cooled to rt. Added water (50 mL) and extracted with EtOAc (50 mL*3). The combined organic layers were washed with brine, dried over Na$_2$SO$_4$, concentrated, and purified by Pre-HPLC to give Example 34 (19 mg, yield 30.3%) as yellow solid. LCMS [M+H]$^+$=381.1. $^1$H NMR (400 MHz, Chloroform-d) δ 12.28 (s, 1H), 10.15 (s, 1H), 9.35 (s, 1H), 9.05 (s, 1H), 7.50 (d, J=4.6 Hz, 1H), 6.29 (dd, J=10.4, 2.2 Hz, 1H), 6.05 (dd, J=10.5, 2.2 Hz, 1H), 5.20 (s, 2H), 4.81 (s, 1H).

Example 35: General Procedure for Synthesis of Example 35

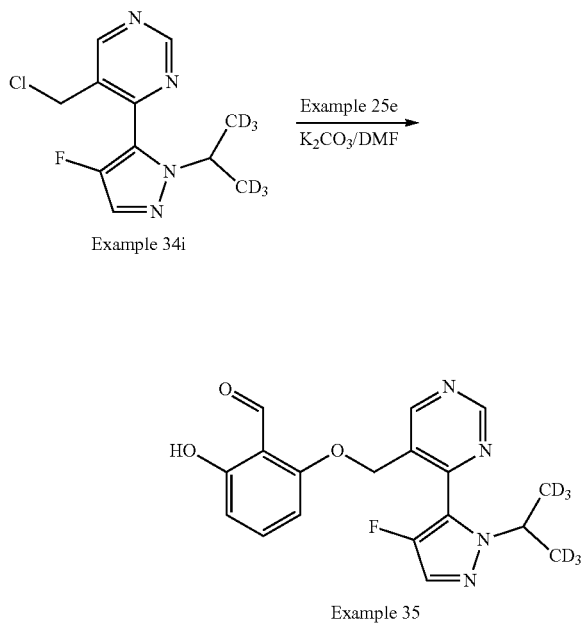

A mixture of 2,6-dihydroxybenzaldehyde (Example 25e, 56 mg, 0.402 mmol) and K$_2$CO$_3$ (111 mg, 0.804 mmol) in DMF (3 mL) was added Example 34i (70 mg, 0.268 mmol) at r.t. The mixture was heated at 55° C. for 1 h; Cooled to r.t. Added water (25 mL) and the residue was extracted with EtOAc (10 mL*2). The combined organic phase was washed with brine, dried over Na$_2$SO$_4$, filtrated and concentrated under reduced pressure to give the crude product which was further purified by silica gel chromatography to give the pure product Example 35 (20 mg, yield 20.6%) as white solid. LCMS [M+H]$^+$=363.1

$^1$H NMR (400 MHz, Chloroform-d) δ 11.92 (s, 1H), 10.29 (s, 1H), 9.34 (s, 1H), 9.07 (s, 1H), 7.49 (d, J=4.6 Hz, 1H), 7.39 (t, J=8.4 Hz, 1H), 6.59 (d, J=8.5 Hz, 1H), 6.32 (d, J=8.2 Hz, 1H), 5.22 (s, 2H), 4.79 (s, 1H).

Example 36: General Procedure for Synthesis of Example 36

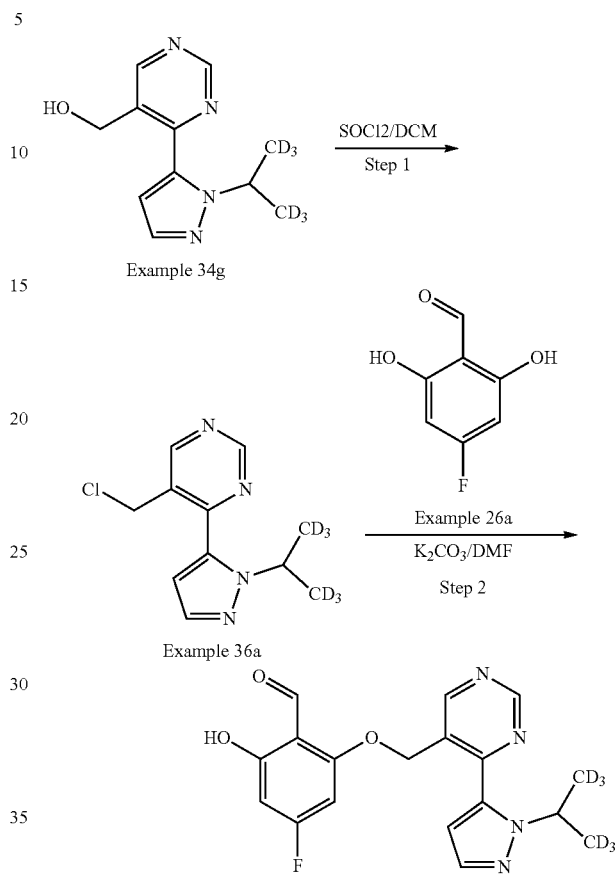

Step 1: Example 36a

To Example 34g (250 mg, 1.12 mmol) in DCM (5 mL) was added SOCl$_2$ (0.5 mL) at r.t. The reaction mixture was stirred at r.t. for 1 h and concentrated to dryness. The crude solid was suspended in toluene and concentrated to dryness to give Example 36a (300 mg) as yellow solid, which was used for next step without further purification.

Step 2: Example 36

A mixture of 2,6-dihydroxybenzaldehyde (Example 26a, 82 mg, 0.52 mmol) and K$_2$CO$_3$ (276 mg, 2.0 mmol) in DMF (5 mL) was added Example 36a (100 mg, 0.4 mmol) at r.t. The mixture was heated at 80° C. for 1 h, Cooled to r.t. Added water (20 mL) and extracted with EtOAc (50 mL*3). The combined organic layers were washed with brine, dried over Na$_2$SO$_4$, concentrated, and purified by Pre-HPLC to give Example 36 (23 mg, yield 16%) as yellow solid. LCMS [M+H]$^+$=363.1

$^1$H NMR (400 MHz, Chloroform-d) δ 12.31 (s, 1H), 10.18 (s, 1H), 9.34 (s, 1H), 8.99 (s, 1H), 7.62 (d, J=2.0 Hz, 1H), 6.43 (d, J=2.0 Hz, 1H), 6.32 (dd, J=10.3, 2.2 Hz, 1H), 6.09 (dd, J=10.5, 2.2 Hz, 1H), 5.13 (s, 2H), 4.95 (s, 1H).

Example 37: General Procedure for Synthesis of Example 37

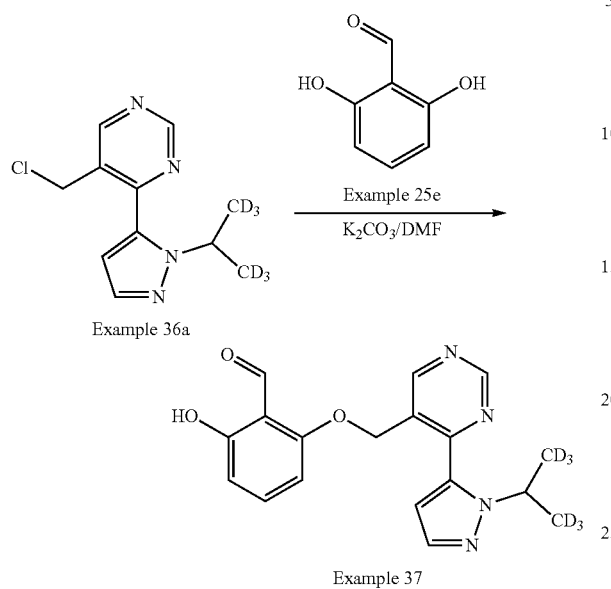

Example 37

A mixture of 2,6-dihydroxybenzaldehyde (Example 25e, 22 mg, 0.159 mmol) and K$_2$CO$_3$ (51 mg, 0.366 mmol) in DMF (5 mL) was added Example 36a (30 mg, 0.122 mmol) at r.t. The mixture was heated at 60° C. for 2.5 h, Cooled to r.t. Added water (25 mL) and extracted with EtOAc (50 mL*3). The combined organic layers were washed with brine, dried over Na$_2$SO$_4$, concentrated, and purified by Pre-HPLC to give Example 37 (25 mg, yield 59.5%) as white solid. LCMS [M+H]$^+$=345.1

$^1$H NMR (400 MHz, Chloroform-d) δ 11.95 (s, 1H), 10.32 (s, 1H), 9.33 (s, 1H), 9.00 (s, 1H), 7.61 (d, J=1.9 Hz, 1H), 7.41 (t, J=8.4 Hz, 1H), 6.61 (d, J=8.5 Hz, 1H), 6.46 (d, J=2.0 Hz, 1H), 6.34 (d, J=8.3 Hz, 1H), 5.15 (s, 2H), 4.94 (s, 1H).

Example 38: General Procedure for Synthesis of Example 38

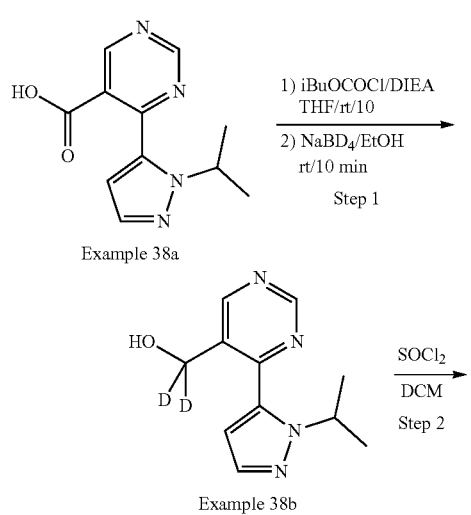

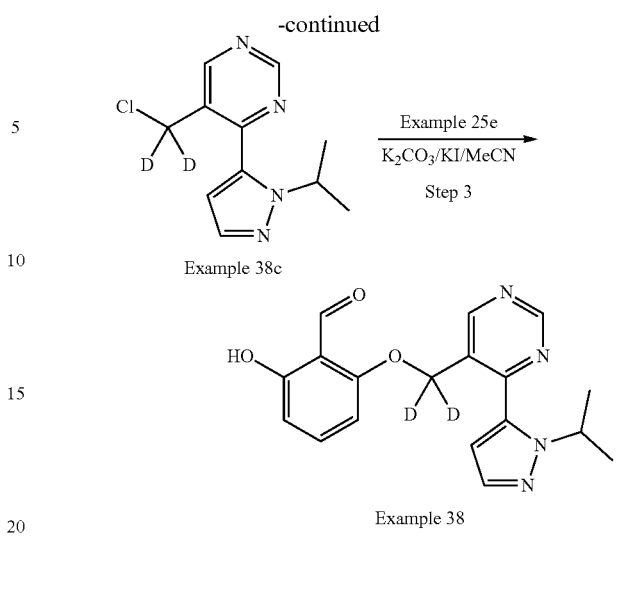

Step 1: Example 38b

To a solution of Example 38a (50 mg, 0.215 mmol, 1.0 eq) in THF (4 mL), tBuOCOCl (35.2 mg, 0.258 mmol) at 0° C. was added TEA (43.4 g, 0.43 mmol, 2.0 eq), the mixture was stirred at 0° C. for 10 min, at 0° C. was added NaBD$_4$ (13 mg, 0322 mmol, 1.5 eq) in EtOH (1 mL) to r.t. for 10 min. The reaction was then quenched by adding 2 mL water, The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product Example 38b (30 mg, yield 50%) as yellow oil. LCMS [M+1]$^+$=220

Step 2: Example 38c

To a solution of Example 38b (200 mg, 0.917 mmol, 1.0 eq) in DCM (2 mL) was added SOCl$_2$ (3 mL) at 0° C. for 15 min, the mixture was stirred at r.t. for 30 min, concentrated under vacuum to give Example 38c (210 mg, yield 97%) as yellow solid. LCMS [M+1]$^+$=238

Step 3: Example 38

To a solution of Example 38c (145 mg, 0.545 mmol, 1.0 eq) in MeCN (5 mL) was added Example 25e (112 mg, 0.817 mmol, 1.5 eq) and K$_2$CO$_3$ (188 mg, 1.36 mmol), KI(cat). the mixture was stirred at 60° C. for 3 hrs, The reaction mixture was then cooled down, the reaction was then quenched by adding 50 mL water, The residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product Example 38 (82 mg, yield 66%) as yellow solid. LCMS [M+1]$^+$=341

$^1$H NMR (400 MHz, Chloroform-d) δ 11.96 (s, 1H), 10.32 (s, 1H), 9.33 (s, 1H), 9.00 (s, 1H), 7.61 (d, J=1.9 Hz, 1H), 7.41 (t, J=8.4 Hz, 1H), 6.61 (d, J=8.5 Hz, 1H), 6.46 (d, J=1.9 Hz, 1H), 6.34 (dd, J=8.2, 0.9 Hz, 1H), 4.98 (p, J=6.6 Hz, 1H), 1.52 (d, J=6.6 Hz, 6H).

Example 39: General Procedure for Synthesis of Example 39

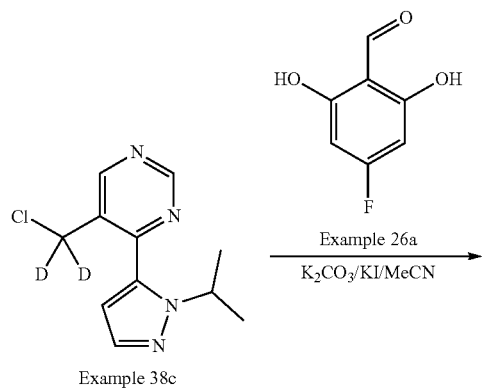

Example 38c

Example 26a
K₂CO₃/KI/MeCN

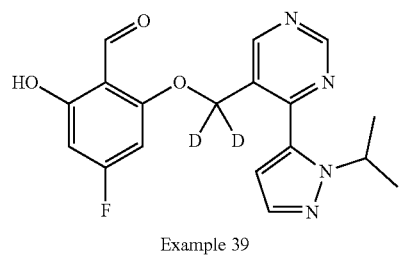

Example 39

To a solution of Example 38c (145 mg, 0.527 mmol, 1.0 eq) in MeCN (5 mL) was added Example 26a (123 mg, 0.798 mmol, 1.5 eq) and K₂CO₃ (218 mg, 1.58 mmol) KI (cat) the mixture was stirred at 60° C. for 3 hrs, The reaction mixture was then cooled down, the reaction was then quenched by adding 50 mL water, The residue was extracted with EtOAc (20 mL*2). The combined organic phase was washed with brine, dried over Na₂SO₄, filtrated and concentrated under reduced pressure to give the crude product which was further purified by silica gel chromatography to give the pure product Example 39 (80 mg, yield 66%) as yellow solid. LCMS [M+1]=360

¹H NMR (400 MHz, Chloroform-d) δ 12.31 (d, J=1.4 Hz, 1H), 10.17 (s, 1H), 9.34 (s, 1H), 8.99 (s, 1H), 7.61 (d, J=1.9 Hz, 1H), 6.43 (d, J=2.0 Hz, 1H), 6.31 (dd, J=10.3, 2.2 Hz, 1H), 6.08 (dd, J=10.5, 2.2 Hz, 1H), 5.06-4.94 (m, 1H), 1.52 (d, J=6.6 Hz, 6H).

Example 40: General Procedure for Synthesis of Example 40

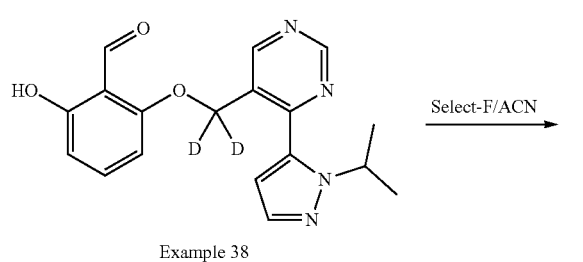

Example 38

Select-F/ACN

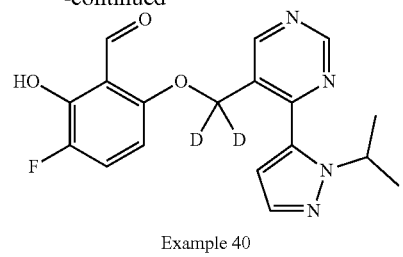

Example 40

To a solution of Example 38 (40 mg, 0.12 mmol) in Acetonitrile (5 mL) was added Select F (62 mg, 0.18 mmol) and sodium sulfate (1.2 g), and then heated to reflux for 1 hrs. After cooled to r.t, water (20 mL) was added, then extracted with EA (20 mL), washed with brine and dried over Na₂SO₄. Then concentrated under reduced pressure and purified by Prep-TLC (eluent: PE/EA=3/1) to give the desired product Example 40 (12 mg, yield 28%) as a yellow solid. LCMS [M+1]⁺=359

¹H NMR (400 MHz, DMSO-d₆) δ 11.14 (s, 1H), 10.05 (s, 1H), 9.30 (s, 1H), 9.11 (s, 1H), 7.59 (t, J=2.7 Hz, 1H), 7.46 (dd, J=11.5, 9.3 Hz, 1H), 6.73-6.68 (m, 2H), 4.83 (dd, J=13.1, 6.5 Hz, 1H), 1.36 (d, J=6.6 Hz, 6H).

Example 41: General Procedure for Synthesis of Example 41

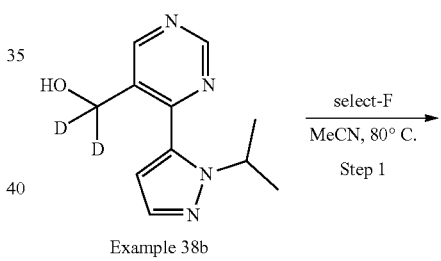

Example 38b select-F
MeCN, 80° C.
Step 1

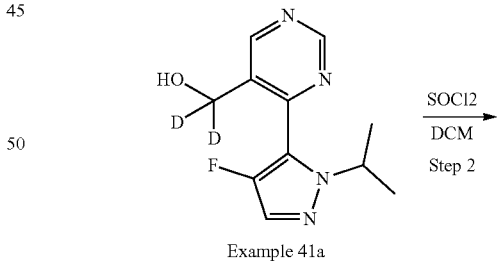

Example 41a

SOCl2
DCM
Step 2

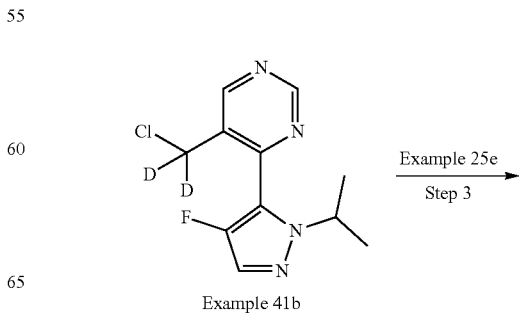

Example 41b

Example 25e
Step 3

-continued

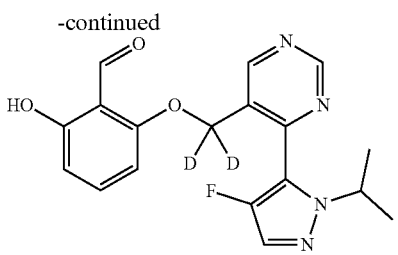

Example 41

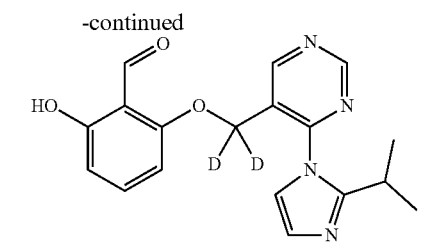

Example 42

Step 1: Example 41a

A solution of Example 38b (217 mg, 1.0 mmol) in CH₃CN (5 mL) was treated with Selectfluor (531 mg, 1.5 mmol) and the reaction mixture was heated at 80° C. for 4 hours. After cooling to room temperature the solution was evaporated and the residue was purified on silica gel using a mixture of (PE:EA=10:3) as elution to give Example 41a (57 mg).

Step 2: Example 41b

To Example 41a (57 mg) in DCM (5 mL) was added SOCl₂ (0.2 mL) at r.t. The reaction mixture was stirred at r.t. for 0.5 h and concentrated to dryness. The crude solid was suspended in toluene and concentrated to dryness to give the desired product (Example 41b, 67 mg) as yellow solid, which was used for next step without further purification.

Step 3: Example 41

A mixture of 2,6-dihydroxybenzaldehyde (Example 25e, 54 mg, 0.4 mmol) and K₂CO₃ (107.6 mg, 0.78 mmol) in MeCN (3 mL) was added Example 41b (67 mg, 0.260 mmol) at r.t. The mixture was heated at 65° C. for 1.5 h, Cooled to r.t. Added water (25 mL) and extracted with EtOAc (50 mL*3). The combined organic layers were washed with brine, dried over Na₂SO₄, concentrated, and purified on silica gel using a mixture of (PE:EA=10:3) as elution to give Example 41 (27 mg, yield 37.36%) as an white solid. LCMS [M+1]⁺=359

¹H NMR (400 MHz, Chloroform-d) δ 11.92 (s, 1H), 10.28 (s, 1H), 9.33 (s, 1H), 9.06 (s, 1H), 7.48 (d, J=4.6 Hz, 1H), 7.38 (t, J=8.4 Hz, 1H), 6.58 (d, J=8.5 Hz, 1H), 6.31 (d, J=8.2 Hz, 1H), 4.83 (p, J=6.6 Hz, 1H), 1.48 (d, J=6.6 Hz, 6H).

Example 42: General Procedure for Synthesis of Example 42

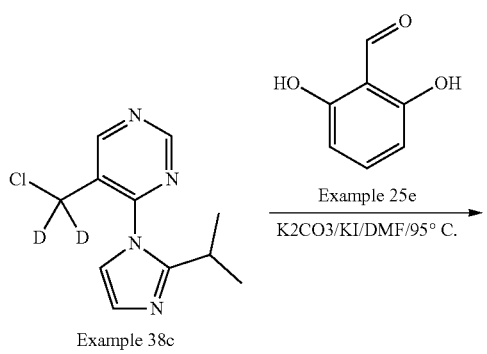

The crude Example 38c (163 mg, 0.68 mmol), Example 25e (93 mg 0.68 mmol), K₂CO₃ (186 mg, 1.35 mmol) KI (8 mg, 0.045 mmol) was suspended in DMF (5 mL) heated to 80° C. for 40 mins, TLC detected the reaction was complete, filtered and purified by doing Prep-HPLC to afford the desired Example 42 (25 mg, yield 17%) was obtained as a yellow solid. LCMS [M+1]⁺=341.

¹H NMR (400 MHz, CDCl₃) δ 11.93 (s, 1H), 10.30 (s, 1H), 9.27 (s, 1H), 9.11 (s, 1H), 7.40 (t, J=8.3 Hz, 1H), 7.08 (d, J=40.4 Hz, 2H), 6.62 (d, J=8.5 Hz, 1H), 6.29 (d, J=8.2 Hz, 1H), 3.24-3.10 (m, 1H), 1.28 (d, J=6.6 Hz, 6H).

Example 43: General Procedure for Synthesis of Example 43

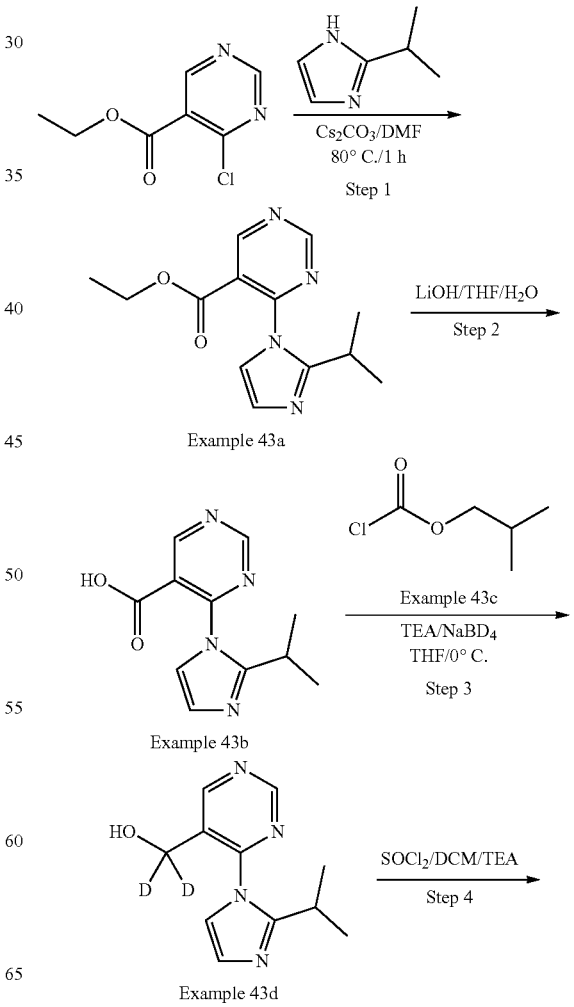

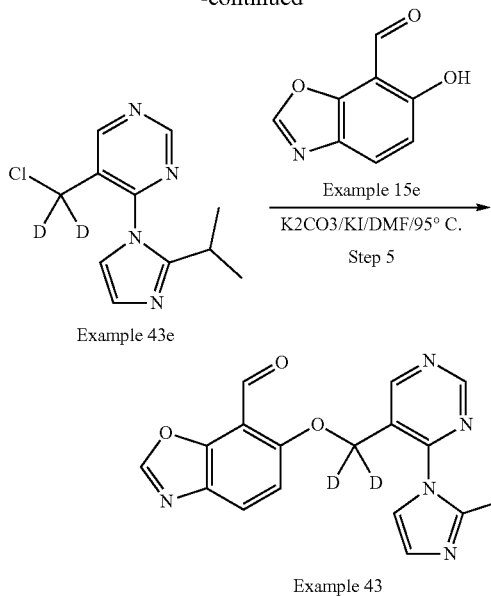

Example 43e

Example 15e
K2CO3/KI/DMF/95° C.
Step 5

Example 43

Step 1: Example 43a

To a solution of ethyl 4-chloropyrimidine-5-carboxylate (10.5 g, 0.056 mol) was dissolved in DMF (100 mL) was added 2-isopropyl-1H-imidazole (6.2 g, 0.056 mol) and $Cs_2CO_3$ (27.6 g), and then heated to 80° C. for 1 hrs, showed reaction completed). After cooled to r.t., water (500 mL) was added, then extracted with EA (200 mL*2), washed with brine and dried over $Na_2SO_4$. Then concentrated under reduced pressure and purified by flash chromatography on silica gel column (elution:PE/EA=3/1) to give Example 43a (9.7 g, yield 66%) as a yellow solid. LCMS [M+1]=261

Step 2: Example 43b

To a solution of Example 43a (2.68 g, 0.01 mol) in MeOH (5 mL), THF (15 mL), $H_2O$ (5 mL) was added $LiOH.H_2O$ (433 mg, 0.1 mol) at 0° C. for 30 mins, the reaction was then quenched by 1NHCl to pH=6, concentrated and purified by flash chromatography on silica gel column eluted with DCM/MeOH 20% to give a crude Example 43b (3 g) which was used directly to the next step.

Step 3: Example 43d

To a solution of Example 43b (3 g, 0.13 mol) in THF (50 mL), Example 43c (2.1 g, 0.016 mol) at 0° C. was added TEA (1.6 g, 0.016 mol), the mixture was stirred at r.t. for 2 hrs, and then $NaBD_4$ (640 mg, 0.016 mol) in EtOH (10 mL) was added at 0° C., which was turned to r.t for another 30 min. The reaction was then quenched by adding 5 mL water, then concentrated. The residue was purified by flash chromatography (eluent: Petroleum Ether/EtOAc=1:1) to give Example 43d (300 mg, yield 11%) as white solid. LCMS [M+1]$^+$=221.1

Step 4: Example 43e

To a solution of Example 43d (300 mg 0.95 mmol) in DCM (6 mL) was treated with $SOCl_2$ (243 mg) at 0° C. After 30 mins TEA (414 mg 4.09 mmol) was added, then the reaction mixture was concentrated to give a crude Example 43e, which was used to next step with any purification.

Step 5: Example 43

The crude Example 43e, Example 15e (111 mg 0.68 mmol), $K_3CO_3$ (188 mg 1.36 mmol), KI (11 mg 0.07 mmol) was suspended in DMF (5 mL) heated to 80° C. for 40 mins, TLC detected the reaction was complete, filtered and the residue was purified by doing Prep-HPLC to afford the desired product Example 43 (40 mg, yield 16%) was obtained as a white solid. LCMS [M+1]$^+$=366.

$^1$H NMR (400 MHz, $CDCl_3$) δ 10.55 (s, 1H), 9.29 (s, 1H), 9.20 (s, 1H), 8.17 (s, 1H), 7.96 (d, J=8.8 Hz, 1H), 7.10 (d, J=19.8 Hz, 2H), 6.98 (d, J=8.8 Hz, 1H), 3.22-3.11 (m, 1H), 1.28 (d, J=6.7 Hz, 6H).

Example 44: General Procedure for Synthesis of Example 44

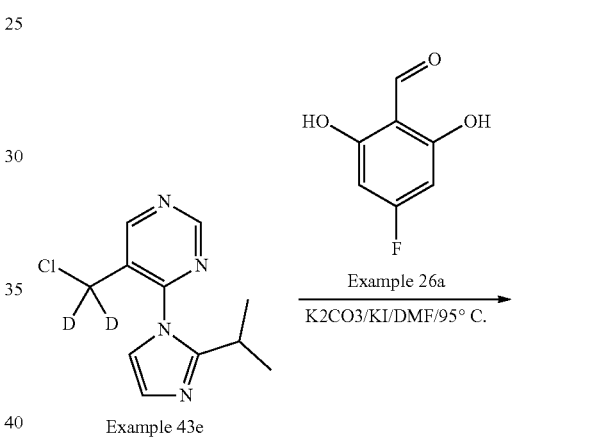

Example 43e

Example 26a
K2CO3/KI/DMF/95° C.

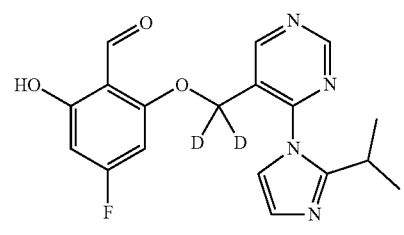

Example 44

The Example 43e, Example 26a (222 mg 1.43 mmol), $K_3CO_3$ (327 mg 2.38 mmol), KI (17 mg, 0.095 mmol) was suspended in DMF (5 mL), heated to 80° C. for 40 mins, TLC detected the reaction was complete, filtered and the residue was purified by doing Prep-HPLC to afford the desired product Example 44 (30 mg) as a white solid. LCMS [M+1]$^+$=359

$^1$H NMR (400 MHz, CDCl3) δ 12.32 (s, 1H), 10.19 (s, 1H), 9.33 (s, 1H), 9.14 (s, 1H), 7.23 (s, 1H), 7.06 (s, 1H), 6.37 (d, J=10.3 Hz, 1H), 6.09 (d, J=10.0 Hz, 1H), 3.23 (s, 1H), 1.35 (d, J=6.8 Hz, 6H).

Example 45: General Procedure for Synthesis of Example 45

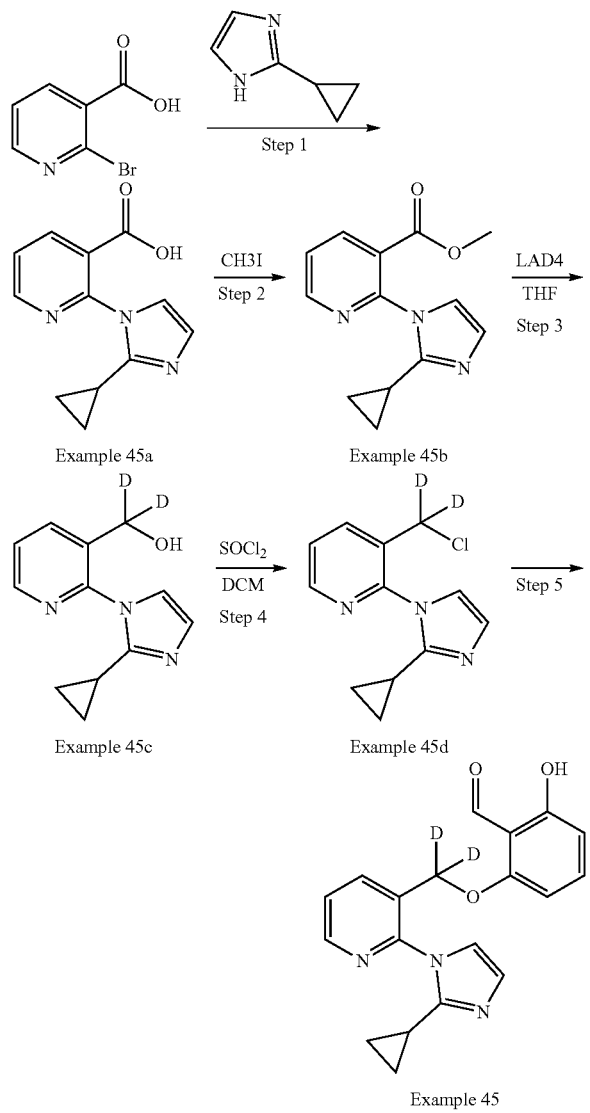

Example 45a

Example 45b

Example 45c

Example 45d

Example 45

Step 1: Example 45a

A mixture of 2-bromonicotinic acid (2.00 g, 9.26 mmol), 2-cyclopropyl-1H-imidazole (1.12 g, 10.2 mmol), cesium carbonate (6.03 g, 18.5 mmol) and copper Iodide (176 mg, 0.92 mmol) in DMSO (8 mL) was heated to 120° C. for 16 h under nitrogen. LCMS analysis showed completed consumption of the starting material. Cooled to r.t., the reaction was used in the next step without work-up. LCMS [M+H]$^+$=230.1.

Step 2: Example 45b

The reaction mixture was cooled to room temperature and CH$_3$I (2 mL, 32.1 mmol) was added. The mixture was stirred for 1 h. The mixture was diluted with water, extracted with ethyl acetate and the combined organic extract was dried over Na$_2$SO$_4$. The solvent was removed under reduced pressure and the residue was purified by flash chromatography on silica gel (PE/EA=1:7) to afford the desired Example 45b (140 mg). LCMS [M+H]$^+$=244.1.

Step 3: Example 45c

A solution of Example 45b (140 mg, 0.576 mmol) in tetrahydrofuran (5.0 mL) was added dropwise to a vigorously stirred suspension of LiAlD4 (50 mg. 1.2 mmol) at 0° C., the resulting mixture was stirred at 0° C. for 1 hour and then at room temperature for 18 hours. The mixture was diluted with water (3 mL), filtered and dried over Na$_2$SO$_4$. The solvent was removed under reduced pressure to afford the crude Example 45c (125 mg, yield 100%). LCMS [M+H]$^+$=218.1.

Step 4: Example 45d

To Example 45c (125 mg, 0.576 mmol) in DCM (5 mL) was added SOCl$_2$ (0.5 mL) at r.t. The reaction mixture was stirred at r.t. for 2 hrs and concentrated to dryness. The crude solid was suspended in toluene and concentrated to dryness to give Example 45d (205 mg) as yellow solid, which was used for next step without further purification. LCMS [M+H]$^+$=236.1.

Step 5: Example 45

To a solution of Example 45d (205 mg, 0.57 mmol) and 2,6-dihydroxybenzaldehyde (Example 25e, 95 mg, 0.69 mmol) in DMF (5 mL) was added potassium carbonate (392 mg, 2.86 mmol) and the mixture was heated at 65° C. for 2 hrs, Cooled to rt. Added water (25 mL) and extracted with EtOAc (50 mL*3). The combined organic layers were washed with brine, dried over Na$_2$SO$_4$, concentrated, and purified by Pre-HPLC to give Example 45 (15 mg, yield 7.8%) as yellow solid. $^1$H NMR (400 MHz, DMSO-d$_6$) δ 10.09 (s, 1H), 8.64 (dd, J=4.8, 1.8 Hz, 1H), 8.31 (dd, J=7.7, 1.8 Hz, 1H), 7.64 (dd, J=7.7, 4.8 Hz, 1H), 7.45 (t, J=8.4 Hz, 1H), 7.35 (d, J=1.4 Hz, 1H), 6.83 (d, J=1.4 Hz, 1H), 6.48 (dd, J=18.2, 8.4 Hz, 2H), 1.61 (ddd, J=13.2, 8.2, 4.9 Hz, 1H), 0.88-0.65 (m, 4H). LCMS (M+H$^+$) 338.1.

Example 46: General Procedure for Synthesis of Example 46

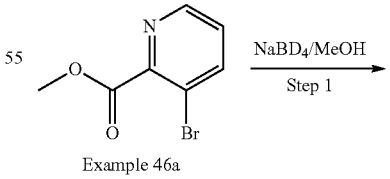

Example 46a

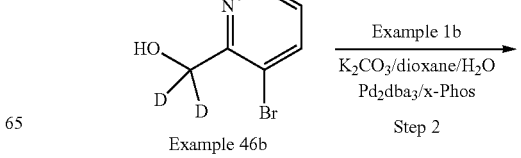

Example 46b

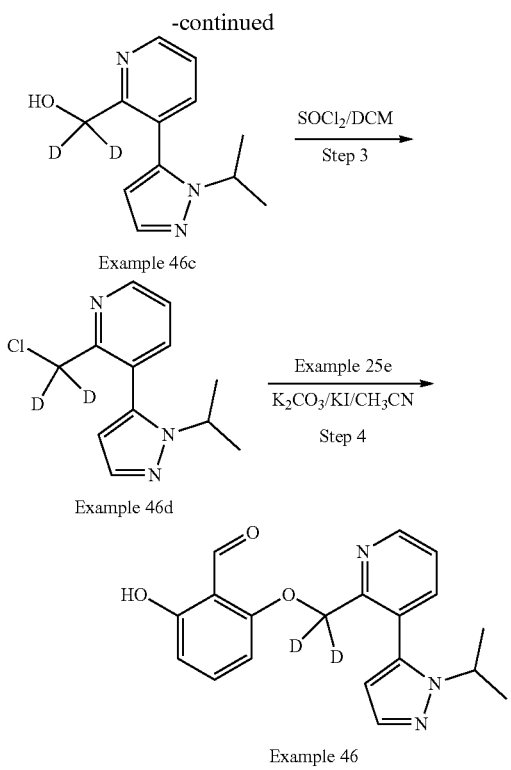

Example 46c

Example 46d

Example 46

Step 1: Example 46b

To a solution of Example 46a (2 g, 9.2 mmol, 1 eq) in methanol (100 mL) was added NaBD₄ (1.8 g, 46.4 mmol, 5 eq) in batch at 0° C. and slowly warmed to r.t. for 16 h. After the reaction was completed, the solvent was removed under reduced pressure, and the residue was dissolved in EtOAc (50 mL), washed with aq. NH₄Cl (20 mL*3), dried over Na₂SO₄, filtered and concentrated to afford the product (Example 46b, 1.4 g, yield 82%) as a white solid. LCMS [M+1]⁺=190

Step 2: Example 46c

To a solution of Example 46b (800 mg, 4.2 mmol, 1 eq) in dioxane/water (8.4 mL/1 mL) was added Example 1b (972 mg, 6.3 mmol, 1.5 eq), K₃PO₄ (2.2 g, 10.5 mmol, 2.5 eq), Pd₂(dba)₃ (192 mg, 0.21 mmol, 0.05 eq) and 2-dicyclohexylphosphino-2',4',6'-triisopropylbiphenyl (99.9 mg, 0.21 mmol, 0.05 eq) under N₂ protection and then heated to 90° C. for 9 hrs. After cooled to room temperature, the solvent was removed under reduced pressure, the residue was extracted with EtOAc (20 mL*2) and combined the organic phase, washed with brine, dried over Na₂SO₄, filtered and concentrated under reduced pressure to give the crude product which was further purified by silica chromatography to give the product (Example 46c, 400 mg, yield 35%) as yellow oil. LCMS [M+1]⁺219.

Step 3: Example 46d

To a solution of Example 46c (600 mg, 1.8 mmol, 1 eq) in DCM (1.8 mL) was added thionyl chloride (0.5 mL) and stirred at r.t for 0.5 h. After the reaction was completed, the solvent was removed under reduced pressure to give the product (Example 46d, 600 mg, yield 92%) as white solid.

Step 4: Example 46

To a solution of Example 46d (600 mg, 2.1 mmol, 1 eq) in acetonitrile (1.7 mL) was added Example 25e (454.9 mg, 3.2 mmol, 1.2 eq), potassium carbonate (724 mg, 5.25 mmol, 2.5 eq) and potassium iodide (2 mg), and then heated to 60° C. for 4 hrs. After cooled to room temperature, water (5 mL) was added to the mixture, then extracted with EA (10 mL*2) and combined the organic phase, washed with brine, dried with Na₂SO₄, filtered and concentrated under reduced pressure to give the crude (600 mg) product which was further purified by Prep-HPLC to give the pure product Example 46 (130 mg, yield 30%) as yellow oil. LCMS [M+1]⁺339

¹H NMR (400 MHz, Chloroform-d) δ 11.91 (s, 1H), 10.18 (s, 1H), 8.75 (dd, J=4.8, 1.8 Hz, 1H), 7.65 (dd, J=7.7, 1.8 Hz, 1H), 7.59 (d, J=1.8 Hz, 1H), 7.43 (dd, J=7.8, 4.8 Hz, 1H), 7.33 (t, J=8.4 Hz, 1H), 6.51 (d, J=8.5 Hz, 1H), 6.38-6.32 (m, 1H), 6.24 (d, J=1.8 Hz, 1H), 4.18 (p, J=6.6 Hz, 1H), 1.39 (d, J=6.6 Hz, 6H).

Example 47: General Procedure for Synthesis of Example 47

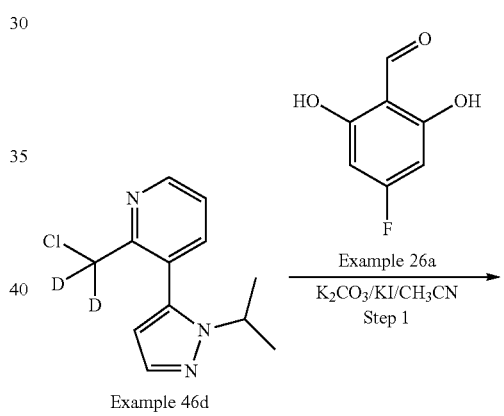

Example 46d

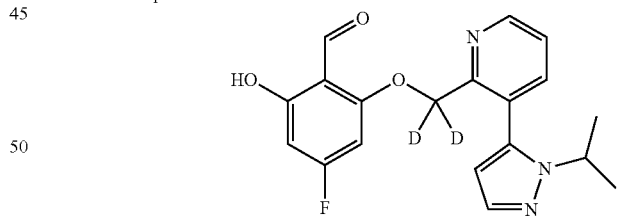

Example 47

Example 47

To a solution of Example 46d (100 mg, 0.42 mmol, 1 eq) in acetonitrile (1.7 mL) was added Example 26a (69 mg, 0.5 mmol, 1.2 eq), potassium carbonate (145 mg, 1.1 mmol, 2.5 eq) and potassium iodide (2 mg), and then heated to 60° C. for 4 hrs. After cooled to room temperature, water (5 mL) was added to the mixture, then extracted with EA (10 mL*2) and combined the organic phase, washed with brine, dried with Na₂SO₄, filtered and concentrated under reduced pressure to give the crude product (120 mg) which was further purified by Prep-HPLC to give the pure product Example 47 (20 mg, yield 20%) as white solid. LCMS [M+1]$^+$=358

$^1$H NMR (400 MHz, Chloroform-d) δ 12.27 (s, 1H), 10.06 (s, 1H), 8.76 (d, J=4.8 Hz, 1H), 7.85-7.53 (m, 2H), 7.45 (dd, J=7.7, 4.8 Hz, 1H), 6.41-6.00 (m, 3H), 4.17 (p, J=6.7 Hz, 1H), 1.41 (d, J=6.6 Hz, 6H).

Example 48: General Procedure for Synthesis of Example 48

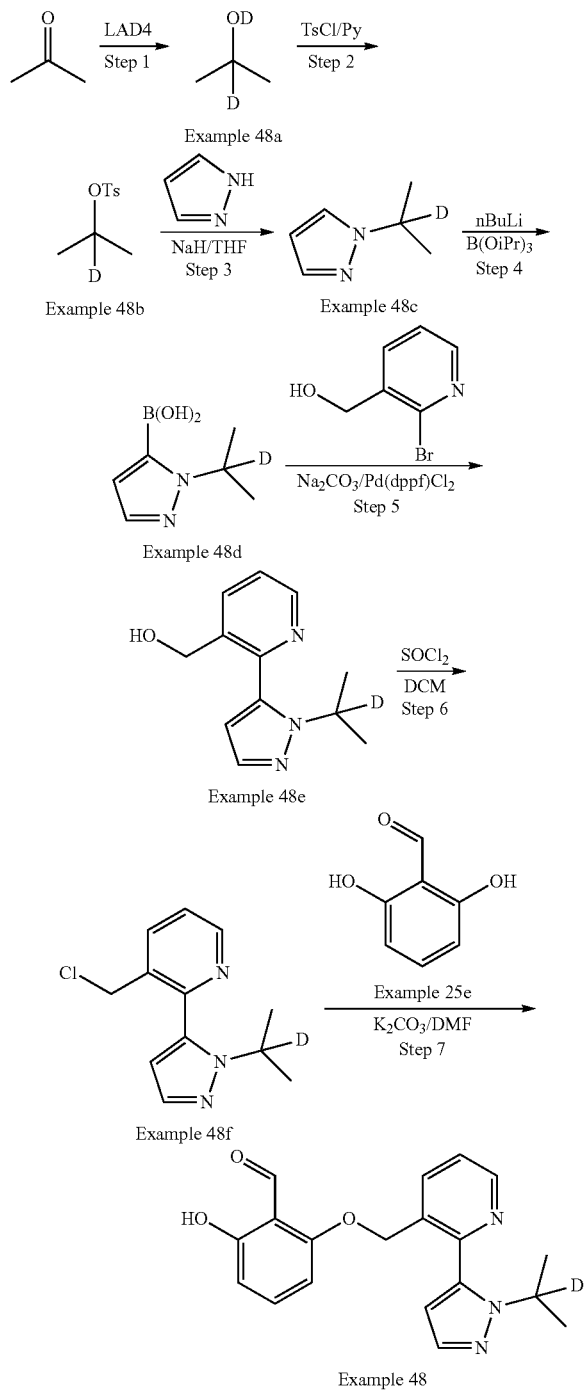

Step 1: Example 48a

To a stirred suspension of LiAlD$_4$ (12.3 g, 307 mmol) in diglyme (200 mL) under N$_2$ at 0° C., was slowly added acetone (35.72 g, 615 mmol). The resulting solution was stirred at 0° C. for 1 h and then diethyl glycol (200 mL) slowly added. The product was distilled from the reaction mixture, and the fraction boiling between 79-105° C. was collected to give the title Example 48a (38.1 g, yield 100%) as colorless oil.

Step 2: Example 48b

Example 48a (38.1 g, 615 mmol) in Piridina (300 mL) was added TsCl (116.8 g, 615 mmol) at 0° C. The reaction was warmed to r.t. and kept for 18 hrs. The reaction liquid was added with water (300 mL). The residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product Example 48b (75 g, yield 56.8%) as colorless oil. LCMS [M+Na]$^+$=238.1.

Step 3: Example 48c

A mixture of 1H-pyrazole (25.00 g, 366 mmol) in THF (500 mL) was added NaH (60%, 20.88 g, 522 mmol) at 0° C., The resulting solution was stirred at 0° C. for 1 h and then Example 48b (75.00 g, 348 mmol) was slowly added. The reaction was warmed at 80° C. and kept for 38 hrs. Cooled to r.t. and filtered. The product was distilled from the mixture, and the fraction boiling between 95-105° C. was collected under reduced pressure to give the title Example 48c (32.0 g, yield 79.8%) as colorless oil. LCMS [M+H]$^+$=112.1.

Step 4: Example 48d

To a solution of Example 48c (1.17 g, 10.0 mmol) in THF (10 mL) at −78° C. was added 2.5M n-BuLi (4.8 mL, 12.0 mmol). The solution was stirred at −78° C. for 1 h and Triisopropyl borate (7.52 g, 40 mmol) was added dropwise. The reaction was continued at −78° C. for 0.5 h, then warmed up to r.t. for 18 hrs. The reaction mixture was quenched with brine, adjusted to pH=5-6 with 1N HCl aqueous solution, the residue was extracted with EtOAc (100 mL*2). The combined organic phase was washed with brine, dried over Na$_2$SO$_4$, filtrated and concentrated under reduced pressure to give the crude product which was further purified by silica gel chromatography to give the pure product Example 48d (1.25 g, yield 80.6%) as white solid. LCMS [M+H]$^+$=156.1

Step 5: Example 48e

To a solution of Example 48d (210.0 mg, 1.35 mmol) in dioxane (7.5 mL) was added (2-bromopyridin-3-yl)methanol (188.0 mg, 1.0 mmol), 2N Na$_2$CO$_3$ aqueous solution (2.5 mL, 5.0 mmol), Pd(dppf)Cl$_2$ (37.0 mg, 0.005 mmol) under N$_2$ protection and then heated to 80° C. for 18 hrs. After cooled to room temperature, the solvent was removed under reduced pressure, the residue was extracted with EtOAc (20 mL*2) and combined the organic phase, washed with brine, dried over Na$_2$SO$_4$, filtered and concentrated under reduced pressure to give the crude and further purified by silica chromatography (PE/EA=1:1) to give the product Example 48e (37 mg, yield 17%) as yellow oil. LCMS [M+1]⁺=219.1

Step 6: Example 48f

To Example 48e (37.0 mg, 0.17 mmol) in DCM (5 mL) was added SOCl₂ (0.3 mL) at r.t. The reaction mixture was stirred at r.t. for 0.5 h and concentrated to dryness. The crude solid was suspended in toluene and concentrated to dryness to give Example 48f (45 mg, yield 100%) as yellow solid, which was used for next step without further purification.

Step 7: Example 48

A mixture of 2,6-dihydroxybenzaldehyde (Example 25e, 28.0 mg, 0.204 mmol) and K₂CO₃ (69.0 mg, 0.495 mmol) in DMF (5 mL) was added Example 48f (45.0 mg, 0.17 mmol) at rt. The mixture was heated at 65° C. for 1.5 hrs. Cooled to r.t., added water (50 mL) and extracted with EtOAc (50 mL*3). The combined organic layers were washed with brine, dried over Na₂SO₄, concentrated, and purified by Pre-HPLC to give Example 48 (40.0 mg, yield 69.5%) as white solid. LCMS [M+1]⁺=339.1

$^1$H NMR (400 MHz, Chloroform-d) δ 11.93 (s, 1H), 10.37 (s, 1H), 8.75 (d, J=4.8 Hz, 1H), 7.97 (d, J=7.9 Hz, 1H), 7.65-7.49 (m, 1H), 7.44-7.30 (m, 2H), 6.57 (d, J=8.5 Hz, 1H), 6.34 (d, J=1.9 Hz, 1H), 6.26 (d, J=8.3 Hz, 1H), 5.08 (s, 2H), 1.47 (s, 6H).

Example 49: General Procedure for Synthesis of Example 49

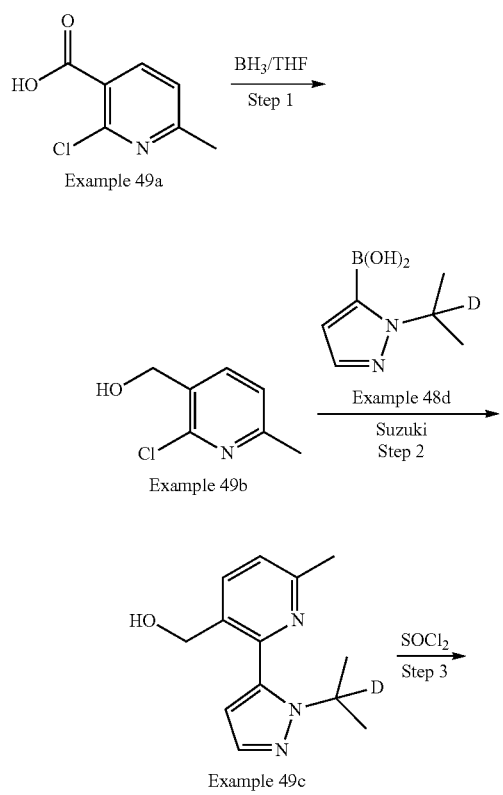

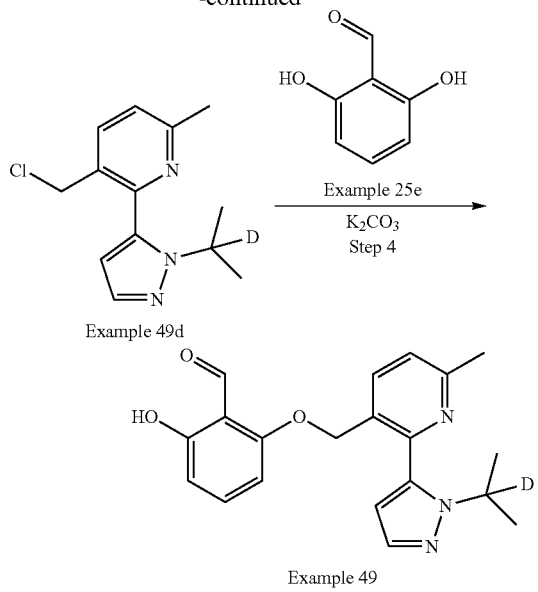

Step 1: Example 49b

To a solution of Example 49a (3.0 g, 0.013 mol, 1.0 eq) in THF (100 mL) was added BH₃ (1M, 70 mL) in batch at 0° C. and slowly warmed to r.t. for 1 h (detected by LCMS). After the reaction was completed, the solvent was removed under reduced pressure, and the residue was dissolved in EtOAc (50 mL), washed with aqueous NH₄Cl solution (20 mL*3), dried over Na₂SO₄, filtered and concentrated to afford the title Example 49b (2.5 g, yield 90.9%) as a white solid.

Step 2: Example 49c

To a solution of Example 49b (130.0 mg, 1.5 mmol, 1.0 eq.) in dioxane/water (8 mL/1 mL) was added Example 48d (130.0 mg, 1.9 mmol, 1.0 eq.), K₃PO₄ (438.0 mg, 3.0 mmol, 2.0 eq.), Pd₂(dba)₃ (13.0 mg) and 2-dicyclohexylphosphino-2',4',6'-triisopropylbiphenyl (13.0 mg) under N₂ protection and then heated to 90° C. for 2 hrs (detected by TLC PE/EA=2/1). After cooled to room temperature, the solvent was removed under reduced pressure, the residue was extracted with EtOAc (20 mL*2) and combined the organic phase, washed with brine, dried over Na₂SO₄, filtered and concentrated under reduced pressure to give the crude and further purified by silica chromatography to give the title Example 49c (100 mg, yield 70%) as yellow oil.

Step 3: Example 49d

To a solution of Example 49c (164 mg) in DCM (18 mL) was added thionyl chloride (0.5 mL) and stirred at r.t for 0.5 h (detected by TLC PE/EA=2/1). After the reaction was completed, the solvent was removed under reduced pressure to give the title Example 49d (193 mg, yield 100%) as yellow oil.

Step 4: Example 49

To a solution of Example 49d (177 mg, 0.71 mmol, 1 eq.) in acetonitrile (5 mL) was added Example 25e (147 mg, 1.06 mmol, 1.5 eq.), potassium carbonate (392 mg, 2.84 mmol, 4 eq.) and potassium iodide (2 mg), and then heated to 60° C. for 4 hrs. After cooled to room temperature, water (5 mL) was added to the mixture, then extracted with EA (10 mL*2) and combined the organic phase, washed with brine, dried with Na$_2$SO$_4$, filtered and concentrated under reduced pressure to give the crude product (120 mg) which was further purified by Prep-HPLC to give the title Example 49 (90 mg, yield 36.1%) as a white solid.

$^1$H NMR (400 MHz, Chloroform-d$_6$) δ 11.93 (s, 1H), 10.34 (s, 1H), 7.85 (d, J=7.9 Hz, 1H), 7.61-7.55 (m, 1H), 7.36 (t, J=8.4 Hz, 1H), 7.27 (s, 1H), 6.55 (d, J=8.5 Hz, 1H), 6.36-6.30 (m, 1H), 6.26 (d, J=8.3 Hz, 1H), 5.03 (s, 2H), 2.65 (s, 3H), 1.48 (s, 6H).

Example 50: General Procedure for Synthesis of Example 50

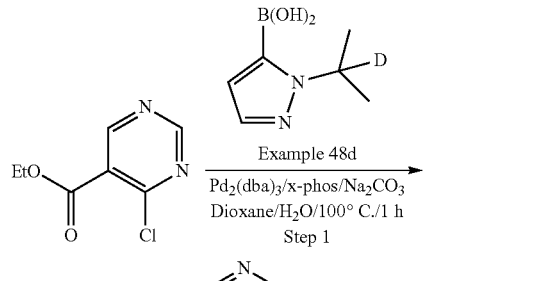

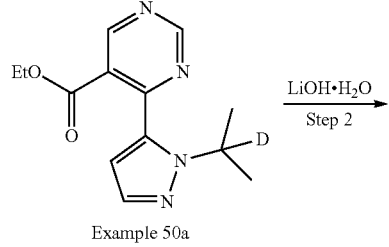

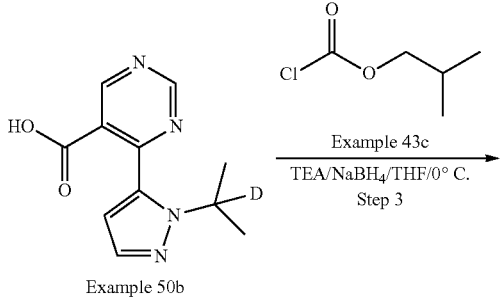

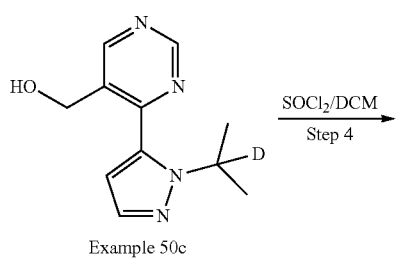

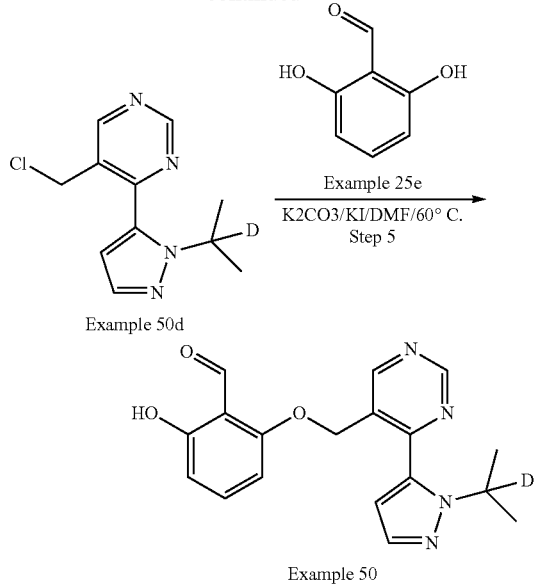

Step 1: Example 50a

To a solution of ethyl 4-chloropyrimidine-5-carboxylate (0.84 g, 4.52 mmol, 1.0 eq.) was dissolved in Dioxane (10 mL) and water (1 mL) was added Example 48d (840 mg, 5.42 mmol, 1.2 eq.) and Na$_2$CO$_3$ (0.95 g, 9.03 mmol, 2.0 eq.), Pd$_2$(dba)$_3$ (50 mg) and x-phos (50 mg), and then heated to 105° C. for 1 hrs. (detected by TLC PE:EA=5:1, showed reaction completed). The reaction was purified by flash chromatography (PE:EA=20%) to give the title Example 50a (530 mg, yield 44.9%) as a yellow oil.

Step 2: Example 50b

To a solution of Example 50a (0.53 g, 2.03 mmol, 1.0 eq.) in MeOH (1 mL)/THF (3 mL)/H$_2$O (1 mL) was added LiOH.H$_2$O (86 mg, 2.03 mmol, 1.0 eq.) at 0° C. for 30 min, the reaction was then quenched by 1NHCl to pH=6, concentrated and purified by flush (eluted with DCM/MeOH=20%) to give a crude title Example 50b (0.5 g, yield 100%) as a white solid which was used to next step.

Step 3: Example 50c

To a solution of Example 50b (500 mg, 2.1 mmol, 1.0 eq.) in THF (10 mL), compound 171 (352 mg, 2.6 mmol, 1.2 eq.) at 0° C. was added TEA (326 mg, 3.2 mmol, 1.5 eq.), the mixture was stirred at r.t. for 10 hrs, and then NaBH$_4$ (98 mg, 2.6 mmol, 1.2 eq.) in EtOH (1.5 mL) was added at 0° C., which was turned to r.t. for another 30 min. The reaction was then quenched by adding 2 mL water and concentrated. The residue was purified by flash chromatography (elution:PE/EA=1:1) to give the title Example 50c (220 mg, yield 47.8%) as yellow oil. LCMS [M+1]$^+$220

Step 4: Example 50d

To a solution of Example 50c (110 mg, 0.50 mmol, 1.0 eq.) in DCM (5 mL) was treated with SOCl$_2$ (120 mg, 1.0 mmol, 2.0 eq.) at 0° C. After 30 min, TEA (253 mg, 2.50 mmol, 5.0 eq.) was added. Then the reaction mixture was concentrated to give a crude title Example 50d which was used to next step directly without any purification.

Step 5: Example 50

The crude Example 50d, Example 25e (87 mg 0.63 mmol), K$_2$CO$_3$ (116 mg, 0.84 mmol), KI (7 mg, 0.04 mmol) was suspended in DMF (2 mL) and heated to 60° C. for 30 min. TLC detected the reaction was completed, filtered and sent to Prep-HPLC to give the title Example 50 (33 mg, yield 23.2%) as a yellow solid. LCMS [M+1]$^+$340

$^1$H NMR (400 MHz, Chloroform-d$_6$) δ 11.95 (s, 1H), 10.32 (s, 1H), 9.34 (s, 1H), 9.04 (s, 1H), 7.61 (d, J=1.8 Hz, 1H), 7.41 (t, J=8.4 Hz, 1H), 6.61 (d, J=8.5 Hz, 1H), 6.46 (d, J=1.9 Hz, 1H), 6.34 (d, J=8.2 Hz, 1H), 5.16 (s, 2H), 1.51 (s, 6H).

Example 51: General Procedure for Synthesis of Example 51

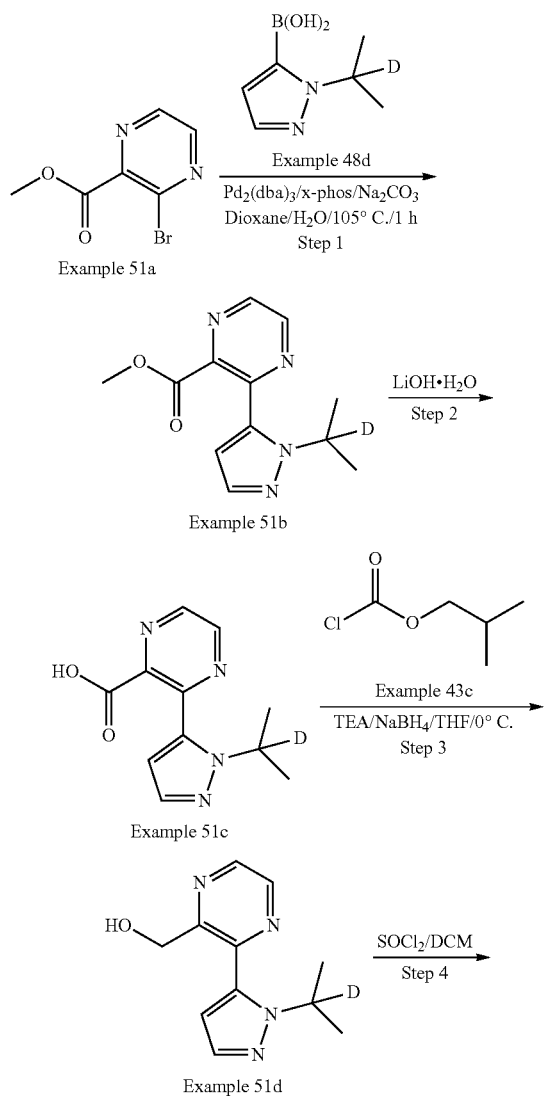

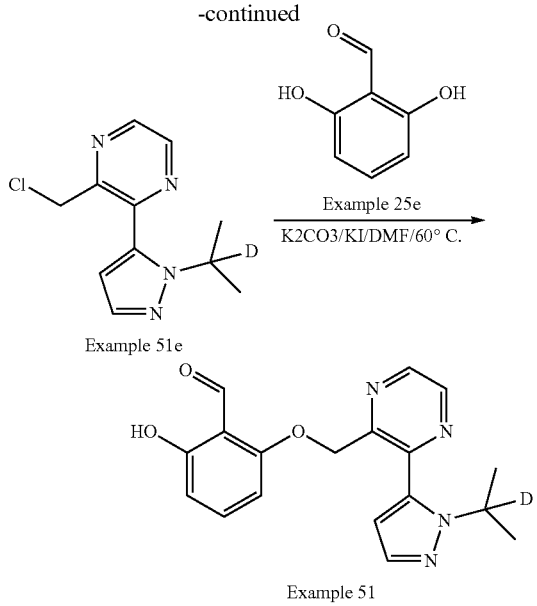

Step 1: Example 51b

To a solution of Example 51a (0.56 g, 2.6 mmol, 1.0 eq.) was dissolved in Dioxane (10 mL) and water (1 mL) was added Example 48d (600 mg, 3.9 mmol, 1.5 eq.), Na$_2$CO$_3$ (0.51 g, 5.2 mmol, 2.1 eq.), Pd$_2$(dba)$_3$ (50 mg) and x-phos (50 mg), and then heated to 105° C. under N$_2$ for 1 h. The reaction was purified by flash (PE:EA=20%) to give the title Example 51b (600 mg, yield 93%) as yellow oil.

Step 2: Example 51c

To a solution of Example 51b (0.6 g, 2.4 mmol, 1.0 eq.) in MeOH (3 mL)/THF (10 mL)/H$_2$O (3 mL) was added LiOH.H$_2$O (102 mg, 2.4 mmol, 1.0 eq.) at 0° C. for 30 min, the reaction was then quenched by 1NHCl to pH=6, concentrated and purified by flash (eluted with DCM/MeOH=20%) to give a crude Example 51c (0.6 g, yield 100%) as a white solid which was used to next step directly.

Step 3: Example 51d

To a solution of Example 51c (360 mg, 1.6 mmol, 1.0 eq.) in THF (10 mL), Example 43c (255 mg, 1.9 mmol, 1.2 eq.) at 0° C. was added TEA (240 mg, 2.4 mmol, 1.5 eq.), the mixture was stirred at r.t. for 10 hrs, and then NaBH$_4$ (71 mg, 1.9 mmol, 1.5 eq.) in EtOH (1.5 mL) was added at 0° C., which was turned to r.t. for another 30 min. The reaction was then quenched by adding 2 mL water, and then concentrated. The residue was purified by flash chromatography (elution as PE/EA=1:1) to give the title Example 51d (150 mg, yield 42.8%) as yellow oil.

Step 4: Example 51e

To a solution of Example 5 d (150 mg, 0.68 mmol, 1.0 eq.) in DCM (5 mL) was treated with SOCl$_2$ (163 mg, 1.4 mmol, 2.0 eq.) at 0° C. After 30 min, TEA (206 mg, 2.04 mmol, 3.0 eq.) was added. The reaction mixture was concentrated to give a crude title Example 51e (180 mg, yield 100%) which was used to next step without any other purification.

Step 5: Example 51

The crude Example 51e, Example 25e (157 mg 1.14 mmol), K$_2$CO$_3$ (210 mg, 1.52 mmol), KI (13 mg, 0.08 mmol) was suspended in DMF (5 mL) and heated to 60° C. for 30 min. TLC detected the reaction was completed. The mixture was filtered and sent to Prep-HPLC to give the title compound Example 51 (80 mg, yield 23.2%) as a white solid. LCMS [M+1]$^+$340

$^1$H NMR (400 MHz, cdcl3) δ 11.93 (s, 1H), 10.22 (s, 1H), 8.73 (d, J=2.3 Hz, 1H), 8.66 (d, J=2.3 Hz, 1H), 7.60 (d, J=1.7 Hz, 1H), 7.37 (t, J=8.4 Hz, 1H), 6.56 (d, J=8.5 Hz, 1H), 6.46 (d, J=1.8 Hz, 1H), 6.40 (d, J=8.3 Hz, 1H), 5.26 (s, 2H), 1.47 (s, 6H).

Example 52: General Procedure for Synthesis of Example 52

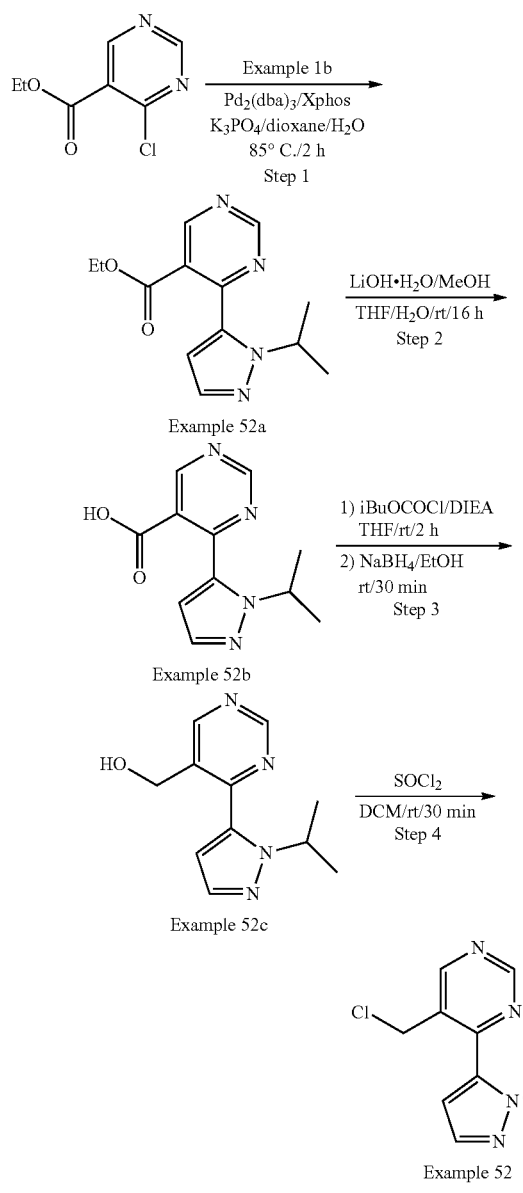

Step 1: Example 52a

To a solution of ethyl 4-chloropyrimidine-5-carboxylate (2.0 g, 10 mmol) in Dioxane (20 mL) was added (1-isopropyl-1H-pyrazol-5-yl)boronic acid (2.4 g, 16 mmol) and Pd$_2$(dpa)$_3$ (0.4 g, 0.5 mmol), K$_3$PO$_4$ (5.3 g, 25 mmol), H$_2$O (2 mL) the mixture was stirred at 85° C. for 3 hrs. The reaction mixture was then cooled down, The reaction was quenched by adding 50 mL water and extracted with EtOAc (100 mL) twice, the organic phase was combined, washed with brine, dried over Na$_2$SO$_4$, and concentrated under vacuum to give the desired product (Example 52a, 2 g, yield 71%) as yellow solid.

Step 2: Example 52b

To a solution of Example 52a (2 g, 7.6 mmol) in MeOH (5 mL), THF (15 mL), H$_2$O (5 mL) was added LiOH.H$_2$O (600 mg, 15.2 mmol) at 0° C. for 15 mins, the mixture was stirred at r.t. for another 16 hrs, the reaction was then quenched by adding 50 mL water, the reaction was added 1N HCl to pH=4 extracted with EtOAc (100 mL) twice, the organic phase was combined, washed with brine, dried over Na$_2$SO$_4$, and concentrated under vacuum to give the desired product (Example 52b, 1.300 g, yield 73%) as yellow solid.

Step 3: Example 52c

To a solution of Example 52b (1.2 g, 5.172 mmol) in THF (20 mL), tBuOCOCl (1.063 g, 7.758 mmol) at 0° C. was added DIEA (1.33 g, 10.34 mmol, 2.0 eq), the mixture was stirred at r.t for 2 hrs, at 0° was added NaBH$_4$ (295 mg, 7.758 mmol) in EtOH (10 mL) to r.t. for 30 min. The reaction was then quenched by adding 20 mL water, extracted with EtOAc (500 mL) twice, the organic phase was combined, washed with brine, dried over Na$_2$SO$_4$, and concentrated The residue was purified by flash chromatography on a 25 g silica gel column (elution as Petroleum Ether/EtOAc=3:2) to give the desired product (Example 52c, 200 mg, yield 18%) as yellow oil. MS [M+1]$^+$=219

Step 4: Example 52

To a solution of Example 52c (200 mg, 0.917 mmol, 1.0 eq) in DCM (2 mL) was added SOCl$_2$ (3 mL) at 0° C. for 15 mins, the mixture was stirred at r.t for 30 min, concentrated under vacuum to give the desired product (Example 52, 210 mg, yield 97%) as yellow solid. LCMS [M+1]$^+$=237.

Example 53: General Procedure for Synthesis of Example 53

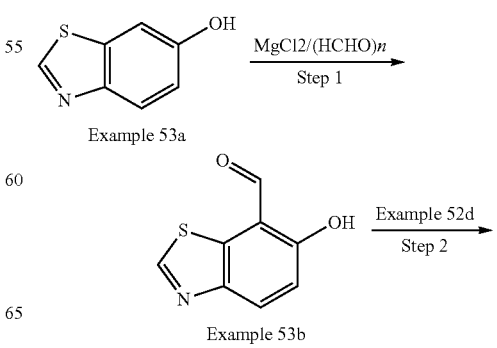

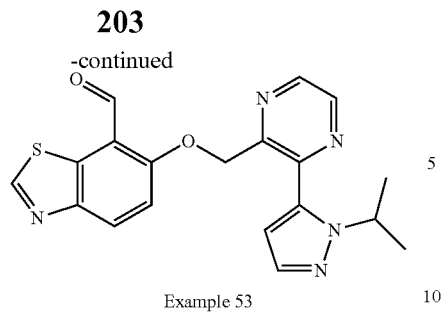

Example 53

Step 1: Example 53b

To the mixture of Example 53a (500 mg, 3.31 mmol), anhydrous magnesium chloride (471 mg, 4.96 mmol) in 15 mL of anhydrous acetonitrile was added TEA (1.75 mL, 12.41 mmol) and (HCHO)n (670 mg, 22.34 mmol). The mixture was then heated to reflux for 3 hours. After cooling to r.t., 50 mL of 5 percent aqueous hydrochloric acid was added. The product was extracted with ethyl acetate. The combined organic extracts were washed with water and brine, dried over $Na_2SO_4$. The residue was purified by column chromatography (n-hexane:ethyl acetate=8:1) to give the desired product (Example 53b, 180 mg, yield 30%) as yellow solid. LCMS $[M+1]^+=180.1$

Step 2: Example 53

A mixture of Example 53b (113 mg, 0.412 mmol), Example 52d (89 mg, 0.495 mmol), potassium carbonate (285 mg, 2.06 mmol) was stirred in DMF (5 mL) at 65° C. for 1.5 hrs, the reaction was quenched by adding 20 mL water, extracted with EtOAc (35 mL*2), the organic phase was combined, washed with brine, dried over $Na_2SO_4$, and concentrated under vacuum and which was further purified by combined-flash (PE/EA=100/60) to give the title Example 53 (55 mg, yield 35.3%) as yellow solid. LCMS $[M+1]^+=380.1$ $^1$H NMR (400 MHz, DMSO-$d_6$) δ 10.34 (s, 1H), 9.34 (d, J=4.9 Hz, 2H), 9.24 (s, 1H), 8.38 (d, J=9.0 Hz, 1H), 7.61-7.48 (m, 2H), 6.75 (d, J=2.0 Hz, 1H), 5.50 (s, 2H), 4.87 (p, J=6.6 Hz, 1H), 1.36 (d, J=6.6 Hz, 6H).

Example 54: General Procedure for Synthesis of Example 54

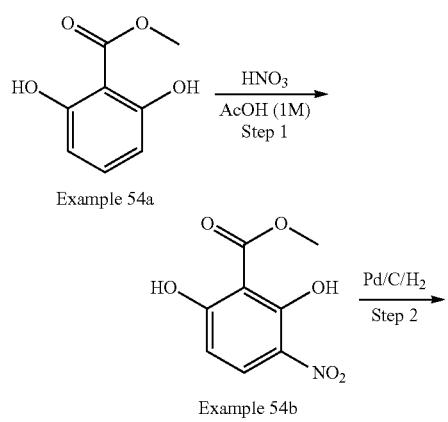

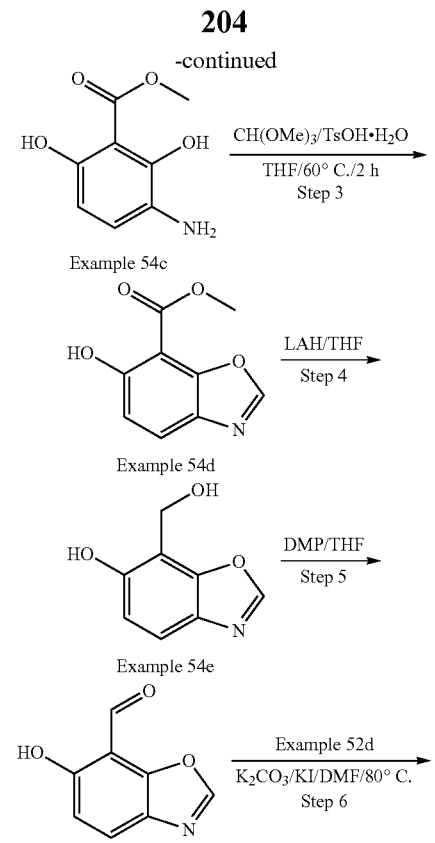

Example 54

Step 1: Example 54b

1M $HNO_3$ in acetic acid (10 mL, 10.0 mmol) was added dropwise to a solution of Example 54a (1.68 g, 10.0 mmol) in acetic acid (10 mL) at ambient temperature. The reaction mixture was stirred at r.t. for 2 hours. The precipitant was filtered and washed with water and acetone, dried to provide the desired product (Example 54b, 1.08 g, yield 51%) as yellow solid.

$^1$H NMR (400 MHz, DMSO-$d_6$) δ 10.92 (s, 2H), 8.02 (d, J=9.4 Hz, 1H), 6.57 (d, J=9.4 Hz, 1H), 3.78 (s, 3H).

Step 2: Example 54c

To a solution of Example 54b (1.02 g, 3.9 mmol) in MeOH (20 mL) was added Pd/C (100 mg) the mixture was stirred at r.t. under $H_2$ overnight for 16 hrs. Filtered and concentrated to give the desired product (Example 54c, 530 mg, yield 62%) as a brown solid.

Step 3: Example 54d

To a solution of Example 54c (46.3 g, 0.25 mol) in THF (500 mL), CH(OMe)$_3$ (80.5 g, 0.76 mol) and TsOH.H$_2$O (4.8 g, 0.025 mol) was added, then heated to 65° C. for 2 hrs, after the completion of the reaction (as indicated by TLC), the mixture was filtered. Further purification by column chromatography eluted with EA/PE (20%) affords the desired product (Example 54d, 25 g, and yields 52%) as a white solid. LCMS [M+1]$^+$=194

$^1$H NMR (400 MHz, DMSO-d$_6$) δ 10.79 (s, 1H), 8.65 (s, 1H), 7.88 (d, J=8.8 Hz, 1H), 7.01 (d, J=8.8 Hz, 1H), 3.95 (s, 3H).

Step 4: Example 54e

To a solution of Example 54d (6.6 g, 0.034 mol) in THF (120 mL) was added LAH (1.3 g, 0.034 mol) at r.t. After addition, the reaction mixture was stirred at r.t. for 1 hour. Water (100 mL) was added. The residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product (Example 54e, 1.6 g, yield 28%) as colorless oil. LCMS [M+1]$^+$=166.

Step 5: Example 15e

Example 54e (3 g, 0.018 mmol) was suspended in THF (100 mL), DMP (9.3 g 0.022 mmol) was added and heated to 40° C. for 4 hrs, TLC detected the reaction was complete, filtered and purified by Prep-TLC to afford the desired product (Example 15e, 125 mg) as a white solid. LCMS [M+1]$^+$=164

Step 6: Example 54

Example 15e (125 mg 0.76 mmol) Example 52d (180 mg 0.76 mmol), K$_2$CO$_3$ (211 mg 1.53 mmol), KI (14 mg, 0.08 mmol) was suspended in DMF (3 mL), heated to 80° C. for 40 min, LCMS detected the reaction was complete, filtered and the residue purified by Prep-HPLC to afford the desired product Example 54 (110 mg) as a white solid. LCMS [M+1]$^+$=364

$^1$H NMR (400 MHz, CDCl$_3$) δ 10.56 (s, 1H), 9.35 (s, 1H), 9.09 (s, 1H), 8.17 (s, 1H), 7.97 (d, J=8.8 Hz, 1H), 7.62 (d, J=1.7 Hz, 1H), 7.04 (d, J=8.9 Hz, 1H), 6.50 (d, J=1.8 Hz, 1H), 5.28 (s, 2H), 4.97 (dd, J=13.2, 6.6 Hz, 1H), 1.53 (d, J=6.6 Hz, 6H).

Example 55: General Procedure for Synthesis of Example 55

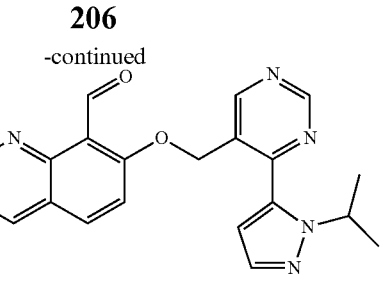

Example 55

Step 1: Example 55b

To a solution of Example 55a (2 g, 13.8 mmol) in chloroform (30 mL) an aqueous NaOH (16 mL, 350 mmol) solution was added. The resulting mixture was stirred at 92° C. for 20 hrs until TLC indicated complete conversion and a thick, dark brown, frothing liquid was show. The reaction was diluted with water (300 mL), and then extracted with DCM (200 mL*3) and combined the organic phase, washed with brine, dried over Na$_2$SO$_4$. Concentration in vacuum to give the crude desired product which was further purified by silica gel chromatography to afford the desired product (Example 55b, 200 mg) as a yellow solid.

Step 2: Example 55

To a solution of Example 55b (110 mg, 0.64 mmol in acetonitrile (5 mL) was added Example 52d (150 mg, 0.5 mmol), potassium carbonate (225 mg, 1.8 mmol) and potassium iodide (2 mg), and then heated to 60° C. for 4 hrs. After cooled to room temperature, water (5 mL) was added to the mixture, then extracted with EA (10 mL*2) and combined the organic phase, washed with brine, dried with Na$_2$SO$_4$, filtered and concentrated under reduced pressure to give the crude product (120 mg) which was further purified by Prep-HPLC to give the desired product Example 55c (10 mg, yield 13%) as yellow oil. LCMS [M+1]$^+$=374

$^1$H NMR (400 MHz, CDCl$_3$) δ 11.43 (s, 1H), 9.37 (d, J=31.2 Hz, 2H), 9.02 (s, 1H), 8.17 (d, J=8.0 Hz, 1H), 8.03 (d, J=8.9 Hz, 1H), 7.64 (s, 1H), 7.46-7.39 (m, 1H), 6.56 (d, J=2.0 Hz, 1H), 5.34 (s, 2H), 4.92 (q, J=6.6 Hz, 1H), 1.52 (d, J=6.6 Hz, 6H).

Example 56: General Procedure for Synthesis of Example 56

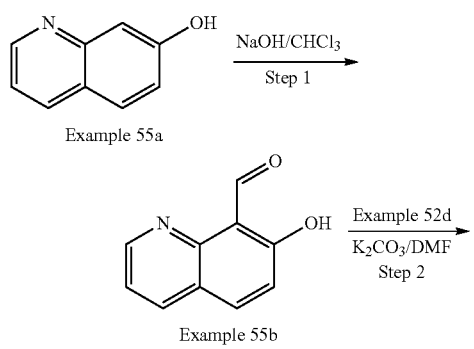

Example 55a

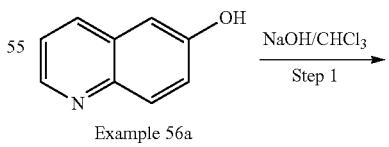

Example 56a

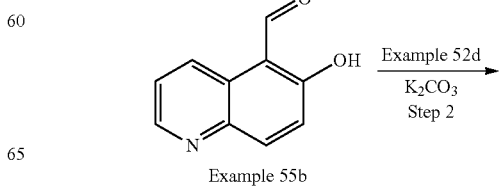

Example 55b

Step 1: Example 56b

To a solution of Example 56a (2 g, 13.8 mmol) in chloroform (30 mL), an aqueous NaOH (16 mL, 350 mmol) solution was added. The resulting mixture was stirred at 92° C. for 20 hrs until TLC indicated complete conversion yielding a thick, dark brown, liquid. The reaction was diluted with water (300 mL), and then extracted with DCM (200 mL*3) and combined the organic phase, washed with brine, dried with Na$_2$SO$_4$, concentration in vacuum to give a brownish solid which was purified by doing flash chromatography to afford the desired product (Example 56b, 200 mg) as yellow solid.

Step 2: Example 56

To a solution of Example 56b (110 mg, 0.64 mmol in acetonitrile (5 mL) was added Example 52d (150 mg, 0.5 mmol), potassium carbonate (225 mg, 1.8 mmol), and potassium iodide (2 mg), and then heated to 60° C. for 4 hrs. After cooled to room temperature, water (5 mL) was added to the mixture, then extracted with EA (10 mL*2) and combined the organic phase, washed with brine, dried with Na$_2$SO$_4$, filtered and concentrated under reduced pressure to give the crude product (120 mg) which was further purified by Prep-HPLC to give the pure desired product Example 56 (30 mg, yield 33%) as yellow oil. LCMS [M+1]$^+$=374

$^1$H NMR (400 MHz, CDCl$_3$) δ 10.82 (s, 1H), 9.64-9.54 (m, 1H), 9.36 (s, 1H), 9.08 (s, 1H), 8.88 (dd, J=4.2, 1.6 Hz, 1H), 8.36 (d, J=9.4 Hz, 1H), 7.62 (d, J=1.9 Hz, 1H), 7.56 (dd, J=8.8, 4.2 Hz, 1H), 7.49 (d, J=9.4 Hz, 1H), 6.52 (d, J=1.9 Hz, 1H), 5.39 (s, 2H), 5.04-4.95 (m, 1H), 1.54 (d, J=6.6 Hz, 6H).

Example 57: General Procedure for Synthesis of Example 57

Step 1: Example 57a

A solution of Example 52c (417 mg, 1.6 mmol) in CH$_3$CN (50 mL) was treated with Select Fluor (960 mg, 12.4 mmol) and the reaction mixture was heated at 80° C. for 4 hours. After cooling to room temperature the solution was evaporated and the residue was purified on silica gel using a mixture of (PE:EA=10:3) as eluent to give the desired product Example 57a (100 mg),

Step 2: Example 57b

To Example 57a (100 mg) in DCM (5 mL) was added SOCl$_2$ (0.2 mL) at r.t. The reaction mixture was stirred at r.t. for 0.5 h and concentrated to dryness. The crude solid was suspended in toluene and concentrated to dryness to give the crude desired product (Example 57b, 110 mg) as yellow solid, which was used for the next step without further purification.

Step 3: Example 57

A mixture of δ-hydroxybenzo[d]oxazole-7-carbaldehyde (Example 15e, 70.5 mg, 0.4 mmol) and K$_2$CO$_3$ (181.6 mg, 1.3 mmol) in DMF (6 mL) was added Example 57b (100 mg, 0.39 mmol) at r.t. The mixture was heated at 80° C. for 0.5 h, Cooled to r.t. Added water (25 mL) and the residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product Example 57 (20 mg) as a white solid.

¹H NMR (400 MHz, CDCl3) δ 10.54 (s, 1H), 9.36 (s, 1H), 9.17 (s, 1H), 8.16 (s, 1H), 7.95 (d, J=8.8 Hz, 1H), 7.50 (d, J=4.6 Hz, 1H), 7.03 (d, J=8.8 Hz, 1H), 5.34 (s, 2H), 4.84 (p, J=6.6 Hz, 1H), 1.49 (d, J=6.6 Hz, 6H).

Example 58: General Procedure for Synthesis of Example 58

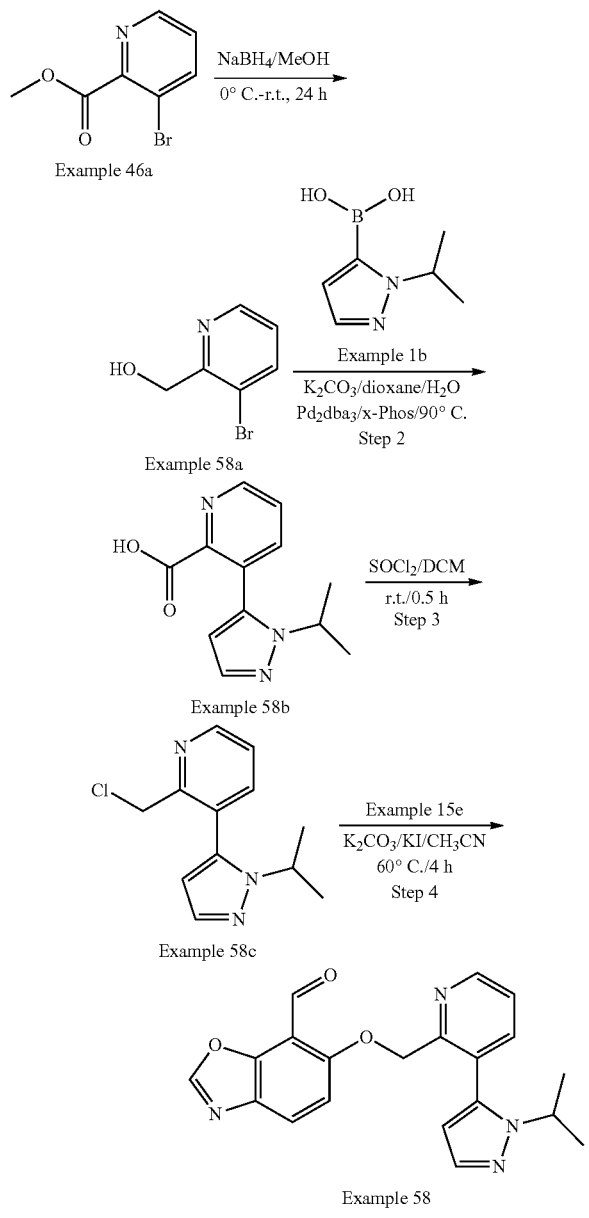

Step 1: Example 58a

To a solution of Example 46a (2 g, 9.2 mmol) in methanol (100 mL) was added NaBH$_4$ (1.8 g, 46.4 mmol) portionwise at 0° C. and slowly warmed to r.t. for 24 hrs. After the reaction was completed, the solvent was removed under reduced pressure, and the residue was dissolved in EtOAc (50 mL), washed with aq. NH$_4$Cl (20 mL*3), dried over Na$_2$SO$_4$, filtered and concentrated to afford the desired product (Example 58a, 1.4 g, yield 82%) as a white solid. LCMS [M+1]$^+$=188

Step 2: Example 58b

To a solution of Example 58a (500 mg, 2.7 mmol) in dioxane/water (20 mL/2 mL) was added Example 1b (614 mg, 4 mmol), K$_3$PO$_4$ (1.4 g, 6.6 mmol), Pd$_2$(dba)$_3$ (121 mg, 0.1 mmol) and 2-dicyclohexylphosphino-2',4',6'-triisopropylbiphenyl (63 mg, 0.1 mmol) under N$_2$ protection and then heated to 90° C. for 9 hrs. After cooled to room temperature, the solvent was removed under reduced pressure, the residue was extracted with EtOAc (20 mL*2) and combined the organic phase, washed with brine, dried over Na$_2$SO$_4$, filtered and concentrated under reduced pressure to give the crude product which was further purified by silica chromatography to give the desired product (Example 58b, 200 mg, yield 35%) as yellow oil. LCMS [M+1]$^+$=218.

Step 3: Example 58c

To a solution of Example 58b (200 mg, 0.9 mmol, 1 eq) in DCM (1.8 mL) was added thionyl chloride (0.5 mL) and stirred at r.t for 0.5 h. After the reaction was completed, the solvent was removed under reduced pressure to give the crude desired product (Example 58c, 200 mg, yield 92%) as white solid.

Step 4: Example 58

To a solution of Example 58c (100 mg, 0.42 mmol) in acetonitrile (3 mL) was added Example 15e (69 mg, 0.5 mmol), potassium carbonate (145 mg, 1.1 mmol) and potassium iodide (2 mg), and then heated to 60° C. for 4 hrs. After cooled to room temperature, water (5 mL) was added to the mixture, then extracted with EA (10 mL*2) and combined the organic phase, washed with brine, dried with Na$_2$SO$_4$, filtered and concentrated under reduced pressure to give the crude (120 mg) which was further purified by Prep-HPLC to give the pure desired product Example 58 (50 mg) as white solid. LCMS [M+1]$^+$=218.

¹H NMR (400 MHz, CDCl$_3$) δ 10.44 (s, 1H), 8.78 (dd, J=4.8, 1.7 Hz, 1H), 8.14 (s, 1H), 7.90 (d, J=8.9 Hz, 1H), 7.69 (dd, J=7.8, 1.8 Hz, 1H), 7.62 (d, J=1.8 Hz, 1H), 7.46 (dd, J=7.7, 4.8 Hz, 1H), 7.10 (d, J=8.9 Hz, 1H), 6.28 (d, J=1.8 Hz, 1H), 5.21 (s, 2H), 4.21 (p, J=6.6 Hz, 1H), 1.41 (d, J=6.5 Hz, 6H).

Example 59: General Procedure for Synthesis of Example 59

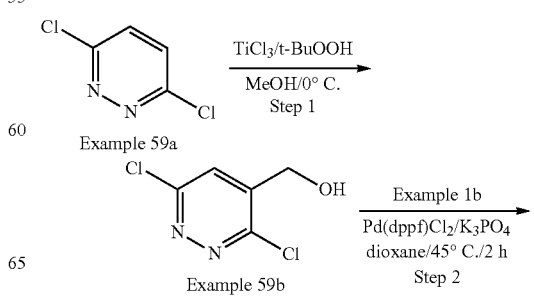

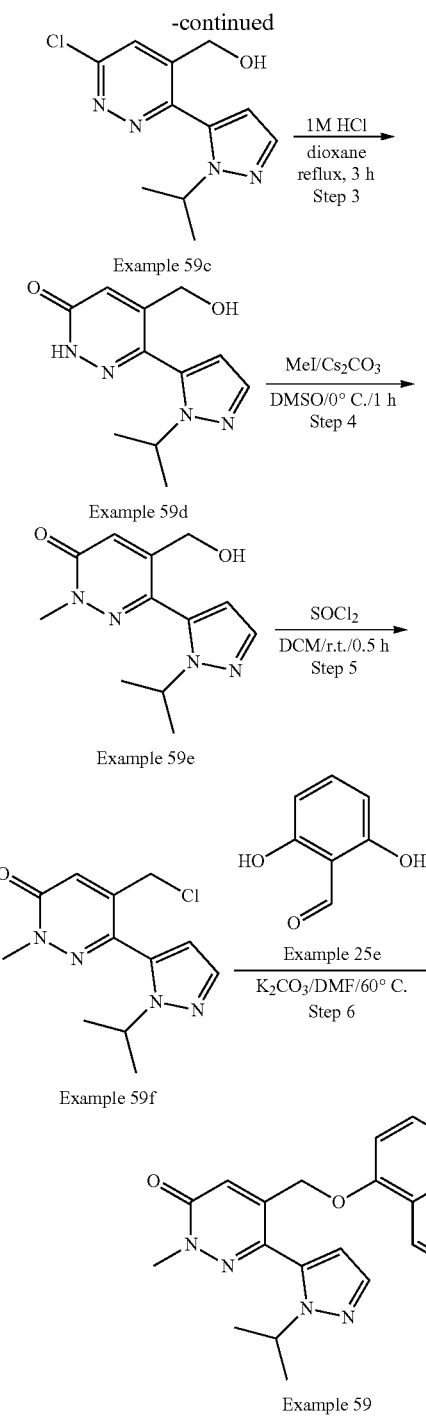

under reduced pressure to give the crude product which was further purified by silica gel chromatography to give the pure product (Example 59b, 3.3 g, yields 9%) as off-white solid. LCMS $[M+1]^+=179$.

Step 2: Example 59c

To a mixture of Example 59b (900 mg, 5 mmol), Example 1b (800 mg, 5 mmol), (dppf)$PdCl_2$ (0.7 g, 1 mmol) and $K_3PO_4$ (1.3 g, 6 mmol) in dioxane (10 mL) was heated to 45° C. for 2 hrs under $N_2$ protection. After the reaction, the reaction solution was diluted with EtOAc (20 mL), washed with brine, dried with $Na_2SO_4$. Then removed the solvent under reduced pressure and purified by silica chromatography to give the desired product (Example 59c, 100 mg, yield 8%) as light brown solid. LCMS $[M+1]^+=253$.

Step 3: Example 59d

To a solution of Example 59c (50 mg, 0.2 mmol) in dioxane (2 mL) was added 1M HCl (2 mL) and then heated to reflux for 3 hrs. After the reaction, the reaction solution was concentrated and the residue was dissolved with water (5 mL), and adjust to pH δ-7 with sat. $NaHCO_3$, then extracted with DCM/MeOH=10:1 (5 mL*10) and combined the organic phase, washed with brine, dried with $Na_2SO_4$. Then removed the solvent under reduced pressure to give the crude product (Example 59d, 42 mg, yield 91%) and will be used in the next step directly. LCMS $[M+1]^+=235$ Step 4: Example 59e To a mixture of Example 59d (25 mg, 0.1 mmol) and $Cs_2CO_3$ (39 mg, 0.12 mmol) in DMSO (1 mL) was added a solution of $CH_3I$ (17 mg, 0.12 mmol) in DMSO (0.5 mL) drop wisely at 0° C. After the addition, the resulting solution was stirred for another 1 h. After the reaction, the resulting solution was diluted with water (3 mL), extracted with DCM (3 mL*5), washed with brine, dried with $Na_2SO_4$. Then removed the solvent under reduced pressure to give the crude product (Example 59e, 30 mg) and will be used in the next step directly. LCMS $[M+1]^+=249$.

Step 5: Example 59f

To a solution of Example 59e (30 mg, 0.12 mmol) in DCM (3 mL) was added 3 drops of $SOCl_2$ and then stirred at r.t for 0.5 hr. After the reaction, removed the solvent under reduced pressure to give the crude product (Example 59f, 30 mg, yield 94%) and will be used in the next step directly.

Step 6: Example 59

To a mixture of Example 59f (30 mg, 0.11 mmol), Example 25e (15 mg, 0.11 mmol) and $K_2CO_3$ (45 mg, 0.33 mmol) in DMF (3 mL) was heated to 60° C. for 0.5 h. After the reaction, the mixture was filtered. The filtrate was concentrated and purified by Prep-HPLC to afford the desired product Example 59 (12 mg, yield 24%) as white solid. LCMS $[M+1]^+=369$.

$^1$H NMR (400 MHz, DMSO-$d_6$) δ 11.62 (s, 1H), 10.17 (s, 1H), 7.54 (d, J=1.8 Hz, 1H), 7.47 (t, J=8.4 Hz, 1H), 7.30 (s, 1H), 6.61 (d, J=1.9 Hz, 1H), 6.54 (d, J=8.4 Hz, 1H), 6.48 (d, J=8.4 Hz, 1H), 5.02 (s, 2H), 4.58 (p, J=6.6 Hz, 1H), 3.71 (s, 3H), 1.35 (d, J=6.6 Hz, 6H).

Step 1: Example 59b

To a vigorously stirred mixture of Example 59a (29.2 g, 0.2 mol), MeOH (200 g, 6 mol) and 70% tert-butyl hydroperoxide (77 g, 0.6 mol) was added titanium trichloride (458 g, 0.6 mol, 20%. w/w in 2N aqueous HCl) drop wise slowly at 0° C. After added, the mixture was stirred at 0° C. for another 30 minutes (detected by TLC PE/EA=3/1). Then quenched with sat. $NH_4Cl$. The residue was extracted with DCM (200 mL*2). The combined organic phase was washed with brine, dried over $Na_2SO_4$, filtrated and concentrated

Example 60: General Procedure for Synthesis of Example 60

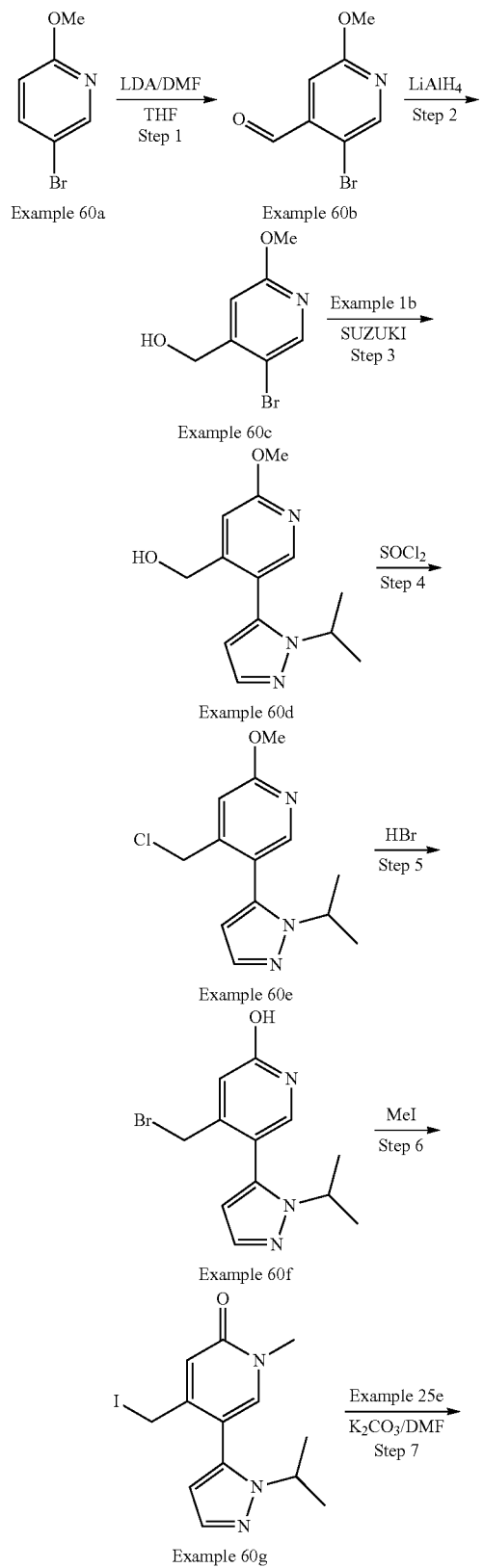

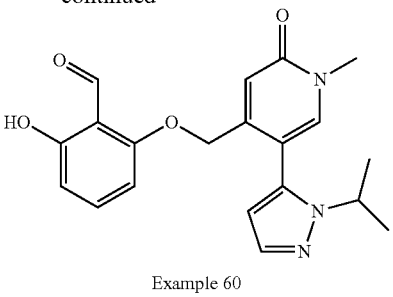

Example 60

Step 1: Example 60b

To a solution of diisopropylamine (22.7 g, 0.22 mol) in THF (0.5 L) was cooled to −30° C., and then added n-BuLi (140 mL, 0.22 mol). After addition, the resulting solution was stirred for 0.5 h. The mixture was cooled to −60° C., Example 60a (35.1 g, 0.19 mol) dissolved in THF (200 mL) was added dropwise, maintained the temperature below −60° C., the resulting solution was stirred for 1 h. DMF (20.4 g 0.28 mol) was added dropwise at −60° C., the resulting solution was stirred for 1 h. The reaction mixture was quenched by saturated NH$_4$Cl (200 mL) aqueous, and allowed warmed to room temperature. the residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product (Example 60b, 26.4 g, yield 64.3%) as a white solid. $^1$H NMR (400 MHz, CDCl$_3$) δ 10.28 (s, 1H), 8.40 (s, 1H), 7.16 (s, 1H), 3.95 (s, 3H)

Step 2: Example 60c

Example 60b (20.5 g, 0.095 mol) was dissolved in THF (400 mL) the resulting solution was stirred at 0° C. under N$_2$ then treated with LiAlH4 (3.9 g 0.1 mol), maintained the temp below 10° C., After addition, the colorless solution turned to purplish red and stirred at r.t. for 2 hrs. TLC showed Compound 232 was consumed, water (4 mL) 15% NaOH (4 mL) and water (12 mL) was added successively the mixture was stirred at r.t for 1 hr, Na$_2$SO$_4$ (50 g) was added, the suspension was filtered off and washed with EA (200 mL), the filtrate was concentrated to give the desired product (Example 60c, 9.4 g, yield 93%) as a brown oil. LCMS [M+H]$^+$=218, 220.

Step 3: Example 60d

Example 60c (19.2 g 0.088 mol), Na$_2$CO$_3$ (18.7 g, 0.18 mol), Example 1b (16.3 g 0.11 mol) and Pd(dppf)Cl$_2$ (1.0 g) was added to a solution of Dioxane (400 mL) and water (20 mL), the suspension was stirred at 90° C. under N$_2$ for 18 hrs. The residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product (Example 60d, 2.2 g, yield 10%) as a yellow oil. LCMS [M+H]$^+$=248

Step 4: Example 60e

Example 60d (990 mg) was dissolved in DCM (20 mL), cooling to 0° C., SOCl$_2$ (4 mL) was added, the mixture was stirred for 2 hrs at r.t. TLC showed Example 60d was consumed, concentrated to give the crude product (Example 60e, 1.2 g) as white solid which used to for the next step without further purification. LCMS [M+H]$^+$=268.

Step 5: Example 60f

Example 60e (1.2 g, 4.52 mmol) was dissolved in HBr (48%10 mL), the mixture was stirred at 100° C. for 2 hrs. TLC showed Example 60e was consumed concentrated to give the crude product (Example 60f, 2.2 g) as brown solid, which used to next step without further purification. LCMS [M+H]$^+$=296.

Step 6: Example 60g

Example 60f (2.1 g 7.09 mmol), Na$_2$CO$_3$ (1.7 g 15.61 mmol), CH$_3$I (2.0 g, 14.09 mmol) was added to DMF (40 mL); the mixture was stirred for 4 hrs at 30° C. TLC showed SM was consumed the mixture was work up and purified by chromatography to give the desired product (Example 60g, 130 mg) as a yellow solid. LCMS [M+H]$^+$=312.

Step 7: Example 60

Example 60g (130 mg, 0.42 mmol) was dissolved in DMF (5 mL), K$_2$CO$_3$ (58 mg, 0.42 mmol) Example 25e (64 mg, 0.46 mmol) was added, the mixture was stirred at 65° C. for 2 hrs under N$_2$. The residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product Example 60 (55 mg) as a yellowish solid. LCMS [M+H]$^+$ =368.

$^1$H NMR (400 MHz, cdcl3) δ 11.95 (s, 1H), 10.37 (s, 1H), 7.68 (s, 1H), 7.34 (t, J=8.4 Hz, 1H), 7.29 (s, 1H), 6.85 (s, 1H), 6.57 (d, J=8.5 Hz, 1H), 6.26 (s, 1H), 6.12 (d, J=8.2 Hz, 1H), 4.68 (s, 2H), 4.38-4.27 (m, 1H), 3.62 (s, 3H), 1.51 (d, J=6.2 Hz, 6H).

Example 61: General Procedure for Synthesis of Example 61g & Example 61h

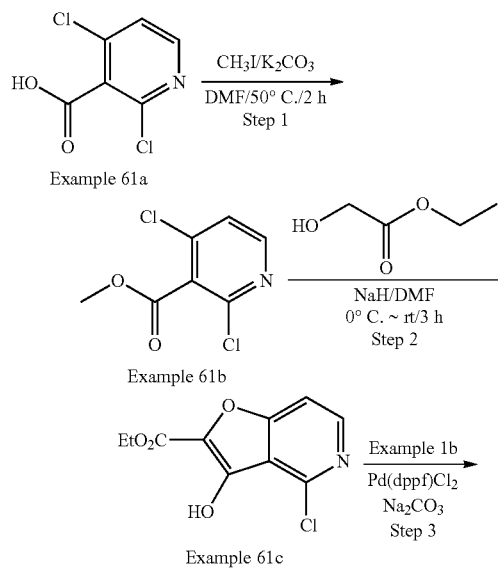

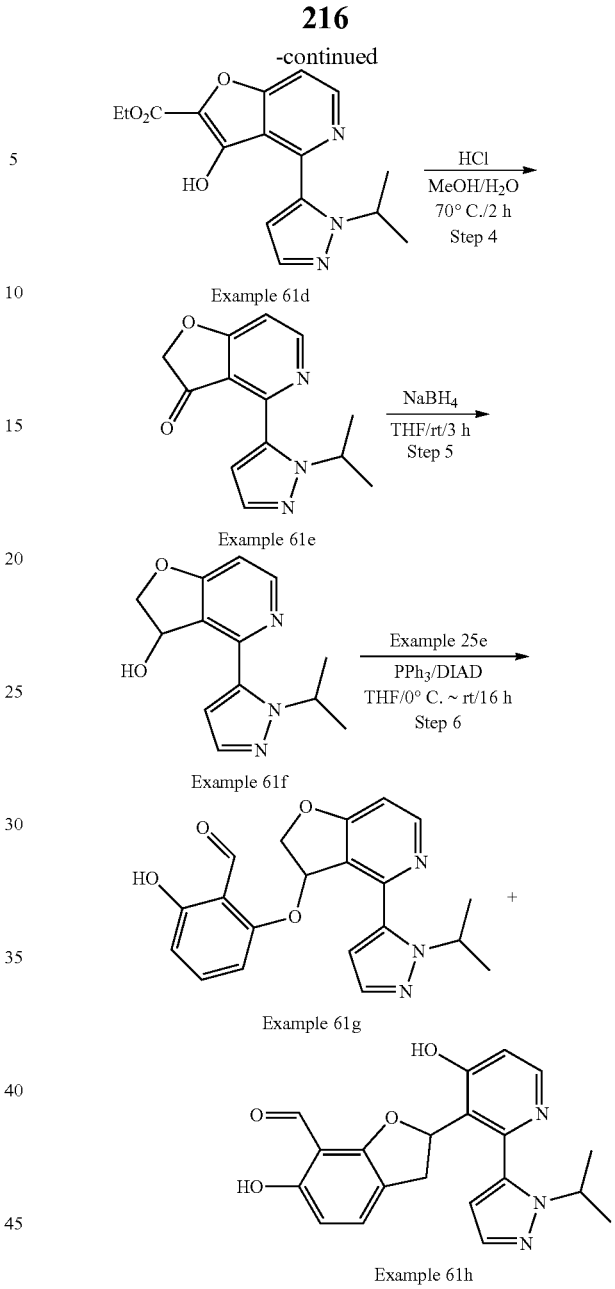

Step 1: Example 61b

To a solution of Example 61a (21 g, 0.11 mol) in 100 mL DMF was added CH$_3$I (28.4 g, 0.2 mol) and potassium carbonate (34.0 g, 0.25 mol) under N$_2$, the mixture was stirred at 50° C. for 2 hrs. The reaction was then quenched by adding 80 mL water, and the mixture was exacted with EA (100 mL) and H$_2$O. The organic layer was dried over Na$_2$SO$_4$ and concentrated to give 20.5 g polar less yellow solid (Example 61b, crude) which was used directly in the next step without further purification. LCMS [M+1]$^+$ 206.1

Step 2: Example 61c

To a solution of Example 61b (20.5 g, 0.10 mol), ethyl 2-hydroxyacetate (11.2 g, 0.11 mol) in 100 mL DMF was added NaH (8.0 g, 0.18 mol) by portions at ice temperature.

The mixture was stirred at 0° C. for 1 hr and then it was turned to r.t. for another 2 hrs. The reaction was quenched by adding 80 mL water. The residue was extracted with EtOAc (200 mL*2). The combined organic phase was washed with brine, dried over $Na_2SO_4$, filtrated and concentrated under reduced pressure to give the crude product which was further purified by silica gel chromatography to give the pure product as yellow solid (Example 61c, 10.2 g, yield 42%). LCMS $[M+1]^+=242.1$ Step 3: Example 61d A mixture of Example 61c (4.83 g, 20.0 mmol), Example 1b (4.0 g, 26.0 mmol), sodium carbonate (4.5 g, 42 mmol) and $Pd(dppf)Cl_2$ (0.5 g, 0.7 mmol) was stirred in 1,4-dioxane (70 mL) and water (10 mL) at 90° C. for 2 hrs under $N_2$. The solvent was then removed; the residue was extracted with EtOAc (100 mL) and $H_2O$ twice. The organic layer was dried over $Na_2SO_4$ and concentrated. The residue was further purified by flash column chromatography (PE:EA=4:1) to give yellow oil (Example 61d, crude yield 18%). LCMS $[M+1]^+316.1$ Step 4: Example 61e To a solution of Example 61d (1.1 g, 3.3 mmol) in methanol (30 mL) was added 10 mL concentrated HCl slowly. The reaction was stirred at 70° C. for 16 hrs. The methanol was then removed; the residue was extracted with EtOAc (100 mL*2). The combined organic phase was washed with brine, dried over $Na_2SO_4$, filtrated and concentrated under reduced pressure to give the crude product which was further purified by silica gel chromatography to give the pure product yellow solid (Example 61e, 0.28 g, crude yield 32%). LCMS $[M+1]^+=244.1$ Step 5: Example 61f To a solution of Example 61e (2.5 g, 10.2 mmol) in 50 mL THF was added $NaBH_4$ (1.1 g, 30.6 mmol). The mixture was stirred at r.t for 3 hrs, then it was quenched by addition of 20 mL methanol. The solvent was then removed under vacuum, the residue was further purified by flash column chromatography (PE:EA=1:1) to afford Example 61f (660 mg, crude yield 29%). LCMS $[M+1]^+=246.1$ Step 6: Example 61g & Example 61h To a solution of Example 61f (138 mg, 0.56 mmol), Example 25e (87 mg, 0.63 mmol), $PPh_3$ (191 mg, 0.73 mmol) in THF (20 mL) was added DIAD (152 mg, 0.75 mmol) dropwise at 0° C., the mixture was then turned to room temperature and stirred for another 16 hrs. The solvent was then removed and the residue was further purified by prep-HPLC to give the two desired products.

Example 61g (21 mg, yellow solid, yield 11%). LCMS $[M+1]^+=366.1$.

$^1$H NMR (400 MHz, Chloroform-d) δ 11.97 (s, 1H), 10.05 (s, 1H), 8.61 (d, J=5.6 Hz, 1H), 7.48 (d, J=1.9 Hz, 1H), 7.42 (t, J=8.4 Hz, 1H), 6.94 (d, J=5.6 Hz, 1H), 6.62 (d, J=8.5 Hz, 1H), 6.42 (d, J=1.9 Hz, 1H), 6.24 (d, J=8.2 Hz, 1H), 5.97 (dd, J=5.3, 2.2 Hz, 1H), 5.27 (h, J=6.7 Hz, 1H), 4.80-4.68 (m, 2H), 1.51 (d, J=6.6 Hz, 3H), 1.45 (d, J=6.6 Hz, 3H).

Example 61h (9 mg grey solid, yield 5%). LCMS $[M+1]^+$ 366.1.

$^1$H NMR (400 MHz, Chloroform-d) δ 12.12 (s, 1H), 10.21 (s, 1H), 7.43 (s, 1H), 7.14 (d, J=6.3 Hz, 1H), 6.65 (d, J=8.4 Hz, 1H), 6.25 (s, 1H), 6.06 (d, J=8.4 Hz, 1H), 5.15 (s, 1H), 4.89-4.80 (m, 2H), 4.24 (s, 1H), 1.51 (d, J=6.5 Hz, 3H), 0.89 (d, J=6.5 Hz, 3H).

Example 62: General Procedure for Synthesis of Example 62a & Example 62b

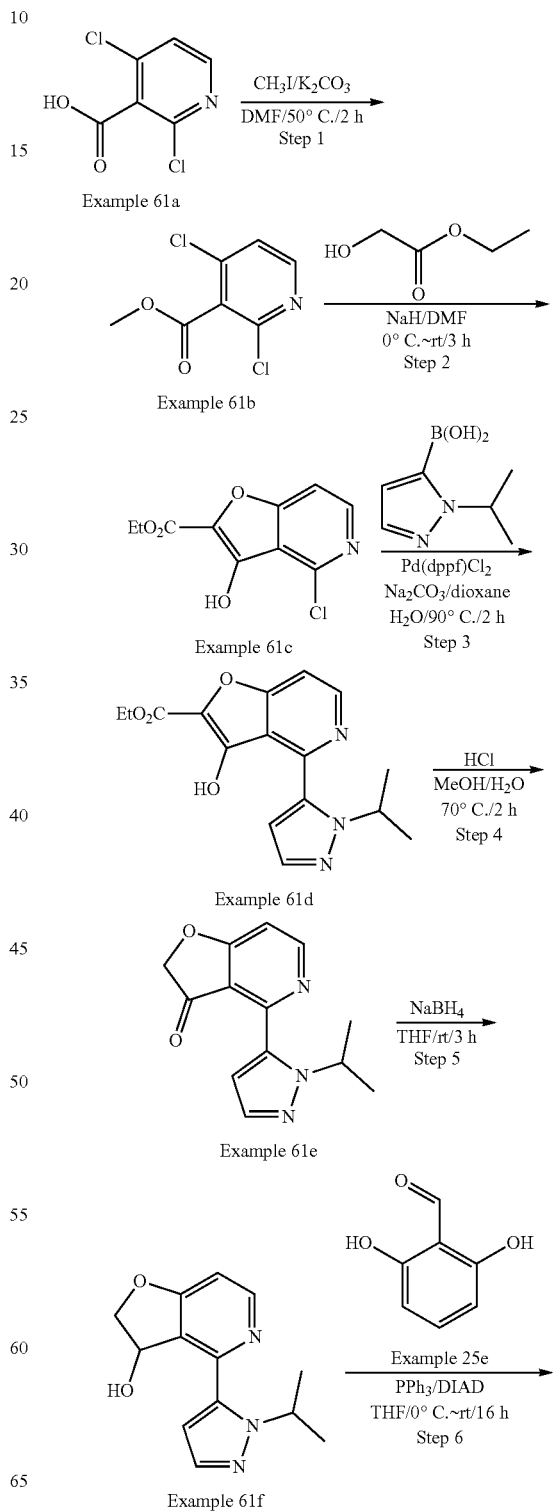

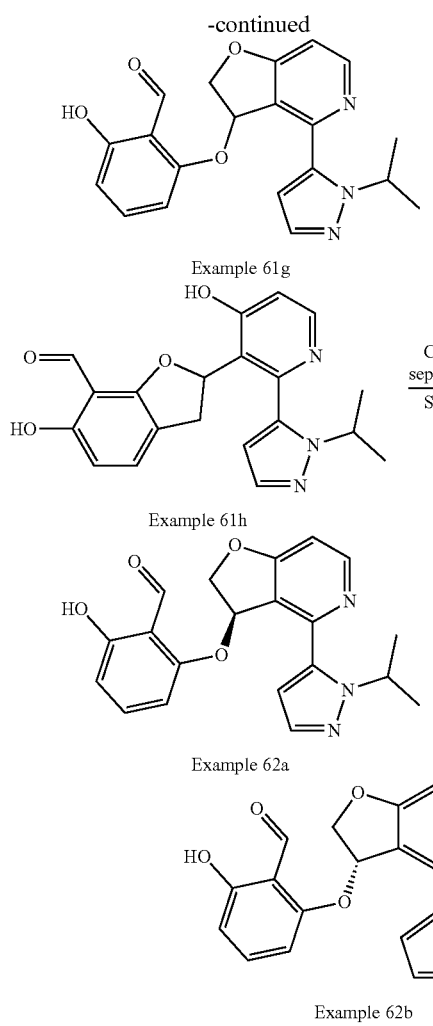

Example 61g

Example 61h

Chiral separation
Step 7 →

Example 62a

Example 62b

Step 7: Example 62a & Example 62b

Example 61g (102 mg, 0.28 mmol) was further purified by Chiral separation (method as Table 1) to afford the Example 62a (42.0 mg, 0.12 mmol, yield 41%) as white solid. LCMS [M+1]$^+$=366.1.

$^1$H NMR (400 MHz, Chloroform-d) δ 11.97 (s, 1H), 10.05 (s, 1H), 8.61 (d, J=5.6 Hz, 1H), 7.48 (d, J=1.9 Hz, 1H), 7.42 (t, J=8.4 Hz, 1H), 6.94 (d, J=5.6 Hz, 1H), 6.62 (d, J=8.5 Hz, 1H), 6.42 (d, J=1.9 Hz, 1H), 6.24 (d, J=8.2 Hz, 1H), 5.97 (dd, J=5.3, 2.2 Hz, 1H), 5.27 (h, J=6.7 Hz, 1H), 4.80-4.68 (m, 2H), 1.51 (d, J=6.6 Hz, 3H), 1.45 (d, J=6.6 Hz, 3H).

Example 62b (34 mg, yield 33%) as white solid. LCMS [M+1]$^+$=366.1.

$^1$H NMR (400 MHz, Chloroform-d) δ 11.97 (s, 1H), 10.05 (s, 1H), 8.61 (d, J=5.6 Hz, 1H), 7.48 (d, J=1.9 Hz, 1H), 7.42 (t, J=8.4 Hz, 1H), 6.94 (d, J=5.6 Hz, 1H), 6.62 (d, J=8.5 Hz, 1H), 6.42 (d, J=1.9 Hz, 1H), 6.24 (d, J=8.2 Hz, 1H), 5.97 (dd, J=5.3, 2.2 Hz, 1H), 5.27 (h, J=6.7 Hz, 1H), 4.80-4.68 (m, 2H), 1.51 (d, J=6.6 Hz, 3H), 1.45 (d, J=6.6 Hz, 3H).

| Column | CHIRALCEL OZ-H |
|---|---|
| Column size | 0.46 cm I.D. × 15 cm L |
| Injection | 1.0 ul |
| Mobile phase | Hexane/EtOH = 80/20 (V/V) |
| Flow rate | 1.0 ml/min |
| Wave length | UV 254 nm |
| Temperature | 35° C. |
| Sample name | Raw Material |

Example 63: General Procedure for Synthesis of Example 63

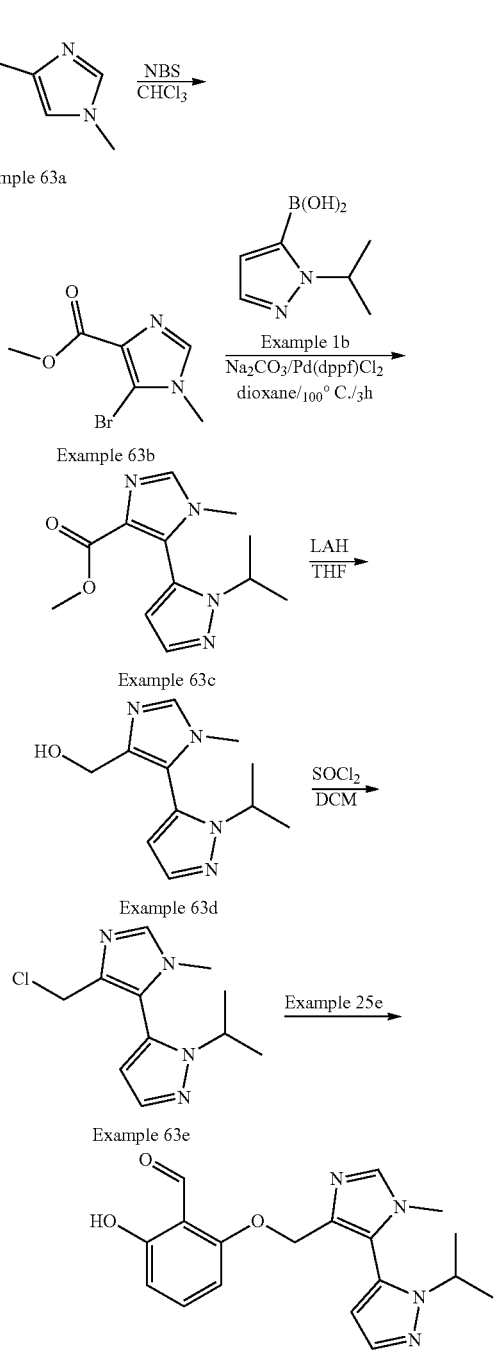

Example 63a

Example 63b

Example 63c

Example 63d

Example 63e

Example 63

Step 1: Example 63b

To a solution of Example 63a (1.40 g, 10.0 mmol) in CHCl$_3$ (30.0 mL) was added NBS (2.13 g, 12.0 mmol). The reaction mixture was then stirred 18 hrs at 50° C. and then cooled to room temperature. The residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product Example 63b (500 mg, yield 22.8%). H NMR (400 MHz, Chloroform-d) δ 7.60 (s, 1H), 3.91 (s, 3H), 3.67 (s, 3H).

Step 2: Example 63c

To a solution of Example 63b (219 mg, 1.0 mmol) in dioxane (7.5 mL) was added Example 1b (231 mg, 1.5 mmol), 2N Na$_2$CO$_3$ (2.5 mL, 5.0 mmol), Pd(dppf)Cl$_2$ (37 mg, 0.005 mmol) under N$_2$ and then heated to 90° C. for 5 hrs. After cooled to room temperature, the solvent was removed under reduced pressure, the residue was extracted with EtOAc (20 mL) and combined the organic phase, washed with brine, dried over Na$_2$SO$_4$, filtered and concentrated under reduced pressure to give the crude product which was further purified by flash column chromatography (PE:EA=3:1) to give the Example 63c (200 mg, yield 81.6%) as a yellow solid. LCMS [M+1]$^+$=249.1.

Step 3: Example 63d

To a suspension of Example 63c (200 mg, 0.805 mmol) in THF (10 mL) at 10° C. added dropwise LiAlH$_4$ (100 mg, 2.42 mmol) and the mixture was stirred for 1 hour. On cooling, water (5 mL) was added followed by Na$_2$SO$_4$ and the resulting precipitate was filtered through a celite pad. The filtrate was concentrated under reduced pressure to afford the title Example 63d (93 mg, yield 52.54%) as yellow oil. LCMS [M+1]$^+$=221.1

Step 4: Example 63e

To Example 63d (93 mg, 0.419 mmol) in DCM (5 mL) was added SOCl$_2$ (0.5 mL) at r.t. The reaction mixture was stirred at r.t. for 0.5 h and concentrated to dryness. The crude solid was suspended in toluene and concentrated to dryness to give Example 63e (100 mg, yield 95%) as yellow solid, which was directly used in the next step without further purification. LCMS [M+1]$^+$=239.1

Step 5: Example 63

A mixture of Example 25e (70 mg, 0.503 mmol) and K$_2$CO$_3$ (290 mg, 2.1 mmol) in DMF (5 mL) was added Example 63e (100 mg, 0.419 mmol) at r.t. The mixture was heated at 55° C. for 1 hr. The mixture was then extracted with EtOAc (75 mL) and H$_2$O. The organic layer was dried over Na$_2$SO$_4$ and concentrated. The residue was further purified by Pre-HPLC to give the product Example 63 (20 mg, yield 14%) as white solid. LCMS [M+H]$^+$ 341.1.
$^1$H NMR (400 MHz, Chloroform-d) δ 11.94 (s, 1H), 10.39 (s, 1H), 7.62 (d, J=1.4 Hz, 1H), 7.42 (t, J=8.4 Hz, 1H), 7.12 (s, 1H), 6.65 (d, J=8.3 Hz, 1H), 6.55 (d, J=8.4 Hz, 1H), 6.41 (s, 1H), 5.20 (s, 2H), 4.92 (p, J=6.6 Hz, 1H), 3.67 (s, 3H), 1.48 (d, J=6.5 Hz, 6H).

Example 64: General Procedure for Synthesis of Example 64

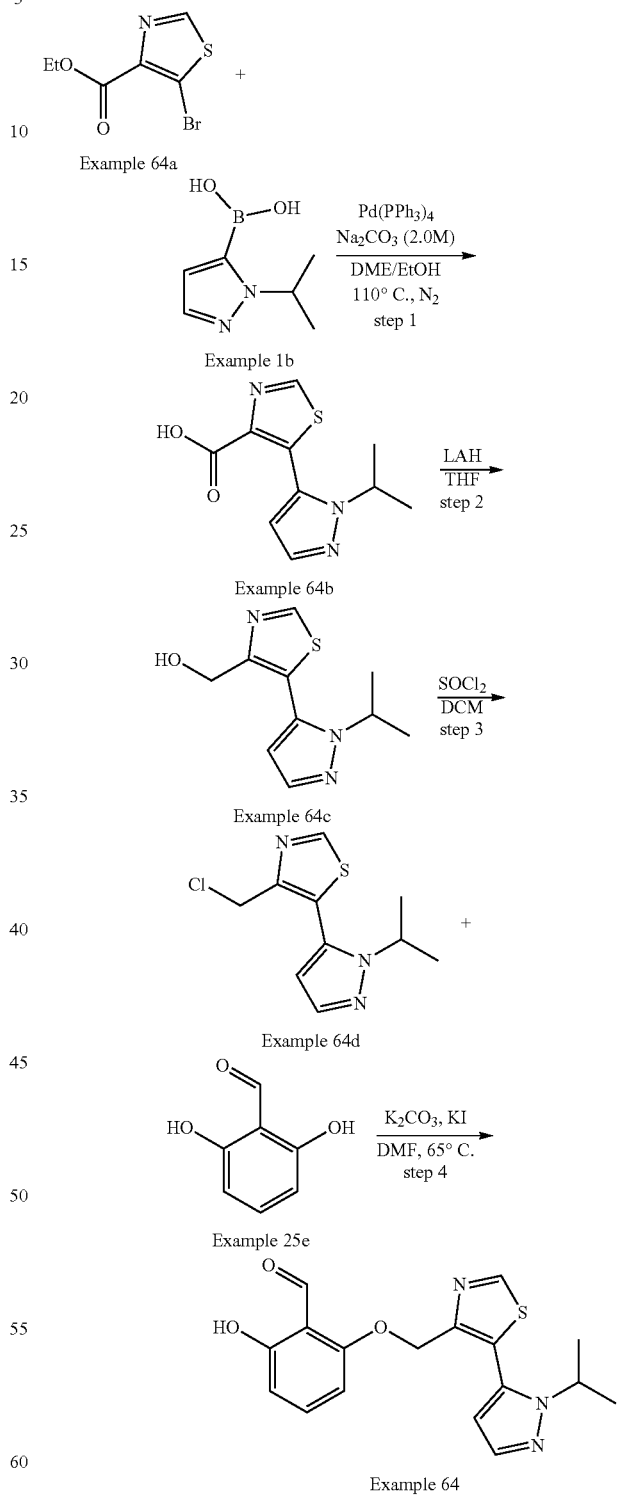

Step 1: Example 64b

To a solution of Example 64a (3.34 g, 14.15 mmol), Example 1b (3.27 g, 21.22 mmol) and Na$_2$CO$_3$ solution (26 mL, 2.0 M) in DME:EtOH=1:1, 160 mL) was added Pd(PPh$_3$)$_4$ (3.27 g, 2.83 mmol) at room temperature under N$_2$. The reaction mixture was heated to 110° C. and stirred overnight under N$_2$. TLC showed the starting material was consumed completely and desired the product was detected. The reaction mixture was filtered and the filter cake was washed with EtOAc and the filtrates were concentrated. The residue was purified by flash column chromatography (PE: EtOAc=3:1) to afford the Example 64b (3.7 g, yield 95%) as yellow solid. LCMS [M+H]$^+$=326.1

Step 2: Example 64c

To a solution of Example 64b (1 g, 4.22 mmol) in dry THF (30 mL) was added LAH (320 mg, 8.44 mmol) at 0° C. under N$_2$. After addition, the reaction mixture was stirred at 0° C. for 1.5 hrs. TLC showed the starting material was consumed completely. The reaction mixture was quenched by H$_2$O (0.5 mL), 10% NaOH solution (0.5 mL) and filtered. The filtered cake was washed with EtOAc and the filtrates was concentrated and purified by flash column chromatography (PE:EtOAc=1:1) to afford Example 64c (75 mg, 7.9% yield) as a yellow solid. LCMS [M+H]$^+$=224.1

Step 3: Example 64d

To a mixture of Example 64c (75 mg, 0.33 mmol, 1.0 eq.) in DCM was added SOCl$_2$ (1 mL) at room temperature and the reaction mixture was stirred for 20 min. The reaction mixture was concentrated under reduced pressure to afford Example 64d (86 mg, 100% yield) as a yellow solid. LCMS [M+H]$^+$=242.1

Step 4: Example 64

A mixture of Example 64d (86 mg, 0.35 mmol), Example 25e (32 mg, 0.23 mmol), K$_2$CO$_3$ (131 mg, 0.95 mmol) and KI (0.4 mg, 0.002 mmol) in MeCN (10 mL) was heated to 60° C. and stirred for 1 hour. TLC showed the starting material was consumed completely. The reaction mixture was filtered and washed with EtOAc and concentrated. The residue was purified by prep-HPLC to afford the product Example 64 (40 mg, yield 33.3%) as yellow oil. LCMS [M+H]$^+$=344.
$^1$H NMR (400 MHz, Chloroform-d) δ 11.93 (s, 1H), 10.16 (s, 1H), 8.98 (s, 1H), 7.63 (s, 1H), 7.40-7.35 (t, J=8.0 Hz, 1H), 6.56-6.54 (d, J=8.0 Hz, 1H), 6.45-6.43 (d, J=8.0 Hz, 1H), 6.35 (s, 1H), 5.14 (s, 2H), 4.42 (m, 1H), 1.44 (d, J=8.0 Hz, 6H).

Example 65: General Procedure for Synthesis of Example 65

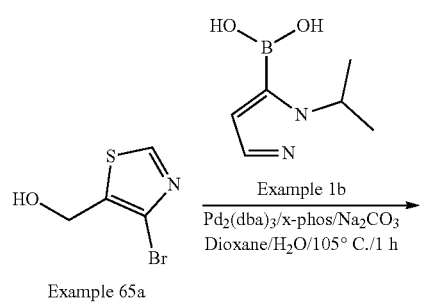

Example 65a

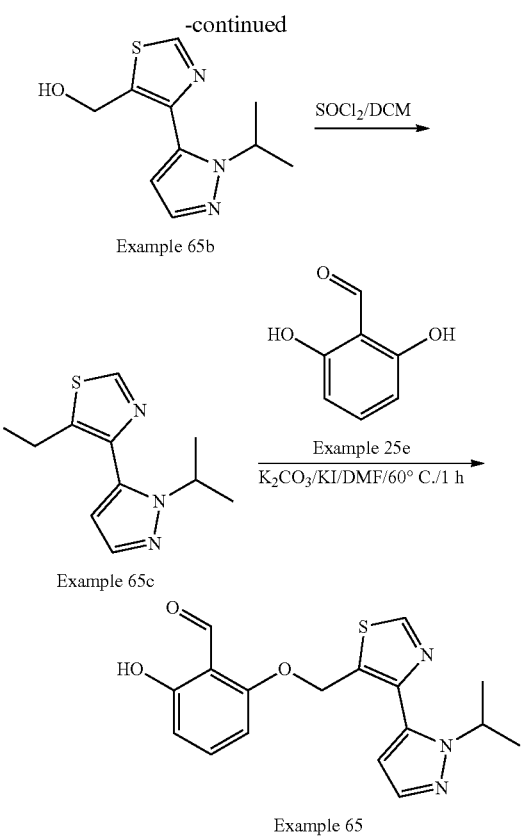

Step 1: Example 65b

To a solution of Example 65a (426 mg, 2.2 mmol) in Dioxane (10 mL) and water (1 mL) was added Example 1b (507 mg, 3.3 mmol) and Na$_2$CO$_3$ (467 mg 4.4 mmol) Pd$_2$(dba)$_3$ (50 mg), X-phos (50 mg) under N$_2$. The mixture was then heated to 105° C. for 1 hr. The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product Example 65b (270 mg, yield 55%) as yellow oil. LCMS [M+1]$^+$=224.1

Step 2: Example 65c

To a solution of Example 65b (105 mg 0.47 mmol) in DCM (2 mL) was added SOCl$_2$ (112 mg 0.94 mmol) at r.t. After stirring 30 min, the reaction was quenched by adding NaHCO$_3$ solution. The residue was extracted with DCM (20 mL*2). The combined organic phase was washed with brine, dried over Na$_2$SO$_4$, filtrated and concentrated under reduced pressure to give the crude product which was further purified by silica gel chromatography to give the pure product Example 65c (110 mg, yield 95% crude) as yellow oil, which was directly used in the next step without further purification. LCMS [M+1]$^+$=242.1

Step 3: Example 65

A mixture of Example 65c (110 mg 0.49 mmol), Example 25e (101 mg 0.73 mmol), K$_2$CO$_3$ (135 mg 0.97 mmol), KI (8 mg, 0.05 mmol) was stirred in DMF (5 mL) at 60° C. for 1 hr, TLC detected the starting material was consumed completely, the mixture was extracted with EtOAc (15 mL) and water. The organic layer was dried over Na$_2$SO$_4$ and concentrated. The residue was further purified by Prep-HPLC to obtain the desired Example 65 (80 mg, yield 47.5%) as yellow solid. LCMS [M+1]$^+$=334.1. $^1$H NMR (400 MHz, CDCl$_3$) δ 11.94 (s, 1H), 10.33 (s, 1H), 8.94 (s, 1H), 7.61 (s, 1H), 7.38 (t, J=8.4 Hz, 1H), 6.59 (d, J=8.5 Hz, 1H), 6.35-6.29 (m, 2H), 5.33 (s, 2H), 4.91-4.84 (m, 1H), 1.49 (d, J=6.5 Hz, 6H).

Example 66: General Procedure for Synthesis of Example 66

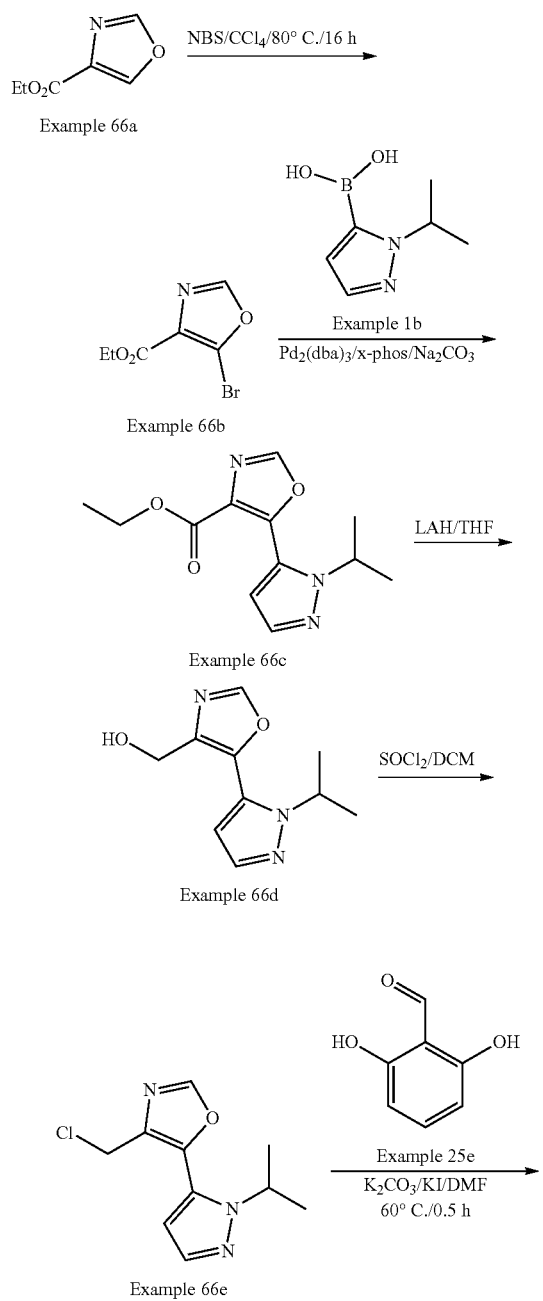

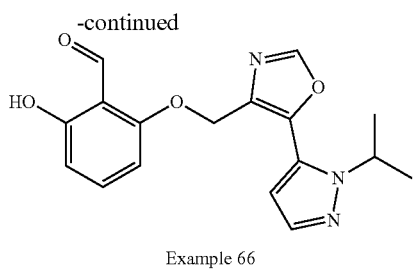

Example 66

Step 1: Example 66b

To a solution of Example 66a (184 mg, 1.3 mmol) in CCl$_4$ (2 mL) was added NBS (348 mg, 1.9 mmol) and 1,1'-Azobis(cyanocyclohexane) (32 mg, 0.13 mol), the mixture was heated to 80° C. overnight. The residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product Example 66b (105 mg, yield 36.7%) as white solid. LCMS [M+1]$^+$=220.1

$^1$H NMR (400 MHz, CDCl$_3$) δ 8.25 (s, 1H), 4.44-4.35 (m, 2H), 1.38 (t, J=7.1 Hz, 3H).

Step 2: Example 66c

To a solution of Example 66b (350 mg, 1.6 mmol) was dissolved in Dioxane (5 mL) and water (0.5 mL) was added Example 1b (366 mg, 2.4 mmol) and Na$_2$CO$_3$ (336 mg, 3.2 mmol) Pd$_2$(dba)$_3$ (30 mg), x-phos (30 mg), and then heated to 105° C. for 1 hrs. TLC (PE:EA=10:1) showed reaction completed. The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product Example 66c (450 mg, yield 100%) as yellow oil. LCMS [M+1]$^+$=250.1

Step 3: Example 66d

To a solution of Example 66c (420 mg, 1.7 mmol) in THF (10 mL) was added LAH (71 mg, 1.9 mmol) at r.t. The reaction mixture was stirred at r.t for 0.5 h, and then it was quenched by water (1 mL). The mixture was stirred at r.t for another 30 mins, then it was concentrated and purified by flash column chromatography (EA:PE=1:1) to give Example 66d (0.2 g, yield 56.8%) as colorless oil. LCMS [M+1]$^+$=208.1

Step 4: Example 66e

To a solution of Example 66d (80 mg 0.39 mmol) in DCM (4.0 mL) was added SOCl$_2$ (92 mg, 0.77 mmol) at r.t. The solvent was removed, and Example 66e (88 mg, crude yield 95%) was successfully obtained which was directly used to next step without further purification. LCMS [M+1]$^+$=208.1

Step 5: Example 66

A mixture of Example 66e (88 mg, 0.39 mmol), Example 25e (81 mg, 0.59 mmol), K$_2$CO$_3$ (135 mg, 0.97 mmol), KI (8 mg, 0.05 mmol) was stirred in DMF (6 mL) at 60° C. for 1 hr, TLC showed the reaction was complete. The residue was extracted with EtOAc (10 mL*2). The combined organic phase was washed with brine, dried over Na₂SO₄, filtrated and concentrated under reduced pressure to give the crude product which was further purified by silica gel chromatography to give the pure product Example 66 (15 mg, yield 11.5%) as yellow solid. LCMS [M+1]⁺=328.1

¹H NMR (400 MHz, CDCl₃) δ 11.95 (s, 1H), 10.39 (s, 1H), 7.74 (s, 1H), 7.57 (d, J=1.8 Hz, 1H), 7.44 (t, J=8.4 Hz, 1H), 6.81 (d, J=1.9 Hz, 1H), 6.59 (d, J=8.6 Hz, 1H), 6.56 (d, J=8.4 Hz, 1H), 5.70-5.60 (m, 1H), 5.16 (s, 2H), 1.54 (d, J=6.6 Hz, 6H).

Example 67: General Procedure for Synthesis of Example 67

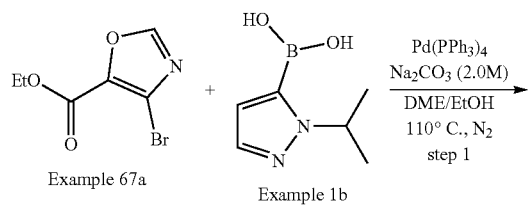

Example 67a + Example 1b

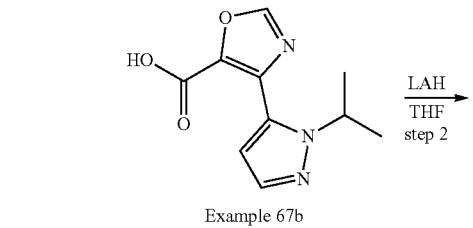

Example 67b

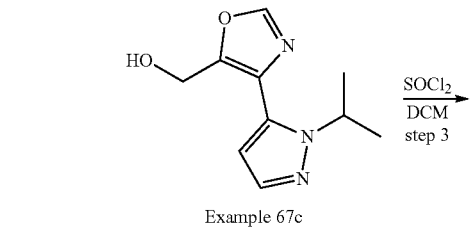

Example 67c

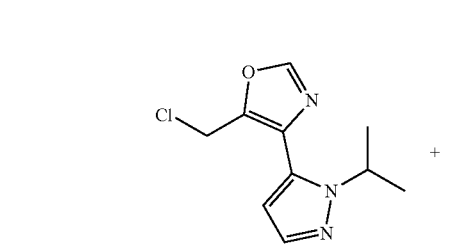

Example 67d +

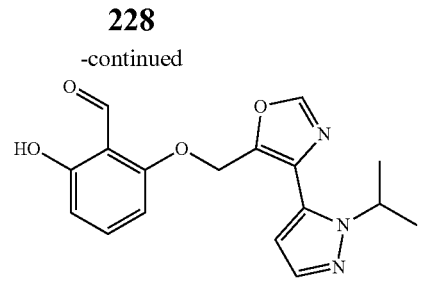

Example 67

Step 1-4: Example 67

The procedure was according to Example 66.

Example 67 (25 mg white solid was obtained) LCMS [M+H]⁺=328.1 ¹H NMR (400 MHz, Chloroform-d) δ 11.95 (s, 1H), 10.29 (s, 1H), 8.03 (s, 1H), 8.58 (s, 1H), 7.40-7.36 (t, J=8.0 Hz, 1H), 6.60-6.58 (d, J=8.0 Hz, 1H), 6.39-6.73 (d, J=8.0 Hz, 1H), 6.32 (s, 1H), 5.21 (s, 2H), 5.00 (m, 1H), 1.51-1.49 (d, J=8.0 Hz, 6H).

Example 68: General Procedure for Synthesis of Example 68

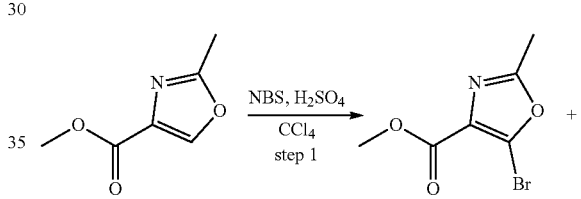

Example 68a → Example 68b +

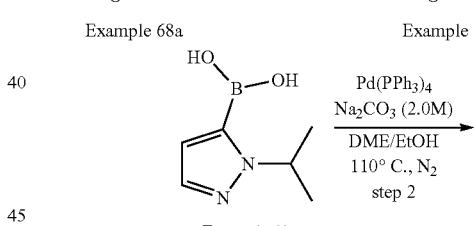

Example 1b

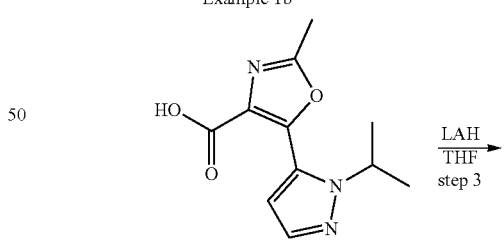

Example 68c

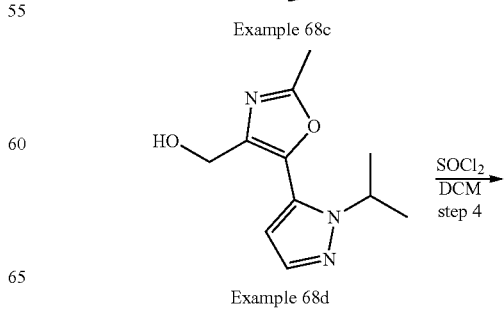

Example 68d

-continued

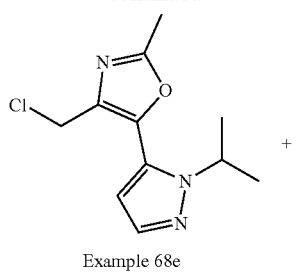

Example 68e

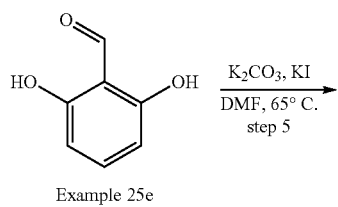

Example 25e

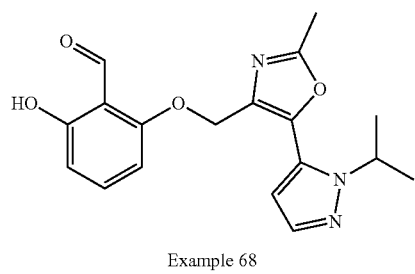

Example 68

Step 1-5: Example 68

The procedure was according to example 66.

Example 68 (12 mg white solid was obtained) LCMS [M+H]$^+$=342.1

$^1$H NMR (400 MHz, Chloroform-d) δ 11.95 (s, 1H), 10.23 (s, 1H), 7.59 (s, 1H), 7.39-7.35 (t, J=8.0 Hz, 1H), 6.56-6.54 (d, J=8.0 Hz, 1H), 6.45-6.43 (d, J=8.0 Hz, 1H), 6.37 (s, 1H), 5.02 (s, 2H), 4.59 (m, 1H), 2.57 (s, 3H), 1.50-1.48 (d, J=8.0 Hz, 6H).

Example 69: General Procedure for Synthesis of Example 69

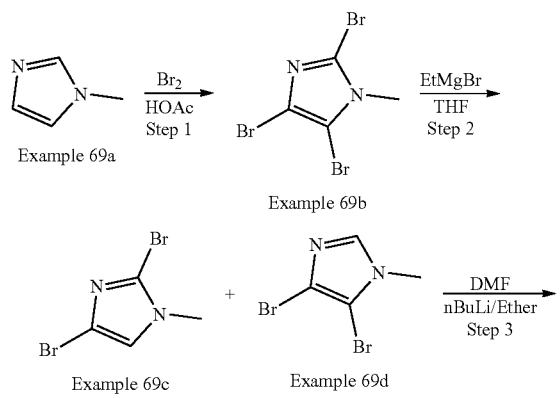

-continued

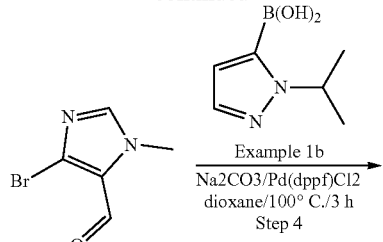

Example 69e

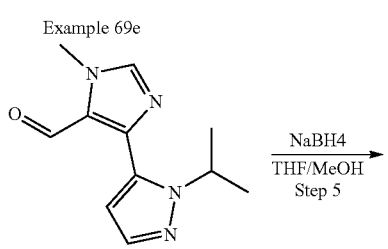

Example 69f

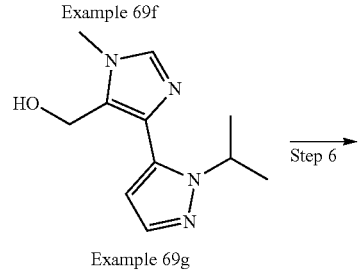

Example 69g

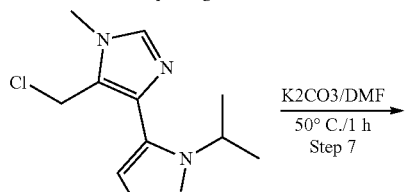

Example 69h

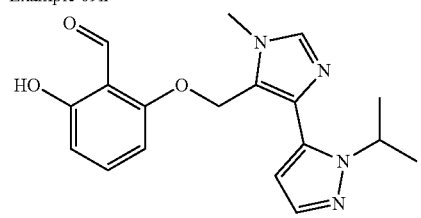

Example 69

Step 1: Example 69b

To a solution of Example 69a (82 g, 1.0 mol) and sodium acetate (125 g, 1.52 mol) in acetic acid (2.0 L) at room temperature was added bromine (480 g, 30 mmol) dropwise as a solution in 1.0 L acetic acid. The resulting mixture was stirred for 2.5 h at room temperature. Acetic acid was removed in vacuo; the residue was suspended in 1.5 L water and stirred at room temperature for 10 minutes. The resultant precipitate was filtered, washed with water and dried under high vacuum to give Example 69b (95.0 g, contained 30% isomer) as light yellow powder. LCMS [M+H]$^+$=319.1

Step 2: Example 69c&d

To a solution of Example 69b (84 g, 263.3 mmol) in dry THF (2 L) was added EtMgBr (88 mL, 263.3 mmol, 3.0M in ether) slowly under N₂. The reaction was stirred at r.t. for 2 hours. Then about 2.0 L water was added and filtered concentrated and the residue was extracted with EtOAc (50 mL*2). The combined organic phase was washed with brine, dried over Na₂SO₄, filtrated and concentrated under reduced pressure to give the crude product which was further purified by silica gel chromatography to give the pure product Example 69d (14.0 g) as white solid ¹H NMR (400 MHz, Chloroform-d) δ 7.48 (s, 1H), 3.63 (s, 3H).

Example 69c (14.0 g) as white solid. ¹H NMR (400 MHz, Chloroform-d) δ 6.94 (s, 1H), 3.60 (s, 3H).

Step 3: Example 69e

A solution of Example 69c&d (2.4 g, 10.0 mol) in ether (100 mL) was cooled to −78° C. under nitrogen atmosphere and then a 2.5 M n-BuLi solution in hexane (4.0 mL, 10.0 mol) added dropwise over 15 mins. The mixture was stirred at −78° C. for 30 min and then DMF (2.0 mL) was added dropwise over 15 min. The mixture was stirred at −78° C. for 30 min and quenched with saturated 1N HCl (50 mL) at −78° C. The residue was extracted with EtOAc (50 mL*2). The combined organic phase was washed with brine, dried over Na₂SO₄, filtrated and concentrated under reduced pressure to give the crude product which was further purified by silica gel chromatography to give the pure product Example 69e (1.8 g, yield 95%) as yellow solid. ¹H NMR (400 MHz, Chloroform-d) δ 9.77 (d, J=0.9 Hz, 1H), 7.51 (s, 1H), 3.93 (s, 3H).

Step 4: Example 69f

To a solution of Example 69e (1.47 g, 7.82 mmol) in dioxane (30 mL) was added Example 1b (2.0 g, 11.73 mmol), 2N Na₂CO₃ (10 mL, 20 mmol), Pd(dppf)Cl₂ (285 mg, 0.391 mmol) under N₂ and then heated to 90° C. for 5 hrs. After cooled to room temperature, the solvent was removed under reduced pressure, the residue was extracted with EtOAc (20 mL*2) and combined the organic phase, washed with brine, dried over Na₂SO₄, filtered and concentrated under reduced pressure. The residue was then further purified by flash column chromatography (PE:EA=2:1) to give the Example 69f (1.32 g, yield 77.6%) as yellow solid. H NMR (400 MHz, Chloroform-d) δ 9.82 (s, 1H), 7.67 (s, 1H), 7.58 (d, J=1.9 Hz, 1H), 6.37 (d, J=1.9 Hz, 1H), 5.06 (p, J=6.6 Hz, 1H), 4.00 (s, 3H), 1.50 (d, J=6.6 Hz, 6H). LC-LCMS [M+1]⁺219.1.

Step 5: Example 69g

To a suspension of Example 69f (100 mg, 0.458 mmol) in THF:MeOH=1:1 (4 mL) at 10° C. added NaBH₄ (70 mg, 1.83 mmol) and the mixture was stirred for 1 hour. 1N HCl (2 mL) was added and stirred for 30 min, dried over Na₂SO₄, filtered through a celite pad. The filtrate was concentrated under reduced pressure to afford the title Example 69g (100 mg, yield 95%) as white solid. LCMS [M+1]⁺=221.1.

Step 6: Example 69h

To a solution of Example 69g (100 mg, 0.458 mmol) in DCM (5 mL) was added SOCl₂ (0.5 mL) at r.t. The reaction mixture was stirred at r.t. for 0.5 h and concentrated to dryness. The crude solid was suspended in toluene and concentrated to dryness to give Example 69h (105 mg) as yellow solid, which was directly used for next step without further purification. LCMS [M+1]⁺=239.1.

Step 7: Example 69

A mixture of Example 25e (83 mg, 0.6 mmol) and K₂CO₃ (276 mg, 2.0 mmol) in DMF (5 mL) was added Example 69h (100 mg, 0.419 mmol) under N₂. The mixture was then heated at 55° C. for 0.5 h, Cooled to r.t. The reaction was then quenched by adding water (50 mL) and extracted with EtOAc (50 mL). The combined organic layers were washed with brine, dried over Na₂SO₄, concentrated, and purified by Pre-HPLC to give the desired product Example 69 (15 mg, yield 14%) as white solid. LCMS [M+1]⁺=341.1

¹H NMR (400 MHz, Chloroform-d) δ 11.93 (s, 1H), 10.30 (s, 1H), 7.72 (s, 1H), 7.56 (d, J=1.7 Hz, 1H), 7.37 (t, J=8.4 Hz, 1H), 6.58 (d, J=8.5 Hz, 1H), 6.31 (d, J=8.3 Hz, 1H), 6.19 (d, J=1.8 Hz, 1H), 5.14 (s, 2H), 5.04 (p, J=6.6 Hz, 1H), 3.79 (s, 3H), 1.48 (d, J=6.6 Hz, 6H).

Example 70: General Procedure for Synthesis of Example 70

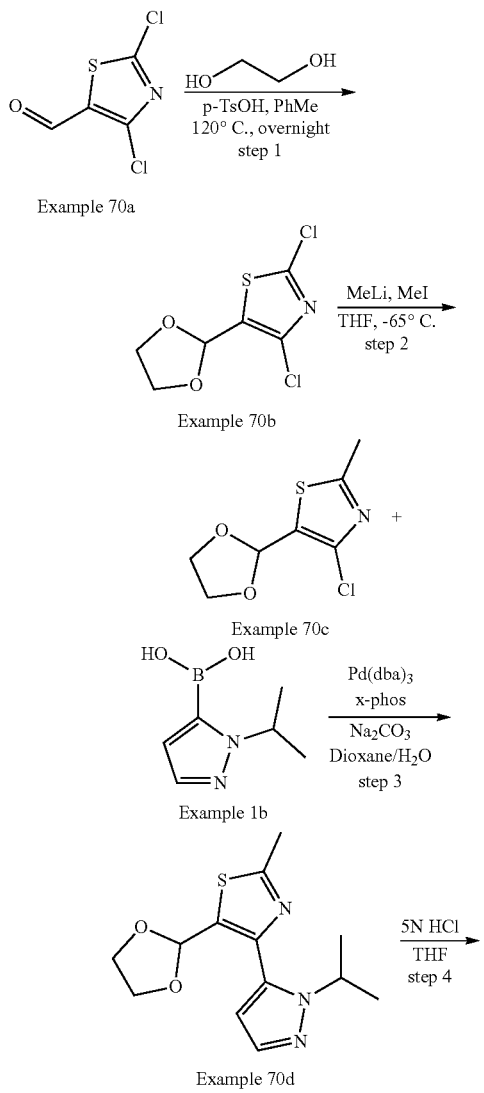

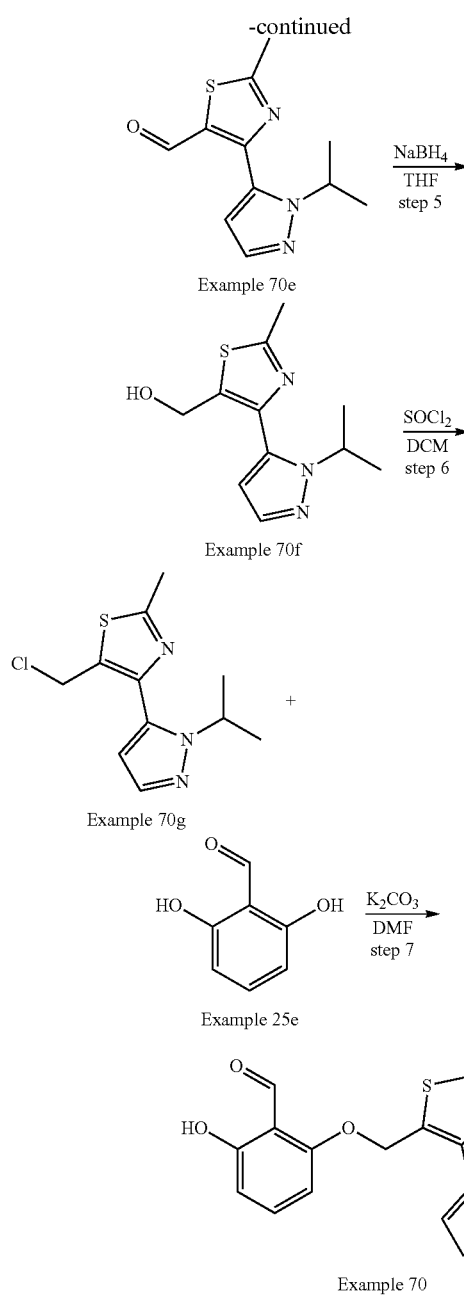

Step 1: Example 70b

A solution of Example 70a (1.0 g, 5.52 mmol, 1.0 eq.), ethane-1,2-diol (1.02 g, 16.57 mmol, 3.0 eq.) and p-TsOH (105 mg, 0.55 mmol, 0.1 eq.) in PhMe (15 mL) at 120° C. with Dean-Stark trap and stirred overnight. TLC (PE/EtOAc=3/1) showed the starting material was consumed completely. The reaction mixture was cooled to room temperature and washed with sat. aq. NaHCO$_3$ (20 mL), brine (2*20 mL), dried over Na$_2$SO$_4$, filtered and concentrated to afford Example 70b (1.29 g, 100% yield) as a yellow liquid. LCMS [M+H]=225.1

Step 2: Example 70c

To a solution of Example 70b (1.0 g, 4.44 mmol, 1.0 eq.) in dry THF (40 mL) was added MeLi (1.6 M, 3.4 mL, 5.55 mmol, 1.25 eq.) at −65° C. under N$_2$. After addition, the reaction mixture was stirred at same temperature for 1 hour. MeI (0.83 mL, 13.33 mmol, 3.0 eq.) in dry THF (10 mL) was added dropwise and then the reaction mixture was stirred for 3 hrs at −65° C. TLC (PE/EtOAc=5/1) showed the starting material was still remained and the desired compound was detected by LCMS. So the reaction mixture was stirred at room temperature overnight. TLC showed the starting material was still remained. The reaction mixture was quenched by sat. aq. NH$_4$Cl (50 mL) and separated. The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product Example 70c (230 mg, 25.2% yield) as a yellow solid. LCMS [M+H]$^+$=206.1

Step 3: Example 70d

To a solution of Example 70c (180 mg, 0.87 mmol), Example 1b (205 mg, 1.31 mmol) and Na$_2$CO$_3$ (185 mg, 1.75 mmol) in dioxane/H$_2$O (10/1, 11 mL) was added Pd$_2$(dba)$_3$ (18 mg, 0.08 mmol) and x-phos (18 mg, 0.08 mmol) at room temperature under N$_2$. The reaction mixture was heated to 105° C. and stirred overnight under N$_2$. TLC showed the starting material was consumed completely. The reaction mixture was concentrated and purified by flash column chromatography to afford Example 70d (230 mg, 8.8% yield) as yellow oil. LCMS [M+H]$^+$=280.1

Step 4: Example 70e

A mixture of Example 70d (230 mg, 0.82 mmol, 1.0 eq.) in THF (10 mL) was added 5N HCl (1.3 mL) at 20° C. for 2 hours. TLC (PE:EtOAc=1:1) showed the starting material was consumed completely. H$_2$O was added and the aqueous layer was extracted with EtOAc (2*15 mL). The organic layer was washed with brine, dried over Na$_2$SO$_4$, filtered and concentrated to afford Example 70e (210 mg, 100% yield) as yellow oil. LCMS: [M+H]=236.1

Step 5: Example 70f

To a mixture of Example 70e (190 mg, 0.8 mmol, 1.5 eq.) in THF (20 mL) was added NaBH$_4$ (61 mg, 1.61 mmol, 2.0 eq.) at room temperature. After addition, the reaction mixture was stirred for 0.5 hr. TLC (PE:EtOAc=5:1) showed the starting material was consumed completely. The reaction mixture was poured into sat. aq. NH$_4$Cl (20 mL) and separated. The organic layer was washed with brine, dried over Na$_2$SO$_4$, filtered and concentrated, which was purified by flash column chromatography to afford Example 70f (90 mg, 47.6% yield) as yellow oil. LCMS [M+H]$^+$=238.1

Step 6: Example 70g

To a mixture of Example 70f (90 mg, 0.38 mmol, 1.0 eq.) in DCM (10 mL) was added SOCl$_2$ (0.5 mL) at 20° C. and stirred for 1 hr. LCMS showed the starting material was consumed completely. The reaction mixture was concentrated under reduced pressure to afford Example 70 g (118 mg, 100% yield) as a yellow solid. LCMS [M+H]$^+$=257.1

Step 7: Example 70

A mixture of Example 70g (118 mg, 0.46 mmol, 1.5 eq.), Example 25e (42 mg, 0.31 mmol, 1.0 eq.) and K$_2$CO$_3$ (425 mg, 3.1 mmol, 10.0 eq.) in DMF (10 mL) was heated to 65° C. and stirred for 0.5 hour. LCMS showed the starting material was consumed completely. Cooled to room temperature and diluted with EtOAc and washed with brine, dried over $Na_2SO_4$, filtered and concentrated, which was purified by prep-HPLC to afford the desired compound Example 70 (26 mg, yield 23.6%) as white solid. LCMS $[M+H]^+$=358.1

$^1$H NMR (400 MHz, Chloroform-d) δ 11.93 (s, 1H), 10.32 (s, 1H), 7.59 (s, 1H), 7.39-7.35 (t, J=8.0 Hz, 1H), 6.58-6.56 (d, J=8.0 Hz, 1H), 6.31-6.29 (d, J=8.0 Hz, 1H), 5.23 (s, 2H), 4.84 (m, 1H), 2.77 (s, 3H), 1.49-1.48 (d, J=4.0 Hz, 6H).

Example 71: General Procedure for Synthesis of Example 71

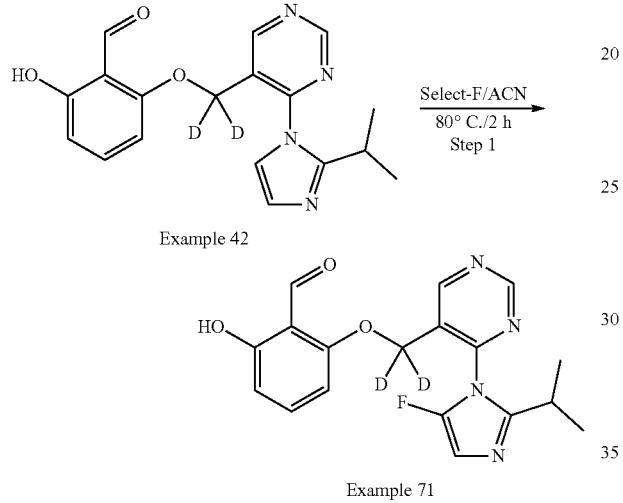

Step 1: Example 71

Example 42a (40 mg, 0.12 mmol, 1.0 eq.), Select-F (62 mg, 0.18 mmol, 1.5 eq.) was suspended in ACN (4 mL) and heated to 80° C. for 2 hrs. TLC detected the reaction was completed. The mixture was concentrated and the residue was purified by Prep-HPLC to give the title compound Example 71 (12 mg, yield 27%) as a yellow solid.

LCMS $[M+1]^+$=359. $^1$H NMR (400 MHz, dmso) δ 11.69 (s, 1H), 10.07 (s, 1H), 9.31 (s, 1H), 9.17 (s, 1H), 7.57 (d, J=1.8 Hz, 1H), 7.51 (dd, J=11.1, 9.2 Hz, 1H), 6.69 (d, J=1.9 Hz, 1H), 6.59 (dd, J=9.1, 3.1 Hz, 1H), 4.86 (dt, J=13.1, 6.6 Hz, 1H), 1.36 (d, J=6.6 Hz, 6H).

Example 72: General Procedure for Synthesis of Example 72

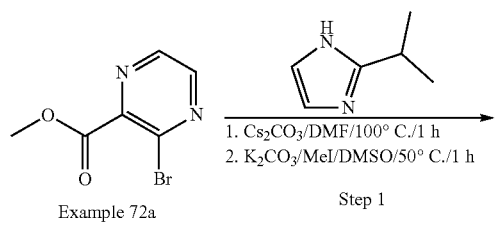

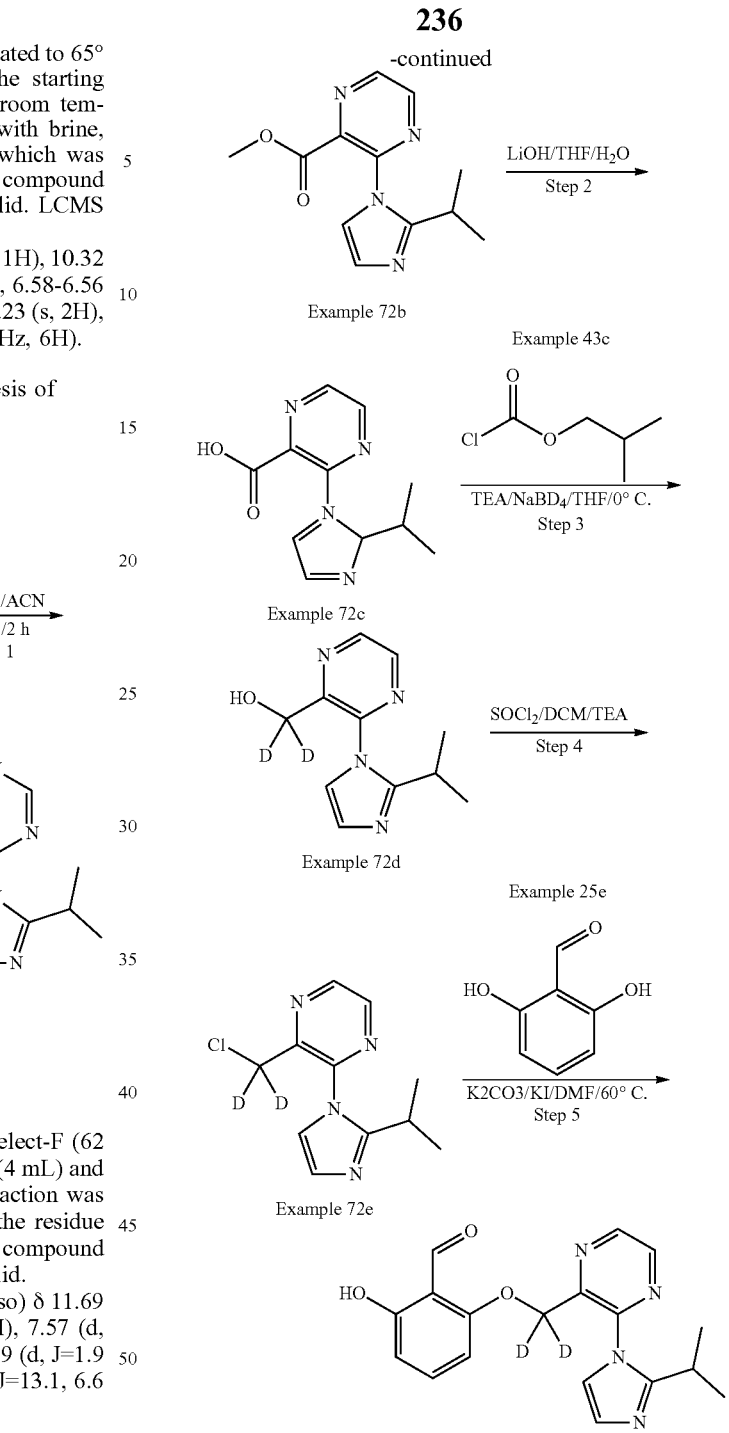

Step 1: Compound 72b

To a solution of Example 72a (1.55 g, 7.1 mmol) was dissolved in DMSO (15 mL) followed by 2-isopropyl-1H-imidazole (866 mg, 7.9 mmol) and $Cs_2CO_3$ (5.8 g, 17.9 mmol), and then heated to 100° C. for 1 h. (detected by TLC PE:EA=2:1, showed reaction completed). After cooled to r.t., filtered and the filtrate was used to next step without purification. The filtrate was added $K_2CO_3$ (1.5 g 10.6 mmol) and $CH_3I$ (1.5 g 10.6 mmol), then stirred at 50° C. for 1 h. The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product Example 72b (480 mg, yield 28.2%) as a yellow oil.

Step 2: Example 72c

To a solution of Example 72b (0.48 g, 2 mmol) in MeOH (1 mL)/THF (3 mL)/H$_2$O (1 mL) was added LiOH.H$_2$O (82 mg, 2 mmol) at 0° C. for 30 min, the reaction was then quenched by 1NHCl to pH=6, concentrated and purified by flash (eluted with DCM/MeOH=20%) to give a crude Example 72c (0.4 g, yield 86.2%) which was applied to the next step directly.

Step 3: Example 72d

To a solution of Example 72c (440 mg, 1.9 mmol) in THF (20 mL) was added Example 43c (311 mg, 2.3 mmol) at 0° C. and TEA (288 mg, 2.8 mmol). The mixture was stirred at r.t for 10 s, and then NaBD$_4$ (96 mg, 2.3 mmol) in EtOH (1.5 mL) was added at 0° C., which was turned to r.t for another 30 min. The reaction was then quenched by adding 2 mL water, then concentrated. The residue was purified by flash chromatography (eluent: PE/EA=1:1) to give the title Example 72d (118 mg, yield 28.2%) as yellow oil. LCMS [M+1]$^+$221.1

Step 4: Example 72e

To a solution of Example 72d (118 mg, 0.54 mmol) in DCM (5 mL) was treated with SOCl$_2$ (77 mg 0.64 mmol) at 0° C. After 30 min, TEA (290 mg, 2.86 mmol) was added, then the reaction mixture was concentrated to give a crude Example 72e which was used to next step without any other purification.

Step 5: Example 72

The crude Example 72e, Example 25e (112 mg, 0.81 mmol), K$_2$CO$_3$ (224 mg, 1.60 mmol), KI (8 mg, 0.05 mmol) was suspended in DMF (5 mL) and heated to 60° C. for 40 min. TLC detected the reaction was completed. The reaction was filtered and sent to Prep-HPLC to give the title compound Example 72 (15 mg, yield 8%) as a white solid. LCMS [M+1]$^+$=341

$^1$H NMR (400 MHz, CDCl$_3$) δ 11.91 (s, 1H), 10.20 (s, 1H), 8.77 (d, J=2.3 Hz, 1H), 8.65 (d, J=2.3 Hz, 1H), 7.36 (t, J=8.4 Hz, 1H), 7.07 (d, J=35.9 Hz, 2H), 6.56 (d, J=8.5 Hz, 1H), 6.35 (d, J=8.3 Hz, 1H), 2.88 (dt, J=13.5, 6.8 Hz, 1H), 1.23 (d, J=6.8 Hz, 6H).

Example 73: General Procedure for Synthesis of Example 73

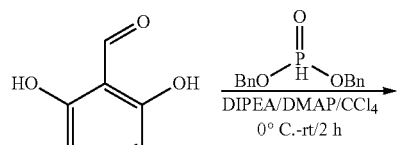

Example 25e

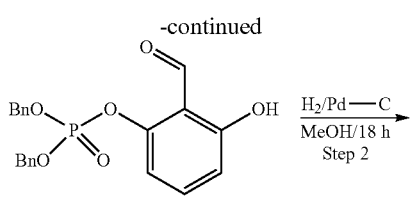

Example 73a

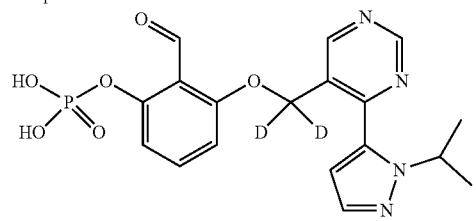

Example 73b

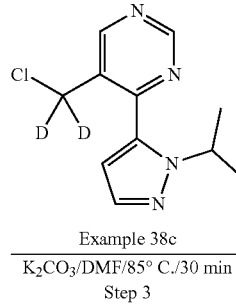

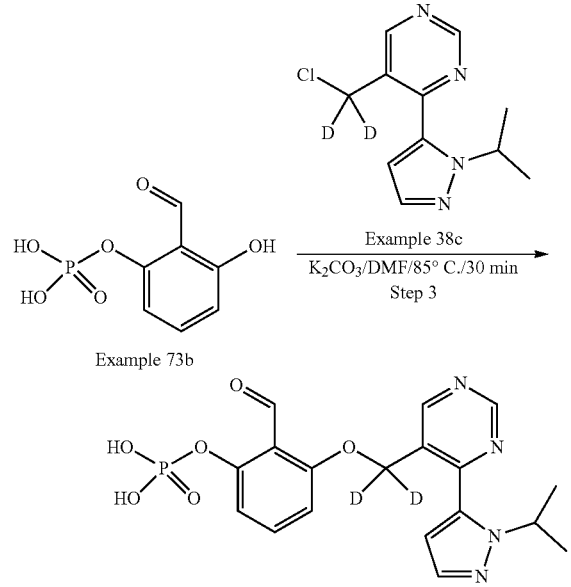

Example 73

Step 1: Example 73a

To a solution of Example 25e (1.7 g 0.006 mol) in dry acetonitrile was added DIPEA (1.86 g 0.014 mol), DMAP (88 mg 0.0007 mol) and CCl$_4$ (5.54 g 0.036 mol). The resulting mixture was purged with argon gas (5 min), cooled to −10° C., and dibenzyl phosphonate (1 g, 0.007 mol) was added dropwise over 3 min. After 1 h the reaction mixture was diluted with water. The residue was extracted with EtOAc (50 mL*2). The combined organic phase was washed with brine, dried over Na$_2$SO$_4$, filtrated and concentrated under reduced pressure to give the crude product which was further purified by silica gel chromatography to give the pure product Example 73a (1.4 g) as crude oil.

Step 2: Example 73b

To a solution of Example 73a (1.4 g) in MeOH (20 mL), was added Pd/C (0.1 g). The reaction vessel was evacuated and then purged with an atmosphere of hydrogen three times. After 1 h, Filtered and concentrated under vacuum to give Example 73b (0.8 g, yield 73%) as yellow oil Step 3: Example 73

To a solution of Example 73b (700 mg, 3.2 mmol, 1.0 eq) in DMF (10 mL) was added Example 38c (968 mg, 3.52 mmol, 1.1 eq) and K$_2$CO$_3$ (2 g, 14.08 mmol) KI (cat) the mixture was stirred at 80° C. for 1 hrs, The reaction mixture was then cooled down, the reaction was then quenched by adding 50 mL water, the residue was extracted with EtOAc (200 mL*2). The combined organic phase was washed with brine, dried over Na$_2$SO$_4$, filtrated and concentrated under reduced pressure to give the crude product which was further purified by silica gel chromatography to give the pure product Example 73 (80 mg) as white solid.

$^1$H NMR (400 MHz, DMSO-d$_6$) δ 13.02 (s, 2H), 10.06 (s, 1H), 9.18 (s, 1H), 8.90 (s, 1H), 7.56 (d, J=1.9 Hz, 1H), 7.36 (d, J=8.3 Hz, 1H), 6.85 (d, J=8.3 Hz, 1H), 6.65 (d, J=1.9 Hz, 1H), 6.49 (d, J=8.4 Hz, 1H), 4.84-4.78 (m, 1H), 1.34 (d, J=6.5 Hz, 6H).

Example 74: General Procedure for Synthesis of Example 74

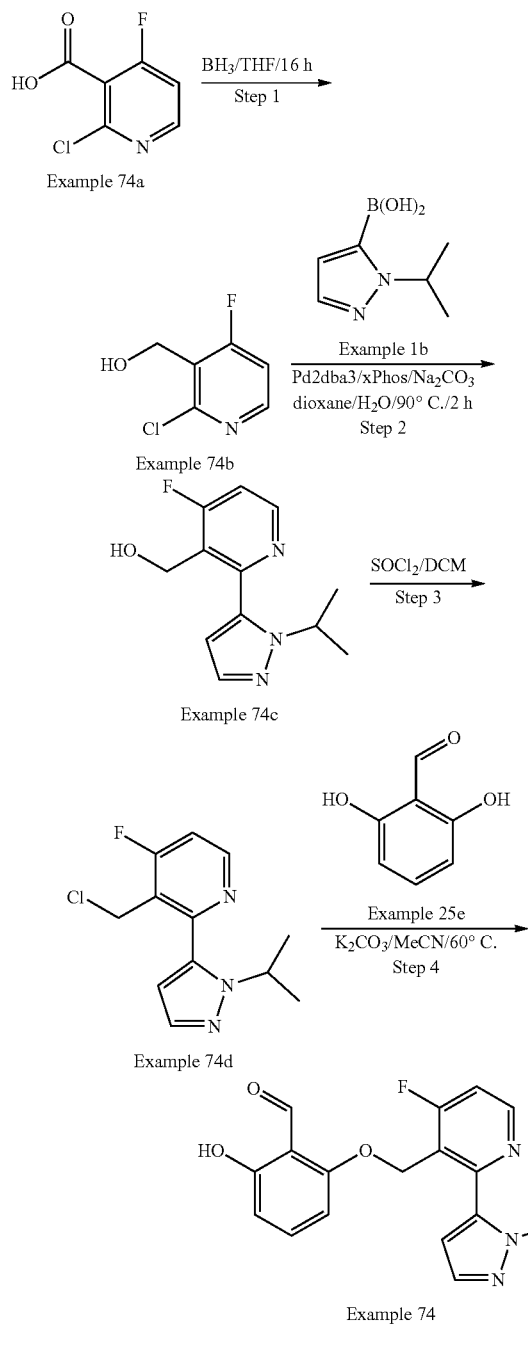

Step 1: Example 74b

To a solution of Example 74a (100 mg, 0.57 mmol) in THF (100 mL) was added BH$_3$ (1M, 10 mL) in batch at 0° C. and slowly warmed to 65° C. for 16 h. After the reaction was completed, the solvent was removed under reduced pressure, and the residue was dissolved in EtOAc (50 mL), washed with aq. NH$_4$Cl (20 mL*3), dried over Na$_2$SO$_4$, filtered and concentrated to afford the desired product (Example 74b, 100 mg) as a yellow oil.

Step 2: Example 74c

To a solution of Example 74b (154 mg, 0.9625 mmol) in dioxane/water (8 mL/1 mL) was added Example 1b (222 mg, 1.442 mmol), K$_3$PO$_4$ (530 g, 2.5 mmol), Pd$_2$(dba)$_3$ (15 mg) and 2-dicyclohexylphosphino-2',4',6'-triisopropylbiphenyl (15 mg,) under N$_2$ protection and then heated to 90° C. for 2 hrs. After cooled to room temperature, the solvent was removed under reduced pressure; the residue was extracted with EtOAc (20 mL*2). The combined organic phase was washed with brine, dried over Na$_2$SO$_4$, filtrated and concentrated under reduced pressure to give the crude product which was further purified by silica gel chromatography to give the pure product (Example 74c, 50 mg, yield 30%) as yellow oil.

Step 3: Example 74d

To a solution of Example 74c (50 mg) in DCM (18 mL) was added thionyl chloride (0.5 mL) and stirred at r.t. for 0.5 h. After the reaction was completed, the solvent was removed under reduced pressure to give the crude product (Example 74d, 50 mg) as yellow oil.

Step 4: Example 74

To a solution of Example 74d (50 mg, 0.197 mmol) in acetonitrile (5 mL) was added Example 25e (40 mg, 0.296 mmol), potassium carbonate (108.7 mg, 0.788 mmol) and potassium iodide (2 mg), and then heated to 60° C. for 4 hrs. After cooled to room temperature, water (5 mL) was added to the mixture, and then extracted with EA (10 mL*2). The combined organic phase was washed with brine, dried over Na$_2$SO$_4$, filtrated and concentrated under reduced pressure to give the crude product which was further purified by Prep-HPLC to give the pure product Example 74 (7 mg) as yellow soild. LCMS [M+1]$^+$=356.1

$^1$H NMR (400 MHz, Chloroform-d) δ 11.93 (s, 1H), 10.22 (s, 1H), 8.75 (dd, J=8.1, 5.5 Hz, 1H), 7.56 (d, J=1.8 Hz, 1H), 7.40 (t, J=8.4 Hz, 1H), 7.18 (dd, J=8.9, 5.6 Hz, 1H), 6.59 (d, J=8.5 Hz, 1H), 6.40-6.33 (m, 2H), 5.10 (d, J=1.3 Hz, 2H), 4.71 (p, J=6.6 Hz, 1H), 1.46 (d, J=6.6 Hz, 6H).

Example 75: General Procedure for Synthesis of Example 75

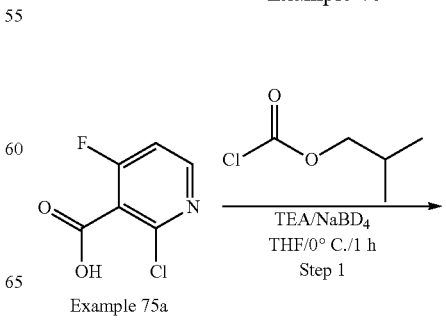

-continued

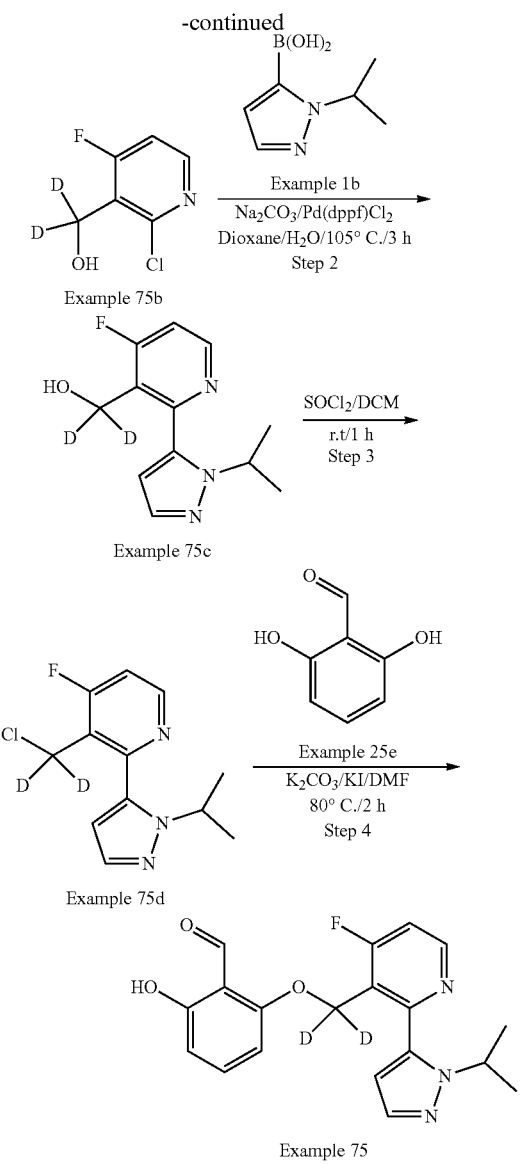

Step 1: Example 75b

To a solution of Example 75a (2.74 g, 15.6 mmol) in THF (50 mL), tBuOCOCl (3.2 g, 23.4 mmol) at 0° C. was added TEA (3.16 g, 31.2 mmol), the mixture was stirred at r.t. for 0.5 min, and then NaBD₄ (1.31 g, 31.2 mmol) in EtOH (10 mL) was added at 0° C., which was turned to r.t for another 30 min. The reaction was then quenched by adding water (10 mL), then concentrated, the residue was purified by flash column chromatography (eluted with EtOAc) to give the desired product (Example 75b, 1.05 g, yield 41%) as yellow oil. LCMS [M+1]⁺=164

Step 2: Example 75c

To a solution of Example 75b (1.3 g, 8.0 mmol) was dissolved in Dioxane (40 mL) and water (1 mL) was added Example 1b (1.8 g, 12 mmol) and Na₂CO₃ (1.78 g, 16 mmol) Pd (dppf)Cl₂ (100 mg), and then heated to 105° C. under N₂ for 2 h. The reaction mixture was cooled to r.t., filtered, and the filtrate was concentrated and purified by flash column chromatography to give the desired product (Example 75c, 700 mg, yield 37%) as yellow solid. LCMS [M+1]⁺=238

Step 3: Example 75d

To a solution of Example 75c (700 mg, 2.95 mmol) in DCM (3 mL) was treated with SOCl₂ (1 mL) at 0° C. After 30 mins the reaction mixture was concentrated to give a crude product (Example 75d, yield 100%), which was used directly to next step without any purification.

Step 4: Example 75

The crude Example 75d obtained from previous step, Example 25e (611 mg, 4.43 mmol), K₂CO₃ (1.2 g, 8.85 mmol), KI (50 mg 0.3 mmol) was suspended in DMF (15 mL). The mixture was heated to 80° C. for 2 h, then filtered and the filtrate was purified by doing Prep-HPLC to give the desired product Example 75 (350 mg, yield 33%) as a brown solid. LCMS [M+1]⁺=358

$^1$H NMR (400 MHz, Chloroform-d) δ 11.93 (s, 1H), 10.22 (s, 1H), 8.76 (s, 1H), 7.56 (d, J=1.5 Hz, 1H), 7.40 (t, J=8.4 Hz, 1H), 7.18 (dd, J=8.7, 5.5 Hz, 1H), 6.58 (d, J=8.5 Hz, 1H), 6.36 (d, J=8.0 Hz, 2H), 4.73 (dd, J=13.2, 6.6 Hz, 1H), 1.46 (d, J=6.6 Hz, 6H).

Example A1: Oxygen Equilibrium Curve (OEC) Studies

Materials: Normal whole blood was collected from adult healthy donors at the Virginia Commonwealth University after informed consent. The use of these human samples is in accordance with regulations of the IRB for Protection of Human Subjects. Compounds (50 mM-100 mM concentration in DMSO) were stored at 15° C. or room temperature until use.

Time-Dependent OEC Studies:

The time-dependent OEC studies were conducted on normal human adult blood samples with hematocrit value of 20% in the absence or presence of effectors solubilized in DMSO at final drug and DMSO concentrations of 2 mM and 2%, respectively. The DMSO-solubilized compound was added to 8 ml of whole blood that had been pre-incubated at 37° C. for 15 min. The mixture was further incubated at 37° C. with shaking. At 1 h, aliquots (2 ml) were taken and equilibrated in IL 237 tonometer (Instrumentation Laboratories, Inc., Lexington, Mass.) for about 7-8 min at 37° C. with gas mixture containing O₂ concentrations of 0.804%, 2.954%, and 5.77% corresponding to oxygen tensions (partial pressure of oxygen; pO₂) of 7, 20 and 40 mmHg, respectively. After equilibration, the sample was removed by syringe and aspirated into a ABL 700 series table top automated blood gas analyzer (Radiometer America, Inc., Westlake, Ohio) to determine values of total hemoglobin (tHb), methemoglobin (metHb), hematocrit (Hct), pH, partial pressure of oxygen (pO2), and Hb oxygen saturation values (sO₂). The measured values of sO₂ and pO₂ at each partial pressure of oxygen are then subjected to a non-linear regression analysis using the program Scientist (Micromath, Salt Lake City, Utah) with the following equation:

$$sO_2\% = 100\, a \frac{pO_2^N \text{mmHg}}{P_{50}^N(\text{mmHg}) + pO_2^N(\text{mmHg})}$$

This equation was used to calculate P50 and Hill coefficient (N) values. Corresponding control experiments without the test compound (P50control) but containing DMSO were also performed. GBT440 was used as a positive control. Table 1 below lists the delta p50% values.

TABLE 1

| Example | delta p50 |
|---|---|
| 2 | −78% |
| 3 | −62% |
| 4 | −51% |
| 5 | −77% |
| 6 | −66% |
| 7 | −59% |
| 8 | −68% |
| 9 | −64% |
| 10 | −68% |
| 13 | −9% |
| 14 | −63% |
| 15 | −81% |
| 20 | −74% |
| 21 | −72% |
| 23 | −62% |
| 24 | −47% |
| 30 | −85% |
| 59 | −54% |
| 60 | −69% |
| 61g | −59% |
| 62a | −63% |
| 62b | −64% |

Dose-Dependent Whole Blood OEC Studies

To 2 ml 20% hct blood, 0.2 or 0.5 or 1 mM compound was added and kept shaking at 37° C. for 1 hr. OEC analysis was performed as described above to determine partial pressure of oxygen (pO2) and Hb oxygen saturation values (sO2). A control without compound but containing equivalent amount of DMSO was performed (1%). GBT440 was used as a positive control. Table 2 below lists the delta p50% values.

TABLE 2

| | delta p50 | |
|---|---|---|
| Example | 0.2 mM | 0.5 mM |
| GBT-440 | −14.2% | −35.1% |
| 11 | −12.80% | −37.60% |
| 12 | −26.60% | −58.40% |
| 16 | −8.90% | −14.70% |
| 17 | −12% | −30% |
| 18 | −2.80% | −8.10% |
| 19 | −8.20% | −18.10% |
| 22 | −12.90% | −35.50% |
| 25 | −14.30% | −36.10% |
| 26 | −11.10% | −26.10% |
| 27b | −18.8% | −56.6% |
| 28 | −11.90% | −40.70% |
| 29e | −24.9% | −66.1% |
| 31 | −9.80% | −36.10% |
| 32 | −12.70% | −39.20% |
| 33 | −12.70% | −39.70% |
| 34 | −6.50% | −10.00% |
| 35 | −10.30% | −29.80% |
| 36 | −9.30% | −14% |
| 37 | −16.20% | −46.10% |
| 38 | −15.20% | −46.80% |
| 39 | −12.20% | −29.30% |
| 40 | −6% | −12% |
| 41 | −14.40% | −30.20% |
| 42 | −10.20% | −23.10% |
| 43 | −9.90% | −28.10% |
| 44 | −6.90% | −22.10% |
| 45 | −10% | −29.80% |
| 46 | −12.80% | −37.90% |
| 47 | −15.30% | −40.80% |

TABLE 2-continued

| | delta p50 | |
|---|---|---|
| Example | 0.2 mM | 0.5 mM |
| 48 | −11% | −38.10% |
| 49 | −13.10% | −33.00% |
| 50 | −16.10% | −38.4.% |
| 51 | −13.10% | −36.40% |
| 53 | −20.50% | −37.80% |
| 54 | −12.00% | −35.00% |
| 55 | −5.30% | −8.80% |
| 56 | −1.60% | −11.30% |
| 57 | −4.90% | −7.60% |
| 58 | −14.30% | −34.30% |
| 63 | −7.00% | −15.20% |
| 64 | −10.00% | −31.00% |
| 65 | −11.20% | −36.20% |
| 66 | −5.70% | −16.50% |
| 67 | −6.80% | −25.30% |
| 68 | −8.70% | −13.00% |
| 69 | −21.40% | −41.80% |
| 70 | −10.40% | −21.90% |
| 72 | −5.10% | −16.80% |
| 74 | −15.8% | −48.4% |
| 75 | −13.0% | −53.7% |

Example A2: Hemoglobin Deoxygenation and Anti-Sickling Assays in HbSS Sickled Blood Materials:
Blood collected after informed consent from sickle cell individuals.
HBS buffer: 10 mM HEPES, 145 mM NaCl, pH 7.4
Hemox buffer: Buffer provided for the hemox analyzer
Control Compound stock solution in DMSO (50 mM) stored at RT
Control Compound work solution (CWS): 10 µl of DMSO was added by Hamilton to 90 µl of HBS buffer (20 mM Hepes, 145 mM NaCl, pH 7.4) to create a working solution with a final concentration of 5 mM drug and 10% DMSO).
Compound stock solution in DMSO (50 mM) stored at RT
Compound work solution (WS): 10 µl of DMSO was added by Hamilton to 90 µl of HBS buffer (20 mM Hepes, 145 mM NaCl, pH 7.4) to create a working solution with a final concentration of 5 mM drug and 10% DMSO).
DMSO buffer: 10% DMSO (DB), same as WS but without drug. This will be used to maintain DMSO the same for different drug incubations.

Test Protocol:
Collect blood from Clinic: Blood were collected after informed consent according to an approved IRB protocol.
Run Advia 120 analysis on SCD blood, to determine Hct.
Dilute blood to 20% Hct with HBS to total volume of 3 ml.
This cell suspension (CS) will be used for all experiments.
Incubation
1. 200 µl CS
2. 200 µl CS+20 µl CWS (5 mM diluted 10 times=0.5 mM control final)–(1% DMSO)
3. 200 µl CS+20 µl WS (5 mM diluted 10 times=0.5 mM control final)–(1% DMSO)
4. 200 µl CS+8 µl WS (0.2 mM drug final)+DB–(1% DMSO)
Incubate 30 minutes at 37° C.
Hemox Analysis:
50 µl into 4 ml Hemox buffer, duplicate.
Note: diluted drug during hemox analysis (80 times dilution as compared to incubation).

Sickling Analysis:

50 μl into 1 ml HBS+2% BSA buffer. Eight time points (0-20 minutes) at 2% oxygen, 10,000 events each)

The sickling runs provide sets samples that need to be run on the AMNIS image flow and are subsequently analyzed with pixel analysis software.

Figure 1B:
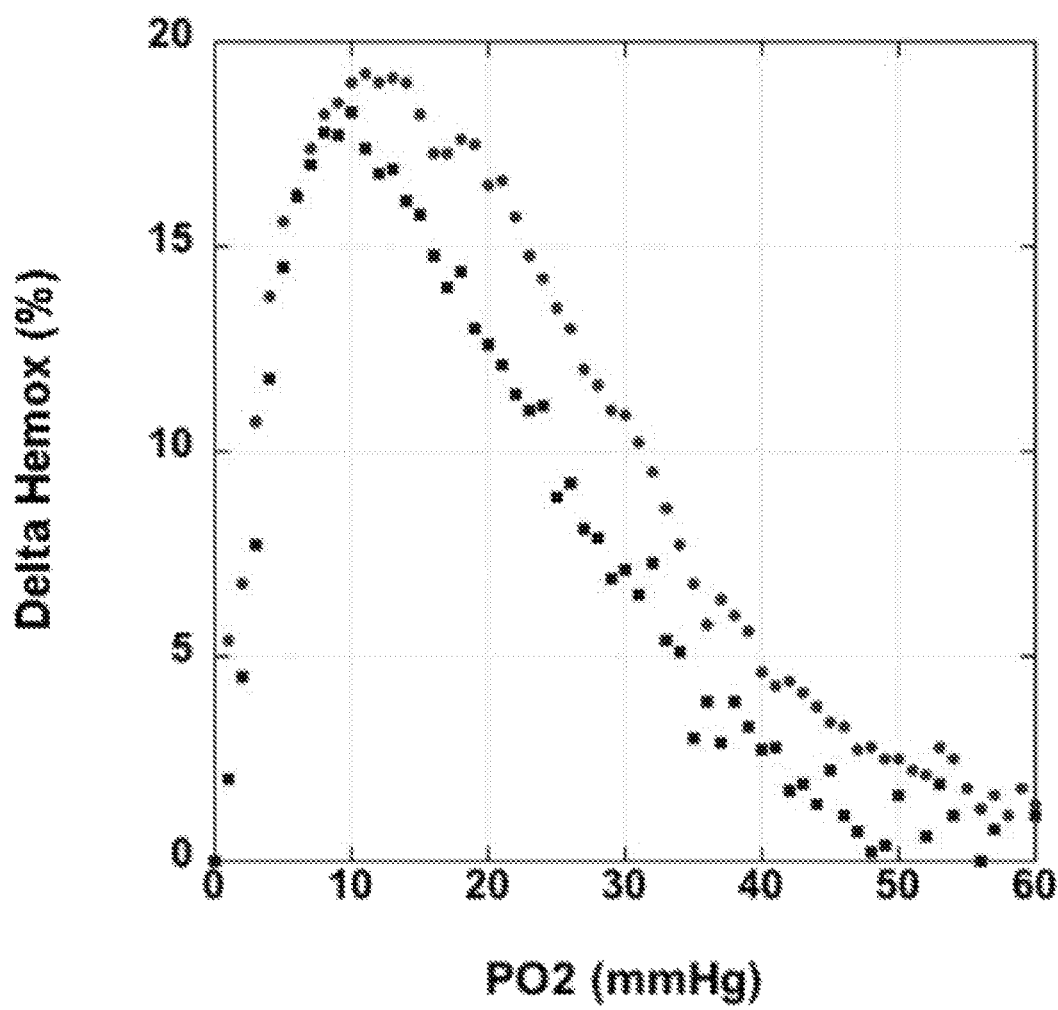
FIG. 1B shows the delta hemox (%) of example 29e as compared with GBT440 at 0.5 mM.

Assay Conditions:

Drug was provided at 50 mM concentration in DMSO, and stored at room temperature until use. 10 μl of DMSO was added by Hamilton to 90 μl of HBS buffer (20 mM Hepes, 145 mM NaCl, pH 7.4) to create a working solution with a final concentration of 5 mM drug and 10% DMSO). Blood was collected from a sickle cell patient in EDTA anticoagulant. To 200 μl of whole blood, a 20 or 8 μl of working solution was added resulting in a final drug concentration of 0.5 mM or 0.2 mM respectively. The DMSO concentration in both was corrected to 1%. The final hematocrit was measured by ADVIA analysis to be 26%. After incubation for 30 minutes at 37° C., oxygen affinity was determined using a Hemox analyzer (TCS Medical product according the manufacturer protocol using 50 μl of the incubation mixture+4 ml Hemox buffer. The kinetics of sickling were determined using a propriety sickling assay, by incubating 50 μl of the incubation mixture in 1 ml HBS with 2% BSA under 1% oxygen for 20 minutes. Samples were collected at set time points (0, 2, 5, 10, 20 minutes), morphology was fixed and 10,000 RBC events were analyzed on shape using the Image stream flow cytometer (AMNIS inc). The percent of non-discoid/sickled cells is expressed as a function of time at 1% oxygen (8 mm Hg $PO_2$) in table 3. The delta hemox (%) comparing Example 29e with GBT440 is shown in FIG. 1A (0.2 mM) and FIG. 1B (0.5 mM).

TABLE 3

| | p50 | |
|---|---|---|
| Example | 0.2 mM | 0.5 mM |
| Untreated | 24.2% | 24.2% |
| GBT-440 | 21.6% | 19.8% |
| 27b | 20.9% | 19.2% |
| 38 | 19.8% | 20.6% |
| 29e | 20.3% | 17.7% |

Figure 2:
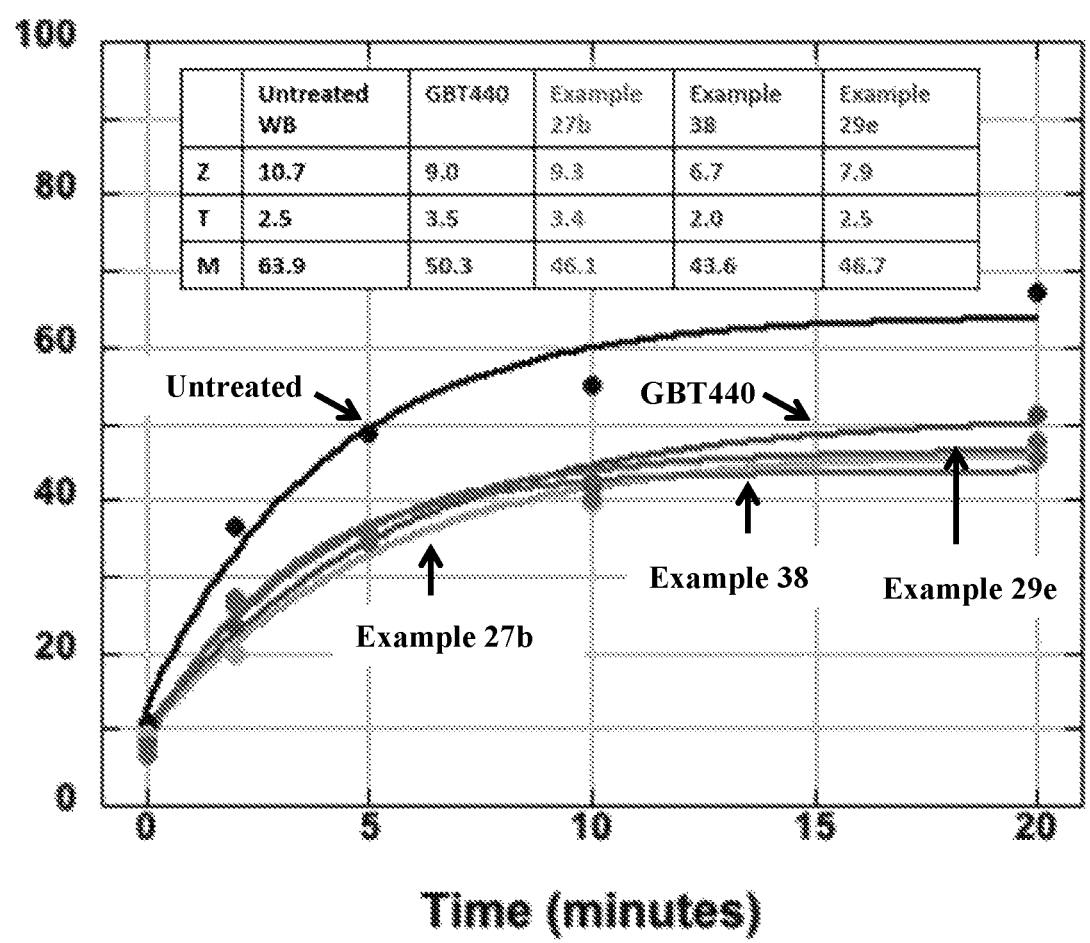
FIG. 2 shows anti-sickling: 0.2 mM compounds in sickled HbSS whole blood 26% Hct under hypoxic induction (M: maximum percentage of sickled cells during 20 mins of hypoxic induction T: time needed to reach 50% of M, and Z: baseline percentage of sickled cells prior to hypoxic induction)

Anti-sickling is shown in FIG. 2 with M: maximum percentage of sickled cells during 20 mins of hypoxic induction, T: time needed to reach 50% of M, and Z: baseline percentage of sickled cells prior to hypoxic induction.

The reduction in % sickled cells compared to untreated in shown in Table 4.

TABLE 4

| | GBT440 | Example 27b | Example 38 | Example 29e |
|---|---|---|---|---|
| Reduction in % sickled cells compared to untreated | −22.4% | −30.8% | −30.6% | −27.1% |

$$\frac{[M - Z \text{ (drug)}] - [M - Z \text{ (vehicle)}]}{[M - Z \text{ (vehicle)}]}$$

Example A3: Pharmacokinetic Study of Example 27, 29, and 38

Rats (Sprague-Dawley, male, 220-280 g) were dosed with GBT-440 (HCl salt) and one of three compounds corresponding to Example 27, 29, and 38. The rats received oral (7.2 mpk) doses of the compound. Rats were fasted overnight before the experiments and provided with food four hours after dosing. The oral dosing formulations was prepared as follows: approximately 10 mg of compound was weighed precisely to an appropriate size of container, to which was added 2 mL of vehicle 0.5% methylcellulose in water and 8 μL 0.5% sodium dodecyl sulfate. The mixture was then transferred into a glass vial, and volume adjusted to appropriate volume with 0.5% methylcellulose to obtain a final concentration of 0.72 mg·mL$^{-1}$, and then vortexed and sonicated briefly.

Whole blood sample collection: Blood samples (~100 L) were collected at pre-dose, 15, 30 min, 1, 2, 4, 8, 12 and 24 h via jugular vein into tubes and anticoagulated with 3.2% TSC (trisodium citrate). The proportion of anticoagulant and blood was 1:9 (v/v). The sampling time was recorded accordingly. The tubes were gently inverted several times to ensure mixing. Then 10 μL doses of whole blood sample was transferred to a new EP tube and duplicated in wet ice.

Plasma sample collection: The remaining whole blood was processed by centrifugation at 5,500 rpm for 10 min. The supernate was collected. All these whole blood and plasma samples were kept below −20° C. for 1 h prior to analysis.

Plasma sample preparation: An aliquot of 20 μL of sample was transferred to sample treatment tube (1.5 mL EP tube), and then 100 μL ACN (0.5% FA) containing Verapamil, 5 ng·mL$^{-1}$ and Glibenclamide, 50 ng·mL$^{-1}$ for protein precipitation was added. The mixture was vortexed for 30 min, and then centrifuged at 13000 rpm for 5 min at room temperature. After that, 70 μL of supernatant was transferred to a 96-Well Plate, to which 70 μL of water added and then vortexed for 10 min at room temperature. An aliquot of 10 μL of this mixture was analyzied using LC-MS/MS.

Whole blood sample preparation: An aliquot of 10 μL of sample was transferred to sample treatment tube (1.5 mL EP tube), and then 500 μL ACN (0.5% FA) containing Verapamil, 5 ng·mL$^{-1}$ and Glibenclamide, 50 ng·mL$^{-1}$ for protein precipitation was added. The mixture was vortexed for 30 min, and then centrifuged at 13000 rpm for 5 min at room temperature. After that, 70 μL of supernatant was transferred to a 96-Well Plate, to which 70 μL of water was added and then vortexed for 10 min at room temperature. An aliquot of 10 μL of this mixture was analyzed using LC-MS/MS.

Plasma and red blood cell concentration-time data were processed by linear regression analysis. All pharmacokinetic parameters were calculated using non-compartment model of Pharsight Phoenix 6.3.

Red blood cell concentrations were calculated according to the method below: Mass balance equation:

$$Cb \cdot VB = Cp \cdot Vp + CBC \cdot VBC$$

Where, Cb=Concentration of whole blood; VB=Volume of whole blood; Cp=Concentration of plasma; Vp=Volume of plasma; CBC=Concentration of blood cell; VBC=Volume of blood cell. VBC=H·VB, where H is the hematocrit number. Vp=(1−H)·VB Key parameters are shown in the Table 5 and Table 6.

TABLE 5

| | Example 27 | | | Example 29 | | | Example 38 | | |
|---|---|---|---|---|---|---|---|---|---|
| | | | | Dose | | | | | |
| | 7.2 mg/kg | | | 7.2 mg/kg | | | 7.2 mg/kg | | |
| | Plasma | RBC | Ratio | Plasma | RBC | Ratio | Plasma | RBC | Ratio |
| $C_{max}$ (µg/mL) | 0.742 | 50.3 | 68:1 | 4.01 | 1236.7 | 308:1 | 0.753 | 115.7 | 154:1 |
| $AUC_{0-24\,h}$ (µg * h/mL) | 10.7 | 565.6 | 53:1 | 42.6 | 11952.8 | 281:1 | 10.7 | 1732.2 | 161:1 |
| $T_{1/2}$ (h) | 18 | 26 | | 12 | 10 | | 11 | 11 | |

TABLE 6

| | GBT-440 (HCl salt) 7.2 mg/kg | | |
|---|---|---|---|
| Dose | Plasma | RBC | Ratio |
| $C_{max}$ (µg/mL) | 2.15 | 216.2 | 100:1 |
| $AUC_{0-24\,h}$ (µg*h/mL) | 22.8 | 3436.3 | 151:1 |
| $T_{1/2}$ (h) | 19 | 17 | |

Example A4: Solubility

Conditions: 1. JP1 buffer (84 mM HCl, 34.22 mM NaCl, pH 1.2); 2. JP2 buffer (50 mM phosphate buffer at pH 6.8); 3. FaSSIF buffer, pH 6.5 (Preparation: In about 0.9 L of purified water dissolve 0.420 g of NaOH (pellets), 4.470 g of $NaH_2PO_4$ (dihydrate), 6.186 g of NaCl; Adjust the pH to 6.5 with Sodium hydroxide 1N or Hydrochloric acid 1N, to make up to volume (1 L) with purified water at room temperature; Add 0.224 g of SIF Powder Original to about 0.5 L of pH 6.5 blank buffer and stir until powder is completely dissolved; Let stand for 2 hour. FaSSIF buffer is now ready to use.

Procedures: 1. accurately weighed about 2 mg test compounds and controls in whatman vials, then transferred 450 µL buffer in to the vials; 2. Filter pistons of miniuniprep vials were placed and compressed to the position of the liquid level to allow for contact. Vortexed for 2 minutes; 3. Incubated and shook the solubility solutions on an orbital shaker for 24 hr at room temperature (25±2° C.); 4. Miniunipreps were compressed to prepare the filtrates for injection into HPLC system; 5. Diluted the filtrates with buffer by a factor of 50 fold to make diluents; 6. Determined the test compound concentration of the diluents and filtrates using HPLC-UV. Results are shown in Table 7.

TABLE 7

| | JP1 Solubility (µg/mL) | JP2 Solubility (µg/mL) | FaSSIF Solubility (µg/mL) |
|---|---|---|---|
| GBT-440 (HCl) | 986.02 | 27.99 | 95.66 |
| Example 27 | 623.32 | 8.16 | 35.67 |
| Example 29 | >4444.44 | 74.43 | 590.91 |
| Example 38 | 19.96 | 15.11 | 26.59 |

Example A5: CYP Inhibition Evaluation in Human Liver Microsomes

Results are shown in Table 8

TABLE 8

| | $IC_{50}$ (µM) | | | | | |
|---|---|---|---|---|---|---|
| | CYP1A2 | CYP2C8 | CYP2C9 | CYP2C19 | CYP2D6 | CYP3A4-M |
| GBT-440 | 17.6 | 12.4 | 28.1 | 7 | >30 | >30 |
| Ex. 27b | 22 | 3.7 | 11 | 6.1 | >30 | 10 |
| Ex. 29e | >50 | >50 | 36.5 | 19.5 | >50 | >50 |
| Ex. 38 | >30 | 25.2 | 10.6 | 8.61 | >30 | >30 |

Example A6: Microsome Stability Evaluation in Human and Rat Liver Microsomes Results are shown in Table 9

TABLE 9

| | Rat microsome, $t^{1/2}$ (min) | Human microsome, $t^{1/2}$ (min) |
|---|---|---|
| GBT-440 | 22 | 24 |
| Ex. 27b | 19 | 24 |
| Ex. 29e | 11 | 11 |
| Ex. 38 | 18 | 38 |

Example B1: Parenteral Pharmaceutical Composition

To prepare a parenteral pharmaceutical composition suitable for administration by injection (subcutaneous, intravenous), 100 mg of a water-soluble salt of a compound of Formulas (I) is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), (II), (II'), (III), (IV), (V), (VI), or (VII), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example B2: Oral Solution

To prepare a pharmaceutical composition for oral delivery, an aqueous 20% propylene glycol solution is prepared. To this is added a sufficient amount of a compound of Formula (I), (II), (II'), (III), (IV), (V), (VI), or (VII), or a pharmaceutically acceptable salt thereof, to provide a 20 mg/mL solution.

Example B3: Oral Capsule

To prepare a pharmaceutical composition for oral delivery, 100-500 mg of a compound of Formula (I), (II), (II'), (III), (IV), (V), (VI), or (VII), or a pharmaceutically acceptable salt thereof, is mixed with starch. The mixture is incorporated into an oral dosage unit such as a hard gelatin capsule, which is suitable for oral administration.

In another embodiment, 100-500 mg of a compound of Formula (I), (II), (II'), (III), (IV), (V), (VI), or (VII), or a pharmaceutically acceptable salt thereof, is placed into Size 4 capsule, or size 1 capsule (hypromellose or hard gelatin) and the capsule is closed.

Example B4: Oral Tablet

A tablet is prepared by mixing 48% by weigh of a compound of Formula (I), (II), (II'), (III), (IV), (V), (VI), or (VII), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example B5: Topical Gel Composition

To prepare a pharmaceutical topical gel composition, a compound of Formula (I), (II), (II'), (III), (IV), (V), (VI), or (VII), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (II), or a pharmaceutically acceptable salt or solvate thereof:

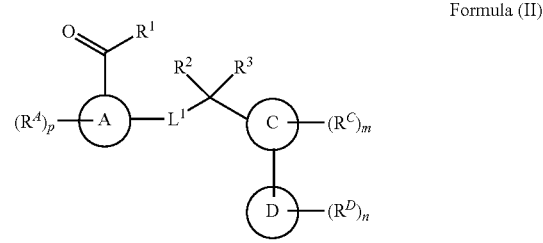

Formula (II)

wherein,
$R^1$ is H or D;
$L^1$ is X;
X is —O—;
$R^2$ is H, D, substituted or unsubstituted $C_1$-$C_6$alkyl, or substituted or unsubstituted $C_1$-$C_6$deuteroalkyl;
$R^3$ is D, substituted or unsubstituted $C_1$-$C_6$alkyl, substituted or unsubstituted $C_1$-$C_6$deuteroalkyl, substituted or unsubstituted $C_1$-$C_6$fluoroalkyl, or substituted or unsubstituted $C_1$-$C_6$heteroalkyl;
or $R^2$ and $R^3$ together with the carbon that they are attached to form a substituted or unsubstituted $C_3$-$C_6$cycloalkyl or a substituted or unsubstituted $C_2$-$C_8$heterocycloalkyl;
or $R^3$ and $R^C$ are taken together with the carbons that they are attached to forma substituted or unsubstituted $C_3$-$C_6$cycloalkyl or a substituted or unsubstituted $C_2$-$C_8$heterocycloalkyl;
or $R^3$ and $R^A$ are taken together with the carbons that they are attached to form a substituted or unsubstituted $C_3$-$C_6$cycloalkyl or a substituted or unsubstituted $C_2$-$C_8$heterocycloalkyl;
ring A is a phenyl;
ring C is a monocyclic heterocycle or a monocyclic carbocycle;
ring D is a monocyclic 5-membered N-containing heterocycle;
each $R^A$, $R^C$, and $R^D$ is independently H, D, halogen, —CN, —OH, —$OR^5$, —$SR^5$, —S(=O)$R^6$, —$NO_2$, —N($R^5$)$_2$, —S(=O)$_2R^6$, —NHS(=O)$_2R^6$, —S(=O)$_2$N(R)$_2$, —C(=O)$R^6$, —OC(=O)$R^6$, —$CO_2R^5$, —$OCO_2R^6$, —C(=O)N(R)$_2$, —OC(=O)N(R)$_2$, —$NR^5$C(=O)N(R)$_2$, —$NR^5$C(=O)$R^6$, —$NR^5$C(=O)$OR^6$, substituted or unsubstituted $C_1$-$C_6$alkyl, substituted or unsubstituted $C_1$-$C_6$deuteroalkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted aryl, or substituted or unsubstituted heteroaryl;
each $R^5$ is independently H, D, substituted or unsubstituted $C_1$-$C_6$alkyl, substituted or unsubstituted $C_1$-$C_6$deuteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;
or two $R^5$ on the same N atom are taken together with the N atom to which they are attached to form a N-containing heterocycloalkyl;

each R⁶ is independently substituted or unsubstituted $C_1$-$C_6$alkyl, substituted or unsubstituted $C_1$-$C_6$deuteroalkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted aryl, or substituted or unsubstituted heteroaryl;

p is 0, 1, 2 or 3;

m is 0, 1, 2 or 3; and n is 0, 1, 2 or 3.

2. The compound of claim 1, or a pharmaceutically acceptable salt or solvate thereof, wherein:

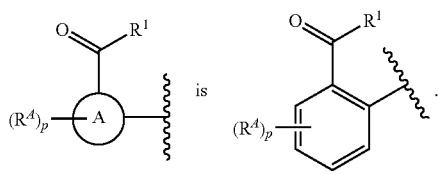

3. The compound of claim 1, or a pharmaceutically acceptable salt or solvate thereof, wherein:
R² is D; and
R³ is D, substituted or unsubstituted $C_1$-$C_3$alkyl, substituted or unsubstituted $C_1$-$C_3$fluoroalkyl, or substituted or unsubstituted $C_1$-$C_3$heteroalkyl.

4. The compound of claim 1, or a pharmaceutically acceptable salt or solvate or solvate thereof, wherein:
R² and R³ are each D.

5. The compound of claim 1, or a pharmaceutically acceptable salt or solvate thereof, wherein:
R² and R³ together with the carbon that they are attached to form a substituted or unsubstituted $C_3$-$C_6$cycloalkyl or a substituted or unsubstituted $C_2$-$C_8$heterocycloalkyl.

6. The compound of claim 1, or a pharmaceutically acceptable salt or solvate thereof, wherein:

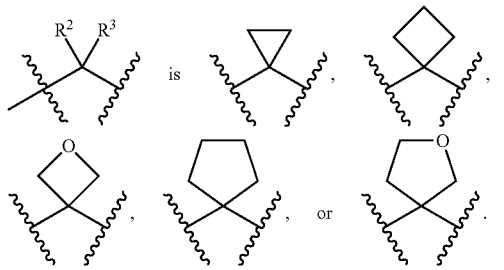

7. The compound of claim 1, or a pharmaceutically acceptable salt or solvate thereof, wherein:
ring C is a monocyclic heterocycle with 1-3 N atoms in the ring.

8. The compound of claim 1, or a pharmaceutically acceptable salt or solvate thereof, wherein:

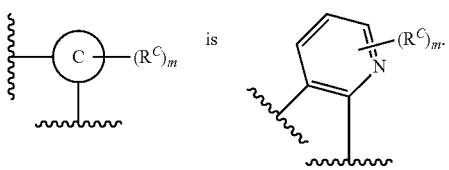

9. The compound of claim 1, wherein the compound of Formula (II) has the structure of Formula (IIa), or a pharmaceutically acceptable salt or solvate thereof:

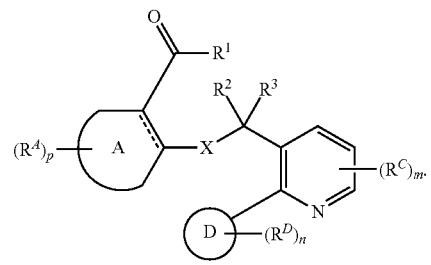

(Formula IIa)

10. The compound of claim 1, or a pharmaceutically acceptable salt or solvate thereof, wherein:

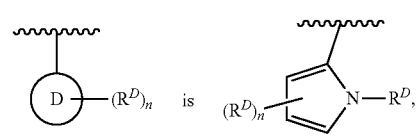

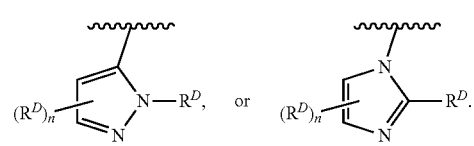

11. The compound of claim 1, wherein the compound of Formula (II) has a structure of Formula (IIb), or pharmaceutically acceptable salt or solvate thereof:

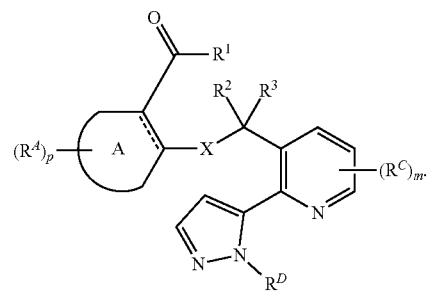

(Formula IIb)

12. The compound of claim 1, wherein the compound of Formula (II) has a structure of Formula (IIc), or pharmaceutically acceptable salt or solvate thereof:

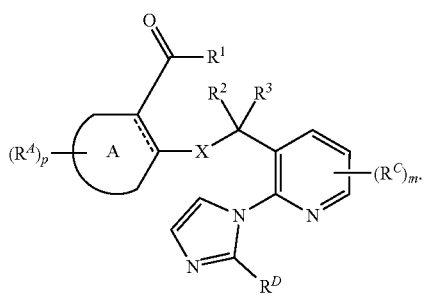

(Formula IIc)

13. The compound of claim 1, or a pharmaceutically acceptable salt or solvate thereof, wherein:

$R^D$ is H, D, substituted or unsubstituted $C_1$-$C_6$alkyl, substituted or unsubstituted $C_1$-$C_6$fluoroalkyl, substituted or unsubstituted $C_1$-$C_6$heteroalkyl.

14. The compound of claim 1, or the pharmaceutically acceptable salt or solvate thereof, wherein the compound has one of the following structures:

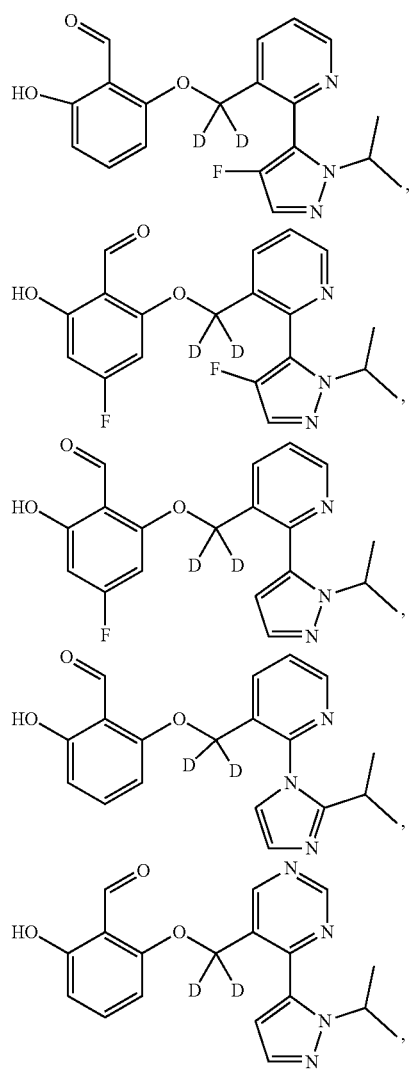

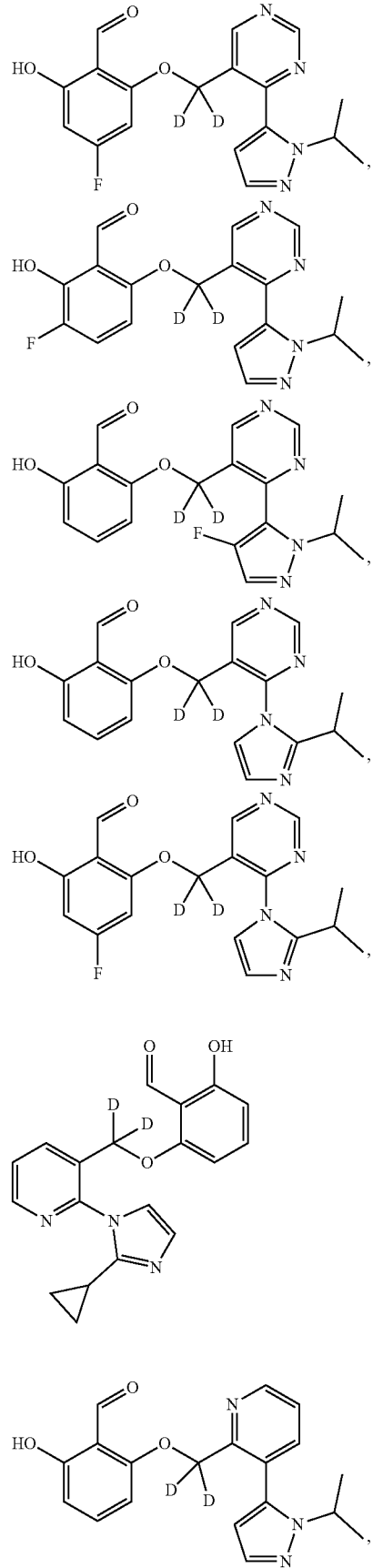

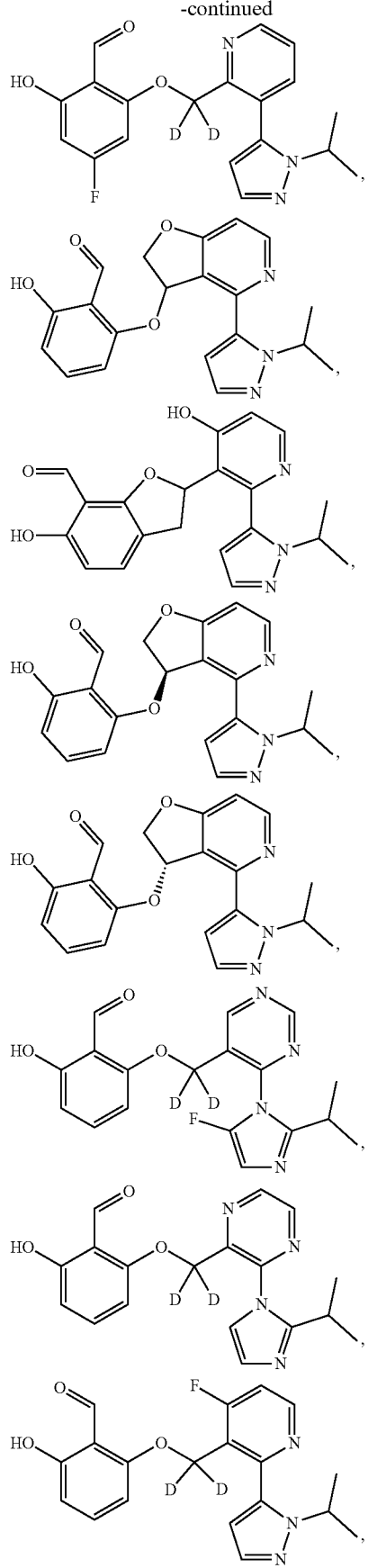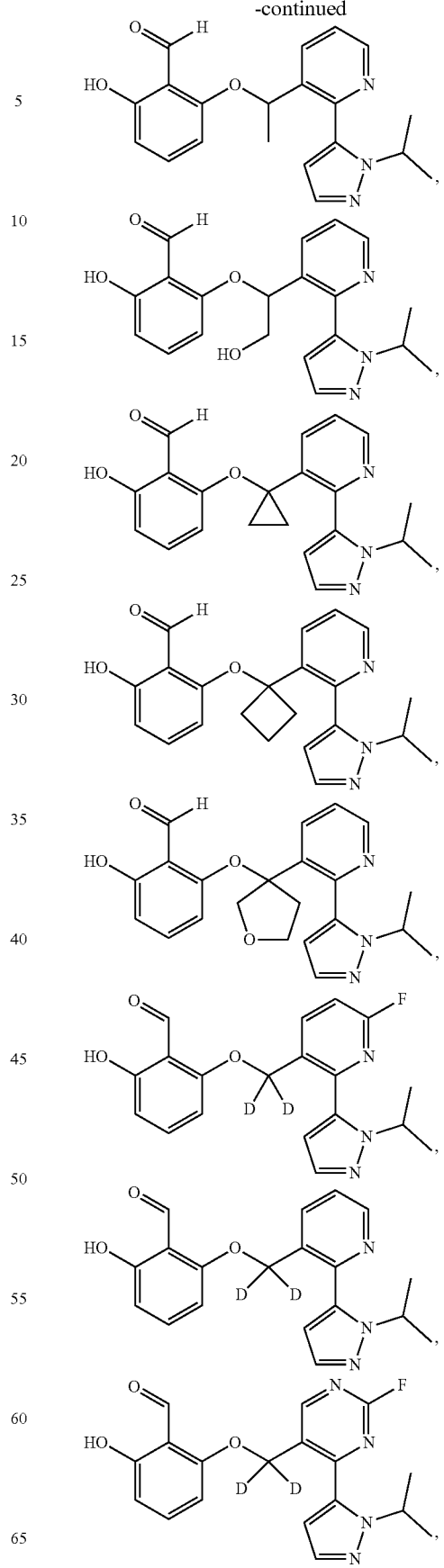

257

-continued

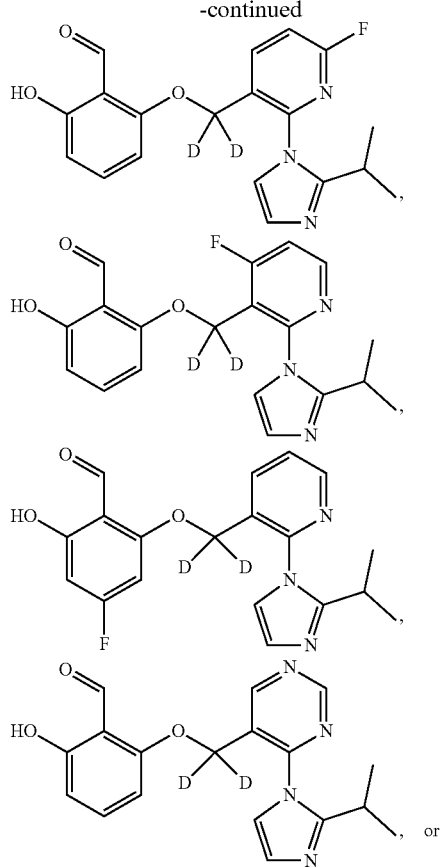

258

-continued

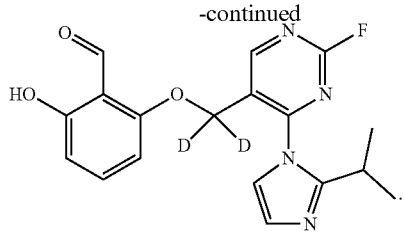

15. A pharmaceutical composition comprising a compound as claimed in claim 1, or a pharmaceutically acceptable salt or solvate thereof, and at least one pharmaceutically acceptable excipient.

16. A method of treating a disease or condition in a subject comprising administering the compound of claim 1, or a pharmaceutically acceptable salt or solvate thereof, to the subject; wherein the disease or condition is associated with oxygen deficiency, a mitochondrial disease, or a hypoxemic pulmonary disorder.

17. The compound of claim 1, or a pharmaceutically acceptable salt or solvate thereof, wherein:

each $R^A$ is independently H, D, halogen, or —OH.

18. The compound of claim 1, or a pharmaceutically acceptable salt or solvate thereof, wherein:

each $R^C$ is independently H, D, or halogen.

* * * * *

UNITED STATES PATENT AND TRADEMARK OFFICE
CERTIFICATE OF CORRECTION

PATENT NO. : 10,787,430 B2
APPLICATION NO. : 16/310258
DATED : September 29, 2020
INVENTOR(S) : Jin et al.

Page 1 of 1

It is certified that error appears in the above-identified patent and that said Letters Patent is hereby corrected as shown below:

In the Claims

Column 250; Lines 48-49; Claim 1, delete: "-S(=O)$_2$N(R)$_2$" and replace with: -- -S(=O)$_2$N(R$^5$)$_2$ --

Column 250; Line 50; Claim 1, delete: "-C(=O)N(R)$_2$" and replace with: -- -C(=O)N(R$^5$)$_2$ --

Column 250; Line 50; Claim 1, delete: "-OC(=O)N(R)$_2$" and replace with: -- -OC(=O)N(R$^5$)$_2$ --

Column 250; Line 51; Claim 1, delete: "-NR$^5$C(=O)N(R)$_2$" and replace with: -- -NR$^5$C(=O)N(R$^5$)$_2$ --

Signed and Sealed this
Tenth Day of November, 2020

Andrei Iancu
*Director of the United States Patent and Trademark Office*